US012564560B1

(12) United States Patent
Forest

(10) Patent No.: US 12,564,560 B1
(45) Date of Patent: Mar. 3, 2026

(54) SELECTIVE SEROTONIN RECEPTOR MODULATORS AND METHODS OF MAKING AND USING THE SAME

(71) Applicant: Park City Bio, LLC, Salt Lake City, UT (US)

(72) Inventor: Jeremy Forest, Richmond Beach, WA (US)

(73) Assignee: Park City Bio, LLC, Salt Lake City, UT (US)

( * ) Notice: Subject to any disclaimer, the term of this patent is extended or adjusted under 35 U.S.C. 154(b) by 0 days.

(21) Appl. No.: 19/098,294

(22) Filed: Apr. 2, 2025

Related U.S. Application Data

(63) Continuation of application No. PCT/US2025/022435, filed on Apr. 1, 2025.

(60) Provisional application No. 63/770,584, filed on Mar. 12, 2025, provisional application No. 63/756,437, filed on Feb. 10, 2025, provisional application No. 63/748,509, filed on Jan. 23, 2025, provisional application No. 63/740,880, filed on Dec. 31, 2024, provisional application No. 63/714,416, filed on Oct. 31, 2024, provisional application No. 63/712,303, filed on Oct. 25, 2024, provisional application No. 63/574,987, filed on Apr. 5, 2024.

(51) Int. Cl.
*A61K 31/135* (2006.01)
*A61P 25/08* (2006.01)

(52) U.S. Cl.
CPC ............ *A61K 31/135* (2013.01); *A61P 25/08* (2018.01)

(58) Field of Classification Search
CPC ... C07C 271/74; C07C 321/28; C07C 391/02; A61K 31/135; A61P 25/08
See application file for complete search history.

(56) References Cited

U.S. PATENT DOCUMENTS

| | | | |
|---|---|---|---|
| 9,629,853 B2 | 4/2017 | Jones et al. | |
| 2004/0260088 A1 | 12/2004 | Connolly et al. | |
| 2018/0002308 A1 | 1/2018 | Asada et al. | |
| 2018/0265453 A1* | 9/2018 | Kozikowski ............ | A61P 25/16 |
| 2020/0148634 A1 | 5/2020 | Leit de Moradei et al. | |

FOREIGN PATENT DOCUMENTS

| | | |
|---|---|---|
| WO | 2000035922 A1 | 6/2000 |
| WO | 2002079152 A1 | 10/2002 |
| WO | 2005007614 A1 | 1/2005 |
| WO | 2005016272 A2 | 2/2005 |
| WO | 2005079391 A2 | 9/2005 |
| WO | 2006077025 A2 | 7/2006 |
| WO | 2011131576 A1 | 8/2011 |
| WO | 2013138687 A1 | 9/2013 |
| WO | 2013192306 A1 | 12/2013 |
| WO | 2016123164 A1 | 8/2016 |
| WO | 2011097336 A2 | 12/2020 |
| WO | 2020260196 A1 | 12/2020 |
| WO | 2021164661 A1 | 8/2021 |
| WO | 2022109408 A1 | 5/2022 |
| WO | 2024077203 A1 | 4/2024 |

OTHER PUBLICATIONS

Venzi et al. Neuropharmacology 2016, 108, 292-304.*
Foster Trends in Pharmacological Sciences 1984, 524-527.*
Patani et al. Chemical Reviews 1996, 96, 3147-3176.*
Jakus et al. Experimental Neurology 2003, 184, 964-972.*
PCT International Search Report and Written Opinion from PCT/US2025/022435, mailed on Jun. 3, 2025, 8 pages.
Pubchem CID 165879667, created Dec. 15, 2022, "{2-[2-(Methylsulfanyl)phenyl]cyclopropyl}methanamine", 7 pages.
Allais et al., "Building Efficient Diastereo- and Enantioselective Synthetic Routes to trans-Cyclopropyl Esters for Rapid Lead Scale-Up," Org. Process. Reg. Dev. pp. A-L, doi: 10.1021/acs.oprd.5c00007 (2025).
Aronov, Alex M., "Predictive in silico modeling for hERG channel blockers," Drug Discovery Today, 10:2, Jan. 2005.
Berg et al., "Fine-tuning serotonin2c receptor function in the brain: Molecular and functional implications," Neuropharmacology 55 (2008) 969-976, doi: 10.1016/j.neuropharm.2008.06.014.
Berger et al., "The Expanded Biology of Serotonin," Annu. Rev. Med. 2009. 60:355-66, doi: 10.1146/annurev.med.60.042307.110802.
BMB-101 Breaking Through, dated Feb. 2025, downloaded from https://brightmindsbio.com/wp-content/uploads/2025/02/BMB-Public-Deck-February-2025.pdf, last visited Mar. 4, 2025.
Callahan et al., "Involvement of 5-HT2c receptors in mediating the discriminative stimulus properties of m-chlorophenylpiperazine (mCPP)," European Journal of Pharmacology 257 (1994) 27-38.
Chen et al., "Rational Drug Design Leading to the Identification of a Potent 5-HT2C Agonist Lacking 5-HT2B Activity," ACS Med. Chem. Lett. 2011, 2, 929-932, doi: 10.1021/ml200206z.
Cheng at al., "Optimization of 2-Phenylcyclopropylmethylamines as Selective Serotonin 2C Receptor Agonists and Their Evaluation as Potential Antipsychotic Agents," J. Med. Chem, pp. 1-44, published online Jan. 29, 2015, doi: 10.1021/jm5019274.
Cheng et al., "Design and Synthesis of (2-(5-Chloro-2,2-dimethyl-2,3-dihydrobenzofuran-7-yl)cyclopropyl) methanamine as a Selective Serotonin 2C Agonist," Tetrahedron Lett. Jun. 3, 2015; 56(23): 3420-3422. doi:10.1016/j.tetlet.2015.01.060.
Cheng et al., "Further Advances in Optimizing (2-Phenylcyclopropyl)methylamines as Novel Serotonin 2C Agonists: Effects in Open Field, Prepulse Inhibition, and Cognition Models," J Med Chem. Jan. 28, 2016; 59(2): 578-591. doi:10.1021/acs.jmedchem.5b01153.
Cheong et al., "T-type Ca2+ channels in absence epilepsy," Acta (2013), pp. 1-12, http://dx.doi.org/10.1016/j.bbamem.2013.02.002.
Cho et al., "Selective 5-Hydroxytryptamine 2C Receptor Agonists Derived from the Lead Compound Tranylcypromine: Identification of Drugs with Antidepressant-Like Action," J. Med. Chem. 2009, 52, 1885-1902, doi: 10.1021/jm801354e.

(Continued)

*Primary Examiner* — Irina Neagu
(74) *Attorney, Agent, or Firm* — McNeill, PLLC

(57) ABSTRACT

This disclosure relates to serotonin receptor modulators, including conformationally constrained serotonin receptor agonists, and methods of making and using the same are disclosed herein.

29 Claims, 2 Drawing Sheets

(56) References Cited

OTHER PUBLICATIONS

Crunelli et al., "Transition to absence seizures and the role of GABAA receptors," Epilepsy Research (2011) 97, 283-289, doi: 10.1016/j.eplepsyres.2011.07.011.
Digiovanni et al., "Preferential Modulation of Mesolimbic Vs. Nigrostriatal Dopaminergic Function by Serotonin2C/2B Receptor Agonists: A Combined In Vivo Electrophysiological and Microdialysis Study," Synapse 35:53-61 (2000).
Dunlop et al., "Characterization of Vabicaserin (SCA-136), a Selective 5-Hydroxytryptamine 2C Receptor Agonist, Characterization of Vabicaserin (SCA-136), a Selective 5-Hydroxytryptamine 2C Receptor Agonist," The Journal of Pharmacology and Experimental Therapeutics, 37:3, 673-680 (2011).
Fiorella et al., "5-HT2c receptor-mediated phosphoinositide turnover and the stimulus effects of m-chlorophenylpiperazine," Psychopharmacology (1995) 122:237-243.
Heijnen et al., "Efficacy of Tranylcypromine in Bipolar Depression," Journal of Clinical Psychopharmacology, vol. 35, No. 6, Dec. 2015, doi: 10.1097/JCP.0000000000000409.
Hogenkamp et al., "Synthesis and in Vitro Activity of 3B-Substituted-3a-hydroxypregnan-20-ones: Allosteric Modulators of the GABAA Receptor," J. Med. Chem. 1997, 40, 61-72.
Kalgutkar et al., "Genotoxicity of 2-(3-Chlorobenzyloxy)-6-(piperazinyl)pyrazine, a Novel 5-Hydroxytryptamine2c Receptor Agonist for the Treatment of Obesity: Role of Metabolic Activation," Drug Metabolism and Disposition, 35:6, 848-858 (2007).
Kang et al., "Quantitative Structure-Activity Relationships in MAO-Inhibitory 2-Phenylcyciopropylamines: Insights into the Topography of MAO-A and MAO-B," Arch. Pharm. Res. 13(1), 82-96 (1990).
Kessler et al., "A Practical Guide to Treatment of Childhood Absence Epilepsy," Pediatric Drugs, Feb. 8, 2019, https://doi.org/10.1007/s40272-019-00325-x.
Kiani, Cameron, "Tranylcypromine: Its Pharmacology, Safety, and Efficacy," The American Journal of Psychiatry Residents' Journal, Jun. 2020, 3-5.
Kozikowski et al., "HTS and Rational Drug Design to Generate a Class of 5-HT2C-Selective Ligands for Possible Use in Schizophrenia," ChemMedChem 2010, 5, 1221-1225, DOI: 10.1002/cmdc.201000186.
Leysen, L.E., "5-HT2 Receptors," Current Drug Targets—CNS & Neurological Disorders, 2004, 3, 11-26.
Liu et al., "Prediction of Efficacy of Vabicaserin, a 5-HT2C Agonist, for the Treatment of Schizophrenia Using a Quantitative Systems Pharmacology Model," CPT Pharmacometrics Syst. Pharmacol. (2014) 3, e111; doi: 10.1038/psp.2014.7.
Marquis et al., "WAY-163909 [(7bR, 10aR)-1,2,3,4,8,9,10,10a-Octahydro-7bHcyclopenta-[b][1,4]diazepino[6,7,1hi] indole]: A Novel 5-Hydroxytryptamine 2C Receptor-Selective Agonist with Preclinical Antipsychotic-Like Activity," The Journal of Pharmacology and Experimental Therapeutics, 320:1, 486-496 (2007).
Meltzer et al., "Lorcaserin and pimavanserin: emerging selectivity of serotonin receptor subtype-targeted drugs," J Clin Invest. 2013;123(12):4986-4991. doi:10.1172/JCI70678.
Mombereau et al, "Functional relevance of serotonin 2C receptor mRNA editing in antidepressant- and anxiety-like behaviors," Neuropharmacology 59 (2010) 468-473.
Nohria et al., "Ganaxolone," Neurotherapeutics: The Journal of the American Society for Experimental NeuroTherapeutics, vol. 4, 102-105, Jan. 2007.
Pazos et al., "The Binding of Serotonergic Ligands to the Porcine Choroid Plexus: Characterization of a New Type of Serotonin Recognition Site," European Journal of Pharmacology, 106 (1985) 539-546.
Thomsen et al., "Lorcaserin, a Novel Selective Human 5-Hydroxytryptamine2C Agonist: in Vitro and in Vivo Pharmacological Characterization," The Journal of Pharmacology and Experimental Therapeutics, 325:2, 577-587 (2008).
Ulrich et al., "Efficacy and Adverse Effects of Tranylcypromine and Tricyclic Antidepressants in the Treatment of Depression," Journal of Clinical Psychopharmacology, vol. 00, No. 00, 2019, doi: 10.1097/JCP.0000000000001153.
Vasilkevich et al., "Safety, Tolerability, and Pharmacokinetics of Novel 5-HT2C Agonist BMB-101 (Phase I Clinical Study)," American Epilepsy Society (AES) Conference, Dec. 6-10, 2024, Los Angeles, retrieved from https://brightmindsbio.com/events-and-presentations/, last visited Dec. 20, 2024.
Yamazaki et al., "Computational Prediction of the Plasma Protein-Binding Percent of Diverse Pharmaceutical Compounds," J Pharm Sci, vol. 93, No. 6, Jun. 2004.
Zhang et al., Design of fluorinated cyclopropane derivatives of 2-phenylcyclopropylmethylamine leading to identification of a selective serotonin 2C (5-HT2C) receptor agonist without 5-HT2B agonism, European Journal of Medicinal Chemistry 182 (2019) 111626, https://doi.org/10.1016/j.ejmech.2019.111626.
*Allergan, Inc.* v. *Sandoz Inc.*, 796 F.3d 1293, 115 USPQ2d 2012 (Fed. Cir. 2015).
De Deurwaerdère et al., "Editorial: Contemporary Perspective on 5-HT2C Receptor Function and Its Pharmacological Targeting," Frontiers in Pharmacology, Article 606414, Nov. 2022, vol. 11, doi: 10.3389/fphar.2020.606414.
He et al., "Barbadin Potentiates Long-Term Effects of Lorcaserin on POMC Neurons and Weight Loss," J. of Neuroscience, Jun. 30, 2021, 41(26): 5734-5746.
*Janssen Pharmaceuticals, Inc.* v. *Teva Pharmaceuticals USA, Inc.*, No. 25 1228 (Fed. Cir. Jul. 8, 2025).
Kalgutkar et al., "Genotoxicity of 2-(3-Chlorobenzyloxy)-6-(piperazinyl)pyrazine, a Novel 5-Hydroxytryptamine2C Receptor Agonist for the Treatment of Obesity: Role of Metabolic Activation," Drug Metabolism and Disposition, 35(6): 848-858.
Bercovici et al., "5-HT2 modulation of AY-9944 induced atypical absence seizures," Neuroscience Letters, May 11, 2027, 418(1): 13-17.
Betchel et al., StatPearls [Internet]. Treasure Island (FL): StatPearls Publishing; Jan. 2023-. Available from: https://www.ncbi.nlm.nih.gov/books/NBK470442/ last visited Aug. 15, 2025.
Chan et al., "Which antiseizure medications are effective for absence seizures in children and adolescents? A Cochrane Review summary with commentary," Dev Med Child Neurol, Oct. 2021, 63(1): 1140-1141.
Fox et al., "Exercise reduces the anxiogenic effects of meta-chlorophenylpiperazine: The role of 5-HT2C receptors in the bed nucleus of the stria terminalis," Front. Synaptic Neurosci., Jan. 12, 2023, (14): 1-13.
In re Wesslau, 353 F.3d 238 (C.C.P.A. 1965).
Johannessen et al., "Valproate: Past, Present, and Future," CNS Drug Reviews, 2003, 9(2): 199-216.
Thomas et al., "Effects of the 5-HTC receptor agonist meta-chlorophenylpiperazine on appetite, food intake, and emotional processing in healthy volunteers," Psychopharmacology, Jan. 10, 2014, DOI: 10.1007/s00213-013-3409-x.
Silenieks, Leonardo B. et al., "Evaluation of Selective 5-HT2C Agonists in Acute Seizure Models", 2019, ACS Chem. Neurosci., doi: 10.1021/acschemneuro.8b00739, 12 pages.
Brandt, Simon D. et al., "An analytical perspective on favoured synthetic routes to the psychoactive tryptamines", Journal of Pharmaceutical and Biomedical Analysis 36 (2004) 675-691.
Coenen, A.M.L. et al., "Absence Epilepsy and the Level of Vigilance in Rats of the WAG/Rij Strain", Neuroscience & Behavioral Revies, 1991, 15: 259-263.
Cortez, Miguel A. et al. "A model of atypical absence seizures: EEG, pharmacology, and developmental characterization", Neurology 2001; 56: 341-349.
Cortez, Miguel A. et al., "Brain Sterols in the AY-9944 Rat Model of Atypical Absence Seizures", Epilepsia, 2002, 43 (1): 3-8.
Gabapentin oral solution, Highlights of Prescribing Information, Initial U.S. Approval: 1993, 34 pages.
Hu, Bing et al., "The generation mechanism of spike-and-slow wave discharges appearing on thalamic relay nuclei", Scientific Reports (2018), 8:4953, 13 pages.

(56) References Cited

OTHER PUBLICATIONS

Jurczak, Ewa et al., "Pharmaceutical Hydrates Analysis—Overview of Methods and Recent Advances", Pharmaceutics 2020, 12, 959, 25 pages.
Kozikowski, Alan., "From Start-Ups to the Chemistry and Biology of Serotonin Inspired Medicines—From Outside to Inside the Cell", 4th Annual Psychedelic Therapeutics and Drug Development Conference, Boston, Massachusetts, May 23-24, 2024.
Lamotrigine Desitin 10 mg/ml Oral Suspension, Package leaflet: Information for the user, 2025.
Lazarini-Lopes, Willian et al., "Absence epilepsy in male and female WAG/Rij rats: a longitudinal EEG analysis of seizure expression", Epilepsy Res. 2021; 176: 106693, 14 pages.
Li, Guoshi et al., "Unified thalamic model generates multiple distinct oscillations with state-dependent entrainment by stimulation", PLoS Comput Biol (2017), 13(10): e1005797, 46 pages.
Stinikova, Evgenia, "Sleep Disturbances in Rats With Genetic Pre-disposition to Spike-Wave Epilepsy (WAG/Rij)", Frontiers in Neurology, 2021, 12:766566, 6 pages.
Sun, Hao et al., "Deuterium isotope effects in drug pharmacokinetics II: Substrate-dependence of the reaction mechanism influences outcome for cytochrome P450 cleared drugs", PLoS One (2018), 13(11): e0206279, 17 p.
Topiramate Rosemont 20mg/ml Oral Suspension, Package Leaflet: Information for the User, Last Revised Apr. 2025, 2 pages.
Tsukahara, Victor Hugo Batista et al., "Data-Drive Network Dynamical Model of Rat Brains During Acute Ictogenesis", Frontiers in Neural Circuits, 2022, 16:747910, 13 pages.
Vasilkevich et al., "BMB-101 and Biased 5-HT2C Agonism: A Novel Approach for Sustained Epilepsy Management," American Epilepsy Society (AES) Conference, Dec. 6-10, 2024, Los Angeles, poster, 1 page.
Nonogaki, Katsunori et al., "The contribution of serotonin 5-HT2C and melanocortin-4 receptors to the satiety signaling of glucagon-like peptide 1 and liragultide, a glucagon-like peptide 1 receptor agonist, in mice", Biochemical and Biophysical Research Communications (2011), 411, pp. 445-448.
Forest, Jeremy, "Selective Serotonin Receptor Modulators and Methods of Making and Using the Same", U.S. Appl. No. 19/311,344, filed Aug. 27, 2025.

* cited by examiner

SELECTIVE SEROTONIN RECEPTOR MODULATORS AND METHODS OF MAKING AND USING THE SAME

CROSS-REFERENCE TO RELATED APPLICATIONS

This application is a continuation of PCT Application No. PCT/US2025/022435, filed Apr. 1, 2025, which claims priority to U.S. Provisional Application No. 63/770,584, filed Mar. 12, 2025, U.S. Provisional Application No. 63/756,437, filed Feb. 10, 2025, U.S. Provisional Application No. 63/748,509, filed Jan. 23, 2025, U.S. Provisional Application No. 63/740,880, filed Dec. 31, 2024, U.S. Provisional Application No. 63/714,416, filed Oct. 31, 2024, U.S. Provisional Application No. 63/712,303, filed Oct. 25, 2024, and U.S. Provisional Application No. 63/574,987, filed Apr. 5, 2024, the entire contents of each are incorporated by reference herein for all purposes.

TECHNICAL FIELD

This disclosure relates to serotonin receptor modulators, including conformationally constrained serotonin receptor agonists, and methods of using them for treating and preventing a variety of human conditions.

BACKGROUND

Serotonin or 5-hydroxy tryptamine (5-HT) is a major neurotransmitter that is primarily found in the gastrointestinal tract, platelets, and the central nervous system (CNS). 5-HT is involved in the regulation of a variety of physiological functions, such as intestinal movements, mood, cognition, and appetite. These functions are mediated through serotonin receptors, which belong to the G-protein coupled receptor (GPCR) superfamily and are composed of seven subfamilies (5-$HT_{1-7}$) and 14 isoforms.

Recently, the serotonin 2C (5-$HT_{2C}$) receptor has been shown to be a promising drug target for the treatment of a variety of CNS disorders, including obesity and mental disorders, such as schizophrenia, depression, and anxiety. Furthermore, based on the study of both its distribution and biological function, 5-$HT_{2C}$ receptors in the basal ganglia likely are essential for the regulation of repetitive motion and in the cingulate gyrus they mediate many of the effects of neurotransmitters on obsessive/compulsive-type behaviors.

One of the many advantages of the 5-$HT_{2C}$ receptor as a CNS drug target stems from the fact that it is found almost exclusively in the CNS. Therefore, compounds that selectively activate this receptor should have limited impact on peripheral tissues. However, the activation of two other closely related 5-HT2 subtypes, i.e., 5-$HT_{2A}$ and 5-$HT_{2B}$ receptors, has been reported to be associated with hallucinations and cardiac valvulopathy, respectively. Therefore, the identification of ligands possessing a high selectivity against the 5-$HT_{2A}$ and 5-$HT_{2B}$ receptors is a key criterion for the therapeutic advancement of 5-$HT_{2C}$ agonists. This goal has been challenging due to the high conservation of molecular determinants involved in ligand recognition within this subfamily of receptors. Accordingly, there remains a need to develop safe and selective 5-$HT_{2A}$ receptor modulators.

SUMMARY

Disclosed herein are compounds of Formula I:

Formula I

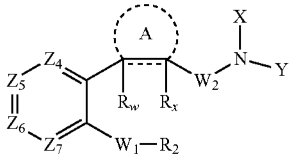

wherein

X and Y are each independently selected from hydrogen, deuterium, optionally substituted $C_1$-$C_8$ alkyl, optionally substituted $C_2$-$C_8$ alkenyl, and optionally substituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from $CF_2$, $NR_1$, O, S(O), $SO_2$, Se, Se(O), and $SeO_2$;

$W_2$ is absent or $C(R_3)(R_{3'})$;

$Z_4$ is selected from N and $CR_4$;

$Z_5$ is selected from N and $CR_5$;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —$C(O)N(R_9)_2$, —$SOR_8$, and —$SO_2R_8$; $R_2$, $R_4$, $R_5$, $R_6$, and $R_7$ are each independently selected from hydrogen, deuterium, —$N(R_9)_2$, —$SR_9$, halo, optionally substituted $C_1$-$C_8$ alkyl, -C1-$C_8$ alkoxy, optionally substituted $C_2$-$C_8$ alkenyl, optionally substituted $C_2$-$C_8$ alkynyl, optionally substituted aryl, optionally substituted heteroaryl, hydroxyl, —$OC(O)R_8$, —$OC(O)OR_8$, —$OP(O)(OR_9)_2$, and —$OSO_2R_8$, or $R_2$ is a residue selected from Formula III Formula III

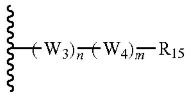

wherein $W_3$ is, for each occurrence, independently selected from optionally substituted alkylene, optionally substituted arylene, optionally substituted heteroarylene, optionally substituted cycloalkylene, optionally substituted heterocycloalkylene, and

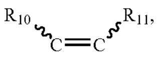

wherein n is an integer selected from 1 to 10, $W_4$ is, for each occurrence, independently selected from O, S, Se, $C(R_{12})(R_{13})$, optionally substituted arylene, optionally substituted heteroarylene, optionally substituted cycloalkylene, optionally substituted heterocycloalkylene, and

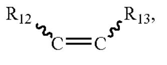

wherein m is an integer selected from 0 to 10, and $R_{10}$, $R_{11}$, $R_{12}$, $R_{13}$, and $R_{15}$ are, for each occurrence, independently selected from optionally substituted $C_1$-$C_8$ alkyl, hydrogen, deuterium, halo, and hydroxyl, or $R_4$ is taken together with $R_5$ and the carbons therebetween to form 3- to 7-membered carbocyclic or heterocyclic ring optionally including 1 to 2 additional ring heteromoieties selected from O, S, S(O), $SO_2$, and $NR_9$, or $R_5$ is taken together with $R_6$ and the carbons therebetween to form 3- to 7-membered carbocyclic or heterocyclic ring optionally including 1 to 2 additional ring heteromoieties selected from O, S, S(O), $SO_2$, and $NR_9$, or $R_6$ is taken together with $R_7$ and the carbons therebetween to form 3- to 7-membered carbocyclic or heterocyclic ring optionally including 1 to 2 additional ring heteromoieties selected from O, S, S(O), $SO_2$, and $NR_9$;

$R_3$ and $R_{3'}$ are each, independently, selected from hydrogen, deuterium, —$N(R_9)_2$, —$SR_9$, halo, optionally substituted $C_1$-$C_8$ alkyl, -C1-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$;

$R_x$ and $R_w$ are absent, or each, independently, is selected from hydrogen, deuterium, —$N(R_9)_2$, —$SR_9$, halo, optionally substituted $C_1$-$C_8$alkyl, -$C_1$-$C_8$ alkoxy, optionally substituted $C_2$-$C_8$ alkenyl, and optionally substituted $C_2$-$C_8$ alkynyl, or $R_2$ is taken together with $W_1$ and the carbon to with $R_x$ is attached, and the carbons therebetween, to form a 3- to 7-membered carbocyclic or heterocyclic ring optionally including 1 to 2 additional ring heteromoieties selected from O, S, S(O), $SO_2$, and $NR_9$;

$R_8$ is selected from optionally substituted $C_1$-$C_8$alkyl, optionally substituted $C_2$-$C_8$ alkenyl, and optionally substituted aryl;

$R_9$ is independently selected from hydrogen, deuterium, optionally substituted $C_1$-$C_8$ alkyl, optionally substituted $C_2$-$C_8$ alkenyl, and optionally substituted aryl;

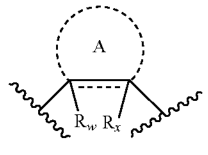

(also referred to as "Group A") represents a fused ring chosen from an optionally substituted cycloalkanyl, optionally substituted cycloalkenyl, optionally substituted heterocyclyl, optionally substituted aryl, and optionally substituted heteroaryl;

the  is a single or double bond, wherein $R_x$ and $R_w$ are absent when it is a double bond;

and salts, solvates, hydrates, prodrugs, and enantiomers thereof.

The disclosure also relates to compositions comprising, consisting of, or consisting essentially of a compound of Formula I and an excipient. The disclosure further relates to pharmaceutical compositions comprising a therapeutically effective amount of a compound of Formula I, wherein the excipient is a pharmaceutically acceptable carrier.

The present disclosure further relates to a method of preventing or treating a psychological disorder comprising the step of administering to a subject in need thereof a therapeutically effective amount of a compound of Formula I or a composition (e.g., a pharmaceutically-acceptable composition) comprising a compound of Formula I.

Embodiments of the disclosure also relate to a composition comprising, consisting of, or consisting essentially of a first compound selected from compounds of Formula I; and a second active compound. In certain embodiments, the second active compound comprises a serotonergic compound.

Also described herein are methods of preventing or treating inflammation and/or pain comprising administering to a subject in need thereof a therapeutically effective amount of a compound of Formula I or a composition (e.g., a pharmaceutically-acceptable composition) comprising a compound of Formula I.

Unless context indicates differently, reference to a compound of Formula I includes all related genera of Formula I (e.g., Formulae II, IV, V, VI, VII, VIII, IX, etc.).

DETAILED DESCRIPTION

Compounds

Figure 1:
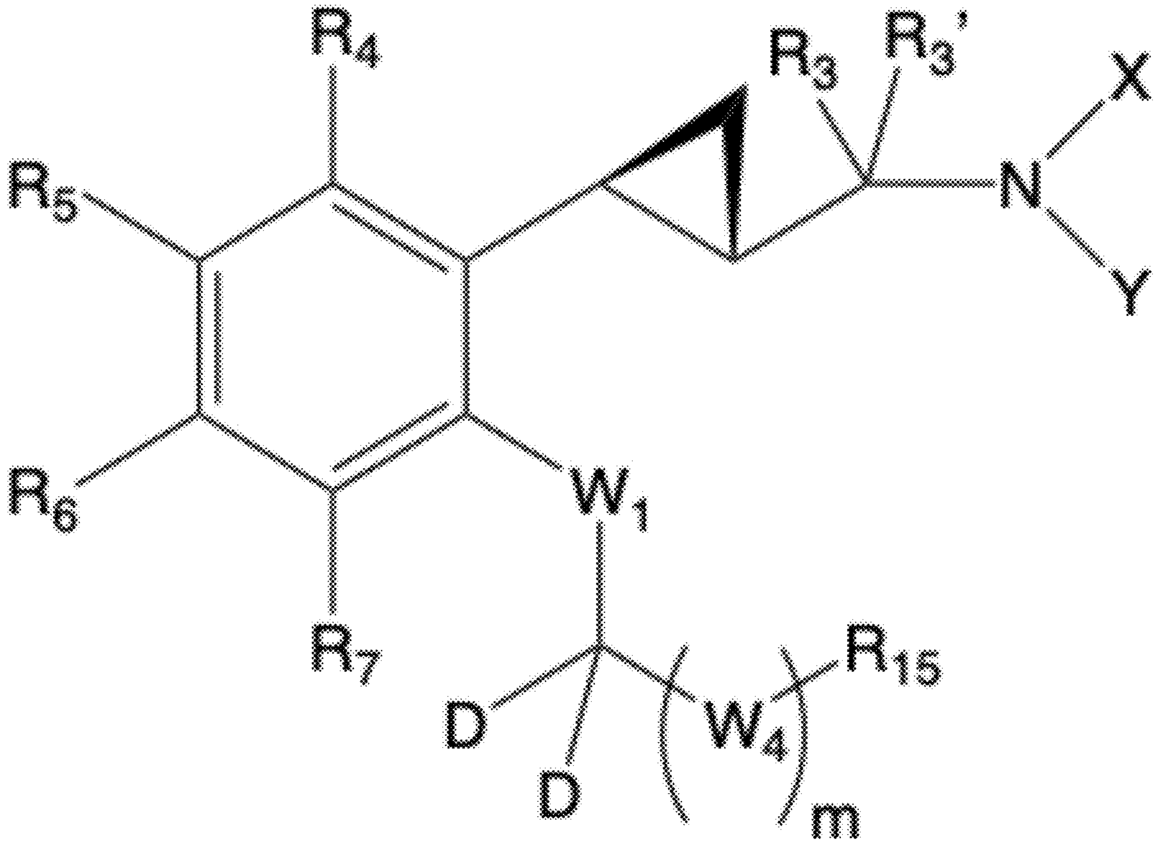
FIG. 1 illustrates the structure of exemplary compounds of Formula VI(a) described herein.
Figure 2:
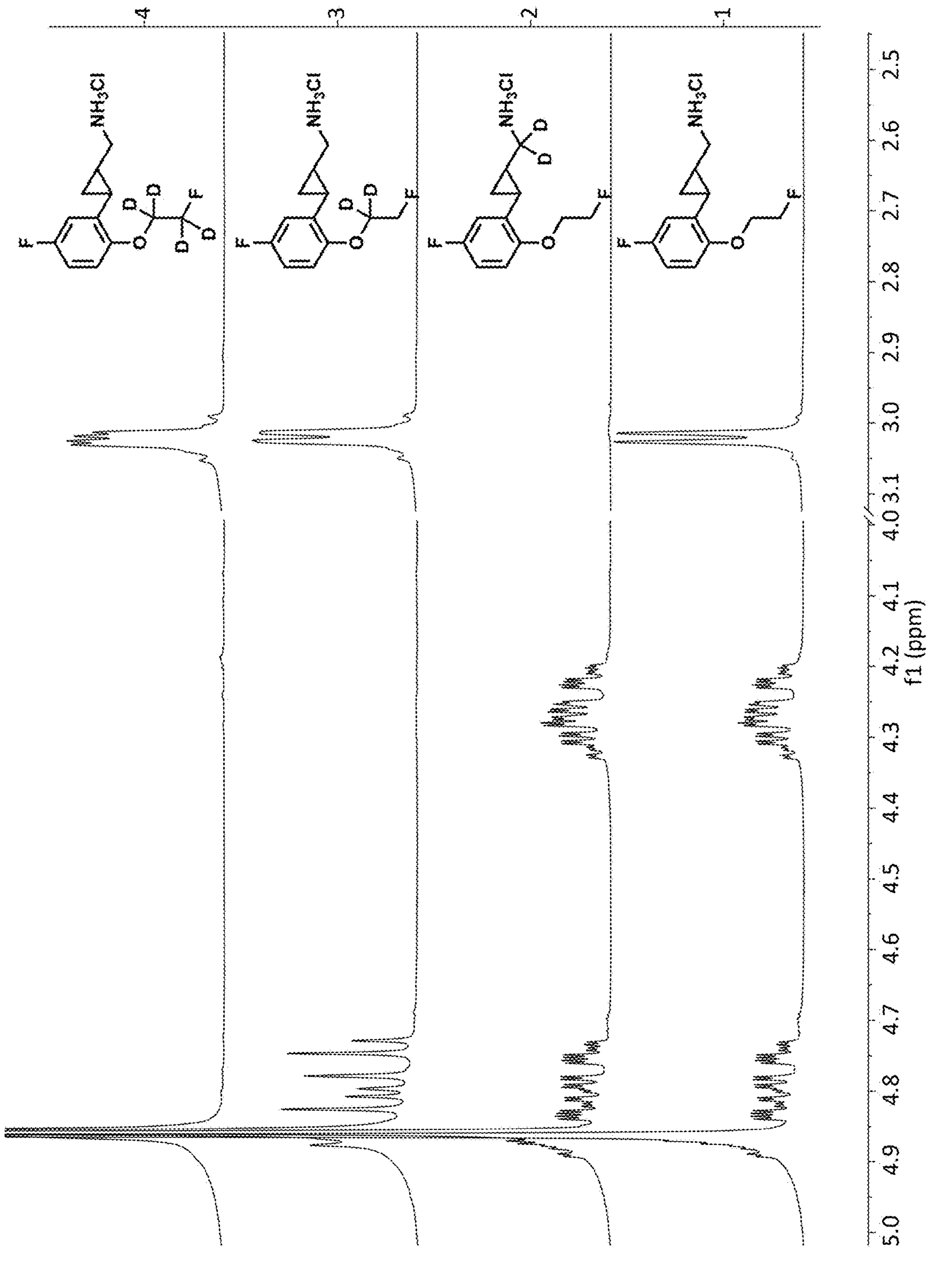
FIG. 2 illustrates the $^1$H NMR chromatogram overlays comparing the presence/absence of protons replaced with deuterium for certain compounds produced in the Examples.

Disclosed herein are compounds of Formula I:

Formula I

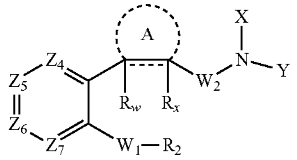

wherein

X and Y are each independently selected from hydrogen, deuterium, optionally substituted $C_1$-$C_8$ alkyl, optionally substituted $C_2$-$C_8$ alkenyl, and optionally substituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$; $W_1$ is selected from $CF_2$, $NR_1$, 0, 5, S(O), $SO_2$, Se, Se(O), and $SeO_2$; $W_2$ is absent or $C(R_3)(R_{3'})$;

$Z_4$ is selected from N and $CR_4$;

$Z_5$ is selected from N and CRS;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —$C(O)N(R_9)_2$, —$SOR_8$, and —$SO_2R_8$;

$R_2$, $R_4$, $R_5$, $R_6$, and $R_7$ are each independently selected from hydrogen, deuterium, —$N(R_9)_2$, —$SR_9$, halo, optionally substituted $C_1$-$C_8$ alkyl, -$C_1$-$C_8$ alkoxy, optionally substituted $C_2$-$C_8$ alkenyl, optionally substituted $C_2$-$C_8$ alkynyl, optionally substituted aryl, optionally substituted heteroaryl, hydroxyl, —$OC(O)R_8$, —$OC(O)OR_8$, —$OP(O)(OR_9)_2$, and —$OSO_2R_8$, or $R_2$ is a residue selected from Formula III:

Formula III

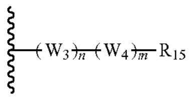

wherein $W_3$ is, for each occurrence, independently selected from optionally substituted alkylene, optionally substituted arylene, optionally substituted heteroarylene, optionally substituted cycloalkylene, optionally substituted heterocycloalkylene, and

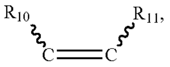

wherein n is an integer selected from 1 to 10, $W_4$ is, for each occurrence, independently selected from O, S, Se, $C(R_{12})(R_{13})$, optionally substituted arylene, optionally substituted heteroarylene, optionally substituted cycloalkylene, optionally substituted heterocycloalkylene, and

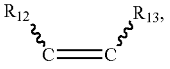

wherein m is an integer selected from 0 to 10, and $R_{10}$, $R_{11}$, $R_{12}$, $R_{13}$, and $R_{15}$ are, for each occurrence, independently selected from optionally substituted $C_1$-$C_8$ alkyl, hydrogen, deuterium, halo, and hydroxyl, or $R_4$ is taken together with $R_5$ and the carbons therebetween to form 3- to 7-membered carbocyclic or heterocyclic ring optionally including 1 to 2 additional ring heteromoieties selected from O, S, S(O), $SO_2$, and $NR_9$, or $R_5$ is taken together with $R_6$ and the carbons therebetween to form 3- to 7-membered carbocyclic or heterocyclic ring optionally including 1 to 2 additional ring heteromoieties selected from O, S, S(O), $SO_2$, and $NR_9$, or $R_6$ is taken together with $R_7$ and the carbons therebetween to form 3- to 7-membered carbocyclic or heterocyclic ring optionally including 1 to 2 additional ring heteromoieties selected from O, S, S(O), $SO_2$, and $NR_9$;

$R_3$ and $R_{3'}$ are each, independently, selected from hydrogen, deuterium, —$N(R_9)_2$, —$SR_9$, halo, optionally substituted $C_1$-$C_8$alkyl, -$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$, or $R_3$ and $R_{3'}$ are taken together with the carbon to which they are attached to form a keto group;

$R_x$ and $R_w$ are absent, or each, independently, is selected from hydrogen, deuterium, —$N(R_9)_2$, —$SR_9$, halo, optionally substituted $C_1$-$C_8$alkyl, -$C_1$-$C_8$ alkoxy, optionally substituted $C_2$-$C_8$ alkenyl, and optionally substituted $C_2$-$C_8$ alkynyl, or $R_2$ is taken together with $W_1$ and the carbon to with $R_x$ is attached, and the carbons therebetween, to form a 3- to 7-membered carbocyclic or heterocyclic ring optionally including 1 to 2 additional ring heteromoieties selected from O, S, S(O), $SO_2$, and $NR_9$;

$R_8$ is selected from optionally substituted $C_1$-$C_8$alkyl, optionally substituted $C_2$-$C_8$ alkenyl, and optionally substituted aryl;

$R_9$ is independently selected from hydrogen, deuterium, optionally substituted $C_2$-$C_8$ alkyl, optionally substituted $C_2$-$C_8$ alkenyl, and optionally substituted aryl;

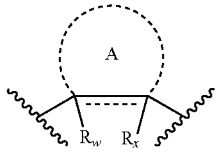

(also referred to as "Group A") represents a fused ring chosen from an optionally substituted cycloalkanyl, optionally substituted cycloalkenyl, optionally substituted heterocyclyl, optionally substituted aryl, and optionally substituted heteroaryl;

the ------ is a single or double bond, wherein $R_x$ and $R_w$ are absent when it is a double bond;

and salts, solvates, hydrates, prodrugs, and enantiomers thereof.

As used herein, the term "alkyl" refers to straight, branched or cyclic saturated hydrocarbon group. As used herein, alkyl has 1 to 20 carbon atoms, 1 to 10 carbon atoms, 1 to 8 carbon atoms, 1 to 6 carbon atoms or 1 to 3 carbon atoms. Examples of alkyl groups include methyl, ethyl, propyl, isopropyl, n-butyl, isobutyl, sec-butyl, tert-butyl pentyl, isopentyl, hexyl, heptyl, octyl, as well as cycloalkyl variants such as cyclopropyl, cyclobutyl, cyclopentyl, cyclohexyl, cycloheptyl, cyclooctyl, cyclononyl, and cyclodecyl. When an alkyl residue having a specific number of carbons is named by chemical name or identified by molecular formula, all positional isomers having that number of carbons may be encompassed; thus, for example, "butyl" includes n-butyl, isobutyl, sec-butyl, and tert-butyl; and "propyl" includes n-propyl and isopropyl. In some embodiments, a deuterium atom maybe be a replacement for a hydrogen atom. The related term "alkylene" refers to a divalent radical derived from an alkyl group by removing at least two hydrogens from one or more carbons. The term "alkylene" includes straight chained and branched alkylene groups. The related term "cycloalkylene" refers to a divalent radical derived from a cycloalkyl group by removing hydrogen from two carbons.

When the alkyl or alkylene groups described herein are said to be "substituted," they may be substituted with any substituent or substituents as those found in the exemplary compounds and embodiments disclosed herein, as well as deuterium, alkyl (including, e.g., cycloalkyl), keto (═O), aryl, heteroaryl, hydroxyl, alkoxy, alkyl sulfonamido, aryl sulfonamido, and halo. In certain embodiments, the optional substituents themselves may be optionally substituted with any of the substituents set forth in the exemplary compounds and embodiments set forth herein. For example, any of the alkyl groups set forth herein may be substituted with an aryl and/or heteroaryl group, wherein the aryl and heteroaryl groups themselves are optionally substituted with one or more groups selected from hydroxyl, halo, or $C_1$-$C_8$ alkoxy.

As used herein, the term "alkenyl" refers to an alkyl group that contains one or more carbon-carbon double bonds, including "cycloalkenyl" groups as defined below. An "alkynyl" group is an alkyl group that contains one or more carbon-carbon triple bonds. Examples of unsaturated alkyl groups include, but are not limited to, vinyl, allyl, $—CH═CH(CH_3)$, $—CH═C(CH_3)_2$, $—C(CH_3)═CH_2$, $—C(CH_3)═CH(CH_3)$, $—C(CH_2CH_3)═CH_2$, $—C≡CH$, $—C≡C(CH_3)$, $—C≡C(CH_2CH_3)$, $—CH_2C≡CH$, $CH_2C≡C(CH_3)$ and $CH_2C≡C(CH_2CH_3)$, among others. When the alkenyl and alkynyl groups described herein are said to be "substituted," they may be substituted with any substituent or substituents as those found in the exemplary compounds and embodiments disclosed herein, as well as those identified above as suitable substituents for substituted "alkyl" groups.

As used herein, the term "cycloalkenyl" refers to a cyclic alkyl group that is partially saturated. The related term "cycloalkanyl" refers to a cyclic alkyl group that is totally saturated.

As used herein, the term "alkoxy" refers to —O-(alkyl), wherein "alkyl" is as defined above and may be optionally substituted as defined above.

As used herein, the term "aryl" refers to an aromatic carbocyclic group of from 6 to 14 carbon atoms having a single ring (e.g., phenyl) or multiple condensed rings (e.g., naphthyl or anthryl). In some embodiments, aryl groups contain 6-14 carbons and in others from 6 to 12 or even 6 to 10 carbon atoms in the ring portions of the groups. Particular aryls include phenyl, biphenyl, naphthyl and the like. The phrase "aryl groups" also includes groups containing fused rings, such as fused aromatic-aliphatic ring systems (e.g., indanyl, tetrahydronaphthyl, and the like). When the aryl groups described herein are said to be "substituted," they may be substituted with any substituent or substituents as those found in the exemplary compounds and embodiments disclosed herein, as well as deuterium, aryl, alkyl, heteroaryl, hydroxyl, and halo, as well as any of the substituents for substituted "alkyl" groups as noted above. The related term "arylene" references a bivalent residue derived from an aryl group by removing at removing a hydrogen atom from two ring carbon atoms.

As used herein, the term "heteroaryl" refers to an aromatic ring system having one to four heteroatoms as ring atoms in a heteroaromatic ring system, wherein the remainder of the atoms are carbon atoms. In some embodiments, heteroaryl groups contain 3 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. When the heteroaryl groups described herein are said to be "substituted," they may be substituted with any substituent or substituents as those found in the exemplary compounds and embodiments disclosed herein, as well as deuterium, aryl, alkyl, heteroaryl, hydroxyl, and halo, as well as any of the substituents for substituted "alkyl" groups as noted above. The related term "heteroarylene" references a bivalent residue derived from a heteroaryl group by removing at removing a hydrogen atom from two ring carbon atoms.

As used herein, the term "heterocyclic ring" or "heterocyclyl" or "heterocycloalkyl" refers to a non-aromatic cycloalkyl in which one to four of the ring carbon atoms are independently replaced with a heteroatom selected from O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass saturated and partially saturated ring systems. Further, the term heterocyclyl is intended to encompass any non-aromatic ring containing at least one heteroatom, which ring may be fused to an aryl or heteroaryl ring, regardless of the attachment to the remainder of the molecule. The phrase also includes bridged polycyclic ring systems containing a heteroatom. When the heterocyclyl groups described herein are said to be "substituted," they may be substituted with any substituent or substituents as those found in the exemplary compounds and embodiments disclosed herein, as well as deuterium, aryl, alkyl, heteroaryl, hydroxyl, and halo, as well as any of the substituents for substituted "alkyl" groups as noted above. The related term "heterocycloalkylene" references a divalent radical derived from a heterocyclic group by removing hydrogens from two carbons.

As used herein, the term "heteromoieties" refers to any groups containing a heteroatom, for example, amino, O, Se, Se(O), $SeO_2$, S, S(O), and $SO_2$.

As used herein, the term "halo" or "halogen" refers to a fluorine, chlorine, bromine or iodine atom.

As used herein, the term "hydroxyl" refers to —OH group.

As used herein, the term "alkyl sulfonamido" refers to a moiety containing $—S(═O)_2—NR_2$, wherein each R group is chosen from an alkyl and H.

As used herein, the term "aryl sulfonamido" refers to a moiety containing $—S(═O)_2—NR_2$, wherein each R group is chosen from an aryl and H.

In some embodiments, the compound of Formula I contains one or more stereocenters.

In some circumstances, the compound of Formula I comprises a racemic mixture. In some embodiments, the compound of Formula I comprises the (S) enantiomer. In some embodiments, the compound of Formula I comprises the (R) enantiomer. In some embodiments, the (S) and (R) designations refer to the absolute stereochemistry of a compound having more than one stereocenter. In such cases, the conformation of one of those stereocenters may be referred to in terms of its relative (D) or (L) configuration.

In some embodiments, X and Y are independently selected from hydrogen, deuterium, and optionally substituted $C_1$-$C_8$alkyl, wherein the alkyl group comprises a cycloalkyl moiety (e.g., cyclopropyl, cyclobutyl, etc.). In some embodiments, at least one of X or Y is an unsubstituted $C_1$-$C_4$ alkyl. In some embodiments, at least one of X or Y is an unsubstituted $C_2$-$C_4$alkyl.

In some embodiments, $R_2$, $R_3$, $R_{3'}$, $R_4$, $R_5$, $R_w$, $R_x$, $R_6$ and $R_7$ are each independently selected from hydrogen, deuterium, halo, $—N(R_9)_2$, $—SR_9$, optionally substituted $C_1$-$C_8$alkyl, $—C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$. In some embodiments, $R_2$, $R_3$, $R_{3'}$, $R_4$, $R_5$, $R_w$, $R_x$, $R_6$ and $R_7$ are each independently selected from hydrogen, deuterium, halo, optionally substituted $C_1$-$C_8$ alkyl, and optionally substituted $C_2$-$C_8$ alkenyl. In some embodiments, $R_2$ is selected from $C_1$-$C_8$ alkyl and $C_2$-$C_8$ alkenyl, each of which are optionally substituted with fluorine or deuterium. In some embodiments, $R_2$ is selected from $C_2$-$C_8$ alkyl and $C_2$-$C_8$ alkenyl, each of which are optionally substituted with fluorine or deuterium.

In some embodiments, $R_3$, $R_{3'}$, $R_x$ and $R_w$, are each, independently, selected from hydrogen, deuterium, —$N(R_9)_2$, —$SR_9$, halo, optionally substituted $C_1$-$C_8$ alkyl, -$C_1$-$C_8$ alkoxy, and optionally substituted $C_2$-$C_8$ alkenyl. In some embodiments, $R_x$ and $R_w$ are both absent. In some embodiments, at least one of $R_3$, $R_{3'}$, $R_x$ or $R_w$ is not hydrogen. In some embodiments, at least one of $R_3$, $R_{3'}$, $R_x$ or $R_w$ is deuterium. In some embodiments, at least one of $R_3$, $R_{3'}$, $R_x$ or $R_w$ is halo. In some embodiments, $R_3$ and $R_3$, are taken together with the carbon to which they are attached to form a keto group (═O). Exemplary compounds where $R_3$ and $R_3$, are taken together with the carbon to which they are attached to form a keto group include intermediates for certain target compounds disclosed herein, such as the target amide compound produced in accordance with Example 20 below.

In some embodiments, $R_4$ and $R_5$ are each independently selected from hydrogen, deuterium, —$N(R_9)_2$, —$SR_9$, optionally substituted $C_1$-$C_8$ alkyl, optionally substituted $C_2$-$C_8$ alkenyl, halo, hydroxyl, -$C_1$-$C_8$ alkoxy, —$OC(O)R_8$, —$OC(O)OR_8$, —$OP(O)(OR_9)_2$, and —$OSO_2R_8$. In some embodiments, $R_4$ and $R_5$ are each independently selected from hydrogen, deuterium, optionally substituted $C_1$-$C_8$ alkyl, optionally substituted $C_2$-$C_8$ alkenyl, halo, hydroxyl, -$C_1$-$C_8$ alkoxy, —$OC(O)R_8$, —$OC(O)OR_8$, —$OP(O)O_2(R_9)_2$, and —$OSO_2R_8$.

In certain embodiments, at least one of $R_4$ and $R_5$ is a $C_1$-$C_8$ alkoxy group, or in some embodiments a $C_2$-$C_4$ alkoxy group, wherein it may be a straight chain or branched $C_1$-$C_8$ alkoxy group or $C_2$-$C_4$ alkoxy group, for example a straight chain, and may be methoxy or ethoxy. In some embodiments, $R_5$ is $C_1$-$C_8$ alkoxy. In some embodiments, $R_4$ is selected from hydrogen and fluorine, and $R_5$ is $C_1$-$C_8$ alkoxy. In some embodiments, at least one of $R_4$ and $R_5$ is a $C_1$-$C_8$ alkyl group or, in some embodiments, a $C_1$-$C_4$ alkyl group, for example a straight chain $C_1$-$C_4$ alkyl. In some embodiments, $R_5$ is selected from methyl, ethyl, n-propyl or n-butyl, and for example methyl or ethyl. In some embodiments, at least one of $R_4$ and $R_5$ is halo. In some embodiments, $R_4$ is fluoro. In some embodiments, $R_4$ is fluoro and $R_5$ is selected from hydrogen and $C_1$-$C_8$ alkoxy. In some embodiments, at least one of $R_4$ and $R_5$ is —$OC(O)R_8$. In some embodiments $R_4$ is —$OC(O)R_8$ and $R_5$ is hydrogen or fluoro.

In some embodiments, $R_8$ is selected from optionally substituted $C_1$-$C_8$ alkyl, optionally substituted $C_2$-$C_8$ alkenyl, and optionally substituted aryl. In some embodiments, $R_9$ is selected from hydrogen, deuterium, optionally substituted $C_1$-$C_8$ alkyl, optionally substituted $C_2$-$C_8$ alkenyl, and optionally substituted aryl. In some embodiments, $R_8$ is selected from methyl, ethyl, propyl, and isopropyl. In some embodiments, $R_9$ is selected from methyl, ethyl, propyl, and isopropyl.

Exemplary halo residues for compounds of Formula I include chloro, bromo, fluoro, and iodo. In certain embodiments, the compounds of Formula I comprise at least one fluoro residue.

In some embodiments, $W_1$ is selected from $CF_2$, $NR_1$, O, S, S(O), $SO_2$, Se, Se(O), and $SeO_2$. In some embodiments, $W_1$ is $NR_1$. In some embodiments, $W_1$ is O. In some embodiments, $W_1$ is S. In some embodiments, $W_1$ is Se.

In some embodiments, $Z_6$ is selected from N and $CR_6$; and $Z_7$ is selected from N and $CR_7$. In some embodiments, $Z_6$ is N. In some embodiments, $Z_7$ is N.

In some embodiments, $R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —$C(O)N(R_9)_2$, —$SOR_8$, and —$SO_2R_8$. In some embodiments, $R_1$ is hydrogen. In some embodiments, $R_1$ is optionally substituted $C_1$-$C_8$ alkyl. In some embodiments, $R_1$ is optionally substituted $C_2$-$C_4$ alkyl. In some embodiments, $R_1$ is methyl. In some embodiments, $R_1$ is ethyl. In some embodiments, $R_1$ is isopropyl.

In certain embodiments, the alkyl groups of Formula I are selected from $C_1$-$C_8$ alkyl, $C_2$-$C_8$ alkyl, $C_3$-$C_8$ alkyl, and $C_4$-$C_8$ alkyl, or methyl, ethyl, propyl, isopropyl, n-butyl, isobutyl, sec-butyl, tert-butyl pentyl, isopentyl, hexyl, heptyl, octyl, etc. In certain embodiments, the alkenyl groups of Formula I are selected from $C_2$-$C_8$ alkenyl, $C_3$-$C_8$ alkenyl, and $C_4$-$C_8$ alkenyl, or ethenyl, propenyl, butenyl, pentenyl, hexenyl, heptenyl, octenyl, etc.

In certain embodiments, the alkyl, alkenyl or alkynyl groups of Formula I may be unsubstituted or substituted with one or more groups selected from deuterium, aryl, heteroaryl, hydroxyl, alkoxy, alkyl sulfonamido, aryl sulfonamido, and halo.

In certain embodiments, the cycloalkenyl and heterocyclyl groups of Formula I may be unsubstituted or substituted with one or more groups selected from deuterium, alkyl, alkenyl, aryl, heteroaryl, hydroxyl, alkoxy, alkyl sulfonamido, aryl sulfonamido, and halo.

In certain embodiments, the aryl and heteroaryl groups of Formula I may be unsubstituted or substituted with one or more groups selected from deuterium, aryl, alkyl, heteroaryl, hydroxyl, and halo. In certain embodiments, the alkoxy groups of Formula I may be unsubstituted or substituted with one or more groups selected from aryl, alkyl, heteroaryl, hydroxyl, and halo.

In some embodiments, X and/or Y are a straight chain $C_1$-$C_4$ alkyl or a $C_2$-$C_4$ alkenyl. In some embodiments, X and Y are each methyl, X and Y are each ethyl, or X is methyl and Y is ethyl. In certain embodiments, X and/or Y are an $C_1$-$C_8$alkyl or $C_2$-$C_8$ alkenyl optionally substituted with at least one halo group, such as fluorine. In certain embodiments, at least one of X or Y is a group selected from —$CF_3$, —$CHF_2$, —$CH_2F$, —$CH_2CF_3$, —$CH_2CHF_2$, and —$CH_2CH_2F$. In certain embodiments, at least one of X or Y is a group selected from -$CD_3$, —$CH_2CD_3$, -$CD_2CH_3$, and -$CD_2CD_3$.

In some embodiments, X is unsubstituted $C_1$-$C_8$alkyl. In some embodiments, X is methyl. In some embodiments, X is ethyl. In some embodiments, X is n-propyl. In some embodiments, X is isopropyl. In some embodiments, X is cyclopropyl. In some embodiments, Y is hydrogen. In some embodiments, Y is unsubstituted $C_1$-$C_8$alkyl. In some embodiments, Y is methyl. In some embodiments, Y is ethyl. In some embodiments, Y is n-propyl. In some embodiments, Y is isopropyl. In some embodiments, Y is cyclopropyl.

In some embodiments, $R_2$, $R_3$, $R_{3'}$, $R_w$, $R_x$, $R_6$ and $R_7$ are each independently selected from hydrogen, deuterium, halo, and $C_1$-$C_4$ alkyl, for example a straight chain $C_1$-$C_4$ alkyl. In some embodiments, $R_2$, $R_3$, $R_{3'}$, $R_w$, $R_x$, $R_6$ and $R_7$ are each independently selected from hydrogen, deuterium, halo, methyl, ethyl, n-propyl, isopropyl, n-butyl, and isobutyl. In other embodiments, $R_2$, $R_3$, $R_{3'}$, $R_w$, $R_x$, $R_6$ and $R_7$ are each independently selected from hydrogen, deuterium, methyl, and ethyl.

In some embodiments, $R_2$ is a $C_1$-$C_4$ alkyl group substituted with at least one group selected from deuterium, halo, aryl, and heteroaryl, wherein the aryl and heteroaryl groups are themselves optionally substituted. In some embodiments, $R_2$ is a $C_2$-$C_4$ alkenyl group substituted with at least one group selected from deuterium, halo, aryl, and heteroaryl, wherein the aryl and heteroaryl groups are themselves optionally substituted. In some embodiments, $R_2$ is a $C_1$-$C_4$ alkyl group substituted with at least one deuterium and at least one fluoro group. In some embodiments, $R_2$ is a $C_2$-$C_4$ alkenyl group substituted with at least one deuterium and at least one fluoro group.

In some embodiments, $R_3$ and $R_{3'}$ are hydrogen. In some embodiments, $R_3$ and $R_{3'}$ are each independently selected from hydrogen, methyl, and ethyl. In some embodiments, $R_3$ is hydrogen. In some embodiments, $R_3$ is methyl and $R_{3'}$ is hydrogen. In some embodiments, $R_3$ and $R_{3'}$ are both hydrogen. In some embodiments, $R_3$ and $R_{3'}$ are both deuterium. In some embodiments, $R_3$ is hydrogen and $R_{3'}$ is deuterium. In some embodiments, when $R_3$ and $R_{3'}$ are not the same, it represents a stereocenter wherein the compound of Formula I comprises a racemic mixture. In some embodiments, when $R_3$ and $R_{3'}$ are not the same or when $R_{3'}$ is not hydrogen, it represents a stereocenter wherein the compound of Formula I comprises the (S) enantiomer. In some embodiments, when $R_3$ and $R_{3'}$ are not the same or when $R_{3'}$ is not hydrogen, it represents a stereocenter wherein the compound of Formula I comprises the (R) enantiomer. In some embodiments, a racemic mixture can be resolved to provide a pure enantiomer or a mixture enhanced with either the (R) or (S) enantiomer.

In some embodiments, $R_6$ and $R_7$ are each independently selected hydrogen, halo, methyl, ethyl, n-propyl, isopropyl, n-butyl and isobutyl. In some embodiments, $R_6$ is selected from hydrogen and halo. In some embodiments, $R_6$ is selected from hydrogen and fluorine. In some embodiments, $R_6$ is fluorine. In some embodiments, $R_6$ is selected from alkoxy and halo.

In some embodiments, $R_6$ is selected from methoxy, chloro, and fluoro. In some embodiments, $R_6$ is fluorine. In some embodiments, $R_6$ is methoxy. In some embodiments, $R_7$ is selected from hydrogen and optionally substituted $C_1$-$C_4$ alkyl. In some embodiments, $R_7$ is selected from hydrogen, methyl, and ethyl. In some embodiments, $R_7$ is optionally substituted $C_1$-$C_4$ alkyl. In some embodiments, when $R_6$ is fluoro, then $R_7$ is selected from hydrogen and optionally substituted $C_1$-$C_4$ alkyl.

In certain embodiments, $R_5$ is selected from hydrogen, $C_1$-$C_8$ alkoxy, and halo. In certain embodiments, $R_5$ is hydrogen. In certain embodiments, $R_5$ is methoxy. In certain embodiments, $R_4$ is selected from hydrogen, $C_1$-$C_8$ alkoxy, hydroxyl, and —OC(O)$R_8$. In certain embodiments, $R_4$ is hydrogen. In certain embodiments, $R_4$ is hydroxyl. In certain embodiments, $R_4$ is —OC(O)$R_8$.

In certain embodiments, $R_1$ is hydrogen. In certain embodiments, $R_1$ is $C_1$-$C_4$ alkyl. In certain embodiments, $R_1$ is methyl.

In certain embodiments, $R_2$ is hydrogen.

In certain embodiments, X and Y are selected from hydrogen and deuterium. In certain embodiments, X is hydrogen and Y is $C_1$-$C_8$ alkyl. In certain embodiments, X is hydrogen. In certain embodiments, Y is selected from methyl, ethyl, and n-propyl. In certain embodiments, X is methyl.

In certain embodiments, one or more hydrogen atoms on compounds of Formula I may be replaced with one or more deuterium atoms. For example, in certain embodiments, $R_6$ may comprise a deuterium atom as a replacement for a hydrogen, or when $R_7$ is a —$CH_3$, each hydrogen atom may be replaced to form a -$CD_3$ residue. Similarly, another non-limiting example includes when X and/or Y is a —$CH_3$, each hydrogen atom may be replaced to form a -$CD_3$ residue.

In some embodiments,

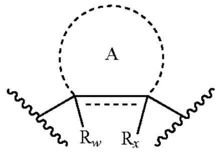

(also referred to as "Group A") represents a fused ring chosen from an optionally substituted cycloalkanyl, an optionally substituted cycloalkenyl, optionally substituted heterocyclyl that is partially saturated, optionally substituted aryl, and optionally substituted heteroaryl. In certain embodiments, Group A is selected from the following:

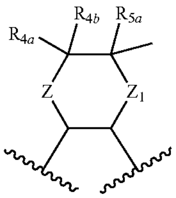 , 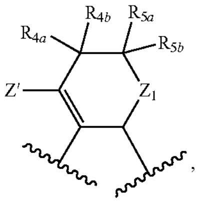 ,

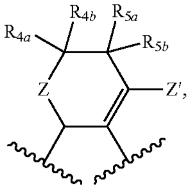 , 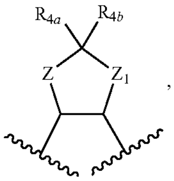 ,

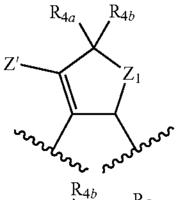 , 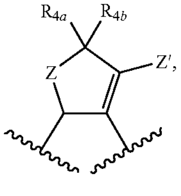 ,

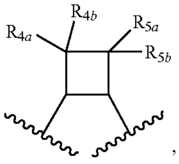 , and 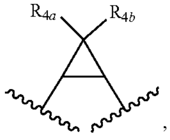 , wherein Z and $Z_1$ are independently selected from O, S and -$CZ'_2$—, and $R_{4a}$, $R_{4b}$, $R_{5a}$, $R_{5b}$ and Z' are each independently selected from hydrogen, deuterium, halogen, hydroxyl, branched or unbranched $C_1$-$C_8$ alkyl, and branched or unbranched $C_2$-$C_8$ alkenyl.

In certain embodiments, Group A may be unsubstituted or optionally substituted with one or more groups selected from deuterium, alkyl, alkenyl, aryl, heteroaryl, hydroxyl, alkoxy, alkyl sulfonamido, aryl sulfonamido, and halo. In some embodiments, Group A may be substituted with one or more groups selected from $C_1$-$C_8$ alkyl or $C_2$-$C_8$ alkenyl, such as methyl, ethyl, n-propyl, isopropyl, and allyl.

In some embodiments, the compounds of Formula I are represented by the subgenus Formula II:

Formula II

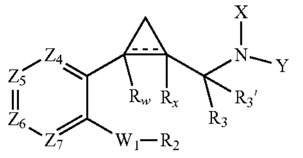

wherein all variables are as defined above.

In certain embodiments for compounds of Formulae I and II, $Z_5$ is $CR_5$, and $R_5$ is selected from hydrogen, $C_1$-$C_8$alkoxy, and halo. In certain embodiments, $Z_5$ is $CR_5$, and $R_5$ is hydrogen. In certain embodiments, $Z_5$ is $CR_5$, and $R_5$ is methoxy. In certain embodiments, $Z_5$ is $CR_5$, and $R_5$ is fluoro.

In certain embodiments, $Z_4$ is $CR_4$, $Z_5$ is $CR_5$, $Z_6$ is $CR_6$ and $Z_7$ is $CR_7$, wherein $R_5$ is halo, $R_4$ is selected from hydrogen, deuterium and halo, $R_6$ is selected from hydrogen, deuterium and halo, and $R_7$ is selected from hydrogen, deuterium and halo.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is selected from hydrogen, deuterium and halo, $R_6$ is selected from hydrogen, deuterium and halo, and $R_7$ is selected from hydrogen, deuterium and halo.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is selected from hydrogen, deuterium and fluoro, $R_6$ is selected from hydrogen, deuterium and fluoro, and $R_7$ is selected from hydrogen, deuterium and fluoro.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is selected from hydrogen, deuterium and fluoro, $R_6$ is selected from hydrogen, deuterium and fluoro, and $R_7$ is selected from hydrogen and deuterium.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is hydrogen, $R_6$ is hydrogen, and $R_7$ is hydrogen.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is hydrogen, $R_6$ is hydrogen, and $R_7$ is hydrogen; $W_2$ is $C(R_3)(R_{3'})$ and $R_3$ and $R_{3'}$ are each selected from hydrogen and deuterium; and X and Y are each hydrogen.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is hydrogen, $R_6$ is hydrogen, and $R_7$ is hydrogen; $W_2$ is $C(R_3)(R_{3'})$ and $R_3$ and $R_{3'}$ are each hydrogen; X and Y are each hydrogen; ------ is a single bond, wherein $R_x$ and $R_w$ are each independently selected from hydrogen, deuterium, and fluoro; and $W_1$ is selected from S and O.

In certain embodiments, $Z_4$ is $CR_4$, $Z_5$ is CRS, $Z_6$ is $CR_6$ and $Z_7$ is $CR_7$, wherein $R_5$ is fluoro, $R_4$ is hydrogen, $R_6$ is hydrogen, and $R_7$ is hydrgg is $C(R_3)(R_{3'})$ and $R_3$ and $R_{3'}$ are each hydrogen; X and Y are each hydrogen; ------ is a single bond, wherein $R_x$ and $R_w$ are each hydrogen; $W_1$ is selected from S and O; and $R_2$ selected from a group selected from $C_1$-$C_8$ alkyl, $C_2$-$C_8$ alkenyl, aryl, and heteroaryl, wherein said group is substituted with at least one of deuterium or fluoro.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is hydrogen, $R_6$ is hydrogen, and $R_7$ is hydrogen; $W_2$ is $C(R_3)(R_{3'})$ and $R_3$ and $R_{3'}$ are each hydrogen; X and Y are each hydrogen; ------ is a single bond, wherein $R_x$ and $R_w$ are each hydrogen; $W_1$ is selected from S and O; and $R_2$ selected from a group selected from $C_1$-$C_8$ alkyl, $C_2$-$C_8$ alkenyl, aryl, and heteroaryl, wherein said group is substituted with at least two deuterium atoms.

In certain embodiments, $Z_4$ is $CR_4$, $Z_5$ is $CR_5$, $Z_6$ is $CR_6$ and $Z_7$ is $CR_7$, wherein $R_5$ is fluoro, $R_4$ is hydrogen, $R_6$ is hydrogen, and $R_7$ is hydrogen; $W_2$ is $C(R_3)(R_{3'})$ and $R_3$ and $R_{3'}$ are each hydrogen; X and Y are each hydrogen; ------ is a single bond, wherein $R_x$ and $R_w$ are each hydrogen; $W_1$ is selected from S and O; and $R_2$ selected from a group selected from $C_1$-$C_4$ alkyl and $C_2$-$C_4$ alkenyl, wherein said group is substituted with at least two deuterium atoms.

In certain embodiments, $R_2$ is a residue selected from Formula III:

Formula III

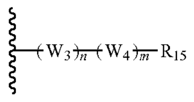

wherein $W_3$ is, for each occurrence, independently selected from arylene, heteroarylene, cycloalkylene, heterocycloalkylene, $C(R_{10})(R_{11})$, and

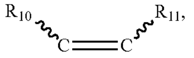

wherein n is an integer selected from 1 to 10;

$W_4$ is, for each occurrence, independently selected from O, S, Se, arylene, heteroarylene, cycloalkylene, heterocycloalkylene, $C(R_{12})(R_{13})$, and

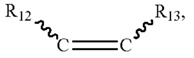

wherein m is an integer selected from 0 to 10; and $R_{10}$, $R_{11}$, $R_{12}$, $R_{13}$, and $R_{15}$ are, for each occurrence, independently selected from hydrogen, deuterium, halo, and hydroxyl.

In certain embodiments of Formula I wherein $W_2$ is $C(R_3)(R_{3'})$ and $R_2$ is a residue of Formula III where $W_3$ is $C(R_{10})(R_{11})$, at least one of $R_3$, $R_{3'}$, $R_{10}$ or $R_{11}$ is deuterium.

In certain embodiments of Formula I wherein $W_2$ is $C(R_3)(R_{3'})$ and $R_2$ is a residue of Formula III where $W_3$ is $C(R_{10})(R_{11})$ and n is 1, at least one of $R_3$, $R_{3'}$, $R_{10}$ or $R_{11}$ is deuterium.

In certain embodiments, $W_3$ is, for each occurrence, independently selected from $C(R_{10})(R_{11})$, wherein n is an integer selected from 1 to 4, and at least one $R_{10}$ is deuterium.

In certain embodiments, $W_3$ is, for each occurrence, independently selected from $C(R_{10})(R_{11})$, wherein n is an integer selected from 1 to 4, and at least one $R_{10}$ and at least one $R_{11}$ are deuterium.

In certain embodiments, $W_3$ is $C(R_{10})(R_{11})$, wherein n is 1, and $R_{10}$ and $R_{11}$ are both deuterium.

In certain embodiments, $W_3$ is $C(R_{10})(R_{11})$, wherein n is 1, and $R_{10}$ and $R_{11}$ are both deuterium; $W_4$ is, for each occurrence, independently selected from arylene, heteroarylene, $C(R_{12})(R_{13})$, and

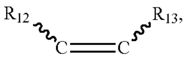

wherein m is an integer selected from 0 to 3, $R_{12}$ and $R_{13}$ are each independently selected from hydrogen, deuterium, and halo for each occurrence; and $R_{15}$ is selected from hydrogen, halo, and deuterium.

In certain embodiments, $W_3$ is $C(R_{10})(R_{11})$, wherein n is 1, and $R_{10}$ and $R_{11}$ are both deuterium; $W_4$ is, for each occurrence, independently selected from $C(R_{12})(R_{13})$ and

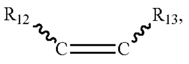

wherein m is an integer selected from 0 to 3, $R_{12}$ and $R_{13}$ are each independently selected from hydrogen, deuterium, and fluoro for each occurrence; and $R_{15}$ is selected from hydrogen, fluoro, and deuterium.

In certain embodiments, $W_3$ is $C(R_{10})(R_{11})$, wherein n is 1, and $R_{10}$ and $R_{11}$ are both deuterium; $W_4$ is, for each occurrence, independently selected from $C(R_{12})(R_{13})$ and

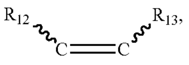

wherein m is an integer selected from 0 to 3, $R_{12}$ and $R_{13}$ are each independently selected from hydrogen and fluoro for each occurrence; and $R_{15}$ is selected from hydrogen and fluoro.

In certain embodiments, at least one occurrence of $R_{10}$, $R_{11}$, $R_{12}$, $R_{13}$ or $R_{15}$ is deuterium. For example, in certain embodiments when n is 1, one or both of $R_{10}$ and $R_{11}$ are deuterium. In certain embodiments when n is 1 and one or both of $R_{10}$ and $R_{11}$ are deuterium, m is an integer selected from 1 to 10 and each occurrence of $R_{12}$ and $R_{13}$ are selected from hydrogen and halo.

In certain embodiments, $R_{15}$ is selected from hydrogen, deuterium, and halo. In certain embodiments, $R_{15}$ is fluoro. In certain embodiments, at least one of $R_{12}$ or $R_{13}$ is fluoro.

Exemplary compounds of Formula I include:

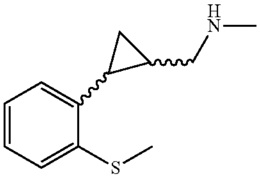

,

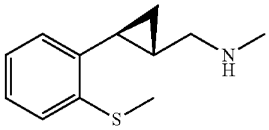

,

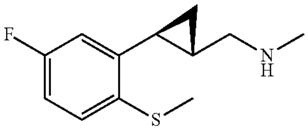

,

-continued

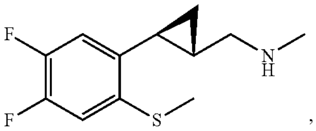

,

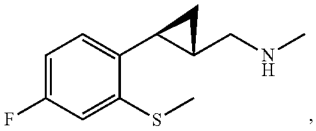

,

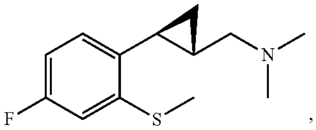

,

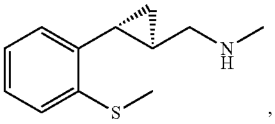

,

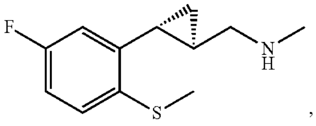

,

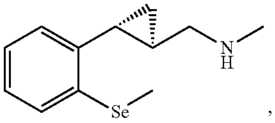

,

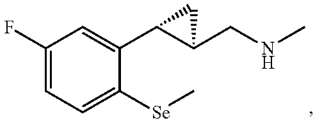

,

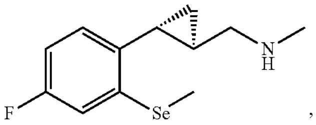

,

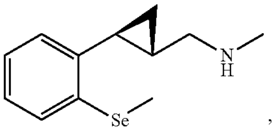

,

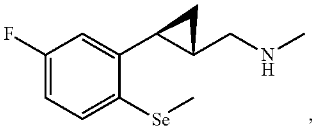

,

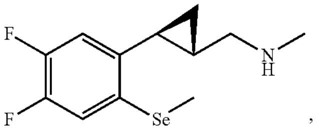

,

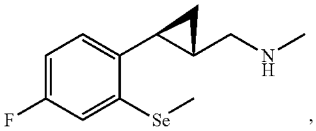

,

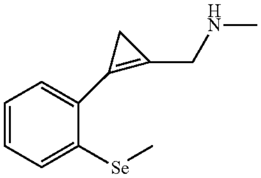

,

-continued
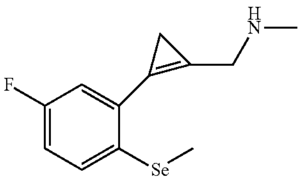
,
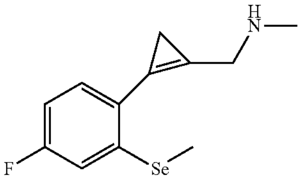
,
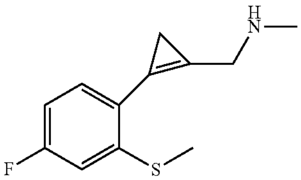
,
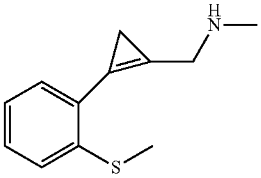
,
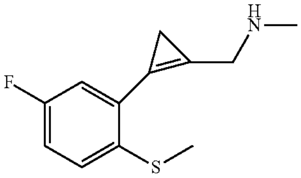
,
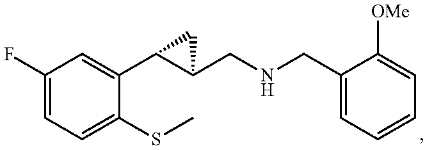
,
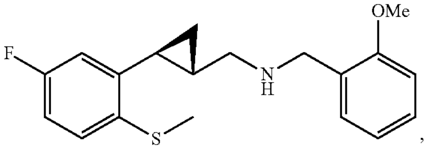
,
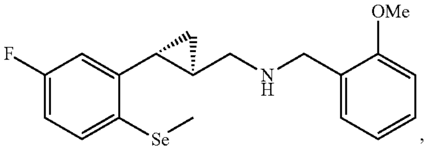
,
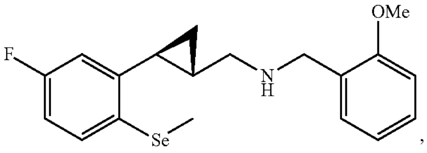
,
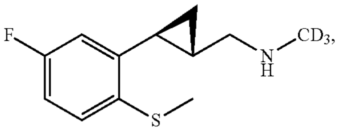
-continued
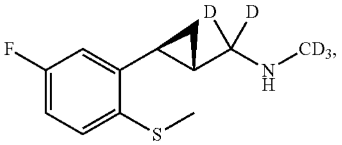
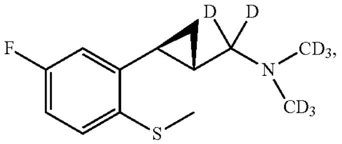
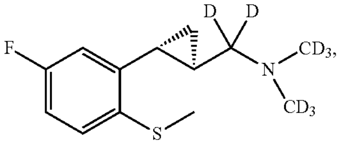
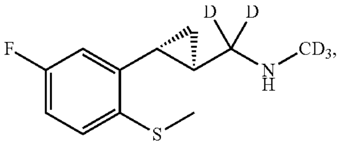
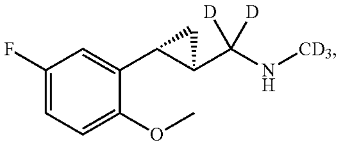
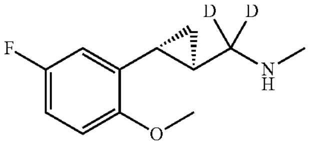
,
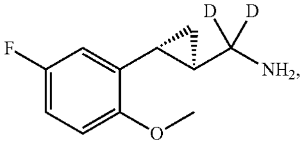
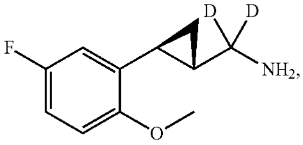
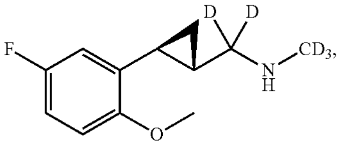
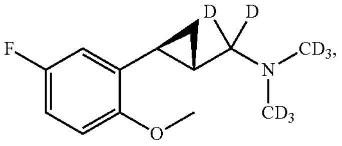
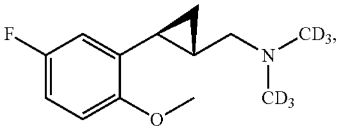
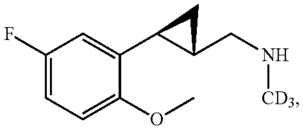

-continued
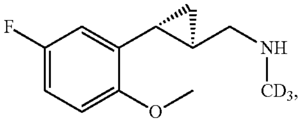
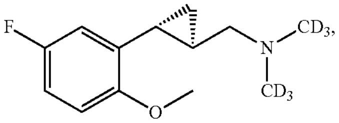
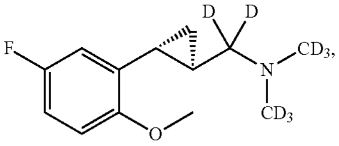
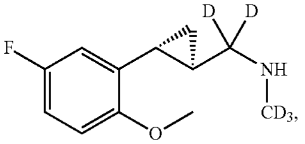
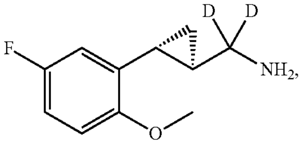
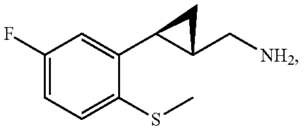
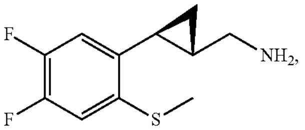
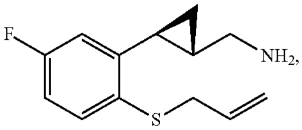
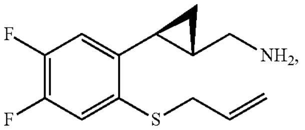
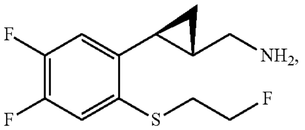
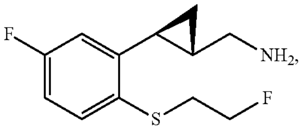
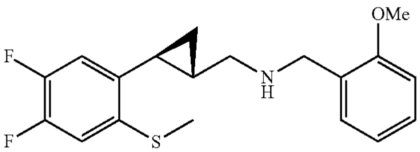
-continued
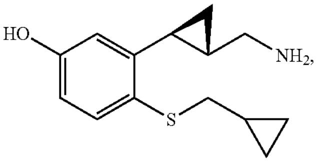
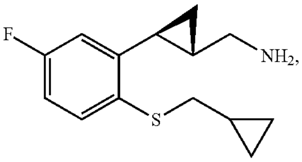
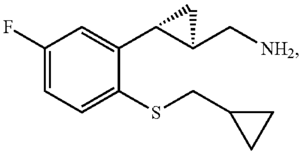
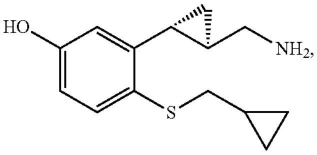
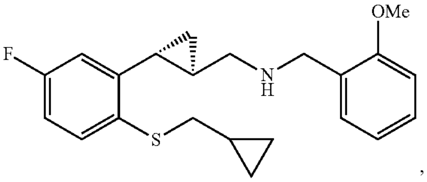
,
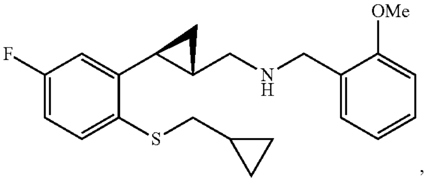
,
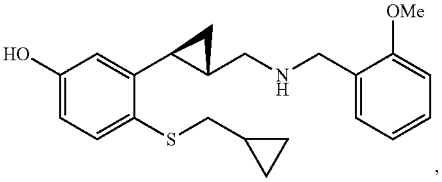
,
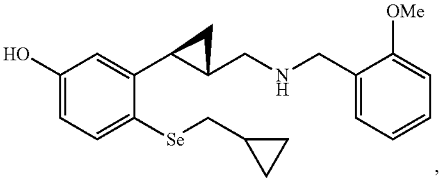
,
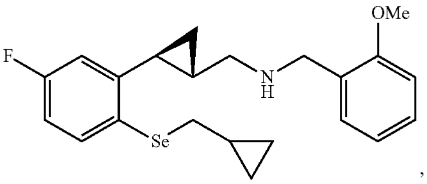
,
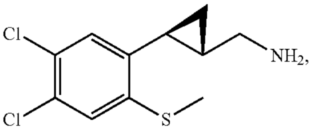

-continued
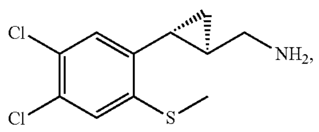
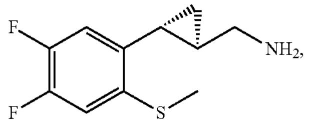
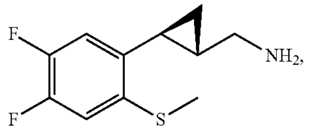
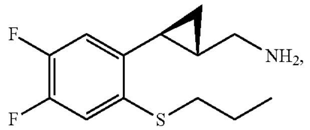
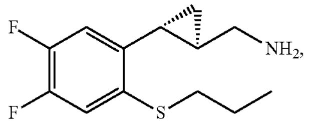
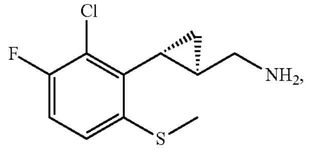
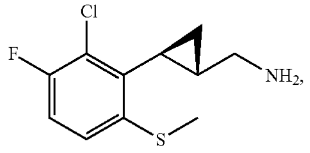
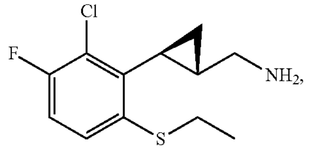
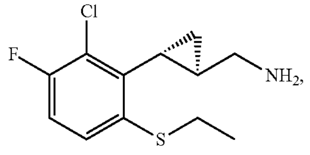
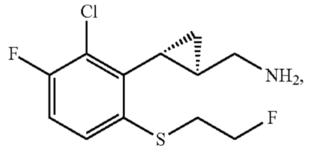
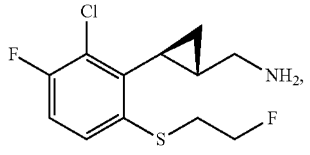
-continued
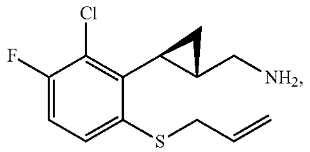
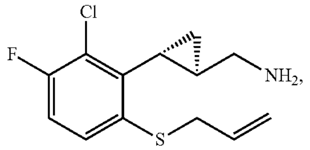
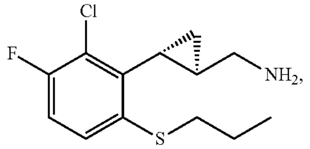
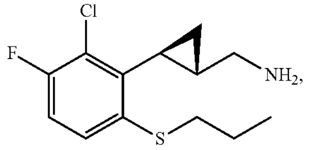
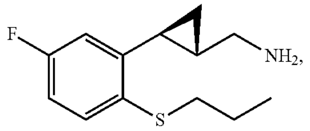
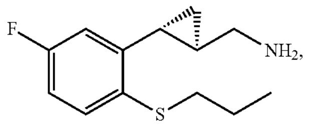
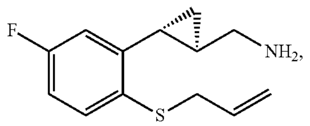
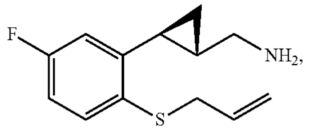
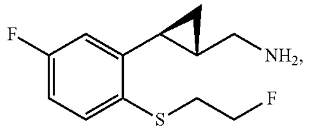
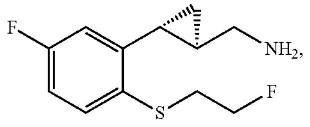
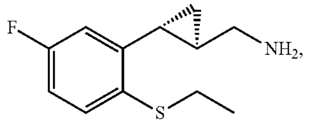
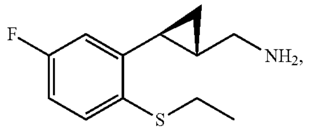

-continued
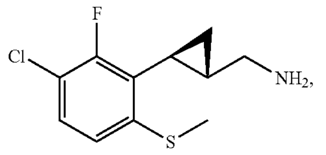
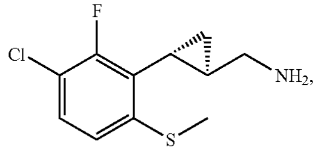
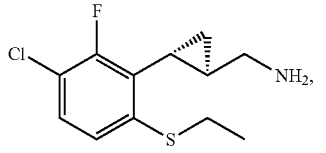
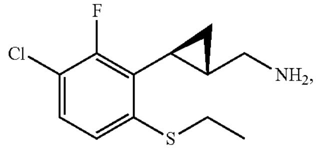
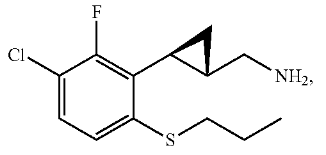
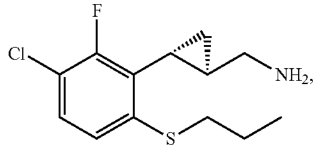
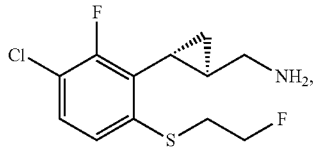
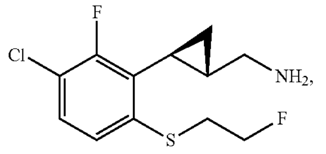
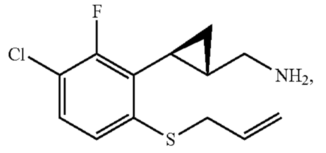
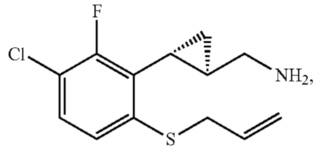
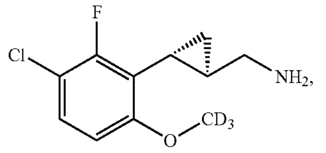
-continued
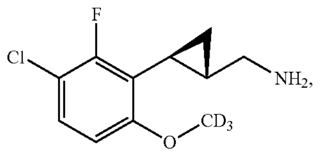
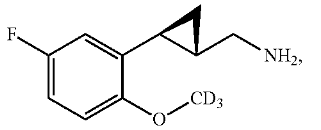
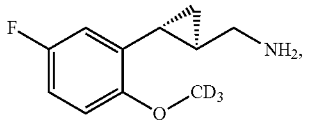
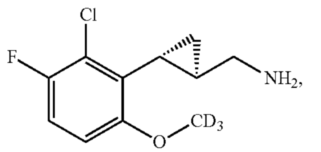
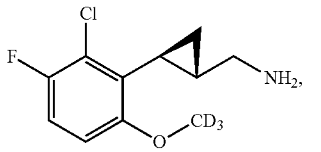
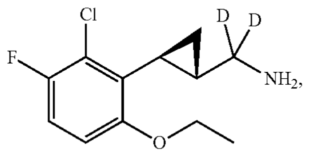
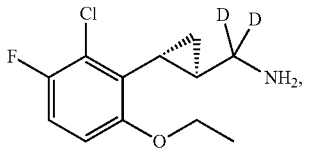
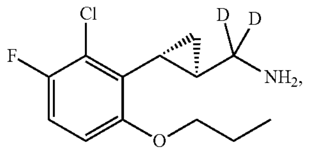
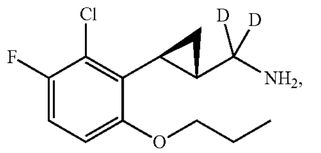
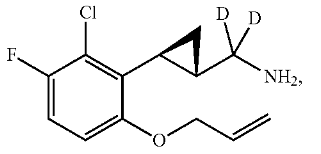
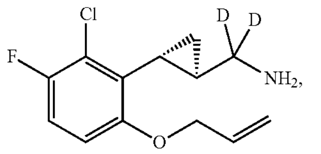

-continued
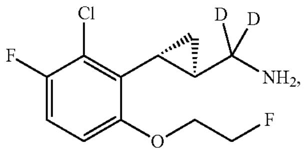
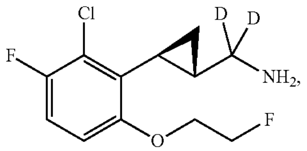
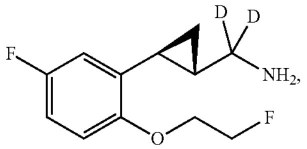
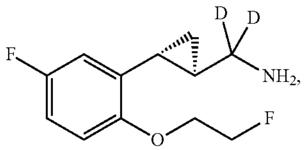
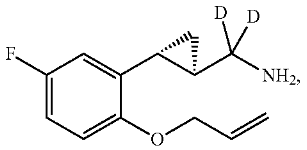
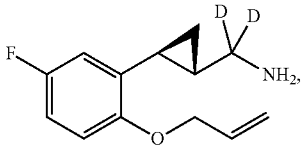
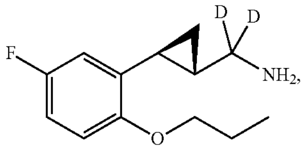
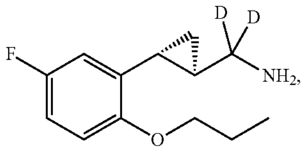
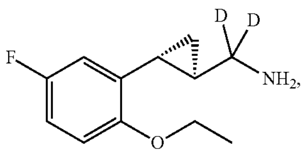
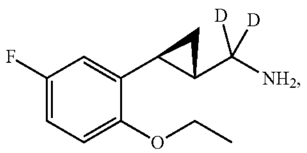
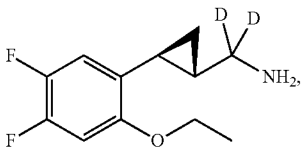
-continued
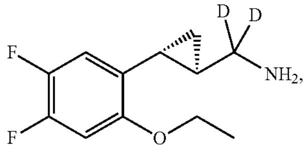
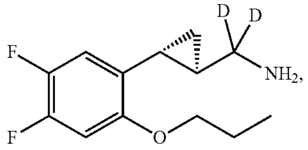
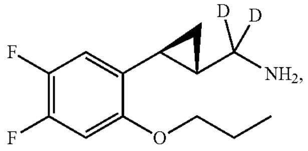
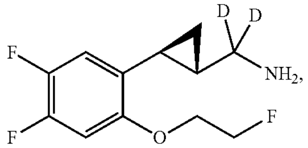
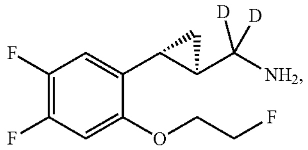
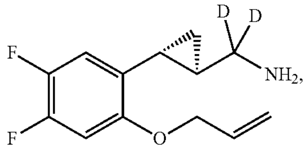
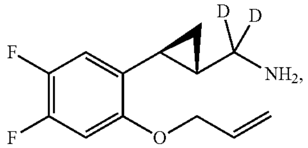
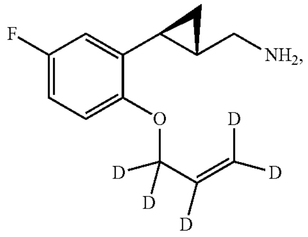
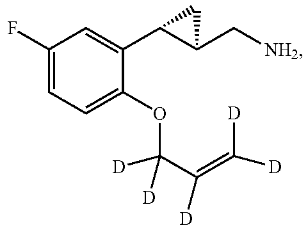
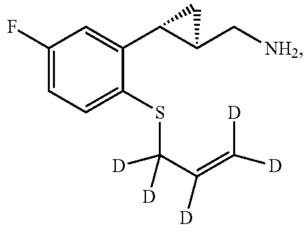

-continued
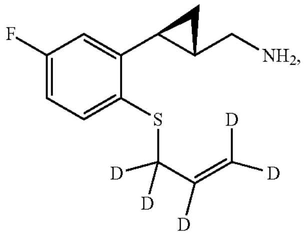
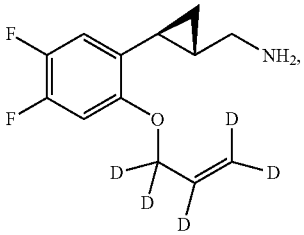
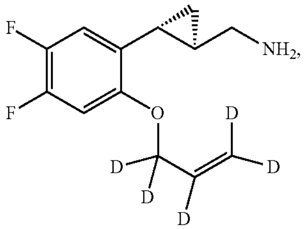
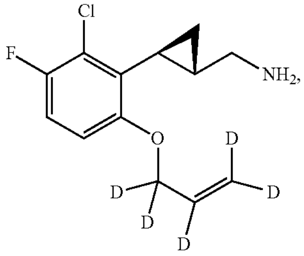
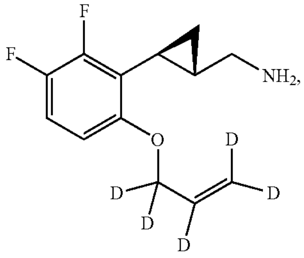
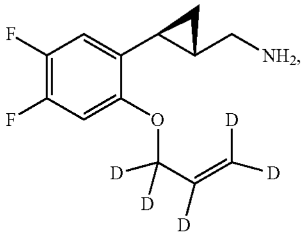
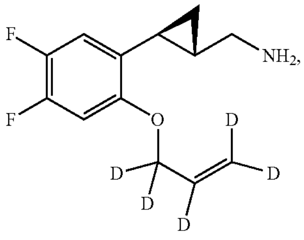
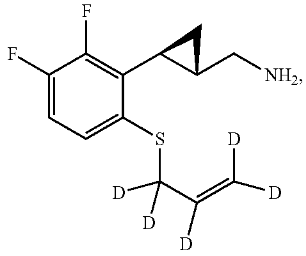
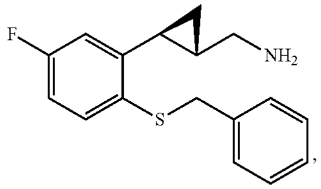
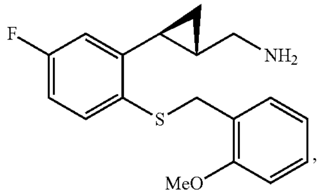
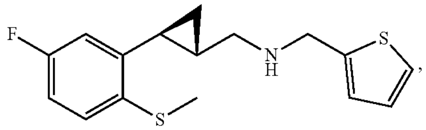
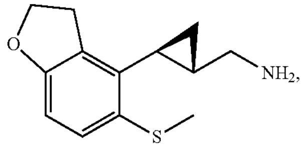
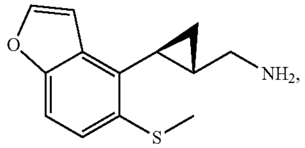
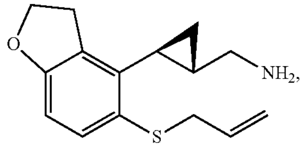
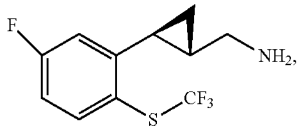
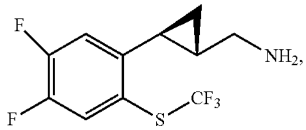
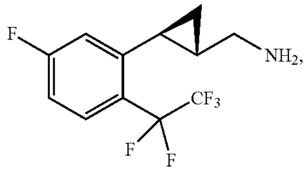

-continued
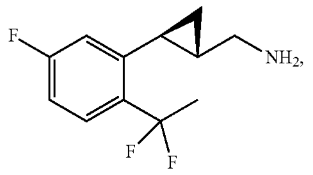
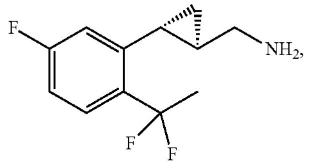
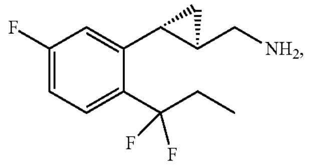
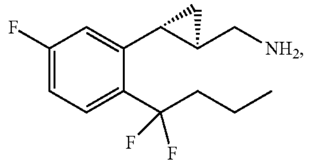
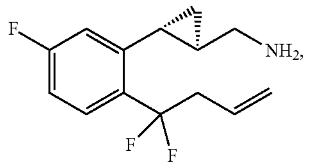
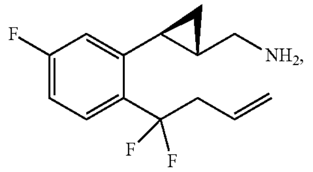
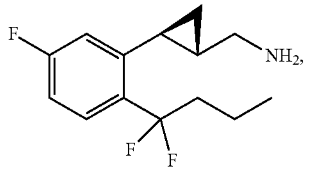
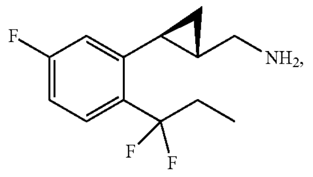
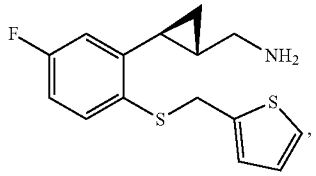
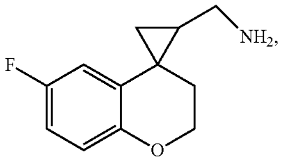
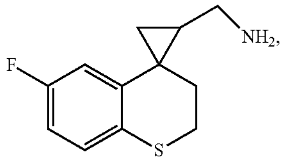
-continued
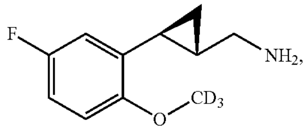
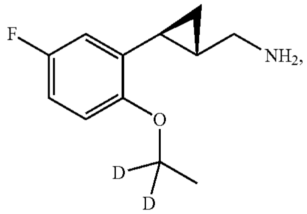
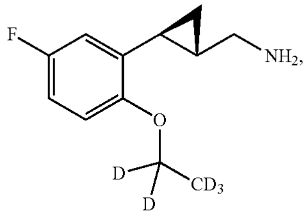
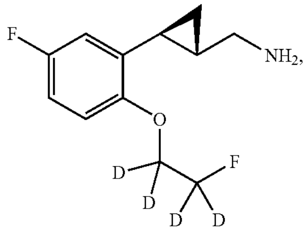
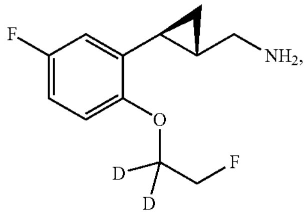
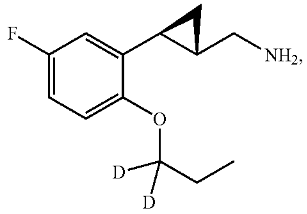
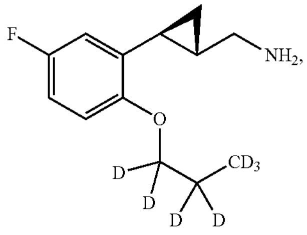
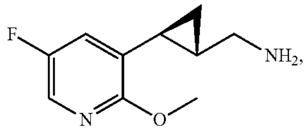
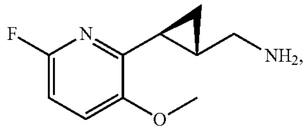

-continued

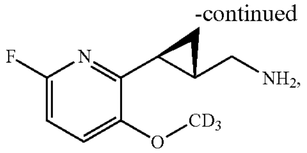

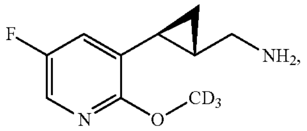

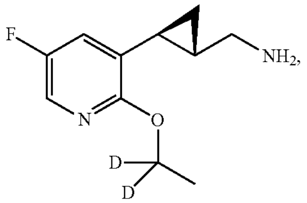

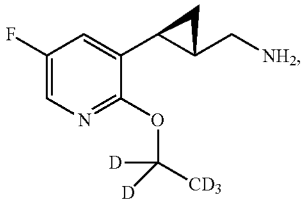

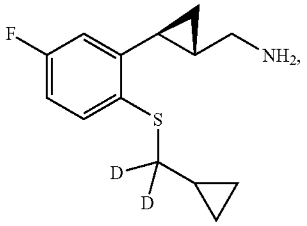

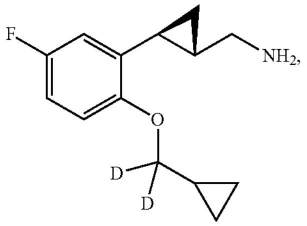

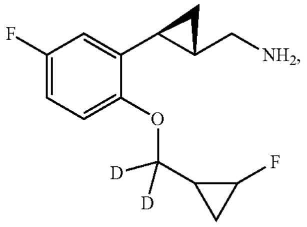

and salts, solvates, hydrates, prodrugs, and enantiomers of any of the foregoing compounds.

In some embodiments, the compounds of Formula I comprise salts. In some embodiments, the compounds of Formula I comprise pharmaceutically-acceptable salts. Exemplary salts include, but are not limited to, HCl, HI, HBr, HF, ascorbate, hydrofumarate, fumarate, oxalate, maleate, and the like. In certain embodiments, the compound of Formula I is in its free-base form. In some embodiments, the compound of Formula I comprises a salt, such as a [1:1] salt (e.g., HCl, hydrofumarate) or a [2:1] salt (e.g., oxalate, fumarate). For the [1:1] salts, one ammonium cation of one compound of Formula I is balanced by a single anion (Cl—, I—, etc.). For the [2:1] salts, two ammonium cations of two molecules of Formula I are balanced by a dianionic species, such as a dianion derived from di-acids such as oxalic acid and fumaric acid. Other exemplary salts include zwitterionic forms of compounds of Formula I, such as when $R_1$ is —$P(O)(OH)_2$, wherein deprotonation of an —OH on $R_1$ may result in intramolecular coordination of the resulting —$O^-$ with the quaternary ethylammonium residue (e.g., —$(CH_2)_2N^+H(CH_3)_2$).

Thus, in some embodiments the compounds described herein may comprise quaternary analogs of the compounds of Formula I, including those of Formula VII:

Formula VII

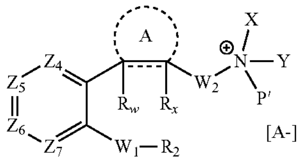

wherein all variables are as previously defined herein, and

P' is selected from hydrogen, deuterium, optionally substituted $C_1$-$C_8$alkyl, optionally substituted $C_2$-$C_8$ alkenyl, optionally substituted $C_2$-$C_8$ alkynyl, and a prodrug residue; and

[A-] is a pharmaceutically acceptable anion;

and salts, solvates, hydrates, and prodrugs thereof.

In some embodiments, P' is selected from hydrogen, deuterium, optionally substituted $C_1$-$C_8$ alkyl, optionally substituted $C_2$-$C_8$ alkenyl, optionally substituted $C_2$-$C_8$ alkynyl, and a prodrug residue. In some embodiments, P' is a prodrug residue. In some embodiments, P' comprises a prodrug residue that is liberated in vivo. In some embodiments, P' is a prodrug residue that is liberated by one or more esterase enzymes in vivo. In some embodiments, the prodrug residue comprises an alkyl residue (e.g., methyl) substituted with an alkylacyloxy residue. In some embodiments, P' is a prodrug residue selected from Formula I-Z:

Formula I-Z

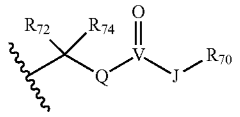

wherein $R_{72}$ and $R_{74}$ are independently selected from hydrogen, deuterium, optionally substituted alkyl, optionally substituted alkenyl, optionally substituted alkynyl, optionally substituted aryl, and optionally substituted heteroaryl;

Q is selected from O and S;

V is selected from C and $P(R_{75})$, wherein $R_{75}$ is selected from —$O^-$ and -OM, wherein M is a pharmaceutically acceptable cation, provided that [A-] is absent when V is $P(R_{75})$ and $R_{75}$ is —$O^-$;

J is absent or is selected from 0, S, and $NR_9$; and $R_{70}$ is selected from hydrogen, optionally substituted alkyl that is branched or unbranched, and optionally substituted alkenyl that is branched or unbranched.

In some embodiments, $R_{72}$ and $R_{74}$ are each hydrogen. In some embodiments, Q is O. In some embodiments, J is absent. In some embodiments, $R_{70}$ is selected from optionally substituted $C_1$-$C_{24}$ alkyl, optionally substituted $C_2$-$C_{24}$ alkenyl, and optionally substituted $C_2$-$C_{24}$ alkynyl, each of which may be branched or unbranched. In some embodiments, $R_{70}$ is selected from branched $C_3$-$C_{24}$ alkyl.

In some embodiments, V is C. In some embodiments, V is $P(R_{75})$, wherein $R_{75}$ is —$O^-$ and the compound of Formula VII is a zwitterion. In some embodiments where V is $P(R_{75})$, $R_{70}$ is H.

In some embodiments, the compounds of Formula VII are selected from compounds of Formula VIIa:

Formula VIIa

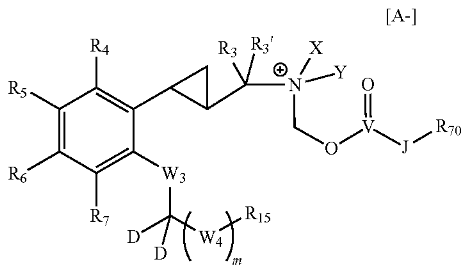

wherein all variables are as previously defined herein. In some embodiments, V is C, J is absent and $R_{70}$ is an optionally substituted $C_1$-$C_{24}$ alkyl. In some embodiments, V is $P(R_{75})$, $R_{75}$ is —$O^-$, J is O, and $R_{70}$ is hydrogen, wherein the compound is zwitterionic and [A-] is absent.

Exemplary compounds of Formula VII include, but are not limited to:

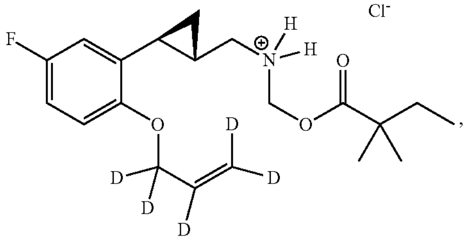

,

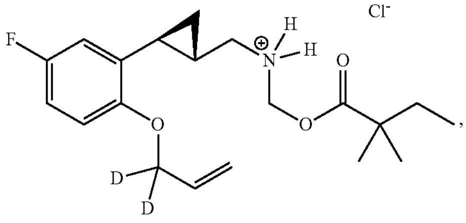

,

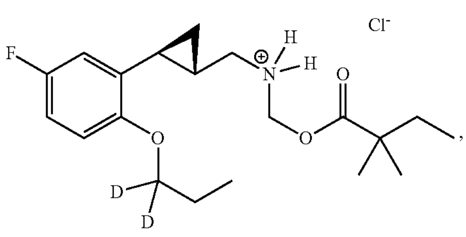

,

-continued

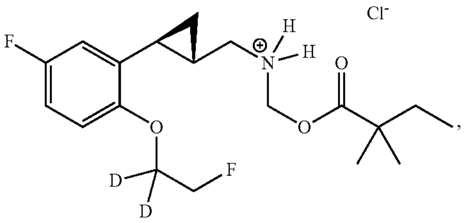

,

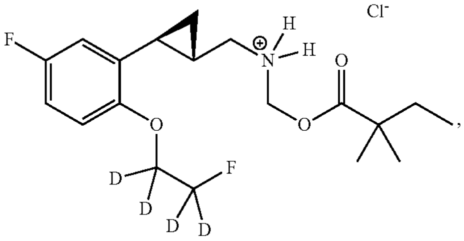

,

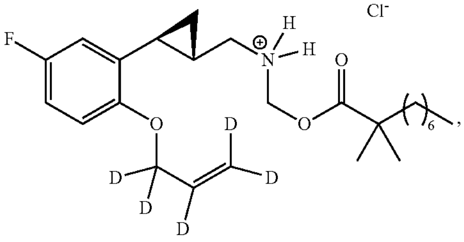

,

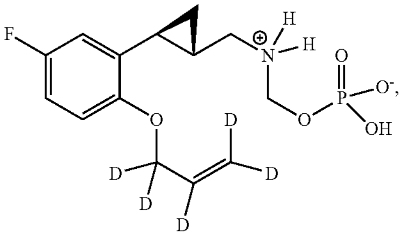

,

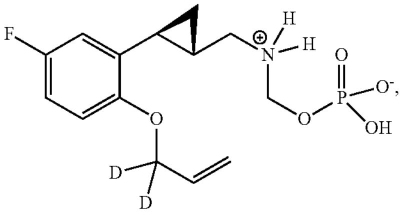

,

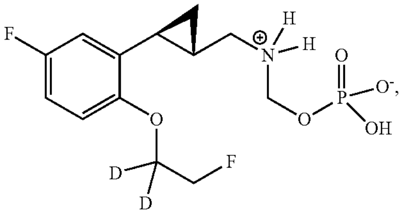

,

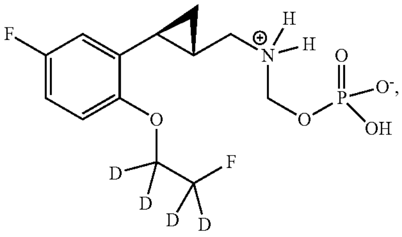

-continued

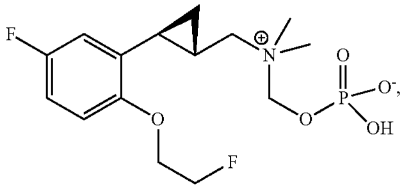

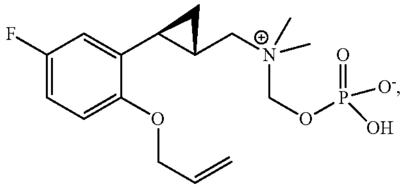

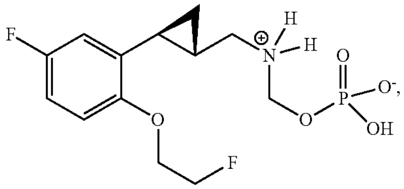
and

-continued

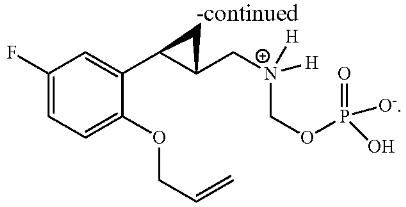

Other exemplary compounds include compounds of Formula II(a) set forth below in Table 1:

Formula II(a)

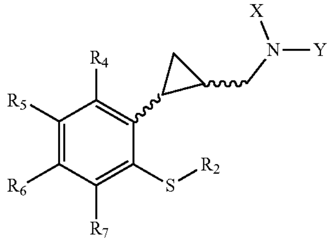

TABLE 1

| Ref. | X | Y | $R_2$ | $R_4$ | $R_5$ | $R_6$ | $R_7$ |
|---|---|---|---|---|---|---|---|
| 1 | $-CH_3$ | $-CH_3$ | $-CH_3$ | $-OH$ | H | H | H |
| 2 | $-CH_3$ | $-CH_2CH_3$ | $-CH_3$ | $-OH$ | H | H | H |
| 3 | $-CH_3$ | $-(CH_2)_2CH_3$ | $-CH_3$ | $-OH$ | H | H | H |
| 4 | $-CH_3$ | $-CH(CH_3)_2$ | $-CH_3$ | $-OH$ | H | H | H |
| 5 | $-CH_3$ | $-(CH_2)_3CH_3$ | $-CH_3$ | $-OH$ | H | H | H |
| 6 | $-CH_3$ | $-CH_2-HC=CH_2$ | $-CH_3$ | $-OH$ | H | H | H |
| 7 | $-CH_2CH_3$ | $-CH_2CH_3$ | $-CH_3$ | $-OH$ | H | H | H |
| 8 | $-CH_2CH_3$ | $-(CH_2)_2CH_3$ | $-CH_3$ | $-OH$ | H | H | H |
| 9 | $-CH_2CH_3$ | $-CH(CH_3)_2$ | $-CH_3$ | $-OH$ | H | H | H |
| 10 | $-CH_2CH_3$ | $-(CH_2)_3CH_3$ | $-CH_3$ | $-OH$ | H | H | H |
| 11 | $-CH_2CH_3$ | $-CH_2-HC=CH_2$ | $-CH_3$ | $-OH$ | H | H | H |
| 12 | $-(CH_2)_2CH_3$ | $-(CH_2)_2CH_3$ | $-CH_3$ | $-OH$ | H | H | H |
| 13 | $-(CH_2)_2CH_3$ | $-CH(CH_3)_2$ | $-CH_3$ | $-OH$ | H | H | H |
| 14 | $-(CH_2)_2CH_3$ | $-(CH_2)_3CH_3$ | $-CH_3$ | $-OH$ | H | H | H |
| 15 | $-(CH_2)_2CH_3$ | $-CH_2-HC=CH_2$ | $-CH_3$ | $-OH$ | H | H | H |
| 16 | $-CH(CH_3)_2$ | $-CH(CH_3)_2$ | $-CH_3$ | $-OH$ | H | H | H |
| 17 | $-CH(CH_3)_2$ | $-(CH_2)_3CH_3$ | $-CH_3$ | $-OH$ | H | H | H |
| 18 | $-CH(CH_3)_2$ | $-CH_2-HC=CH_2$ | $-CH_3$ | $-OH$ | H | H | H |
| 19 | $-(CH_2)_3CH_3$ | $-(CH_2)_3CH_3$ | $-CH_3$ | $-OH$ | H | H | H |
| 20 | $-(CH_2)_3CH_3$ | $-CH_2-HC=CH_2$ | $-CH_3$ | $-OH$ | H | H | H |
| 21 | $-CH_2-HC=CH_2$ | $-CH_2-HC=CH_2$ | $-CH_3$ | $-OH$ | H | H | H |
| 22 | $-CH_3$ | $-CH_2CH_3$ | $-CH_3$ | $-OC(O)CH_3$ | H | H | H |
| 23 | $-CH_3$ | $-(CH_2)_2CH_3$ | $-CH_3$ | $-OC(O)CH_3$ | H | H | H |
| 24 | $-CH_3$ | $-CH(CH_3)_2$ | $-CH_3$ | $-OC(O)CH_3$ | H | H | H |
| 25 | $-CH_3$ | $-(CH_2)_3CH_3$ | $-CH_3$ | $-OC(O)CH_3$ | H | H | H |
| 26 | $-CH_3$ | $-CH_2-HC=CH_2$ | $-CH_3$ | $-OC(O)CH_3$ | H | H | H |
| 27 | $-CH_2CH_3$ | $-CH_2CH_3$ | $-CH_3$ | $-OC(O)CH_3$ | H | H | H |
| 28 | $-CH_2CH_3$ | $-(CH_2)_2CH_3$ | $-CH_3$ | $-OC(O)CH_3$ | H | H | H |
| 29 | $-CH_2CH_3$ | $-CH(CH_3)_2$ | $-CH_3$ | $-OC(O)CH_3$ | H | H | H |
| 30 | $-CH_2CH_3$ | $-(CH_2)_3CH_3$ | $-CH_3$ | $-OC(O)CH_3$ | H | H | H |
| 31 | $-CH_2CH_3$ | $-CH_2-HC=CH_2$ | $-CH_3$ | $-OC(O)CH_3$ | H | H | H |
| 32 | $-(CH_2)_2CH_3$ | $-(CH_2)_2CH_3$ | $-CH_3$ | $-OC(O)CH_3$ | H | H | H |
| 33 | $-(CH_2)_2CH_3$ | $-CH(CH_3)_2$ | $-CH_3$ | $-OC(O)CH_3$ | H | H | H |
| 34 | $-(CH_2)_2CH_3$ | $-(CH_2)_3CH_3$ | $-CH_3$ | $-OC(O)CH_3$ | H | H | H |
| 35 | $-(CH_2)_2CH_3$ | $-CH_2-HC=CH_2$ | $-CH_3$ | $-OC(O)CH_3$ | H | H | H |
| 36 | $-CH(CH_3)_2$ | $-CH(CH_3)_2$ | $-CH_3$ | $-OC(O)CH_3$ | H | H | H |
| 37 | $-CH(CH_3)_2$ | $-(CH_2)_3CH_3$ | $-CH_3$ | $-OC(O)CH_3$ | H | H | H |
| 38 | $-CH(CH_3)_2$ | $-CH_2-HC=CH_2$ | $-CH_3$ | $-OC(O)CH_3$ | H | H | H |
| 39 | $-(CH_2)_3CH_3$ | $-(CH_2)_3CH_3$ | $-CH_3$ | $-OC(O)CH_3$ | H | H | H |
| 40 | $-(CH_2)_3CH_3$ | $-CH_2-HC=CH_2$ | $-CH_3$ | $-OC(O)CH_3$ | H | H | H |
| 41 | $-CH_2-HC=CH_2$ | $-CH_2-HC=CH_2$ | $-CH_3$ | $-OC(O)CH_3$ | H | H | H |
| 42 | $-CH_3$ | $-CH_3$ | $-CH_3$ | $-OC(O)CH_3$ | H | H | H |
| 43 | $-CH_3$ | $-CH_2CH_3$ | $-CH_3$ | $-OC(O)CH_3$ | H | H | H |
| 44 | $-CH_3$ | $-(CH_2)_2CH_3$ | $-CH_3$ | $-OC(O)CH_3$ | H | H | H |
| 45 | $-CH_3$ | $-CH(CH_3)_2$ | $-CH_3$ | $-OC(O)CH_3$ | H | H | H |
| 46 | $-CH_3$ | $-(CH_2)_3CH_3$ | $-CH_3$ | $-OC(O)CH_3$ | H | H | H |

TABLE 1-continued

| Ref. | X | Y | $R_2$ | $R_4$ | $R_5$ | $R_6$ | $R_7$ |
|---|---|---|---|---|---|---|---|
| 47 | $-CH_3$ | $-CH_2-HC=CH_2$ | $-CH_3$ | $-OC(O)CH_3$ | H | H | H |
| 48 | $-CH_2CH_3$ | $-CH_2CH_3$ | $-CH_3$ | $-OC(O)CH_3$ | H | H | H |
| 49 | $-CH_2CH_3$ | $-(CH_2)_2CH_3$ | $-CH_3$ | $-OC(O)CH_3$ | H | H | H |
| 50 | $-CH_2CH_3$ | $-CH(CH_3)_2$ | $-CH_3$ | $-OC(O)CH_3$ | H | H | H |
| 51 | $-CH_2CH_3$ | $-(CH_2)_3CH_3$ | $-CH_3$ | $-OC(O)CH_3$ | H | H | H |
| 52 | $-CH_2CH_3$ | $-CH_2-HC=CH_2$ | $-CH_3$ | $-OC(O)CH_3$ | H | H | H |
| 53 | $-(CH_2)_2CH_3$ | $-(CH_2)_2CH_3$ | $-CH_3$ | $-OC(O)CH_3$ | H | H | H |
| 54 | $-(CH_2)_2CH_3$ | $-CH(CH_3)_2$ | $-CH_3$ | $-OC(O)CH_3$ | H | H | H |
| 55 | $-(CH_2)_2CH_3$ | $-(CH_2)_3CH_3$ | $-CH_3$ | $-OC(O)CH_3$ | H | H | H |
| 56 | $-(CH_2)_2CH_3$ | $-CH_2-HC=CH_2$ | $-CH_3$ | $-OC(O)CH_3$ | H | H | H |
| 57 | $-CH(CH_3)_2$ | $-CH(CH_3)_2$ | $-CH_3$ | $-OC(O)CH_3$ | H | H | H |
| 58 | $-CH(CH_3)_2$ | $-(CH_2)_3CH_3$ | $-CH_3$ | $-OC(O)CH_3$ | H | H | H |
| 59 | $-CH(CH_3)_2$ | $-CH_2-HC=CH_2$ | $-CH_3$ | $-OC(O)CH_3$ | H | H | H |
| 60 | $-(CH_2)_3CH_3$ | $-(CH_2)_3CH_3$ | $-CH_3$ | $-OC(O)CH_3$ | H | H | H |
| 61 | $-(CH_2)_3CH_3$ | $-CH_2-HC=CH_2$ | $-CH_3$ | $-OC(O)CH_3$ | H | H | H |
| 62 | $-CH_2-HC=CH_2$ | $-CH_2-HC=CH_2$ | $-CH_3$ | $-OC(O)CH_3$ | H | H | H |
| 63 | $-CH_3$ | $-CH_3$ | $-CH_3$ | H | H | H | H |
| 64 | $-CH_3$ | $-CH_2CH_3$ | $-CH_3$ | H | H | H | H |
| 65 | $-CH_3$ | $-(CH_2)_2CH_3$ | $-CH_3$ | H | H | H | H |
| 66 | $-CH_3$ | $-CH(CH_3)_2$ | $-CH_3$ | H | H | H | H |
| 67 | $-CH_3$ | $-(CH_2)_3CH_3$ | $-CH_3$ | H | H | H | H |
| 68 | $-CH_3$ | $-CH_2-HC=CH_2$ | $-CH_3$ | H | H | H | H |
| 69 | $-CH_2CH_3$ | $-CH_2CH_3$ | $-CH_3$ | H | H | H | H |
| 70 | $-CH_2CH_3$ | $-(CH_2)_2CH_3$ | $-CH_3$ | H | H | H | H |
| 71 | $-CH_2CH_3$ | $-CH(CH_3)_2$ | $-CH_3$ | H | H | H | H |
| 72 | $-CH_2CH_3$ | $-(CH_2)_3CH_3$ | $-CH_3$ | H | H | H | H |
| 73 | $-CH_2CH_3$ | $-CH_2-HC=CH_2$ | $-CH_3$ | H | H | H | H |
| 74 | $-(CH_2)_2CH_3$ | $-(CH_2)_2CH_3$ | $-CH_3$ | H | H | H | H |
| 75 | $-(CH_2)_2CH_3$ | $-CH(CH_3)_2$ | $-CH_3$ | H | H | H | H |
| 76 | $-(CH_2)_2CH_3$ | $-(CH_2)_3CH_3$ | $-CH_3$ | H | H | H | H |
| 77 | $-(CH_2)_2CH_3$ | $-CH_2-HC=CH_2$ | $-CH_3$ | H | H | H | H |
| 78 | $-CH(CH_3)_2$ | $-CH(CH_3)_2$ | $-CH_3$ | H | H | H | H |
| 79 | $-CH(CH_3)_2$ | $-(CH_2)_3CH_3$ | $-CH_3$ | H | H | H | H |
| 80 | $-CH(CH_3)_2$ | $-CH_2-HC=CH_2$ | $-CH_3$ | H | H | H | H |
| 81 | $-(CH_2)_3CH_3$ | $-(CH_2)_3CH_3$ | $-CH_3$ | H | H | H | H |
| 82 | $-(CH_2)_3CH_3$ | $-CH_2-HC=CH_2$ | $-CH_3$ | H | H | H | H |
| 83 | $-CH_2-HC=CH_2$ | $-CH_2-HC=CH_2$ | $-CH_3$ | H | H | H | H |
| 84 | $-CH_3$ | $-CH_2CH_3$ | $-CH_3$ | H | $-OCH_3$ | H | H |
| 85 | $-CH_3$ | $-(CH_2)_2CH_3$ | $-CH_3$ | H | $-OCH_3$ | H | H |
| 86 | $-CH_3$ | $-CH(CH_3)_2$ | $-CH_3$ | H | $-OCH_3$ | H | H |
| 87 | $-CH_3$ | $-(CH_2)_3CH_3$ | $-CH_3$ | H | $-OCH_3$ | H | H |
| 88 | $-CH_3$ | $-CH_2-HC=CH_2$ | $-CH_3$ | H | $-OCH_3$ | H | H |
| 89 | $-CH_2CH_3$ | $-CH_2CH_3$ | $-CH_3$ | H | $-OCH_3$ | H | H |
| 90 | $-CH_2CH_3$ | $-(CH_2)_2CH_3$ | $-CH_3$ | H | $-OCH_3$ | H | H |
| 91 | $-CH_2CH_3$ | $-CH(CH_3)_2$ | $-CH_3$ | H | $-OCH_3$ | H | H |
| 92 | $-CH_2CH_3$ | $-(CH_2)_3CH_3$ | $-CH_3$ | H | $-OCH_3$ | H | H |
| 93 | $-CH_2CH_3$ | $-CH_2-HC=CH_2$ | $-CH_3$ | H | $-OCH_3$ | H | H |
| 94 | $-(CH_2)_2CH_3$ | $-(CH_2)_2CH_3$ | $-CH_3$ | H | $-OCH_3$ | H | H |
| 95 | $-(CH_2)_2CH_3$ | $-CH(CH_3)_2$ | $-CH_3$ | H | $-OCH_3$ | H | H |
| 96 | $-(CH_2)_2CH_3$ | $-(CH_2)_3CH_3$ | $-CH_3$ | H | $-OCH_3$ | H | H |
| 97 | $-(CH_2)_2CH_3$ | $-CH_2-HC=CH_2$ | $-CH_3$ | H | $-OCH_3$ | H | H |
| 98 | $-CH(CH_3)_2$ | $-CH(CH_3)_2$ | $-CH_3$ | H | $-OCH_3$ | H | H |
| 99 | $-CH(CH_3)_2$ | $-(CH_2)_3CH_3$ | $-CH_3$ | H | $-OCH_3$ | H | H |
| 100 | $-CH(CH_3)_2$ | $-CH_2-HC=CH_2$ | $-CH_3$ | H | $-OCH_3$ | H | H |
| 101 | $-(CH_2)_3CH_3$ | $-(CH_2)_3CH_3$ | $-CH_3$ | H | $-OCH_3$ | H | H |
| 102 | $-(CH_2)_3CH_3$ | $-CH_2-HC=CH_2$ | $-CH_3$ | H | $-OCH_3$ | H | H |
| 103 | $-CH_2-HC=CH_2$ | $-CH_2-HC=CH_2$ | $-CH_3$ | H | $-OCH_3$ | H | H |
| 104 | $-CH_3$ | $-CH_3$ | $-CH_3$ | H | $-OCH_3$ | H | H |
| 105 | $-CH_3$ | $-CH_2CH_3$ | $-CH_3$ | H | H | F | H |
| 106 | $-CH_3$ | $-(CH_2)_2CH_3$ | $-CH_3$ | H | H | F | H |
| 107 | $-CH_3$ | $-CH(CH_3)_2$ | $-CH_3$ | H | H | F | H |
| 108 | $-CH_3$ | $-(CH_2)_3CH_3$ | $-CH_3$ | H | H | F | H |
| 109 | $-CH_3$ | $-CH_2-HC=CH_2$ | $-CH_3$ | H | H | F | H |
| 110 | $-CH_2CH_3$ | $-CH_2CH_3$ | $-CH_3$ | H | H | F | H |
| 111 | $-CH_2CH_3$ | $-(CH_2)_2CH_3$ | $-CH_3$ | H | H | F | H |
| 112 | $-CH_2CH_3$ | $-CH(CH_3)_2$ | $-CH_3$ | H | H | F | H |
| 113 | $-CH_2CH_3$ | $-(CH_2)_3CH_3$ | $-CH_3$ | H | H | F | H |
| 114 | $-CH_2CH_3$ | $-CH_2-HC=CH_2$ | $-CH_3$ | H | H | F | H |
| 115 | $-(CH_2)_2CH_3$ | $-(CH_2)_2CH_3$ | $-CH_3$ | H | H | F | H |
| 116 | $-(CH_2)_2CH_3$ | $-CH(CH_3)_2$ | $-CH_3$ | H | H | F | H |
| 117 | $-(CH_2)_2CH_3$ | $-(CH_2)_3CH_3$ | $-CH_3$ | H | H | F | H |
| 118 | $-(CH_2)_2CH_3$ | $-CH_2-HC=CH_2$ | $-CH_3$ | H | H | F | H |
| 119 | $-CH(CH_3)_2$ | $-CH(CH_3)_2$ | $-CH_3$ | H | H | F | H |
| 120 | $-CH(CH_3)_2$ | $-(CH_2)_3CH_3$ | $-CH_3$ | H | H | F | H |
| 121 | $-CH(CH_3)_2$ | $-CH_2-HC=CH_2$ | $-CH_3$ | H | H | F | H |
| 122 | $-(CH_2)_3CH_3$ | $-(CH_2)_3CH_3$ | $-CH_3$ | H | H | F | H |
| 123 | $-(CH_2)_3CH_3$ | $-CH_2-HC=CH_2$ | $-CH_3$ | H | H | F | H |
| 124 | $-CH_2-HC=CH_2$ | $-CH_2-HC=CH_2$ | $-CH_3$ | H | H | F | H |

TABLE 1-continued

| Ref. | X | Y | $R_2$ | $R_4$ | $R_5$ | $R_6$ | $R_7$ |
|---|---|---|---|---|---|---|---|
| 125 | $-CH_3$ | $-CH_3$ | $-CH_3$ | H | H | F | H |
| 126 | $-CH_3$ | $-CH_2CH_3$ | $-CH_3$ | H | H | H | $-CH_3$ |
| 127 | $-CH_3$ | $-(CH_2)_2CH_3$ | $-CH_3$ | H | H | H | $-CH_3$ |
| 128 | $-CH_3$ | $-CH(CH_3)_2$ | $-CH_3$ | H | H | H | $-CH_3$ |
| 129 | $-CH_3$ | $-(CH_2)_3CH_3$ | $-CH_3$ | H | H | H | $-CH_3$ |
| 130 | $-CH_3$ | $-CH_2-HC{=}CH_2$ | $-CH_3$ | H | H | H | $-CH_3$ |
| 131 | $-CH_2CH_3$ | $-CH_2CH_3$ | $-CH_3$ | H | H | H | $-CH_3$ |
| 132 | $-CH_2CH_3$ | $-(CH_2)_2CH_3$ | $-CH_3$ | H | H | H | $-CH_3$ |
| 133 | $-CH_2CH_3$ | $-CH(CH_3)_2$ | $-CH_3$ | H | H | H | $-CH_3$ |
| 134 | $-CH_2CH_3$ | $-(CH_2)_3CH_3$ | $-CH_3$ | H | H | H | $-CH_3$ |
| 135 | $-CH_2CH_3$ | $-CH_2-HC{=}CH_2$ | $-CH_3$ | H | H | H | $-CH_3$ |
| 135 | $-(CH_2)_2CH_3$ | $-(CH_2)_2CH_3$ | $-CH_3$ | H | H | H | $-CH_3$ |
| 137 | $-(CH_2)_2CH_3$ | $-CH(CH_3)_2$ | $-CH_3$ | H | H | H | $-CH_3$ |
| 138 | $-(CH_2)_2CH_3$ | $-(CH_2)_3CH_3$ | $-CH_3$ | H | H | H | $-CH_3$ |
| 139 | $-(CH_2)_2CH_3$ | $-CH_2-HC{=}CH_2$ | $-CH_3$ | H | H | H | $-CH_3$ |
| 140 | $-CH(CH_3)_2$ | $-CH(CH_3)_2$ | $-CH_3$ | H | H | H | $-CH_3$ |
| 141 | $-CH(CH_3)_2$ | $-(CH_2)_3CH_3$ | $-CH_3$ | H | H | H | $-CH_3$ |
| 142 | $-CH(CH_3)_2$ | $-CH_2-HC{=}CH_2$ | $-CH_3$ | H | H | H | $-CH_3$ |
| 143 | $-(CH_2)_3CH_3$ | $-(CH_2)_3CH_3$ | $-CH_3$ | H | H | H | $-CH_3$ |
| 144 | $-(CH_2)_3CH_3$ | $-CH_2-HC{=}CH_2$ | $-CH_3$ | H | H | H | $-CH_3$ |
| 145 | $-CH_2-HC{=}CH_2$ | $-CH_2-HC{=}CH_2$ | $-CH_3$ | H | H | H | $-CH_3$ |
| 146 | $-CH_3$ | $-CH_2CH_3$ | $-CH_3$ | H | F | H | H |
| 147 | $-CH_3$ | $-(CH_2)_2CH_3$ | $-CH_3$ | H | F | H | H |
| 148 | $-CH_3$ | $-CH(CH_3)_2$ | $-CH_3$ | H | F | H | H |
| 149 | $-CH_3$ | $-(CH_2)_3CH_3$ | $-CH_3$ | H | F | H | H |
| 150 | $-CH_3$ | $-CH_2-HC{=}CH_2$ | $-CH_3$ | H | F | H | H |
| 151 | $-CH_2CH_3$ | $-CH_2CH_3$ | $-CH_3$ | H | F | H | H |
| 152 | $-CH_2CH_3$ | $-(CH_2)_2CH_3$ | $-CH_3$ | H | F | H | H |
| 153 | $-CH_2CH_3$ | $-CH(CH_3)_2$ | $-CH_3$ | H | F | H | H |
| 154 | $-CH_2CH_3$ | $-(CH_2)_3CH_3$ | $-CH_3$ | H | F | H | H |
| 155 | $-CH_2CH_3$ | $-CH_2-HC{=}CH_2$ | $-CH_3$ | H | F | H | H |
| 156 | $-(CH_2)_2CH_3$ | $-(CH_2)_2CH_3$ | $-CH_3$ | H | F | H | H |
| 157 | $-(CH_2)_2CH_3$ | $-CH(CH_3)_2$ | $-CH_3$ | H | F | H | H |
| 158 | $-(CH_2)_2CH_3$ | $-(CH_2)_3CH_3$ | $-CH_3$ | H | F | H | H |
| 159 | $-(CH_2)_2CH_3$ | $-CH_2-HC{=}CH_2$ | $-CH_3$ | H | F | H | H |
| 160 | $-CH(CH_3)_2$ | $-CH(CH_3)_2$ | $-CH_3$ | H | F | H | H |
| 161 | $-CH(CH_3)_2$ | $-(CH_2)_3CH_3$ | $-CH_3$ | H | F | H | H |
| 162 | $-CH(CH_3)_2$ | $-CH_2-HC{=}CH_2$ | $-CH_3$ | H | F | H | H |
| 163 | $-(CH_2)_3CH_3$ | $-(CH_2)_3CH_3$ | $-CH_3$ | H | F | H | H |
| 164 | $-(CH_2)_3CH_3$ | $-CH_2-HC{=}CH_2$ | $-CH_3$ | H | F | H | H |
| 165 | $-CH_2-HC{=}CH_2$ | $-CH_2-HC{=}CH_2$ | $-CH_3$ | H | F | H | H |
| 166 | $-CH_3$ | $-CH_3$ | $-CH_3$ | H | F | H | H |
| 167 | $-CH_3$ | $-CH_2CH_3$ | $-CH_3$ | $-OC(O)CH_3$ | F | H | H |
| 168 | $-CH_3$ | $-(CH_2)_2CH_3$ | $-CH_3$ | $-OC(O)CH_3$ | F | H | H |
| 169 | $-CH_3$ | $-CH(CH_3)_2$ | $-CH_3$ | $-OC(O)CH_3$ | F | H | H |
| 170 | $-CH_3$ | $-(CH_2)_3CH_3$ | $-CH_3$ | $-OC(O)CH_3$ | F | H | H |
| 171 | $-CH_3$ | $-CH_2-HC{=}CH_2$ | $-CH_3$ | $-OC(O)CH_3$ | F | H | H |
| 172 | $-CH_2CH_3$ | $-CH_2CH_3$ | $-CH_3$ | $-OC(O)CH_3$ | F | H | H |
| 173 | $-CH_2CH_3$ | $-(CH_2)_2CH_3$ | $-CH_3$ | $-OC(O)CH_3$ | F | H | H |
| 174 | $-CH_2CH_3$ | $-CH(CH_3)_2$ | $-CH_3$ | $-OC(O)CH_3$ | F | H | H |
| 175 | $-CH_2CH_3$ | $-(CH_2)_3CH_3$ | $-CH_3$ | $-OC(O)CH_3$ | F | H | H |
| 176 | $-CH_2CH_3$ | $-CH_2-HC{=}CH_2$ | $-CH_3$ | $-OC(O)CH_3$ | F | H | H |
| 177 | $-(CH_2)_2CH_3$ | $-(CH_2)_2CH_3$ | $-CH_3$ | $-OC(O)CH_3$ | F | H | H |
| 178 | $-(CH_2)_2CH_3$ | $-CH(CH_3)_2$ | $-CH_3$ | $-OC(O)CH_3$ | F | H | H |
| 179 | $-(CH_2)_2CH_3$ | $-(CH_2)_3CH_3$ | $-CH_3$ | $-OC(O)CH_3$ | F | H | H |
| 180 | $-(CH_2)_2CH_3$ | $-CH_2-HC{=}CH_2$ | $-CH_3$ | $-OC(O)CH_3$ | F | H | H |
| 181 | $-CH(CH_3)_2$ | $-CH(CH_3)_2$ | $-CH_3$ | $-OC(O)CH_3$ | F | H | H |
| 182 | $-CH(CH_3)_2$ | $-(CH_2)_3CH_3$ | $-CH_3$ | $-OC(O)CH_3$ | F | H | H |
| 183 | $-CH(CH_3)_2$ | $-CH_2-HC{=}CH_2$ | $-CH_3$ | $-OC(O)CH_3$ | F | H | H |
| 184 | $-(CH_2)_3CH_3$ | $-(CH_2)_3CH_3$ | $-CH_3$ | $-OC(O)CH_3$ | F | H | H |
| 185 | $-(CH_2)_3CH_3$ | $-CH_2-HC{=}CH_2$ | $-CH_3$ | $-OC(O)CH_3$ | F | H | H |
| 186 | $-CH_2-HC{=}CH_2$ | $-CH_2-HC{=}CH_2$ | $-CH_3$ | $-OC(O)CH_3$ | F | H | H |
| 187 | $-CH_3$ | $-CH_3$ | $-CH_3$ | $-OC(O)CH_3$ | F | F | H |
| 188 | $-CH_3$ | $-CH_2CH_3$ | $-CH_3$ | H | H | F | H |
| 189 | $-CH_3$ | $-(CH_2)_2CH_3$ | $-CH_3$ | H | H | F | H |
| 190 | $-CH_3$ | $-CH(CH_3)_2$ | $-CH_3$ | H | H | F | H |
| 191 | $-CH_3$ | $-(CH_2)_3CH_3$ | $-CH_3$ | H | H | F | H |
| 192 | $-CH_3$ | $-CH_2-HC{=}CH_2$ | $-CH_3$ | H | H | F | H |
| 193 | $-CH_2CH_3$ | $-CH_2CH_3$ | $-CH_3$ | H | H | F | H |
| 194 | $-CH_2CH_3$ | $-(CH_2)_2CH_3$ | $-CH_3$ | H | H | F | H |
| 195 | $-CH_2CH_3$ | $-CH(CH_3)_2$ | $-CH_3$ | H | H | F | H |
| 196 | $-CH_2CH_3$ | $-(CH_2)_3CH_3$ | $-CH_3$ | H | H | F | H |
| 197 | $-CH_2CH_3$ | $-CH_2-HC{=}CH_2$ | $-CH_3$ | H | H | F | H |
| 198 | $-(CH_2)_2CH_3$ | $-(CH_2)_3CH_3$ | $-CH_3$ | H | H | F | H |
| 199 | $-(CH_2)_2CH_3$ | $-CH(CH_3)_2$ | $-CH_3$ | H | H | F | H |
| 200 | $-(CH_2)_2CH_3$ | $-(CH_2)_3CH_3$ | $-CH_3$ | H | H | F | H |
| 201 | $-(CH_2)_2CH_3$ | $-CH_2-HC{=}CH_2$ | $-CH_3$ | H | H | F | H |
| 202 | $-CH(CH_3)_2$ | $-CH(CH_3)_2$ | $-CH_3$ | H | H | F | H |

TABLE 1-continued

| Ref. | X | Y | $R_2$ | $R_4$ | $R_5$ | $R_6$ | $R_7$ |
|---|---|---|---|---|---|---|---|
| 203 | $—CH(CH_3)_2$ | $—(CH_2)_3CH_3$ | $—CH_3$ | H | H | F | H |
| 204 | $—CH(CH_3)_2$ | $—CH_2—HC{=}CH_2$ | $—CH_3$ | H | H | F | H |
| 205 | $—(CH_2)_3CH_3$ | $—(CH_2)_3CH_3$ | $—CH_3$ | H | H | F | H |
| 206 | $—(CH_2)_3CH_3$ | $—CH_2—HC{=}CH_2$ | $—CH_3$ | H | H | F | H |
| 207 | $—CH_2—HC{=}CH_2$ | $—CH_2—HC{=}CH_2$ | $—CH_3$ | H | H | F | H |
| 208 | $—CH_3$ | $—CH_2CH_3$ | $—CH_3$ | H | H | F | H |
| 209 | $—CH_3$ | $—(CH_2)_2CH_3$ | $—CH_3$ | $—OC(O)CH_3$ | H | F | H |
| 210 | $—CH_3$ | $—CH(CH_3)_2$ | $—CH_3$ | $—OC(O)CH_3$ | H | F | H |
| 211 | $—CH_3$ | $—(CH_2)_3CH_3$ | $—CH_3$ | $—OC(O)CH_3$ | H | F | H |
| 212 | $—CH_3$ | $—CH_2—HC{=}CH_2$ | $—CH_3$ | $—OC(O)CH_3$ | H | F | H |
| 213 | $—CH_2CH_3$ | $—CH_2CH_3$ | $—CH_3$ | $—OC(O)CH_3$ | H | F | H |
| 214 | $—CH_2CH_3$ | $—(CH_2)_2CH_3$ | $—CH_3$ | $—OC(O)CH_3$ | H | F | H |
| 215 | $—CH_2CH_3$ | $—CH(CH_3)_2$ | $—CH_3$ | $—OC(O)CH_3$ | H | F | H |
| 216 | $—CH_2CH_3$ | $—(CH_2)_3CH_3$ | $—CH_3$ | $—OC(O)CH_3$ | H | F | H |
| 217 | $—CH_2CH_3$ | $—CH_2—HC{=}CH_2$ | $—CH_3$ | $—OC(O)CH_3$ | H | F | H |
| 218 | $—(CH_2)_2CH_3$ | $—(CH_2)_2CH_3$ | $—CH_3$ | $—OC(O)CH_3$ | H | F | H |
| 219 | $—(CH_2)_2CH_3$ | $—CH(CH_3)_2$ | $—CH_3$ | $—OC(O)CH_3$ | H | F | H |
| 220 | $—(CH_2)_2CH_3$ | $—(CH_2)_3CH_3$ | $—CH_3$ | $—OC(O)CH_3$ | H | F | H |
| 221 | $—(CH_2)_2CH_3$ | $—CH_2—HC{=}CH_2$ | $—CH_3$ | $—OC(O)CH_3$ | H | F | H |
| 222 | $—CH(CH_3)_2$ | $—CH(CH_3)_2$ | $—CH_3$ | $—OC(O)CH_3$ | H | F | H |
| 223 | $—CH(CH_3)_2$ | $—(CH_2)_3CH_3$ | $—CH_3$ | $—OC(O)CH_3$ | H | F | H |
| 224 | $—CH(CH_3)_2$ | $—CH_2—HC{=}CH_2$ | $—CH_3$ | $—OC(O)CH_3$ | H | F | H |
| 225 | $—(CH_2)_3CH_3$ | $—(CH_2)_3CH_3$ | $—CH_3$ | $—OC(O)CH_3$ | H | F | H |
| 226 | $—(CH_2)_3CH_3$ | $—CH_2—HC{=}CH_2$ | $—CH_3$ | $—OC(O)CH_3$ | H | F | H |
| 227 | $—CH_2—HC{=}CH_2$ | $—CH_2—HC{=}CH_2$ | $—CH_3$ | $—OC(O)CH_3$ | H | F | H |
| 228 | $—CH_3$ | $—CH_3$ | $—CH_3$ | $—OC(O)CH_3$ | H | F | H |
| 229 | $—CH_3$ | $—CH_2CH_3$ | allyl | H | H | H | H |
| 230 | $—CH_3$ | $—(CH_2)_2CH_3$ | allyl | H | H | H | H |
| 231 | $—CH_3$ | $—CH(CH_3)_2$ | allyl | H | H | H | H |
| 232 | $—CH_3$ | $—(CH_2)_3CH_3$ | allyl | H | H | H | H |
| 233 | $—CH_3$ | $—CH_2—HC{=}CH_2$ | allyl | H | H | H | H |
| 234 | $—CH_2CH_3$ | $—CH_2CH_3$ | allyl | H | H | H | H |
| 235 | $—CH_2CH_3$ | $—(CH_2)_2CH_3$ | allyl | H | H | H | H |
| 236 | $—CH_2CH_3$ | $—CH(CH_3)_2$ | allyl | H | H | H | H |
| 237 | $—CH_2CH_3$ | $—(CH_2)_3CH_3$ | allyl | H | H | H | H |
| 238 | $—CH_2CH_3$ | $—CH_2—HC{=}CH_2$ | allyl | H | H | H | H |
| 239 | $—(CH_2)_2CH_3$ | $—(CH_2)_2CH_3$ | allyl | H | H | H | H |
| 240 | $—(CH_2)_2CH_3$ | $—CH(CH_3)_2$ | allyl | H | H | H | H |
| 241 | $—(CH_2)_2CH_3$ | $—(CH_2)_3CH_3$ | allyl | H | H | H | H |
| 242 | $—(CH_2)_2CH_3$ | $—CH_2—HC{=}CH_2$ | allyl | H | H | H | H |
| 243 | $—CH(CH_3)_2$ | $—CH(CH_3)_2$ | allyl | H | H | H | H |
| 244 | $—CH(CH_3)_2$ | $—(CH_2)_3CH_3$ | allyl | H | H | H | H |
| 245 | $—CH(CH_3)_2$ | $—CH_2—HC{=}CH_2$ | allyl | H | H | H | H |
| 246 | $—(CH_2)_3CH_3$ | $—(CH_2)_3CH_3$ | allyl | H | H | H | H |
| 247 | $—(CH_2)_3CH_3$ | $—CH_2—HC{=}CH_2$ | allyl | H | H | H | H |
| 248 | $—CH_2—HC{=}CH_2$ | $—CH_2—HC{=}CH_2$ | allyl | H | H | H | H |
| 249 | H | $—CH_3$ | $—CH_3$ | H | H | H | H |
| 250 | H | $—CH_2CH_3$ | $—CH_3$ | H | H | H | H |
| 251 | H | $—(CH_2)_2CH_3$ | $—CH_3$ | H | H | H | H |
| 252 | H | $—CH(CH_3)_2$ | $—CH_3$ | H | H | H | H |
| 253 | H | $—(CH_2)_3CH_3$ | $—CH_3$ | H | H | H | H |
| 254 | H | $—CH_2—HC{=}CH_2$ | $—CH_3$ | H | H | H | H |
| 255 | H | $—CH_3$ | $—CH_3$ | H | F | H | H |
| 256 | H | $—CH_2CH_3$ | $—CH_3$ | H | F | H | H |
| 257 | H | $—(CH_2)_2CH_3$ | $—CH_3$ | H | F | H | H |
| 258 | H | $—CH(CH_3)_2$ | $—CH_3$ | H | F | H | H |
| 259 | H | $—(CH_2)_3CH_3$ | $—CH_3$ | H | F | H | H |
| 260 | H | $—CH_2—HC{=}CH_2$ | $—CH_3$ | H | F | H | H |
| 261 | H | $—CH_3$ | $—CH_3$ | H | H | F | H |
| 262 | H | $—CH_2CH_3$ | $—CH_3$ | H | H | F | H |
| 263 | H | $—(CH_2)_2CH_3$ | $—CH_3$ | H | H | F | H |
| 264 | H | $—CH(CH_3)_2$ | $—CH_3$ | H | H | F | H |
| 265 | H | $—(CH_2)_3CH_3$ | $—CH_3$ | H | H | F | H |
| 266 | H | $—CH_2—HC{=}CH_2$ | $—CH_3$ | H | H | F | H |
| 267 | H | $—CH_3$ | $—CH_3$ | $—OC(O)CH_3$ | H | H | H |
| 268 | H | $—CH_2CH_3$ | $—CH_3$ | $—OC(O)CH_3$ | H | H | H |
| 269 | H | $—(CH_2)_2CH_3$ | $—CH_3$ | $—OC(O)CH_3$ | H | H | H |
| 270 | H | $—CH(CH_3)_2$ | $—CH_3$ | $—OC(O)CH_3$ | H | H | H |
| 271 | H | $—(CH_2)_3CH_3$ | $—CH_3$ | $—OC(O)CH_3$ | H | H | H |
| 272 | H | $—CH_2—HC{=}CH_2$ | $—CH_3$ | $—OC(O)CH_3$ | H | H | H |
| 273 | H | $—CH_3$ | $—CH_3$ | $—OC(O)CH_3$ | F | H | H |
| 274 | H | $—CH_2CH_3$ | $—CH_3$ | $—OC(O)CH_3$ | F | H | H |
| 275 | H | $—(CH_2)_2CH_3$ | $—CH_3$ | $—OC(O)CH_3$ | F | H | H |
| 276 | H | $—CH(CH_3)_2$ | $—CH_3$ | $—OC(O)CH_3$ | F | H | H |
| 277 | H | $—(CH_2)_3CH_3$ | $—CH_3$ | $—OC(O)CH_3$ | F | H | H |
| 278 | H | $—CH_2—HC{=}CH_2$ | $—CH_3$ | $—OC(O)CH_3$ | F | H | H |
| 279 | H | $—CH_3$ | $—CH_3$ | $—OC(O)CH_3$ | H | F | H |
| 280 | H | $—CH_2CH_3$ | $—CH_3$ | $—OC(O)CH_3$ | H | F | H |

TABLE 1-continued

| Ref. | X | Y | $R_2$ | $R_4$ | $R_5$ | $R_6$ | $R_7$ |
|---|---|---|---|---|---|---|---|
| 281 | H | $—(CH_2)_2CH_3$ | $—CH_3$ | $—OC(O)CH_3$ | H | F | H |
| 282 | H | $—CH(CH_3)_2$ | $—CH_3$ | $—OC(O)CH_3$ | H | F | H |
| 283 | H | $—(CH_2)_3CH_3$ | $—CH_3$ | $—OC(O)CH_3$ | H | F | H |
| 284 | H | $—CH_2—HC═CH_2$ | $—CH_3$ | $—OC(O)CH_3$ | H | F | H |
| 285 | H | $—CH_3$ | $—CH_3$ | H | F | F | H |
| 286 | H | $—CH_2CH_3$ | $—CH_3$ | H | F | F | H |
| 287 | H | $—(CH_2)_2CH_3$ | $—CH_3$ | H | F | F | H |
| 288 | H | $—CH(CH_3)_2$ | $—CH_3$ | H | F | F | H |
| 289 | H | $—(CH_2)_3CH_3$ | $—CH_3$ | H | F | F | H |
| 290 | H | $—CH_2—HC═CH_2$ | $—CH_3$ | H | F | F | H |
| 291 | H | $—CH_3$ | $—CH_3$ | H | H | H | H |
| 292 | H | $—CH_2CH_3$ | $—CH_3$ | H | H | H | H |
| 293 | H | $—(CH_2)_2CH_3$ | $—CH_3$ | H | H | H | H |
| 294 | H | $—CH(CH_3)_2$ | $—CH_3$ | H | H | H | H |
| 295 | H | $—(CH_2)_3CH_3$ | $—CH_3$ | H | H | H | H |
| 296 | H | $—CH_2—HC═CH_2$ | $—CH_3$ | H | H | H | H |
| 297 | H | $—CH_3$ | $—CH_3$ | H | $—OCH_3$ | H | H |
| 298 | H | $—CH_2CH_3$ | $—CH_3$ | H | $—OCH_3$ | H | H |
| 299 | H | $—(CH_2)_2CH_3$ | $—CH_3$ | H | $—OCH_3$ | H | H |
| 300 | H | $—CH(CH_3)_2$ | $—CH_3$ | H | $—OCH_3$ | H | H |
| 301 | H | $—(CH_2)_3CH_3$ | $—CH_3$ | H | $—OCH_3$ | H | H |
| 302 | H | $—CH_2—HC═CH_2$ | $—CH_3$ | H | $—OCH_3$ | H | H |
| 303 | H | $—CH_3$ | $—CH_3$ | H | H | F | H |
| 304 | H | $—CH_2CH_3$ | $—CH_3$ | H | H | F | H |
| 305 | H | $—(CH_2)_2CH_3$ | $—CH_3$ | H | H | F | H |
| 306 | H | $—CH(CH_3)_2$ | $—CH_3$ | H | H | F | H |
| 307 | H | $—(CH_2)_3CH_3$ | $—CH_3$ | H | H | F | H |
| 308 | H | $—CH_2—HC═CH_2$ | $—CH_3$ | H | H | F | H |
| 309 | H | cyclopropyl | $—CH_3$ | H | H | H | H |
| 310 | H | cyclopropyl | $—CH_3$ | H | H | H | H |
| 311 | H | cyclopropyl | $—CH_3$ | $—OH$ | H | H | H |
| 312 | H | cyclopropyl | $—CH_3$ | $—OC(O)CH_3$ | H | H | H |
| 313 | H | cyclopropyl | $—CH_3$ | H | $—OCH_3$ | H | H |
| 314 | H | cyclopropyl | $—CH_3$ | H | H | H | H |
| 315 | H | cyclopropyl | $—CH_3$ | H | H | H | H |
| 316 | H | cyclopropyl | $—CH_3$ | $—OH$ | F | H | H |
| 317 | H | cyclopropyl | $—CH_3$ | $—OH$ | H | H | H |
| 318 | H | cyclopropyl | $—CH_3$ | $—OC(O)CH_3$ | H | H | H |
| 319 | H | cyclopropyl | $—CH_3$ | H | F | H | H |
| 320 | H | cyclopropyl | $—CH_3$ | H | H | F | H |
| 321 | H | $—CH_3$ | $—CH_3$ | H | H | H | H |
| 322 | H | $—CH_3$ | $—CH_3$ | $—OH$ | H | H | H |
| 323 | H | $—CH_3$ | $—CH_3$ | $—OC(O)CH_3$ | H | H | H |
| 324 | H | $—CH_3$ | $—CH_3$ | H | $—OCH_3$ | H | H |
| 325 | H | $—CH_3$ | $—CH_3$ | H | F | H | H |
| 326 | H | $—CH_3$ | $—CH_3$ | $—OH$ | F | H | H |
| 327 | H | $—CH_3$ | $—CH_3$ | $—OC(O)CH_3$ | F | F | H |
| 328 | H | $—CH_3$ | $—CH_3$ | H | F | F | H |
| 329 | H | $—CD_2CD_3$ | H | H | F | H | H |
| 330 | H | $—CD_2CD_3$ | H | $—OH$ | H | H | H |
| 331 | H | $—CD_2CD_3$ | H | $—OC(O)CH_3$ | H | H | H |
| 332 | H | $—CD_2CD_3$ | H | H | F | F | H |
| 333 | H | $—CD_2CD_3$ | H | H | H | F | H |
| 334 | H | $—CD_2CD_3$ | H | $—OH$ | F | H | H |
| 335 | H | $—CD_2CD_3$ | H | $—OC(O)CH_3$ | F | H | H |
| 336 | H | $—CD_2CD_3$ | H | H | $—OCH_3$ | F | H |

Other exemplary compounds include compounds of Formula II(b) set forth below in Table 2:

Formula II(b)

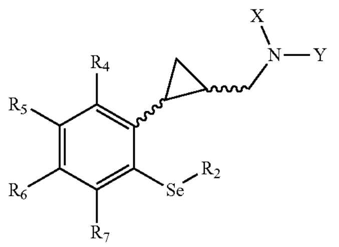

TABLE 2

| Ref. | X | Y | $R_2$ | $R_4$ | $R_5$ | $R_6$ | $R_7$ |
|---|---|---|---|---|---|---|---|
| 1 | —$CH_3$ | —$CH_3$ | —$CH_3$ | —OH | H | H | H |
| 2 | —$CH_3$ | —$CD_2CD_3$ | —$CH_3$ | —OH | H | H | H |
| 3 | —$CH_3$ | —$(CH_2)_2CH_3$ | —$CH_3$ | —OH | H | H | H |
| 4 | —$CH_3$ | —$CH(CH_3)_2$ | —$CH_3$ | —OH | H | H | H |
| 5 | —$CH_3$ | —$(CH_2)_3CH_3$ | —$CH_3$ | —OH | H | H | H |
| 6 | —$CH_3$ | —$CH_2$—HC═$CH_2$ | —$CH_3$ | —OH | H | H | H |
| 7 | —$CH_2CH_3$ | —$CH_2CH_3$ | —$CH_3$ | —OH | H | H | H |
| 8 | —$CH_2CH_3$ | —$(CH_2)_2CH_3$ | —$CH_3$ | —OH | H | H | H |
| 9 | —$CH_2CH_3$ | —$CH(CH_3)_2$ | —$CH_3$ | —OH | H | H | H |
| 10 | —$CH_2CH_3$ | —$(CH_2)_3CH_3$ | —$CH_3$ | —OH | H | H | H |
| 11 | —$CH_2CH_3$ | —$CH_2$—HC═$CH_2$ | —$CH_3$ | —OH | H | H | H |
| 12 | —$(CH_2)_2CH_3$ | —$(CH_2)_2CH_3$ | —$CH_3$ | —OH | H | H | H |
| 13 | —$(CH_2)_2CH_3$ | —$CH(CH_3)_2$ | —$CH_3$ | —OH | H | H | H |
| 14 | —$(CH_2)_2CH_3$ | —$(CH_2)_3CH_3$ | —$CH_3$ | —OH | H | H | H |
| 15 | —$(CH_2)_2CH_3$ | —$CH_2$—HC═$CH_2$ | —$CH_3$ | —OH | H | H | H |
| 16 | —$CH(CH_3)_2$ | —$CH(CH_3)_2$ | —$CH_3$ | —OH | H | H | H |
| 17 | —$CH(CH_3)_2$ | —$(CH_2)_3CH_3$ | —$CH_3$ | —OH | H | H | H |
| 18 | —$CH(CH_3)_2$ | —$CH_2$—HC═$CH_2$ | —$CH_3$ | —OH | H | H | H |
| 19 | —$(CH_2)_3CH_3$ | —$(CH_2)_3CH_3$ | —$CH_3$ | —OH | H | H | H |
| 20 | —$(CH_2)_3CH_3$ | —$CH_2$—HC═$CH_2$ | —$CH_3$ | —OH | H | H | H |
| 21 | —$CH_2$—HC═$CH_2$ | —$CH_2$—HC═$CH_2$ | —$CH_3$ | —OH | H | H | H |
| 22 | —$CH_3$ | —$CH_2CH_3$ | —$CH_3$ | —OC(O)$CH_3$ | H | H | H |
| 23 | —$CH_3$ | —$(CH_2)_2CH_3$ | —$CH_3$ | —OC(O)$CH_3$ | H | H | H |
| 24 | —$CH_3$ | —$CH(CH_3)_2$ | —$CH_3$ | —OC(O)$CH_3$ | H | H | H |
| 25 | —$CH_3$ | —$(CH_2)_3CH_3$ | —$CH_3$ | —OC(O)$CH_3$ | H | H | H |
| 26 | —$CH_3$ | —$CH_2$—HC═$CH_2$ | —$CH_3$ | —OC(O)$CH_3$ | H | H | H |
| 27 | —$CH_2CH_3$ | —$CH_2CH_3$ | —$CH_3$ | —OC(O)$CH_3$ | H | H | H |
| 28 | —$CH_2CH_3$ | —$(CH_2)_2CH_3$ | —$CH_3$ | —OC(O)$CH_3$ | H | H | H |
| 29 | —$CH_2CH_3$ | —$CH(CH_3)_2$ | —$CH_3$ | —OC(O)$CH_3$ | H | H | H |
| 30 | —$CH_2CH_3$ | —$(CH_2)_3CH_3$ | —$CH_3$ | —OC(O)$CH_3$ | H | H | H |
| 31 | —$CH_2CH_3$ | —$CH_2$—HC═$CH_2$ | —$CH_3$ | —OC(O)$CH_3$ | H | H | H |
| 32 | —$(CH_2)_2CH_3$ | —$(CH_2)_2CH_3$ | —$CH_3$ | —OC(O)$CH_3$ | H | H | H |
| 33 | —$(CH_2)_2CH_3$ | —$CH(CH_3)_2$ | —$CH_3$ | —OC(O)$CH_3$ | H | H | H |
| 34 | —$(CH_2)_2CH_3$ | —$(CH_2)_3CH_3$ | —$CH_3$ | —OC(O)$CH_3$ | H | H | H |
| 35 | —$(CH_2)_2CH_3$ | —$CH_2$—HC═$CH_2$ | —$CH_3$ | —OC(O)$CH_3$ | H | H | H |
| 36 | —$CH(CH_3)_2$ | —$CH(CH_3)_2$ | —$CH_3$ | —OC(O)$CH_3$ | H | H | H |
| 37 | —$CH(CH_3)_2$ | —$(CH_2)_3CH_3$ | —$CH_3$ | —OC(O)$CH_3$ | H | H | H |
| 38 | —$CH(CH_3)_2$ | —$CH_2$—HC═$CH_2$ | —$CH_3$ | —OC(O)$CH_3$ | H | H | H |
| 39 | —$(CH_2)_3CH_3$ | —$(CH_2)_3CH_3$ | —$CH_3$ | —OC(O)$CH_3$ | H | H | H |
| 40 | —$(CH_2)_3CH_3$ | —$CH_2$—HC═$CH_2$ | —$CH_3$ | —OC(O)$CH_3$ | H | H | H |
| 41 | —$CH_2$—HC═$CH_2$ | —$CH_2$—HC═$CH_2$ | —$CH_3$ | —OC(O)$CH_3$ | H | H | H |
| 42 | —$CH_3$ | —$CH_3$ | —$CH_3$ | —OC(O)$CH_3$ | H | H | H |
| 43 | —$CH_3$ | —$CH_2CH_3$ | —$CH_3$ | —OC(O)$CH_3$ | H | H | H |
| 44 | —$CH_3$ | —$(CH_2)_2CH_3$ | —$CH_3$ | —OC(O)$CH_3$ | H | H | H |
| 45 | —$CH_3$ | —$CH(CH_3)_2$ | —$CH_3$ | —OC(O)$CH_3$ | H | H | H |
| 46 | —$CH_3$ | —$(CH_2)_3CH_3$ | —$CH_3$ | —OC(O)$CH_3$ | H | H | H |
| 47 | —$CH_3$ | —$CH_2$—HC═$CH_2$ | —$CH_3$ | —OC(O)$CH_3$ | H | H | H |
| 48 | —$CH_2CH_3$ | —$CH_2CH_3$ | —$CH_3$ | —OC(O)$CH_3$ | H | H | H |
| 49 | —$CH_2CH_3$ | —$(CH_2)_2CH_3$ | —$CH_3$ | —OC(O)$CH_3$ | H | H | H |
| 50 | —$CH_2CH_3$ | —$CH(CH_3)_2$ | —$CH_3$ | —OC(O)$CH_3$ | H | H | H |
| 51 | —$CH_2CH_3$ | —$(CH_2)_3CH_3$ | —$CH_3$ | —OC(O)$CH_3$ | H | H | H |
| 52 | —$CH_2CH_3$ | —$CH_2$—HC═$CH_2$ | —$CH_3$ | —OC(O)$CH_3$ | H | H | H |
| 53 | —$(CH_2)_2CH_3$ | —$(CH_2)_2CH_3$ | —$CH_3$ | —OC(O)$CH_3$ | H | H | H |
| 54 | —$(CH_2)_2CH_3$ | —$CH(CH_3)_2$ | —$CH_3$ | —OC(O)$CH_3$ | H | H | H |
| 55 | —$(CH_2)_2CH_3$ | —$(CH_2)_3CH_3$ | —$CH_3$ | —OC(O)$CH_3$ | H | H | H |
| 56 | —$(CH_2)_2CH_3$ | —$CH_2$—HC═$CH_2$ | —$CH_3$ | —OC(O)$CH_3$ | H | H | H |
| 57 | —$CH(CH_3)_2$ | —$CH(CH_3)_2$ | —$CH_3$ | —OC(O)$CH_3$ | H | H | H |
| 58 | —$CH(CH_3)_2$ | —$(CH_2)_3CH_3$ | —$CH_3$ | —OC(O)$CH_3$ | H | H | H |
| 59 | —$CH(CH_3)_2$ | —$CH_2$—HC═$CH_2$ | —$CH_3$ | —OC(O)$CH_3$ | H | H | H |
| 60 | —$(CH_2)_3CH_3$ | —$(CH_2)_3CH_3$ | —$CH_3$ | —OC(O)$CH_3$ | H | H | H |
| 61 | —$(CH_2)_3CH_3$ | —$CH_2$—HC═$CH_2$ | —$CH_3$ | —OC(O)$CH_3$ | H | H | H |
| 62 | —$CH_2$—HC═$CH_2$ | —$CH_2$—HC═$CH_2$ | —$CH_3$ | —OC(O)$CH_3$ | H | H | H |
| 63 | —$CH_3$ | —$CH_3$ | —$CH_3$ | H | H | H | H |
| 64 | —$CH_3$ | —$CH_2CH_3$ | —$CH_3$ | H | H | H | H |
| 65 | —$CH_3$ | —$(CH_2)_2CH_3$ | —$CH_3$ | H | H | H | H |
| 66 | —$CH_3$ | —$CH(CH_3)_2$ | —$CH_3$ | H | H | H | H |
| 67 | —$CH_3$ | —$(CH_2)_3CH_3$ | —$CH_3$ | H | H | H | H |
| 68 | —$CH_3$ | —$CH_2$—HC═$CH_2$ | —$CH_3$ | H | H | H | H |
| 69 | —$CH_2CH_3$ | —$CH_2CH_3$ | —$CH_3$ | H | H | H | H |
| 70 | —$CH_2CH_3$ | —$(CH_2)_2CH_3$ | —$CH_3$ | H | H | H | H |
| 71 | —$CH_2CH_3$ | —$CH(CH_3)_2$ | —$CH_3$ | H | H | H | H |
| 72 | —$CH_2CH_3$ | —$(CH_2)_3CH_3$ | —$CH_3$ | H | H | H | H |
| 73 | —$CH_2CH_3$ | —$CH_2$—HC═$CH_2$ | —$CH_3$ | H | H | H | H |
| 74 | —$(CH_2)_2CH_3$ | —$(CH_2)_2CH_3$ | —$CH_3$ | H | H | H | H |
| 75 | —$(CH_2)_2CH_3$ | —$CH(CH_3)_2$ | —$CH_3$ | H | H | H | H |
| 76 | —$(CH_2)_2CH_3$ | —$(CH_2)_3CH_3$ | —$CH_3$ | H | H | H | H |
| 77 | —$(CH_2)_2CH_3$ | —$CH_2$—HC═$CH_2$ | —$CH_3$ | H | H | H | H |
| 78 | —$CH(CH_3)_2$ | —$CH(CH_3)_2$ | —$CH_3$ | H | H | H | H |

TABLE 2-continued

| Ref. | X | Y | $R_2$ | $R_4$ | $R_5$ | $R_6$ | $R_7$ |
|---|---|---|---|---|---|---|---|
| 79 | —$CH(CH_3)_2$ | —$(CH_2)_3CH_3$ | —$CH_3$ | H | H | H | H |
| 80 | —$CH(CH_3)_2$ | —$CH_2$—HC═$CH_2$ | —$CH_3$ | H | H | H | H |
| 81 | —$(CH_2)_3CH_3$ | —$(CH_2)_3CH_3$ | —$CH_3$ | H | H | H | H |
| 82 | —$(CH_2)_3CH_3$ | —$CH_2$—HC═$CH_2$ | —$CH_3$ | H | H | H | H |
| 83 | —$CH_2$—HC═$CH_2$ | —$CH_2$—HC═$CH_2$ | —$CH_3$ | H | H | H | H |
| 84 | —$CH_3$ | —$CH_2CH_3$ | —$CH_3$ | H | —$OCH_3$ | H | H |
| 85 | —$CH_3$ | —$(CH_2)_2CH_3$ | —$CH_3$ | H | —$OCH_3$ | H | H |
| 86 | —$CH_3$ | —$CH(CH_3)_2$ | —$CH_3$ | H | —$OCH_3$ | H | H |
| 87 | —$CH_3$ | —$(CH_2)_3CH_3$ | —$CH_3$ | H | —$OCH_3$ | H | H |
| 88 | —$CH_3$ | —$CH_2$—HC═$CH_2$ | —$CH_3$ | H | —$OCH_3$ | H | H |
| 89 | —$CH_2CH_3$ | —$CH_2CH_3$ | —$CH_3$ | H | —$OCH_3$ | H | H |
| 90 | —$CH_2CH_3$ | —$(CH_2)_2CH_3$ | —$CH_3$ | H | —$OCH_3$ | H | H |
| 91 | —$CH_2CH_3$ | —$CH(CH_3)_2$ | —$CH_3$ | H | —$OCH_3$ | H | H |
| 92 | —$CH_2CH_3$ | —$(CH_2)_3CH_3$ | —$CH_3$ | H | —$OCH_3$ | H | H |
| 93 | —$CH_2CH_3$ | —$CH_2$—HC═$CH_2$ | —$CH_3$ | H | —$OCH_3$ | H | H |
| 94 | —$(CH_2)_2CH_3$ | —$(CH_2)_2CH_3$ | —$CH_3$ | H | —$OCH_3$ | H | H |
| 95 | —$(CH_2)_2CH_3$ | —$CH(CH_3)_2$ | —$CH_3$ | H | —$OCH_3$ | H | H |
| 96 | —$(CH_2)_2CH_3$ | —$(CH_2)_3CH_3$ | —$CH_3$ | H | —$OCH_3$ | H | H |
| 97 | —$(CH_2)_2CH_3$ | —$CH_2$—HC═$CH_2$ | —$CH_3$ | H | —$OCH_3$ | H | H |
| 98 | —$CH(CH_3)_2$ | —$CH(CH_3)_2$ | —$CH_3$ | H | —$OCH_3$ | H | H |
| 99 | —$CH(CH_3)_2$ | —$(CH_2)_3CH_3$ | —$CH_3$ | H | —$OCH_3$ | H | H |
| 100 | —$CH(CH_3)_2$ | —$CH_2$—HC═$CH_2$ | —$CH_3$ | H | —$OCH_3$ | H | H |
| 101 | —$(CH_2)_3CH_3$ | —$(CH_2)_3CH_3$ | —$CH_3$ | H | —$OCH_3$ | H | H |
| 102 | —$(CH_2)_3CH_3$ | —$CH_2$—HC═$CH_2$ | —$CH_3$ | H | —$OCH_3$ | H | H |
| 103 | —$CH_2$—HC═$CH_2$ | —$CH_2$—HC═$CH_2$ | —$CH_3$ | H | —$OCH_3$ | H | H |
| 104 | —$CH_3$ | —$CH_3$ | —$CH_3$ | H | —$OCH_3$ | H | H |
| 105 | —$CH_3$ | —$CH_2CH_3$ | —$CH_3$ | H | H | F | H |
| 106 | —$CH_3$ | —$(CH_2)_2CH_3$ | —$CH_3$ | H | H | F | H |
| 107 | —$CH_3$ | —$CH(CH_3)_2$ | —$CH_3$ | H | H | F | H |
| 108 | —$CH_3$ | —$(CH_2)_3CH_3$ | —$CH_3$ | H | H | F | H |
| 109 | —$CH_3$ | —$CH_2$—HC═$CH_2$ | —$CH_3$ | H | H | F | H |
| 110 | —$CH_2CH_3$ | —$CH_2CH_3$ | —$CH_3$ | H | H | F | H |
| 111 | —$CH_2CH_3$ | —$(CH_2)_2CH_3$ | —$CH_3$ | H | H | F | H |
| 112 | —$CH_2CH_3$ | —$CH(CH_3)_2$ | —$CH_3$ | H | H | F | H |
| 113 | —$CH_2CH_3$ | —$(CH_2)_3CH_3$ | —$CH_3$ | H | H | F | H |
| 114 | —$CH_2CH_3$ | —$CH_2$—HC═$CH_2$ | —$CH_3$ | H | H | F | H |
| 115 | —$(CH_2)_2CH_3$ | —$(CH_2)_2CH_3$ | —$CH_3$ | H | H | F | H |
| 116 | —$(CH_2)_2CH_3$ | —$CH(CH_3)_2$ | —$CH_3$ | H | H | F | H |
| 117 | —$(CH_2)_2CH_3$ | —$(CH_2)_3CH_3$ | —$CH_3$ | H | H | F | H |
| 118 | —$(CH_2)_2CH_3$ | —$CH_2$—HC═$CH_2$ | —$CH_3$ | H | H | F | H |
| 119 | —$CH(CH_3)_2$ | —$CH(CH_3)_2$ | —$CH_3$ | H | H | F | H |
| 120 | —$CH(CH_3)_2$ | —$(CH_2)_3CH_3$ | —$CH_3$ | H | H | F | H |
| 121 | —$CH(CH_3)_2$ | —$CH_2$—HC═$CH_2$ | —$CH_3$ | H | H | F | H |
| 122 | —$(CH_2)_3CH_3$ | —$(CH_2)_3CH_3$ | —$CH_3$ | H | H | F | H |
| 123 | —$(CH_2)_3CH_3$ | —$CH_2$—HC═$CH_2$ | —$CH_3$ | H | H | F | H |
| 124 | —$CH_2$—HC═$CH_2$ | —$CH_2$—HC═$CH_2$ | —$CH_3$ | H | H | F | H |
| 125 | —$CH_3$ | —$CH_3$ | —$CH_3$ | H | H | F | H |
| 126 | —$CH_3$ | —$CH_2CH_3$ | —$CH_3$ | H | H | H | —$CH_3$ |
| 127 | —$CH_3$ | —$(CH_2)_2CH_3$ | —$CH_3$ | H | H | H | —$CH_3$ |
| 128 | —$CH_3$ | —$CH(CH_3)_2$ | —$CH_3$ | H | H | H | —$CH_3$ |
| 129 | —$CH_3$ | —$(CH_2)_3CH_3$ | —$CH_3$ | H | H | H | —$CH_3$ |
| 130 | —$CH_3$ | —$CH_2$—HC═$CH_2$ | —$CH_3$ | H | H | H | —$CH_3$ |
| 131 | —$CH_2CH_3$ | —$CH_2CH_3$ | —$CH_3$ | H | H | H | —$CH_3$ |
| 132 | —$CH_2CH_3$ | —$(CH_2)_2CH_3$ | —$CH_3$ | H | H | H | —$CH_3$ |
| 133 | —$CH_2CH_3$ | —$CH(CH_3)_2$ | —$CH_3$ | H | H | H | —$CH_3$ |
| 134 | —$CH_2CH_3$ | —$(CH_2)_3CH_3$ | —$CH_3$ | H | H | H | —$CH_3$ |
| 135 | —$CH_2CH_3$ | —$CH_2$—HC═$CH_2$ | —$CH_3$ | H | H | H | —$CH_3$ |
| 135 | —$(CH_2)_2CH_3$ | —$(CH_2)_2CH_3$ | —$CH_3$ | H | H | H | —$CH_3$ |
| 137 | —$(CH_2)_2CH_3$ | —$CH(CH_3)_2$ | —$CH_3$ | H | H | H | —$CH_3$ |
| 138 | —$(CH_2)_2CH_3$ | —$(CH_2)_3CH_3$ | —$CH_3$ | H | H | H | —$CH_3$ |
| 139 | —$(CH_2)_2CH_3$ | —$CH_2$—HC═$CH_2$ | —$CH_3$ | H | H | H | —$CH_3$ |
| 140 | —$CH(CH_3)_2$ | —$CH(CH_3)_2$ | —$CH_3$ | H | H | H | —$CH_3$ |
| 141 | —$CH(CH_3)_2$ | —$(CH_2)_3CH_3$ | —$CH_3$ | H | H | H | —$CH_3$ |
| 142 | —$CH(CH_3)_2$ | —$CH_2$—HC═$CH_2$ | —$CH_3$ | H | H | H | —$CH_3$ |
| 143 | —$(CH_2)_3CH_3$ | —$(CH_2)_3CH_3$ | —$CH_3$ | H | H | H | —$CH_3$ |
| 144 | —$(CH_2)_3CH_3$ | —$CH_2$—HC═$CH_2$ | —$CH_3$ | H | H | H | —$CH_3$ |
| 145 | —$CH_2$—HC═$CH_2$ | —$CH_2$—HC═$CH_2$ | —$CH_3$ | H | H | H | —$CH_3$ |
| 146 | —$CH_3$ | —$CH_2CH_3$ | —$CH_3$ | H | F | H | H |
| 147 | —$CH_3$ | —$(CH_2)_2CH_3$ | —$CH_3$ | H | F | H | H |
| 148 | —$CH_3$ | —$CH(CH_3)_2$ | —$CH_3$ | H | F | H | H |
| 149 | —$CH_3$ | —$(CH_2)_3CH_3$ | —$CH_3$ | H | F | H | H |
| 150 | —$CH_3$ | —$CH_2$—HC═$CH_2$ | —$CH_3$ | H | F | H | H |
| 151 | —$CH_2CH_3$ | —$CH_2CH_3$ | —$CH_3$ | H | F | H | H |
| 152 | —$CH_2CH_3$ | —$(CH_2)_2CH_3$ | —$CH_3$ | H | F | H | H |
| 153 | —$CH_2CH_3$ | —$CH(CH_3)_2$ | —$CH_3$ | H | F | H | H |
| 154 | —$CH_2CH_3$ | —$(CH_2)_3CH_3$ | —$CH_3$ | H | F | H | H |
| 155 | —$CH_2CH_3$ | —$CH_2$—HC═$CH_2$ | —$CH_3$ | H | F | H | H |
| 156 | —$(CH_2)_2CH_3$ | —$(CH_2)_2CH_3$ | —$CH_3$ | H | F | H | H |

TABLE 2-continued

| Ref. | X | Y | $R_2$ | $R_4$ | $R_5$ | $R_6$ | $R_7$ |
|---|---|---|---|---|---|---|---|
| 157 | $-(CH_2)_2CH_3$ | $-CH(CH_3)_2$ | $-CH_3$ | H | F | H | H |
| 158 | $-(CH_2)_2CH_3$ | $-(CH_2)_3CH_3$ | $-CH_3$ | H | F | H | H |
| 159 | $-(CH_2)_2CH_3$ | $-CH_2-HC=CH_2$ | $-CH_3$ | H | F | H | H |
| 160 | $-CH(CH_3)_2$ | $-CH(CH_3)_2$ | $-CH_3$ | H | F | H | H |
| 161 | $-CH(CH_3)_2$ | $-(CH_2)_3CH_3$ | $-CH_3$ | H | F | H | H |
| 162 | $-CH(CH_3)_2$ | $-CH_2-HC=CH_2$ | $-CH_3$ | H | F | H | H |
| 163 | $-(CH_2)_3CH_3$ | $-(CH_2)_3CH_3$ | $-CH_3$ | H | F | H | H |
| 164 | $-(CH_2)_3CH_3$ | $-CH_2-HC=CH_2$ | $-CH_3$ | H | F | H | H |
| 165 | $-CH_2-HC=CH_2$ | $-CH_2-HC=CH_2$ | $-CH_3$ | H | F | H | H |
| 166 | $-CH_3$ | $-CH_3$ | $-CH_3$ | H | F | H | H |
| 167 | $-CH_3$ | $-CH_2CH_3$ | $-CH_3$ | $-OC(O)CH_3$ | F | H | H |
| 168 | $-CH_3$ | $-(CH_2)_2CH_3$ | $-CH_3$ | $-OC(O)CH_3$ | F | H | H |
| 169 | $-CH_3$ | $-CH(CH_3)_2$ | $-CH_3$ | $-OC(O)CH_3$ | F | H | H |
| 170 | $-CH_3$ | $-(CH_2)_3CH_3$ | $-CH_3$ | $-OC(O)CH_3$ | F | H | H |
| 171 | $-CH_3$ | $-CH_2-HC=CH_2$ | $-CH_3$ | $-OC(O)CH_3$ | F | H | H |
| 172 | $-CH_2CH_3$ | $-CH_2CH_3$ | $-CH_3$ | $-OC(O)CH_3$ | F | H | H |
| 173 | $-CH_2CH_3$ | $-(CH_2)2CH_3$ | $-CH_3$ | $-OC(O)CH_3$ | F | H | H |
| 174 | $-CH_2CH_3$ | $-CH(CH_3)_2$ | $-CH_3$ | $-OC(O)CH_3$ | F | H | H |
| 175 | $-CH_2CH_3$ | $-(CH_2)_3CH_3$ | $-CH_3$ | $-OC(O)CH_3$ | F | H | H |
| 176 | $-CH_2CH_3$ | $-CH_2-HC=CH_2$ | $-CH_3$ | $-OC(O)CH_3$ | F | H | H |
| 177 | $-(CH_2)_2CH_3$ | $-(CH_2)_2CH_3$ | $-CH_3$ | $-OC(O)CH_3$ | F | H | H |
| 178 | $-(CH_2)_2CH_3$ | $-CH(CH_3)_2$ | $-CH_3$ | $-OC(O)CH_3$ | F | H | H |
| 179 | $-(CH_2)_2CH_3$ | $-(CH_2)_3CH_3$ | $-CH_3$ | $-OC(O)CH_3$ | F | H | H |
| 180 | $-(CH_2)_2CH_3$ | $-CH_2-HC=CH_2$ | $-CH_3$ | $-OC(O)CH_3$ | F | H | H |
| 181 | $-CH(CH_3)_2$ | $-CH(CH_3)_2$ | $-CH_3$ | $-OC(O)CH_3$ | F | H | H |
| 182 | $-CH(CH_3)_2$ | $-(CH_2)_3CH_3$ | $-CH_3$ | $-OC(O)CH_3$ | F | H | H |
| 183 | $-CH(CH_3)_2$ | $-CH_2-HC=CH_2$ | $-CH_3$ | $-OC(O)CH_3$ | F | H | H |
| 184 | $-(CH_2)_3CH_3$ | $-(CH_2)_3CH_3$ | $-CH_3$ | $-OC(O)CH_3$ | F | H | H |
| 185 | $-(CH_2)_3CH_3$ | $-CH_2-HC=CH_2$ | $-CH_3$ | $-OC(O)CH_3$ | F | H | H |
| 186 | $-CH_2-HC=CH_2$ | $-CH_2-HC=CH_2$ | $-CH_3$ | $-OC(O)CH_3$ | F | H | H |
| 187 | $-CH_3$ | $-CH_3$ | $-CH_3$ | $-OC(O)CH_3$ | F | F | H |
| 188 | $-CH_3$ | $-CH_2CH_3$ | $-CH_3$ | H | H | F | H |
| 189 | $-CH_3$ | $-(CH_2)_2CH_3$ | $-CH_3$ | H | H | F | H |
| 190 | $-CH_3$ | $-CH(CH_3)_2$ | $-CH_3$ | H | H | F | H |
| 191 | $-CH_3$ | $-(CH_2)_3CH_3$ | $-CH_3$ | H | H | F | H |
| 192 | $-CH_3$ | $-CH_2-HC=CH_2$ | $-CH_3$ | H | H | F | H |
| 193 | $-CH_2CH_3$ | $-CH_2CH_3$ | $-CH_3$ | H | H | F | H |
| 194 | $-CH_2CH_3$ | $-(CH_2)_2CH_3$ | $-CH_3$ | H | H | F | H |
| 195 | $-CH_2CH_3$ | $-CH(CH_3)_2$ | $-CH_3$ | H | H | F | H |
| 196 | $-CH_2CH_3$ | $-(CH_2)_3CH_3$ | $-CH_3$ | H | H | F | H |
| 197 | $-CH_2CH_3$ | $-CH_2-HC=CH_2$ | $-CH_3$ | H | H | F | H |
| 198 | $-(CH_2)_2CH_3$ | $-(CH_2)_2CH_3$ | $-CH_3$ | H | H | F | H |
| 199 | $-(CH_2)_2CH_3$ | $-CH(CH_3)_2$ | $-CH_3$ | H | H | F | H |
| 200 | $-(CH_2)_2CH_3$ | $-(CH_2)_3CH_3$ | $-CH_3$ | H | H | F | H |
| 201 | $-(CH_2)_2CH_3$ | $-CH_2-HC=CH_2$ | $-CH_3$ | H | H | F | H |
| 202 | $-CH(CH_3)_2$ | $-CH(CH_3)_2$ | $-CH_3$ | H | H | F | H |
| 203 | $-CH(CH_3)_2$ | $-(CH_2)_3CH_3$ | $-CH_3$ | H | H | F | H |
| 204 | $-CH(CH_3)_2$ | $-CH_2-HC=CH_2$ | $-CH_3$ | H | H | F | H |
| 205 | $-(CH_2)_3CH_3$ | $-(CH_2)_3CH_3$ | $-CH_3$ | H | H | F | H |
| 206 | $-(CH_2)_3CH_3$ | $-CH_2-HC=CH_2$ | $-CH_3$ | H | H | F | H |
| 207 | $-CH_2-HC=CH_2$ | $-CH_2-HC=CH_2$ | $-CH_3$ | H | H | F | H |
| 208 | $-CH_3$ | $-CH_2CH_3$ | $-CH_3$ | H | H | F | H |
| 209 | $-CH_3$ | $-(CH_2)_2CH_3$ | $-CH_3$ | $-OC(O)CH_3$ | H | F | H |
| 210 | $-CH_3$ | $-CH(CH_3)_2$ | $-CH_3$ | $-OC(O)CH_3$ | H | F | H |
| 211 | $-CH_3$ | $-(CH_2)_3CH_3$ | $-CH_3$ | $-OC(O)CH_3$ | H | F | H |
| 212 | $-CH_3$ | $-CH_2-HC=CH_2$ | $-CH_3$ | $-OC(O)CH_3$ | H | F | H |
| 213 | $-CH_2CH_3$ | $-CH_2CH_3$ | $-CH_3$ | $-OC(O)CH_3$ | H | F | H |
| 214 | $-CH_2CH_3$ | $-(CH_2)_2CH_3$ | $-CH_3$ | $-OC(O)CH_3$ | H | F | H |
| 215 | $-CH_2CH_3$ | $-CH(CH_3)_2$ | $-CH_3$ | $-OC(O)CH_3$ | H | F | H |
| 216 | $-CH_2CH_3$ | $-(CH_2)_3CH_3$ | $-CH_3$ | $-OC(O)CH_3$ | H | F | H |
| 217 | $-CH_2CH_3$ | $-CH_2-HC=CH_2$ | $-CH_3$ | $-OC(O)CH_3$ | H | F | H |
| 218 | $-(CH_2)_2CH_3$ | $-(CH_2)_2CH_3$ | $-CH_3$ | $-OC(O)CH_3$ | H | F | H |
| 219 | $-(CH_2)_2CH_3$ | $-CH(CH_3)_2$ | $-CH_3$ | $-OC(O)CH_3$ | H | F | H |
| 220 | $-(CH_2)_2CH_3$ | $-(CH_2)_3CH_3$ | $-CH_3$ | $-OC(O)CH_3$ | H | F | H |
| 221 | $-(CH_2)_2CH_3$ | $-CH_2-HC=CH_2$ | $-CH_3$ | $-OC(O)CH_3$ | H | F | H |
| 222 | $-CH(CH_3)_2$ | $-CH(CH_3)_2$ | $-CH_3$ | $-OC(O)CH_3$ | H | F | H |
| 223 | $-CH(CH_3)_2$ | $-(CH_2)_3CH_3$ | $-CH_3$ | $-OC(O)CH_3$ | H | F | H |
| 224 | $-CH(CH_3)_2$ | $-CH_2-HC=CH_2$ | $-CH_3$ | $-OC(O)CH_3$ | H | F | H |
| 225 | $-(CH_2)_3CH_3$ | $-(CH_2)_3CH_3$ | $-CH_3$ | $-OC(O)CH_3$ | H | F | H |
| 226 | $-(CH_2)_3CH_3$ | $-CH_2-HC=CH_2$ | $-CH_3$ | $-OC(O)CH_3$ | H | F | H |
| 227 | $-CH_2-HC=CH_2$ | $-CH_2-HC=CH_2$ | $-CH_3$ | $-OC(O)CH_3$ | H | F | H |
| 228 | $-CH_3$ | $-CH_3$ | $-CH_3$ | $-OC(O)CH_3$ | H | F | H |
| 229 | $-CH_3$ | $-CH_2CH_3$ | allyl | H | H | H | H |
| 230 | $-CH_3$ | $-(CH_2)_2CH_3$ | allyl | H | H | H | H |
| 231 | $-CH_3$ | $-CH(CH_3)_2$ | allyl | H | H | H | H |
| 232 | $-CH_3$ | $-(CH_2)_3CH_3$ | allyl | H | H | H | H |
| 233 | $-CH_3$ | $-CH_2-HC=CH_2$ | allyl | H | H | H | H |
| 234 | $-CH_2CH_3$ | $-CH_2CH_3$ | allyl | H | H | H | H |

TABLE 2-continued

| Ref. | X | Y | $R_2$ | $R_4$ | $R_5$ | $R_6$ | $R_7$ |
|---|---|---|---|---|---|---|---|
| 235 | $—CH_2CH_3$ | $—(CH_2)_2CH_3$ | allyl | H | H | H | H |
| 236 | $—CH_2CH_3$ | $—CH(CH_3)_2$ | allyl | H | H | H | H |
| 237 | $—CH_2CH_3$ | $—(CH_2)_3CH_3$ | allyl | H | H | H | H |
| 238 | $—CH_2CH_3$ | $—CH_2—HC{=}CH_2$ | allyl | H | H | H | H |
| 239 | $—(CH_2)_2CH_3$ | $—(CH_2)_2CH_3$ | allyl | H | H | H | H |
| 240 | $—(CH_2)_2CH_3$ | $—CH(CH_3)_2$ | allyl | H | H | H | H |
| 241 | $—(CH_2)_2CH_3$ | $—(CH_2)_3CH_3$ | allyl | H | H | H | H |
| 242 | $—(CH_2)_2CH_3$ | $—CH_2—HC{=}CH_2$ | allyl | H | H | H | H |
| 243 | $—CH(CH_3)_2$ | $—CH(CH_3)_2$ | allyl | H | H | H | H |
| 244 | $—CH(CH_3)_2$ | $—(CH_2)_3CH_3$ | allyl | H | H | H | H |
| 245 | $—CH(CH_3)_2$ | $—CH_2—HC{=}CH_2$ | allyl | H | H | H | H |
| 246 | $—(CH_2)_3CH_3$ | $—(CH_2)_3CH_3$ | allyl | H | H | H | H |
| 247 | $—(CH_2)_3CH_3$ | $—CH_2—HC{=}CH_2$ | allyl | H | H | H | H |
| 248 | $—CH_2—HC{=}CH_2$ | $—CH_2—HC{=}CH_2$ | allyl | H | H | H | H |
| 249 | H | $—CH_3$ | $—CH_3$ | H | H | H | H |
| 250 | H | $—CH_2CH_3$ | $—CH_3$ | H | H | H | H |
| 251 | H | $—(CH_2)_2CH_3$ | $—CH_3$ | H | H | H | H |
| 252 | H | $—CH(CH_3)_2$ | $—CH_3$ | H | H | H | H |
| 253 | H | $—(CH_2)_3CH_3$ | $—CH_3$ | H | H | H | H |
| 254 | H | $—CH_2—HC{=}CH_2$ | $—CH_3$ | H | H | H | H |
| 255 | H | $—CH_3$ | $—CH_3$ | H | F | H | H |
| 256 | H | $—CH_2CH_3$ | $—CH_3$ | H | F | H | H |
| 257 | H | $—(CH_2)_2CH_3$ | $—CH_3$ | H | F | H | H |
| 258 | H | $—CH(CH_3)_2$ | $—CH_3$ | H | F | H | H |
| 259 | H | $—(CH_2)_3CH_3$ | $—CH_3$ | H | F | H | H |
| 260 | H | $—CH_2—HC{=}CH_2$ | $—CH_3$ | H | F | H | H |
| 261 | H | $—CH_3$ | $—CH_3$ | H | H | F | H |
| 262 | H | $—CH_2CH_3$ | $—CH_3$ | H | H | F | H |
| 263 | H | $—(CH_2)_2CH_3$ | $—CH_3$ | H | H | F | H |
| 264 | H | $—CH(CH_3)_2$ | $—CH_3$ | H | H | F | H |
| 265 | H | $—(CH_2)_3CH_3$ | $—CH_3$ | H | H | F | H |
| 266 | H | $—CH_2—HC{=}CH_2$ | $—CH_3$ | H | H | F | H |
| 267 | H | $—CH_3$ | $—CH_3$ | $—OC(O)CH_3$ | H | H | H |
| 268 | H | $—CH_2CH_3$ | $—CH_3$ | $—OC(O)CH_3$ | H | H | H |
| 269 | H | $—(CH_2)_2CH_3$ | $—CH_3$ | $—OC(O)CH_3$ | H | H | H |
| 270 | H | $—CH(CH_3)_2$ | $—CH_3$ | $—OC(O)CH_3$ | H | H | H |
| 271 | H | $—(CH_2)_3CH_3$ | $—CH_3$ | $—OC(O)CH_3$ | H | H | H |
| 272 | H | $—CH_2—HC{=}CH_2$ | $—CH_3$ | $—OC(O)CH_3$ | H | H | H |
| 273 | H | $—CH_3$ | $—CH_3$ | $—OC(O)CH_3$ | F | H | H |
| 274 | H | $—CH_2CH_3$ | $—CH_3$ | $—OC(O)CH_3$ | F | H | H |
| 275 | H | $—(CH_2)_2CH_3$ | $—CH_3$ | $—OC(O)CH_3$ | F | H | H |
| 276 | H | $—CH(CH_3)_2$ | $—CH_3$ | $—OC(O)CH_3$ | F | H | H |
| 277 | H | $—(CH_2)_3CH_3$ | $—CH_3$ | $—OC(O)CH_3$ | F | H | H |
| 278 | H | $—CH_2—HC{=}CH_2$ | $—CH_3$ | $—OC(O)CH_3$ | F | H | H |
| 279 | H | $—CH_3$ | $—CH_3$ | $—OC(O)CH_3$ | H | F | H |
| 280 | H | $—CH_2CH_3$ | $—CH_3$ | $—OC(O)CH_3$ | H | F | H |
| 281 | H | $—(CH_2)_2CH_3$ | $—CH_3$ | $—OC(O)CH_3$ | H | F | H |
| 282 | H | $—CH(CH_3)_2$ | $—CH_3$ | $—OC(O)CH_3$ | H | F | H |
| 283 | H | $—(CH_2)_3CH_3$ | $—CH_3$ | $—OC(O)CH_3$ | H | F | H |
| 284 | H | $—CH_2—HC{=}CH_2$ | $—CH_3$ | $—OC(O)CH_3$ | H | F | H |
| 285 | H | $—CH_3$ | $—CH_3$ | H | F | F | H |
| 286 | H | $—CH_2CH_3$ | $—CH_3$ | H | F | F | H |
| 287 | H | $—(CH_2)_2CH_3$ | $—CH_3$ | H | F | F | H |
| 288 | H | $—CH(CH_3)_2$ | $—CH_3$ | H | F | F | H |
| 289 | H | $—(CH_2)_3CH_3$ | $—CH_3$ | H | F | F | H |
| 290 | H | $—CH_2—HC{=}CH_2$ | $—CH_3$ | H | F | F | H |
| 291 | H | $—CH_3$ | $—CH_3$ | H | H | H | H |
| 292 | H | $—CH_2CH_3$ | $—CH_3$ | H | H | H | H |
| 293 | H | $—(CH_2)_2CH_3$ | $—CH_3$ | H | H | H | H |
| 294 | H | $—CH(CH_3)_2$ | $—CH_3$ | H | H | H | H |
| 295 | H | $—(CH_2)_3CH_3$ | $—CH_3$ | H | H | H | H |
| 296 | H | $—CH_2—HC{=}CH_2$ | $—CH_3$ | H | H | H | H |
| 297 | H | $—CH_3$ | $—CH_3$ | H | $—OCH_3$ | H | H |
| 298 | H | $—CH_2CH_3$ | $—CH_3$ | H | $—OCH_3$ | H | H |
| 299 | H | $—(CH_2)_2CH_3$ | $—CH_3$ | H | $—OCH_3$ | H | H |
| 300 | H | $—CH(CH_3)_2$ | $—CH_3$ | H | $—OCH_3$ | H | H |
| 301 | H | $—(CH_2)_3CH_3$ | $—CH_3$ | H | $—OCH_3$ | H | H |
| 302 | H | $—CH_2—HC{=}CH_2$ | $—CH_3$ | H | $—OCH_3$ | H | H |
| 303 | H | $—CH_3$ | $—CH_3$ | H | H | F | H |
| 304 | H | $—CH_2CH_3$ | $—CH_3$ | H | H | F | H |
| 305 | H | $—(CH_2)_2CH_3$ | $—CH_3$ | H | H | F | H |
| 306 | H | $—CH(CH_3)_2$ | $—CH_3$ | H | H | F | H |
| 307 | H | $—(CH_2)_3CH_3$ | $—CH_3$ | H | H | F | H |
| 308 | H | $—CH_2—HC{=}CH_2$ | $—CH_3$ | H | H | F | H |
| 309 | H | cyclopropyl | $—CH_3$ | H | H | H | H |
| 310 | H | cyclopropyl | $—CH_3$ | H | H | H | H |
| 311 | H | cyclopropyl | $—CH_3$ | —OH | H | H | H |
| 312 | H | cyclopropyl | $—CH_3$ | $—OC(O)CH_3$ | H | H | H |

TABLE 2-continued

| Ref. | X | Y | $R_2$ | $R_4$ | $R_5$ | $R_6$ | $R_7$ |
|---|---|---|---|---|---|---|---|
| 313 | H | cyclopropyl | —$CH_3$ | H | —$OCH_3$ | H | H |
| 314 | H | cyclopropyl | —$CH_3$ | H | H | H | H |
| 315 | H | cyclopropyl | —$CH_3$ | H | H | H | H |
| 316 | H | cyclopropyl | —$CH_3$ | —OH | F | H | H |
| 317 | H | cyclopropyl | —$CH_3$ | —OH | H | H | H |
| 318 | H | cyclopropyl | —$CH_3$ | —$OC(O)CH_3$ | H | H | H |
| 319 | H | cyclopropyl | —$CH_3$ | H | F | H | H |
| 320 | H | cyclopropyl | —$CH_3$ | H | H | F | H |
| 321 | H | —$CD_3$ | —$CH_3$ | H | H | H | H |
| 322 | H | —$CD_3$ | —$CH_3$ | —OH | H | H | H |
| 323 | H | —$CD_3$ | —$CH_3$ | —$OC(O)CH_3$ | H | H | H |
| 324 | H | —$CD_3$ | —$CH_3$ | H | —$OCH_3$ | H | H |
| 325 | H | —$CD_3$ | —$CH_3$ | H | F | H | H |
| 326 | H | —$CD_3$ | —$CH_3$ | —OH | F | H | H |
| 327 | H | —$CD_3$ | —$CH_3$ | —$OC(O)CH_3$ | F | F | H |
| 328 | H | —$CD_3$ | —$CH_3$ | H | F | F | H |
| 329 | H | —$CD_2CD_3$ | H | H | F | H | H |
| 330 | H | —$CD_2CD_3$ | H | —OH | H | H | H |
| 331 | H | —$CD_2CD_3$ | H | —$OC(O)CH_3$ | H | H | H |
| 332 | H | —$CD_2CD_3$ | H | H | F | F | H |
| 333 | H | —$CD_2CD_3$ | H | H | H | F | H |
| 334 | H | —$CD_2CD_3$ | H | —OH | F | H | H |
| 335 | H | —$CD_2CD_3$ | H | —$OC(O)CH_3$ | F | H | H |
| 336 | H | —$CD_2CD_3$ | H | H | —$OCH_3$ | F | H |

Compositions and Methods

As used herein, the term “5-HT1A” refers to a 5-HT1A receptor. As used herein, the term “5-HT2A” refers to a 5-HT2A receptor. As used herein, “5-HT2C” refers to a 5-HT2C receptor.

As used herein, the term “effective amount” in connection with a compound disclosed herein means an amount capable of treating or preventing a disorder, disease or condition, or symptoms thereof, disclosed herein.

As used herein, the term “hallucination” (and related terms such as “hallucinogenic” and “hallucinogen”) refers to a perception in the absence of external stimulus that has qualities of real perception. In some embodiments, hallucinations may be vivid, substantial, and are perceived to be located in external objective space. As used herein, hallucinations may occur in any sensory modality including, but not limited to visual, auditory, olfactory, gustatory, tactile, proprioceptive, equilibrioceptive, nociceptive, thermoceptive and chronoceptive. In some embodiments, the hallucinations are selected from visual hallucinations, auditory hallucinations, olfactory hallucinations, gustatory hallucinations, tactile hallucinations, proprioceptive hallucinations, equilibrioceptive hallucinations, nociceptive hallucinations, thermoceptive hallucinations, chronoceptive hallucinations and any combination thereof. In some embodiments, hallucinations are visual hallucinations.

As used herein, the terms “prevent” or “preventing” refers to means a method of delaying and/or precluding the onset, recurrence or spread, in whole or in part, of a disorder, disease or condition; barring a subject from acquiring a disorder, disease, or condition; or reducing a subject’s risk of acquiring a disorder, disease, or condition.

As used herein, the term “treat” or “treating” refers to an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

For example, in certain embodiments, some seizures disorders are the result of genetic dysfunction, wherein therapeutic modalities for such seizures are not treating the underlying cause. Instead, in certain embodiments, “treating” such diseases or disorders may instead be affected by reducing or eliminating the symptoms of such seizures (e.g., staring spells) or the behavior associated with such.

In further embodiments of the present disclosure, described are novel compounds and compositions, as well as methods of administering the same. In some embodiments, a compound provided herein is for use in the methods provided herein. In some embodiments, the disclosure provides the use of a compound provided herein in the preparation of a medicament for treating one or more of the diseases or disorders provided herein.

In certain embodiments, the method comprises administering a serotonin 5-HT1A agonist and a serotonin 5-HT2A agonist. Without being bound to any particular theory, in certain embodiments it has been surprisingly discovered that administering a serotonin 5-HT1A agonist and a serotonin 5-HT2A agonist can be effective in preventing or treating one or more of the conditions described herein. In certain embodiments, it has also been surprisingly discovered that administering a serotonin 5-HT1A agonist and a hallucinogenic 5-HT2A agonist can effectively treat patients without the patients experiencing the hallucinogenic effects of the 5-HT2A agonist. Without intending to be bound by any particular theory, it is believed that the patient can experience a therapeutic effect without experiencing a hallucinogenic manifestation that typically results from the administration of a 5-HT2A agonist because the 5-HT1A agonist can “turn off” the hallucinogenic effects of the of the 5-HT2A agonist without otherwise significantly altering its agonism at a 5-HT2A receptor. In some embodiments, the 5-HT1A agonist is a partial agonist. In some embodiments, the 5-HT1A agonist is a full agonist. In some embodiments, the 5-HT2A agonist is a partial agonist. In some embodiments, the 5-HT2A agonist is a full agonist. In some embodiments, the 5-HT1A and/or 5-HT2A agonists may be selected from compounds of Formula I herein. In some embodiments, the 5-HT1A and the 5-HT2A agonists are the same compound (e.g., a compound of Formula I).

As defined herein, a “full agonist” shall mean an agonist having an Emax % of at least 90% for the relevant serotonin receptor agonist assay (e.g., BRET2, calcium mobilization, beta-arrestin) when compared to an industry-accepted control compound for that particular receptor assay (e.g., serotonin (5-OH-tryptamine)). In some embodiments, a "full agonist" will exhibit an Emax % of at least 90, at least 91, at least 92, at least 93, at least 94, at least 95, at least 96, at least 97, at least 98, or at least 99%. Also defined herein, a "partial agonist" shall mean an agonist having an Emax % of less than 90% for the relevant serotonin receptor when compared to an industry-accepted control compound for that particular receptor (e.g., serotonin (5-OH-tryptamine)). In some embodiments, a "partial agonist" will exhibit an Emax % of less than 85, 80, 75, 70, 65, 60, 55, 50, 45, 40, 35, 30, 25, 20, 15, 10, or even less than 5%. In some embodiments, a partial agonist will exhibit an Emax % of from about 0.1 to to about 89.9%, such as about 1 to about 89, about 5 to about 85, about 50 to about 88, about 40 to about 85, about 35 to about 75, about 25 to about 65, or about 20 to about 55%.

In some embodiment, the 5-HT1A agonist as used herein is selected from buspirone (8-[4-(4-pyrimidin-2-ylpiperazin-1-yl)butyl]-8-azaspiro[4.5]decane-7,9-dione), 5-OH-buspirone, 6-OH-buspirone, tandospirone ((1R,2R,6S,7S)-4-{4-[4-(pyrimidin-2-yl)piperazin-1-yl]butyl}-4-azatricyclo[5.2.1.02,6]decane-3,5-dione), gepirone (4,4-dimethyl-1-[4-(4-pyrimidin-2-ylpiperazin-1-yl)butyl]piperid-ine-2,6-dione), alnespirone ((+)-4-dihydro-2H-chromen-3-yl]-propylamino]butyl]-8-azaspiro[4.5]decane-7,9-dione), binospirone (8-[2-(2,3-dihydro-1,4-benzodioxin-2-ylmethylamino)ethyl]-8-azaspiro[4.5]-decane-7,9-dione), ipsapirone (9,9-dioxo-8-[4-(4-pyrimidin-2-ylpiperazin-1-yl) butyl]-9.lamda.6-thia-8-a-zabicyclo[4.3.0]nona-1,3,5-trien-7-one), perospirone (3aR, 7aS)-2-{4-[4-(1,2-benzisothiazol-3-yl)piperazin-1-yl]butyl}hexahydro-1H-isoindole-1,3 (2H)-dione, befiradol (F-13,640) (3-chloro-4-fluorophenyl-[4-fluoro-4-([(5-methylpyridin-2-yl)methylamino]methyl) piperidin-1-yl]methanone, repinotan ((R)-(−)-2-[4-[(chroman-2-ylmethyl)-amino]-butyl]-1,1-dioxo-benzo[d] isothiazolone), piclozotan (3-chloro-4-[4-[4-(2-pyridinyl)-1,2,3,6-tetrahydropyridin-1-yl]butyl]-1,4--benzoxazepin-5 (4H)-one), osemozotan (5-(3-[((2S)-1,4-benzodioxan-2-ylmethyl)amino]propoxy)-1,3-benzodioxole), flesinoxan (4-fluoro-N-[2-[4-[(3S)-3-(hydroxymethyl)-2,3-dihydro-1,4-benzodioxin-8-yl]piperazin-1-yl]ethyl]benzamide), flibanserin (1-(2-{4-[3-(trifluoromethyl)phenyl]piperazin-1-yl}ethyl)-1,3-dihydro-2H-benzimidazol-2-one), 8-OH-DPAT (7-(Dipropylamino)-5,6,7,8-tetrahydronaphthalen-1-ol), and sarizotan (EMD-128,130) (1-[(2R)-3,4-dihydro-2H-chromen-2-yl]-N-([5-(4-fluorophenyl)pyridin-3-yl]methyl) methanamine), a compound of Formula I, or a prodrug, salt, or derivative thereof.

In some embodiments, the serotonin 5-HT1A agonist and 5-HT2A agonist are administered at the same time. In some embodiments, the serotonin 5-HT1A agonist and 5-HT2A agonist are administered at different times. In some embodiments, the serotonin 5-HT1A agonist and 5-HT2A agonist are administered sequentially. In some embodiments, the serotonin 5-HT1A agonist is administered first, and 5-HT2A agonist is administered second. In some embodiments, the serotonin 5-HT2A agonist is administered about 30 minutes to about 12 hrs after administration of 5-HT1A agonist, such as about 1 hr to about 6 hrs afterwards. In some embodiments, the serotonin 5-HT1A agonist and 5-HT2A agonist are administered at the same time in the same composition. In some embodiments, 5-HT1A agonist is selected from buspirone, 5-OH-buspirone, 6-OH-buspirone, and 8-OH-DPAT. In some embodiments, the 5-HT1A agonist is buspirone. In some embodiments, the 5-HT1A agonist is selected from compounds of Formula I, such as for example compounds of Formula I(e). In some embodiments, the 5-HT2A agonist is hallucinogenic. In some embodiments, the 5-HT2A agonist is non-hallucinogenic. In some embodiments, the 5-HT2A agonist is selected from compounds of Formula I, such as for example compounds of Formula I(e).

In some embodiments, the 5-HT2A agonist and the 5-HT1A agonist may comprise the same compound. In some embodiments, the compounds of Formula I described herein (e.g., compounds of Formula I(e)) can act as both 5-HT1A and 5-HT2A receptor agonists. In some embodiments, the compounds described herein are full agonists for both 5-HT1A and 5-HT2A.

In some embodiments, the 5-HT1A agonist and 5-HT2A agonist are full agonists for a 5-HT1A receptor and a 5-HT2A receptor, respectively. In some embodiments, the 5-HT1A agonist exhibits a higher level of molar potency (i.e., lower ECSO) for activating a 5-HT1A receptor than the 5-HT2A agonist exhibits for activating the 5-HT2A receptor. Without being bound to any particular scientific theory, in certain embodiments it has been surprisingly discovered that compounds that are agonists for 5-HT1A and 5-HT2A—but which exhibit a higher molar potency for 5-HT1A—may be useful to patients needing/desiring non-hallucinogenic 5-HT2A modulation. In other embodiments, the 5-HT1A agonist is a partial agonist (e.g., buspirone) and 5-HT2A agonist is a full agonist for a 5-HT1A receptor and a 5-HT2A receptors, respectively. In other embodiments, the 5-HT1A agonist is a partial agonist (e.g., buspirone) and 5-HT2A agonist is a partial agonist for a 5-HT1A receptor and a 5-HT2A receptors, respectively.

In certain embodiments are described methods for treating, preventing, ameliorating, or curing a disease or disorder via a non-hallucinogenic therapeutic treatment regimen that includes modulation of a 5-HT1A receptor. In certain embodiments, the method comprises identifying a subject in need of treatment for a disease or condition associated with modulation of a 5-HT1A receptor; selecting a compound of Formula I (e.g., Formula I(e)); and administering the compound to the subject in need of treatment, wherein the compound modulates activity at both a 5-HT1A and 5-HT2A receptor. In certain embodiments, the compound of Formula I is a full agonist of a 5-HT1A receptor. In certain embodiments, the compound of Formula I is a full agonist for both 5-HT1A and 5-HT2A receptors. In certain embodiments, the compound of Formula I is a partial agonist for a 5-HT1A receptor and a full agonist for a 5-HT2A receptor. In certain embodiments, the compound of Formula I is a partial agonist for a 5-HT1A receptor and a partial agonist for a 5-HT2A receptor. In certain embodiments, the compound of Formula I, exhibits a higher molar potency (lower $EC_{50}$) for a 5-HT1A receptor when compared to a 5-HT2A receptor.

In certain embodiments, the 5-HT1A agonist has an $EC_{50}$ for activating a 5-HT1A receptor of less than about 100 nM, such as less than about 75 nm, less than about 50 nm, less than about 25 nm, less than about 15 nm, less than about 10 nm, or less than about 5 nm. In certain embodiments, the 5-HT2A agonist has an $EC_{50}$ for activating a 5-HT2A receptor of less than about 100 nM, such as less than about 75 nm, less than about 50 nm, less than about 25 nm, less than about 15 nm, less than about 10 nm, or less than about 5 nm. In certain embodiments, the 5-HT1A agonist exhibits an $EC_{50}$ for activating a 5-HT1A receptor of about 0.01 nM to about 100 nM, such as about 0.05 to about 50 nm, about 0.1 to about 25 nM, or about 0.5 to about 10 nM. In certain embodiments, the 5-HT2A agonist has an $EC_{50}$ for activating a 5-HT2A receptor of about 0.01 nM to about 100 nM, such as about 0.05 to about 50 nm, about 0.1 to about 25 nM, or about 0.5 to about 10 nM. In certain embodiments, the 5-HT2A agonist has an $EC_{50}$ for activating a 5-HT2A receptor of about 5 to about 75 nM, such as about 10 to about 60 nm, about 15 to about 50 nM, or about 20 to about 40 nM. In some embodiments, the 5-HT1A agonist/5-HT2A agonist exhibits a 5-HT1A receptor: 5-HT2A receptor $EC_{50}$ ratio range of about 1:2 to about 1:100, such as about 1:5 to about 1:50 or about 1:10 to about 1:40. In some embodiments, one or more of the compounds of Formula I independently exhibit a 5-HT1A receptor: 5-HT2A receptor $EC_{50}$ ratio range of about 1:2 to about 1:100, such as about 1:5 to about 1:50 or about 1:10 to about 1:40. Relevant testing parameters to determine full vs. partial agonism (Emax %) and molar potency ($EC_{50}$) include those known to persons of skill in the art, such as the 5-HT Functional Assays described further below.

In some embodiments, also described are novel compounds and compositions, as well as methods of administering the same. In certain embodiments, the method comprises administering a serotonin 5-HT2A agonist and a serotonin 5-HT2B antagonist. Without being bound to any particular theory, in certain embodiments it has been surprisingly discovered that administering a serotonin 5-HT2A agonist and a serotonin 5-HT2B antagonist can be effective in preventing or treating one or more of the conditions described herein. In some embodiments, it has been surprisingly discovered that administering a serotonin 5-HT2A agonist and a serotonin 5-HT2B antagonist can effectively treat patients while also reducing serotonin 5-HT2B-induced cardiotoxicity (e.g., heart valve fibrosis and hypertrophy). In certain embodiments, it has also been surprisingly discovered that administering a serotonin 5-HT2B antagonist and a 5-HT2A agonist can be safely and effectively used treat patients as described herein without the patients experiencing the hallucinogenic effects that can be associated with hallucinogenic 5-HT2A agonists. In some embodiments, the 5-HT2A agonist is a full agonist.

In some embodiments, the 5-HT2A agonist is a partial agonist. In some embodiments, the 5-HT2B antagonist is a full antagonist. In some embodiments, the 5-HT2B antagonist is a partial antagonist.

Exemplary serotonin 5-HT2B receptor antagonists include, but are not limited to, agomelatine, amisulpride, ariprazole, carprazine, clozapine, cyproheptadine, mCCP, sarpogrelate, lisuride, tegasurod, metadoxine, and promethazine. In certain embodiments, the 5-HT2B antagonist is not an antagonist at any of the other serotonin 5-HT type receptor subtypes, such as 5-HT1A and 5-HT2A. In certain embodiments, the 5-HT2B receptor antagonist will also be a full or partial agonist at a 5-HT1A and/or 5-HT2A receptor.

In some embodiments, the serotonin 5-HT2A agonist and 5-HT2B antagonist are administered at the same time. In some embodiments, the serotonin 5-HT2A agonist and 5-HT2B antagonist are administered at different times. In some embodiments, the serotonin 5-HT2A agonist and 5-HT2B antagonist are administered at the same time in the same composition. In some embodiments, the serotonin 5-HT1A agonist and 5-HT2B antagonist are administered sequentially. In some embodiments, the serotonin 5-HT2B antagonist is administered first, and 5-HT2A agonist is administered second. In some embodiments, the serotonin 5-HT2A agonist is administered about 30 minutes to about 12 hrs after administration of 5-HT2B antagonist, such as about 1 hr to about 6 hrs afterwards. In some embodiments, the 5-HT2A agonist is hallucinogenic. In some embodiments, the 5-HT2A agonist is non-hallucinogenic. In some embodiments, the 5-HT2A agonist is selected from compounds of Formula I, such as for example compounds of Formulae II(a) or II(b).

In some embodiments, also described are novel compounds and compositions, as well as methods of administering the same. In certain embodiments, the method comprises administering a serotonin 5-HT2A agonist and a serotonin 5-HT2C agonist. Without being bound to any particular theory, in certain embodiments it has been surprisingly discovered that administering a serotonin 5-HT2A agonist and a serotonin 5-HT2C agonist can be effective in preventing or treating one or more of the conditions described herein. In some embodiments, it has been surprisingly discovered that administering a serotonin 5-HT2A agonist and a serotonin 5-HT2C agonist can effectively treat patients while also reducing or eliminating the hallucinogenic "trip" typically associated with 5-HT2A agonists. In some embodiments, the 5-HT2A agonist is a full agonist. In some embodiments, the 5-HT2A agonist is a partial agonist.

In some embodiments, the 5-HT2C agonist is a full agonist. In some embodiments, the 5-HT2C agonist is a partial agonist.

Exemplary serotonin 5-HT2C receptor agonists include, but are not limited to, lorcaserin, vabicaserin, aripiprazole, YM-348, PRX-00933, and meta-chlorophenylpiperazine.

In certain embodiments, the 5-HT2C agonist is not an agonist at any of the other serotonin 5-HT type receptor subtypes, such as 5-HT1A and 5-HT2B. In certain embodiments, the 5-HT2C receptor agonist will be inactive or only a partial agonist at a 5-HT1A and/or 5-HT2B receptor.

In some embodiments, the serotonin 5-HT2A agonist and 5-HT2C agonist are administered at the same time. In some embodiments, the serotonin 5-HT2A agonist and 5-HT2C agonist are administered at different times. In some embodiments, the serotonin 5-HT2A agonist and 5-HT2C agonist are administered at the same time in the same composition. In some embodiments, the serotonin 5-HT2A agonist and 5-HT2C agonist are administered sequentially. In some embodiments, the serotonin 5-HT2C agonist is administered first, and 5-HT2A agonist is administered second. In some embodiments, the serotonin 5-HT2A agonist is administered about 30 minutes to about 12 hrs after administration of 5-HT2C agonist, such as about 1 hr to about 6 hrs afterwards. In some embodiments, the 5-HT2A agonist is hallucinogenic. In some embodiments, the 5-HT2A agonist is non-hallucinogenic. In some embodiments, the 5-HT2A agonist is selected from compounds of Formula I, such as for example compounds of Formulae II(a) or II(b).

In some embodiments, the 5-HT2A agonist and the 5-HT2C agonist may comprise the same compound. In some embodiments, the compounds of Formula I described herein (e.g., compounds of Formula I(e)) can act as both 5-HT2C and 5-HT2A receptor agonists. In some embodiments, the compounds described herein are full agonists for both 5-HT2A and 5-HT2C.

In some embodiments, the compounds described herein act as partial agonists at 5-HT2A and full agonists at 5-HT2C. In some embodiments, the compounds described herein are partial agonists for both 5-HT2A and 5-HT2C. In some embodiments, the compounds described herein act as agonists at 5-HT2A and 5-HT2C but are only partial agonists (or inactive) at a 5-HT2B receptor.

In some embodiments, the compounds of Formula I are selective agonists of 5-HT2C, wherein said compounds are more potent and/or efficacious (Emax) when compared to the other serotonin receptor subtypes (e.g., 5-HT2A and 5-HT2B). Without being bound to any particular theory, it has been surprisingly discovered that compounds of the present disclosure are orthosteric ligands of 5-HT2C that exhibit a $G_q$-mediated signaling bias and no/minimal β-arrestin recruitment or β-arrestin-mediated intracellular signaling. Applicant theorizes that this $G_q$-biased signaling mechanism results in reduced signal attenuation caused from β-arrestin recruitment, resulting in a greater therapeutic effect and fewer side effects for certain therapeutic indications (e.g., Alzheimer's psychosis, schizophrenia, addition, obesity, etc.).

In certain embodiments for compounds of Formula I, Applicant has discovered that the size and nature of alkyl groups for X and/or Y can dramatically affect the metabolism of such compounds. For example, it has been theorized that compounds such as 5-MeO-Dimethyltryptamine (5-MeO-DMT) and Dimethyltryptamine (DMT) are inactive upon oral administration due to rapid metabolism of the methylamino residues by monoamine oxidase (MAO) enzymes. It has also been theorized that the oral stability of psilocin (4-OH-dimethyltryptamine), on the other hand, is due largely to intramolecular coordination (hydrogen bonding) between the 4-OH group and the dimethylamino residue, which effectively shields/inhibits rapid MAO degradation.

Without being bound to any particular scientific theory, Applicant has surprisingly found that, in some embodiments, substituting the alkyl groups X and/or Y with substituents such as deuterium and fluorine can help inhibit MAO degradation of those groups. In addition, or in the alternative, Applicant has discovered that using non-methyl alkyl groups such as ethyl or n-propyl for X and/or Y can also slow or inhibit rapid MAO metabolism upon oral administration.

This, in turn, permits the preparation of orally available compounds of Formula I that are highly active serotonergic drugs that do not require special formulating procedures (e.g., dosages containing MAO inhibitors), or the presence of hydrogen bond-forming donors in the molecular structure that —in some cases —can negatively impact the properties of the underlying compound (e.g., reduction of 5-HT1A and/or 5-HT2A agonism).

In some embodiments, Applicant has also surprisingly discovered that deuteration of the —$W_1$-$R_2$ residue can help to substantially enhance the half lives of those compounds when compared to proteo (hydrogen) variants. It has been generally shown that the primary metabolites formed in the enzymatic metabolism of most phenalkylamines such as mescaline proceeds via the oxidation of the aminoalkyl residue, as shown below. Notably, the metabolism of mescaline does not proceed through the demethylation of any of the three methoxy residues:

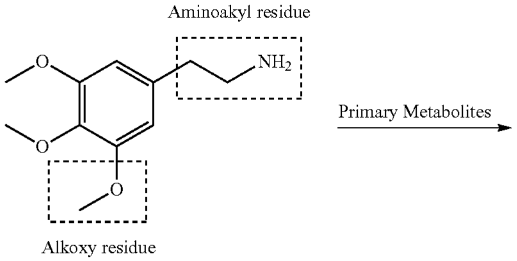

-continued

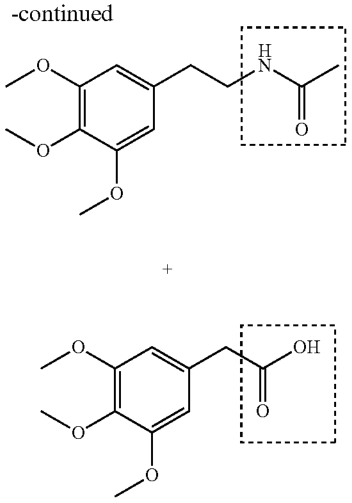

Contrariwise, metabolism (e.g., first-pass metabolism in the liver) for compounds in some of the embodiments described herein proceeds through a previously-unidentified mechanism. Indeed, the primary metabolites of certain compounds described herein takes place on the —$W_1$-$R_1$ residue of those compounds, including the following exemplary study conducted in human and mouse liver microsomes showing no major metabolites resulting from the metabolism of the aminoalkyl residue. Instead, primary metabolites appear to be limited to those resulting from the dealkylation and oxidation/hydrogenation (2 oxygens/2 hydrogens gained as shown via mass spec) of the —$W_1$-$R_2$ residue:

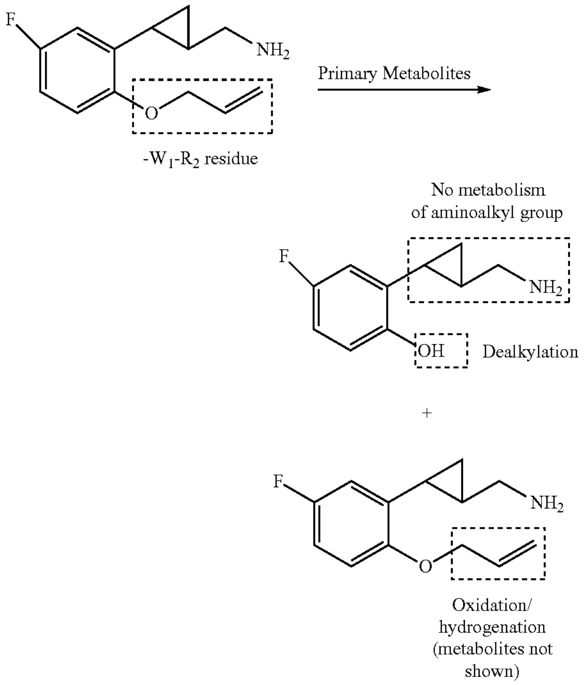

In view of the foregoing, Applicant set out to slow the metabolism of such compounds in an effort to enhance pharmacokineticss (e.g., plasma half life ($T_{1/2}$) and concentration (AUC)) by introducing deuterium atoms to, e.g., the alkoxy and alkylthio groups represented by the —$W_1$-$R_2$ residue of Formula I. Without being bound to any particular scientific theory, it is believed that the heavier deuterium isotope disrupts the enzymatic metabolism of those compounds. In certain embodiments, it is believed that activity of CYP450 enzymes is reduced by the introduction of deuterium at the sites of metabolic breakdown. However, in some embodiments it may not be desirable to "over deuterate" the compound, such as further including deuterated species for other portions of the compound, which can further alter the compounds' pharmacokinetic profiles in an undesirable manner (e.g., reduction in blood-brain barrier penetration; poor solubility in water). Accordingly, in some embodiments, Applicant has discovered that minimal deuteration may be used to achieve the desired pharmacokinetic outcome. Exemplary deuterated compounds have been previously disclosed herein, including those set forth below:

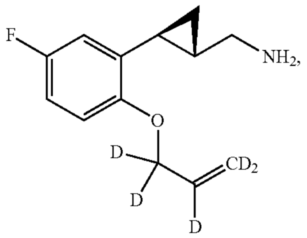

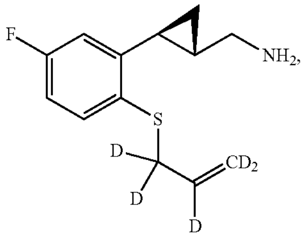

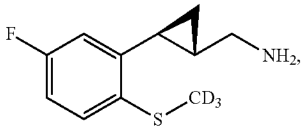

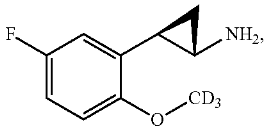

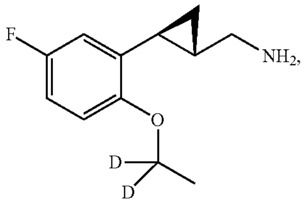

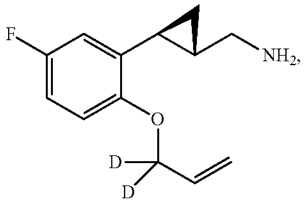

-continued

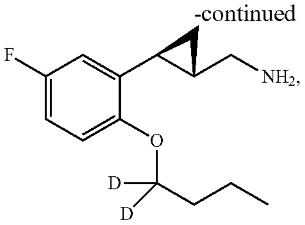

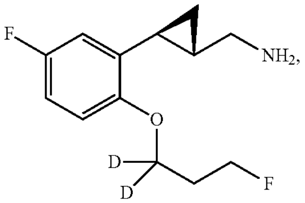

and

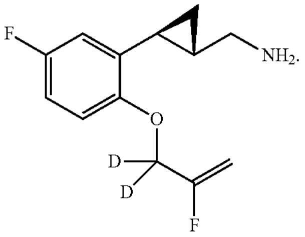

In other embodiments, the nature of the —$W_1$-$R_2$ residue of Formula I may result in "metabolic switching" on the molecular scaffold, which may result in primary metabolism at another site on the molecule. For example, certain compounds having the structure —$W_1$—$CF_3$ may hinder dealkylation of that residue, resulting in primary metabolism at the methylene group between the cyclopropyl residue and the —N(X)(Y) residue. Thus, in such embodiments, the metabolism of those analogs may be slowed by making at least one of $R_3$ and $R_{3'}$ a deuterium. An exemplary compound includes the analog demonstrated below:

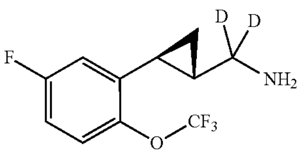 [SMILES: [2H]C([2H])(N)[C@H]1C[C@@H]1c1cc(F)ccc1OC(F)(F)F]

In one embodiment, the compounds of Formula I, the methods, and the pharmaceutical compositions described herein are used to modulate the activity of a neurotransmitter receptor by administering a therapeutically effective amount of a compound of Formula I. Methods include the administration of a therapeutically effective amount of a compound of Formula I to prevent or treat a psychological disorder such as those discussed herein. Compounds of Formula I may be administered neat or as a pharmaceutical composition comprising a compound of Formula I as discussed herein.

In some embodiments, the compounds of Formula I may be used to prevent and/or treat a psychological disorder. The disclosure provides a method for preventing and/or treating a psychological disorder by administering to a subject in need thereof a therapeutically effective amount of a compound of Formula I, including the exemplary embodiments discussed above. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar II disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome; post-traumatic stress disorder (PTSD); premenstrual dysphoric disorder (PMDD); and premenstrual syndrome (PMS).

In some embodiments, the compounds of Formula I may be used to prevent and/or treat a brain disorder. The disclosure provides a method for preventing and/or treating a brain disorder by administering to a subject in need thereof a therapeutically effective amount of a compound of Formula I, including the exemplary embodiments discussed above. The brain disorder may be chosen from Huntington's disease, Alzheimer's disease, dementia, and Parkinson's disease.

In some embodiments, the compounds of Formula I may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of a compound of Formula I, including the exemplary embodiments discussed above.

In some embodiments, the compounds of Formula I may be used to prevent and/or treat inflammation and/or pain, such as, for example, inflammation and/or pain associated with inflammatory skeletal or muscular diseases or conditions. Accordingly, the disclosure relates to a method for preventing and/or treating inflammation and/or pain by administering to a subject in need thereof a therapeutically effective amount of a compound of Formula I, including the exemplary embodiments discussed herein. Generally speaking, treatable "pain" includes nociceptive, neuropathic, and mix-type. A method of the disclosure may reduce or alleviate the symptoms associated with inflammation, including, but not limited to, treating localized manifestation of inflammation characterized by acute or chronic swelling, pain, redness, increased temperature, or loss of function in some cases. A method of the disclosure may reduce or alleviate the symptoms of pain regardless of the cause of the pain, including, but not limited to, reducing pain of varying severity, i.e. mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include, but are not limited to, musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

In other embodiments, the methods and compositions disclosed herein comprise regulating the activity of a neurotransmitter receptor with a formulation comprising a compound of Formula I. In one embodiment, the methods and compositions disclosed herein comprise administering a first dosage formulation comprising at least one compound of Formula I and a second active compound. In one embodiment, the methods disclosed herein comprise administering a first dosage formulation comprising a compound of Formula I and a neurotransmitter activity modulator (e.g., a second serotonergic drug). In one embodiment, the methods disclosed herein comprise administering a first dosage formulation comprising at least one compound of Formula I and a second dosage form comprising at least one cannabinoid, at least one terpene, or a second serotonergic drug.

The present disclosure relates to compositions comprising, consisting essentially of, or consisting of an effective amount of a compound of Formula I and an excipient. The terms "composition" and "formulation" are used interchangeably herein. Other embodiments relate to pharmaceutical compositions comprising, consisting essentially of, or consisting of a therapeutically effective amount of a compound of Formula I, including those discussed above, and a pharmaceutically acceptable excipient (also known as a pharmaceutically acceptable carrier). As discussed above, a compound of Formula I may be therapeutically useful to prevent and/or treat, for example, psychological disorders, brain disorders, pain and inflammation as well as other disorders such as those discussed above.

Exemplary pharmaceutically-acceptable carriers include, but are not limited to, any pharmaceutically-acceptable material, composition or vehicle, such as a liquid or solid filler, diluent, excipient, solvent or encapsulating material, which may be involved in carrying or transporting the subject chemical from one organ, or portion of the body, to another organ, or portion of the body, e.g., oral dosage form enabling transport of compound to the stomach and/or intestinal tract. In certain embodiments, such oral dosage forms may comprise a tablet or capsule (e.g., gel or solid capsule). Each carrier is preferably "acceptable" in the sense of being compatible with the other ingredients of the formulation and not injurious to the subject.

Some examples of materials which can serve as pharmaceutically-acceptable carriers include, but are not imted to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In some embodiments, wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

In some embodiments, the composition may further comprise one or more pharmaceutically-acceptable antioxidants. In certain embodiments, such antioxidants include: (1) water soluble antioxidants, such as ascorbic acid, cysteine hydrochloride, sodium bisulfate, sodium rnetabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In some embodiments, the compounds described herein may be administered orally to a subject in a liquid dosage form. In some embodiments, such a liquid oral formulation may be desirable, particularly for certain seizure disorders (e.g., DEEs) in which administering solid dosage forms (e.g., tablets) to subjects may be difficult. In some embodiments, the liquid dosage form may comprise the at least one compound, water, and an excipient (e.g., a sugar, such as sucrose). In some embodiments, the liquid dosage form is administered to the subject 2-3 times per day.

In some embodiments, the compounds described herein may be administered orally to a subject in a solid dosage form. In some embodiments, such a solid oral formulation may comprise an extended release tablet, which may be administered once a day. In some embodiments, the extended release tablet may be used to effectively release the at least one compound to the subject over an extended period, such as 8-36 hrs or 12-24 hrs. In some embodiments, the extended release tablet can deliver at least some of the compound to the subject's small intestine.

In some embodiments, the compositions described herein may comprise at least one compound of Formula I, and a second compound selected from at least one of a second serotonergic drug, a cannabinoid, a terpene, or an MAO inhibitor In one embodiment, the term "purified" refers to a compound or composition that has been crystallized. In one embodiment, the term "purified" refers to a compound or composition that has been chromatographed, for example by gas chromatography, liquid chromatography (e.g., LC, HPLC, etc.), etc. In one embodiment, the term "purified" refers to a compound or composition that has been distilled. In one embodiment, the term "purified" refers to a compound or composition that has been sublimed. In one embodiment, the term "purified" refers to a compound or composition that has been subject to two or more steps chosen from crystallization, chromatography, distillation, and sublimation.

In one embodiment, the term "purified" refers to a compound that has a purity ranging from about 80% to about 100%, meaning that the compound makes up about 80% to about 100% of the total mass of the composition. In one embodiment, the term "purified" refers to a compound that is has a purity ranging from about 90% to about 100%, meaning that the compound makes up about 90% to about 100% of the total mass of the composition. In one embodiment, the term "purified" refers to a compound that has a purity ranging from about 95% to about 100%, meaning that the compound makes up about 95% to about 100% of the total mass of the composition. In one embodiment, the term "purified" refers to a compound that has a purity ranging from about 99% to about 100% pure, meaning that the compound makes up about 99% to about 100% of the total mass of the composition. In one embodiment, the term "purified" refers to a compound that has a purity ranging from about 99.9% to about 100%, meaning that the compound makes up about 99.9% to about 100% of the total mass of the composition.

As used herein, the term "particular ratio" refers to the amount of a compound in relation to the amount of another compound or compounds. In one embodiment, there is about 1:1 ratio of a 4-acetoxy-3-[2-(dimethylamino)ethyl]-benzo[b]thiophene) to 4-hydroxy-N,N-dimethyltryptamine. In one embodiment, a particular ratio of compounds is measured by the same unit, e.g., grams, kilograms, pounds, ounces, etc. In one embodiment, a particular ratio of compounds is measured in moles, i.e., molar proportions or molar ratios.

As used herein, the term "particular amount" refers to the quantity of a compound or compounds. In one embodiment, a particular amount is the combined quantity of two compounds within a sample. In one embodiment, a particular amount is measured by dry weight. In one embodiment, the particular amount has 1, 2, 3, or 4 significant figures.

Disclosed herein are compositions comprising a compound of Formula I and a second compound. In one embodiment, the compositions disclosed herein comprise a molar ratio ranging from about 10:1 to about 1:10 of the compound of Formula I (e.g., a 5-HT2A receptor agonist) to the second compound (e.g., a 5-HT1A receptor agonist). In one embodiment, the compositions disclosed herein comprise a molar ratio ranging from about 100:1 to about 1:100 of the compound of Formula I to the second compound. In one embodiment, the compositions disclosed herein comprise a molar ratio ranging from about 1,000:1 to about 1:1,000 of the compound of Formula I to the second compound. In one embodiment, the compositions disclosed herein comprise a molar ratio ranging from about 10,000:1 to about 1:10,000 of the compound of Formula I to the second compound.

Within the context of this disclosure, unless otherwise specified, the serotonergic compounds (e.g., tryptamine compounds) described herein may be present in their protonated or deprotonated (salt or free base) forms or mixtures thereof depending on the context, for example, the pH of the solution or composition. However, in certain embodiments, the serotonergic compounds described herein are lipophilic, meaning they will tend to combine with lipids and fats and can readily pass though biological membranes in the body of an animal or human (e.g., blood brain barrier). In certain embodiments, the serotonergic compound in free base form is lipophilic.

As used herein, the term "salt" refers to a neutralized ionic compound. In one embodiment, a salt is formed from the neutralization of acids and bases. In one embodiment, a salt is electrically neutral.

As used herein, the term "serotonergic drug" refers to a compound that binds to, blocks, or otherwise influences (e.g., via an allosteric or orthosteric binding) activity at a serotonin receptor. In one embodiment, a serotonergic drug binds to a serotonin receptor. In one embodiment, a serotonergic drug indirectly affects a serotonin receptor, e.g., via interactions affecting the reactivity of other molecules at the serotonin receptor. In one embodiment, a serotonergic drug is an agonist, e.g., a compound activating a serotonin receptor. In one embodiment, a serotonergic drug is an antagonist, e.g., a compound binding but not activating a serotonin receptor, e.g., blocking a receptor. In one embodiment, a serotonergic drug is an effector molecule, e.g., a compound binding to an enzyme for allosteric regulation. In one embodiment, a serotonergic drug acts (either directly or indirectly) at more than one type of receptor (e.g., SHT, dopamine, adrenergic, acetylcholine, etc.).

In one embodiment, a serotonergic drug is an antidepressant.

In one embodiment, a serotonergic drug is an anxiolytic.

In one embodiment, a serotonergic drug is a selective serotonin reuptake inhibitor (SSRI).

In one embodiment, a serotonergic drug is a selective serotonin norepinephrine reuptake inhibitor (SNRI).

In some embodiments, the compounds of Formula I are serotonergic drugs. In some embodiments, at least one compound of Formula I is administered with a second serotonergic drug, such as one of the serotonergic drugs identified below.

Some exemplary serotonergic drugs include the following molecules: 4-hydroxy-N-methyltryptamine (aka 3-[2-(methylamino)ethyl]-1H-indol-4-ol), aeruginascin (aka [3-[2-(trimethylazaniumyl)ethyl]-1H-indol-4-yl]hydrogen phosphate), baeocystin (aka [3-[2-(methylamino)ethyl]-1H-indol-4-yl]dihydrogen phosphate), bufotenidine (aka 3-[2-(trimethylazaniumypethyl]-1H-indol-5-olate), bufotenin (aka 3-[2-(dimethylamino)ethyl]-1H-indol-5-ol), ethocybin (aka [3-[2-(diethylamino)ethyl]-1H-indol-4-yl]dihydrogen phosphate), norbaeocystin (aka [3-(2-aminoethyl)-1H-indol-4-yl]dihydrogen phosphate), norpsilocin, psilocin (aka 3-[2-(dimethylamino)ethyl]-1H-indol-4-ol), psilocybin (aka [3-[2-(dimethylamino)ethyl]-1H-indol-4-yl]dihydrogen phosphate), serotonin (aka 3-(2-aminoethyl)-1H-indol-5-ol), 1 P-LSD (aka (6aR,9R)-N,N-diethyl-7-methyl-4-propanoyl-6,6a,8,9-tetrahydroindolo [4,3-fg]quinoline-9-carboxamide), ALD-52 (aka (6aR,9R)-4-acetyl-N,N-diethyl-7-methyl-6,6a,8,9-tetrahydroindolo[4,3-fg]q-uinoline-9-carboxamide), AL-LAD (aka (6aR,9R)-N,N-diethyl-7-prop-2-enyl-6,6a,8,9-tetrahydro-4H-indolo[4,3-fg]q-uinoline-9-carboxamide), BU-LAD (aka (6aR,9R)-7-butyl-N,N-diethyl-6,6a,8,9-tetrahydro-4H-indolo[4,3-fg]quinoli-ne-9-carboxamide), DAL (aka (6aR,9R)-7-methyl-N,N-bis(prop-2-enyl)-6,6a,8,9-tetrahydro-4H-indolo[4,3-fg]quinoline-9-carboxamide), DAM-57 (aka (6aR,9R)-N,N,7-trimethyl-6, 6a,8,9-tetrahydro-4H-indolo[4,3-fg]quinoline-9--carboxamide), EIPLA (aka (6aR,9R)-N-ethyl-7-methyl-N-propan-2-yl-6,6a,8,9-tetrahydro-4H-indolo[4,3--fg] quinoline-9-carboxamide), ETH-LAD (aka (6aR,9R)-N,N, 7-triethyl-6,6a,8,9-tetrahydro-4H-indolo[4,3-fg]quinoline-9-carboxamide), LAE-32 (aka (6aR,9R)-N-ethyl-7-methyl-6,6a,8,9-tetrahydro-4H-indolo[4,3-fg]quinoline-9-carboxamide), LPD-824 (aka [(6aR,9R)-7-methyl-6,6a,8,9-tetrahydro-4H-indolo[4,3-fg]quinoline-9-yl]-p-yrrolidin-1-ylmethanone), LSB (aka (6aR,9R)-N-butan-2-yl-7-methyl-6,6a,8,9-tetrahydro-4H-indolo[4,3-fg]quino-line-9-carboxamide), LSA (aka (6aR,9R)-7-methyl-6,6a,8,9-tetrahydro-4H-indolo[4,3-fg]quinoline-9-carbox-amide), LSD-25 (aka (6aR,9R)-N,N-diethyl-7-methyl-6,6a,8,9-tetrahydro-4H-indolo[4,3-fg]quinol-ine-9-carboxamide), LSD-PiP (aka (7-methyl-6,6a,8,9-tetrahydro-4H-indolo[4,3-fg]quinoline-9-yl)-piperidin-1-ylmethanone), LSM-775 (aka [(6aR,9R)-7-methyl-6,6a,8,9-tetrahydro-4H-indolo[4, 3-fg]quinoline-9-yl]-m-orpholin-4-ylmethanone), LSP (aka (6aR,9R)-7-methyl-N-pentan-3-yl-6,6a,8,9-tetrahydro-4H-indolo[4,3-fg]quin-oline-9-carboxamide), LSZ (aka [(6aR, 9R)-7-methyl-6,6a,8,9-tetrahydro-4H-indolo[4,3-fg]quinoline-9-yl]-[-(2S,4S)-2,4-dimethylazetidin-1-yl]methanone), methergine (aka (6aR,9R)-N-(1-hydroxybutan-2-yl)-7-methyl-6,6a,8,9-tetrahydro-4H-indolo[4-,3-fg]quinoline-9-carboxamide), MiPLA (aka (6aR,9R)-N,7-dimethyl-N-propan-2-yl-6,6a,8,9-tetrahydro-4H-indolo[4,3-fg]-quinoline-9-carboxamide), NDTDI, PARGY-LAD, PRO-LAD (aka (6aR,9R)-N,N-diethyl-7-propyl-6,6a,8,9-tetrahydro-4H-indolo[4,3-fg]quinol-ine-9-carboxamide), 2-Me-DET (aka N,N-diethyl-2-(2-methyl-1H-indol-3-yl)ethanamine), 2-Me-DMT (aka N,N-dimethyl-2-(2-methyl-1H-indol-3-yl) ethanamine), 2,alpha-DMT (aka 1-(2-methyl-1H-indol-3-yl) propan-2-amine), 4-AcO-DALT (aka [3-[2-[bis(prop-2-enyl)amino]ethyl]-1H-indol-4-yl]acetate), 4-AcO-DET (aka [3-[2-(diethylamino)ethyl]-1H-indol-4-yl]acetate), 4-AcO-DIPT (aka 3-[2-(Diisopropylamino)ethyl]-1H-indol-4-yl acetate), 4-AcO-DMT (aka [3-[2-(dimethylamino)ethyl]-1H-indol-4-yl]acetate), 4-AcO-DPT (aka [3-[2-(dipropylamino)ethyl]-1H-indol-4-yl]acetate), 4-AcO-EPT (aka 3-{2-[Ethyl(propyl)amino]ethyl}-1H-indol-4-yl acetate), 4-AcO-MET (aka [3-[2-[ethyl(methyl)amino]ethyl]-1H-indol-4-yl]acetate), 4-AcO-MIPT (aka [3-[2-[methyl(propan-2-yl)amino]ethyl]-1H-indol-4-yl]acetate), 4-AcO-MPT, 4-HO-DBT (aka 3-[2-(dibutylamino)ethyl]-1H-indol-4-ol), 4-HO-DET (aka 3-[2-(diethylamino)ethyl]-1H-indol-4-ol), 4-HO-DIPT (aka 3-[2-[di(propan-2-yl)amino]ethyl]-1H-indol-4-ol), 4-HO-DPT (aka 3-[2-(dipropylamino)ethyl]-1H-indol-4-ol), 4-HO-EPT, 4-HO-MCPT, 4-HO-MET (aka 3-[2-[ethyl(methyl)amino]ethyl]-1H-indol-4-ol), 4-HO-MIPT (aka 3-[2-[methyl(propan-2-yl)amino]ethyl]-1H-indol-4-ol), 4-HO-MPMI (aka 3-[(1-methylpyrrolidin-2-yl) methyl]-1H-indol-4-ol), 4-HO-MPT (aka 3-[2-[methyl (propyl)amino]ethyl]-1H-indol-4-ol), 4-HO-pyr-T (aka 3-(2-pyrrolidin-1-ylethyl)-1H-indol-4-ol), 4-MeO-MIPT (aka N-[2-(4-methoxy-1H-indol-3-yl)ethyl]-N-methylpropan-2-amine), 4,5-MDO-DIPT (aka N-[2-(6H-[1,3]dioxolo [4,5-e]indol-8-yl)ethyl]-N-propan-2-ylpropan-2-amine-), 4,5-MDO-DMT (aka 2-(6H-[1,3]dioxolo[4,5-e]indol-8-yl)-N,N-dimethylethanamine), 5-BROMO-DMT (aka 2-(5-bromo-1H-indol-3-yl)-N,N-dimethylethanamine), 5-chloro-alpha-MT (aka 1-(5-chloro-1H-indol-3-yl)propan-2-amine), 5-fluoro-AMT (aka 1-(5-fluoro-1H-indol-3-yl)propan-2-amine), 5-MeO-AET (aka 1-(5-methoxy-1H-indol-3-yl)butan-2-amine), 5-MeO-AMT (aka 1-(5-methoxy-1H-indol-3-yl)propan-2-amine), 5-MeO-DALT (aka N-[2-(5-methoxy-1H-indol-3-yl)ethyl]-N-prop-2-enylprop-2-en-1-amine), 5-MeO-DET (aka N,N-diethyl-2-(5-methoxy-1H-indol-3-yl)ethanamine), 5-MeO-DiPT (aka N-[2-(5-methoxy-1H-indol-3-yl)ethyl]-N-propan-2-ylpropan-2-amine), 5-MeO-DMT (aka 2-(5-methoxy-1H-indol-3-yl)-N,N-dimethylethanamine), 5-MeO-DPT (aka N-[2-(5-methoxy-1H-indol-3-yl)ethyl]-N-propylpropan-1-amine), 5-MeO-EiPT (aka N-ethyl-N-[2-(5-methoxy-1H-indol-3-yl)ethyl] propan-2-amine), 5-MeO-MALT (aka N-[2-(5-Methoxy-1H-indol-3-yl)ethyl]-N-methylprop-2-en-1-amine), 5-MeO-MiPT (aka N-[2-(5-methoxy-1H-indol-3-yl)ethyl]-N-methylpropan-2-amine), 5-MeO-NMT (aka 2-(5-methoxy-1H-indol-3-yl)-N-methylethanamine; hydrochloride), 5-MeO-pyr-T (aka 4-fluoro-5-methoxy-3-(2-pyrrolidin-1-ylethyl)-1H-indole), 5-MeO-TMT (aka 2-(5-methoxy-2-methyl-1H-indol-3-yl)-N,N-dimethylethanamine), 5-MeS-DMT (aka N,N-dimethyl-2-(5-methylsulfanyl-1H-indol-3-yl)ethanamine), 5,6-MDO-DIPT (aka N-[2-(5H-[1,3] dioxolo[4,5-f]indol-7-yl)ethyl]-N-propan-2-ylpropan-2-amine-), 5,6-MDO-DMT (aka 2-(5H-[1,3]dioxolo[4,5-f] indol-7-yl)-N,N-dimethylethanamine), 5,6-MDO-MIPT (aka N-[2-(5H-[1,3]dioxolo[4,5-f]indol-7-yl)ethyl]-N-ethylpropan-2-amine), 5,6-MeO-MIPT (aka N-[2-(5,6-dimethoxy-1H-indol-3-yl)ethyl]-N-methylpropan-2-amine), 5,N, N-TMT (aka N,N-dimethyl-2-(5-methyl-1H-indol-3-ethanamine), 6-MeO-THH (aka 6-methoxy-1-methyl-2,3,4, 9-tetrahydro-1H-pyrido [3,4-b]indole), alpha-ET (aka 1-(1H-indol-3-yl)butan-2-amine), alpha-MT (aka 1-(1H-indol-3-yl)propan-2-amine), alpha-TMT (aka 1-(1H-indol-3- yl)-N,N-dimethylpropan-2-amine), alpha,N-DMT (aka 2-(1H-indol-3-yl)-N,N-dimethylethanamine), alpha,N,O-TMS (aka 1-(5-methoxy-1H-indol-3-yl)-N-methylpropan-2-amine), alpha,O-DMS (aka 1-(5-methoxy-1H-indol-3-yl) propan-2-amine), DALT (aka N-[2-(1H-indol-3-yl)ethyl]-N-prop-2-enylprop-2-en-1-amine), DBT (aka N-butyl-N-[2-(1H-indol-3-yl)ethyl]butan-1-amine), DET (aka N,N-diethyl-2-(1H-indol-3-yl)ethanamine), DiPT (aka N-[2-(5-methoxy-1H-indol-3-yl)ethyl]-N-propan-2-ylpropan-2-amine), DMT (aka 2-(1H-indol-3-yl)-N,N-dimethylethanamine), DPT (aka N-[2-(1H-indol-3-yl) ethyl]-N-propylpropan-1-amine), EiPT (aka N-ethyl-N-[2-(1H-indol-3-yl)ethyl]propan-2-amine), Harmaline (aka 7-methoxy-1-methyl-3,4-dihydro-2H-pyrido [3,4-b]indole), Harmine (aka 7-methoxy-1-methyl-9H-pyrido[3,4-b]indole), MALT, MBT (aka 3H-1,3-benzothiazole-2-thione), Melatonin (aka N-[2-(5-methoxy-1H-indol-3-yl)ethyl]acetamide), MET (aka N-ethyl-2-(1H-indol-3-yl)-N-methylethanamine), MiPT (aka N-[2-(1H-indol-3-yl)ethyl]-N-methylpropan-2-amine), MPT (aka 3-[2-[methyl(propyl) amino]ethyl]-1H-indol-4-ol), NET (aka N-ethyl-2-(1H-indol-3-yl)ethanamine), NMT (aka 2-(1H-indol-3-yl)-N-methylethanamine), PiPT (aka N-[2-(1H-indol-3-yl)ethyl]-N-propan-2-ylpropan-1-amine), pyr-T (aka 3-(2-pyrrolidin-1-ylethyl)-1H-indole), T (aka 2-(1H-indol-3-yl) ethanamine), Tetrahydroharmine (aka 7-methoxy-1-methyl-2,3,4,9-tetrahydro-1H-pyrido[3,4-b]indole), 2-Br-4,5-MDA (aka 1-(6-bromo-1,3-benzodioxol-5-yl)propan-2-amine), 2-TIM (aka 2-(3,4-dimethoxy-2-methylsulfanylphenyl) ethanamine), 2-TOET (aka 1-(4-ethyl-5-methoxy-2-methylsulfanylphenyl)propan-2-amine), 2-TOM (aka 1-(5-methoxy-4-methyl-2-methylsulfanylphenyl)propan-2-amine), 2,4-DMA (aka 1-(2,4-dimethoxyphenyl)propan-2-amine), 2,5-DMA (aka 1-(2,5-dimethoxyphenyl)propan-2-amine), 2C-B (aka 2-(4-bromo-2,5-dimethoxyphenyl) ethanamine), 2C-C(aka 2-(4-chloro-2,5-dimethoxyphenyl) ethanamine), 2C-D (aka 2-(2,5-dimethoxy-4-methylphenyl) ethanamine), 2C-E (aka 2-(4-ethyl-2,5-dimethoxyphenyl) ethanamine), 2C-F (aka 2-(4-fluoro-2,5-dimethoxyphenyl) ethanamine), 2C-G (aka 2-(2,5-dimethoxy-3,4-dimethylpheny)ethanamine), 2C-G-3 (aka 2-(4,7-dimethoxy-2,3-dihydro-1H-inden-5-yl)ethanamine), 2C-G-4 (aka 2-(1,4-dimethoxy-5,6,7,8-tetrahydronaphthalen-2-yl)ethanamine), 2C-G-5 (aka CAS 207740-20-3), 2C-G-N(aka 2-(1,4-dimethoxynaphthalen-2-yl) ethanamine), 2C-H (aka 2-(2,5-dimethoxyphenyl) ethanamine), 2C-I (aka 2-(4-iodo-2,5-dimethoxyphenyl) ethanamine), 2C-N(aka 2-(2,5-dimethoxy-4-nitrophenyl) ethanamine), 2C-O-4 (aka 2-(2,5-dimethoxy-4-propan-2-yloxyphenyl)ethanamine), 2C-P (aka 2-(2,5-dimethoxy-4-propylphenyl)ethanamine), 2C-SE (aka 2-(2,5-dimethoxy-4-methylselanylphenyl)ethanamine), 2C-T (aka 2-(2,5-dimethoxy-4-methylsulfanylphenyl)ethanamine), 2C-T-13 (aka 2-[2,5-dimethoxy-4-(2-methoxyethylsulfanyl)phenyl] ethanamine), 2C-T-15 (aka 2-(4-cyclopropylsulfanyl-2,5-dimethoxyphenyl)ethanamine), 2C-T-17 (aka 2-(4-butan-2-ylsulfanyl-2,5-dimethoxyphenyl)ethanamine), 2C-T-2 (aka 2-(4-ethylsulfanyl-2,5-dimethoxypheny)ethanamine), 2C-T-2 (aka 2-[4-(2-fluoroethylsulfanyl)-2,5-dimethoxyphenyl]ethanamine), 2C-T-4 (aka 2-(2,5-dimethoxy-4-propan-2-ylsulfanylpheny)ethanamine), 2C-T-7 (aka 2-(2,5-dimethoxy-4-propylsulfanylphenyl)ethanamine), 2C-T-8 (aka 2-[4-(cyclopropylmethylsulfanyl)-2,5-dimethoxyphenyl] ethanamine), 2C-T-9 (aka 2-(4-butylsulfanyl-2,5-dimethoxypheny)ethanamine), 2C-TFM (aka 2-[2,5-dimethoxy-4-(trifluoromethyl)phenyl]ethanamine), 2T-MMDA-3a (aka 1-(4-methylsulfanyl-1,3-benzodioxol-5-yl)propan-2-amine), 3-T-TRIS (aka 2-(3,4-diethoxy-5-ethylsulfanylphenyl)ethanamine), 3-TASB (aka 2-(3-ethoxy-4-ethylsulfanyl-5-methoxyphenyl)ethanamine), 3-TE (aka 2-(4-ethoxy-3-methoxy-5-methylsulfanylphenyl)ethanamine), 3-TFM (aka 2-(2,4-dimethoxy-3-methylsulfanylphenyl)ethanamine), 3-TM (aka 2-(3,4-dimethoxy-5-methylsulfanylpheny) ethanamine), 3-TME (aka 2-(3-ethylsulfanyl-4,5-dimethoxyphenyl)ethanamine), 3-TSB (aka 2-(3-ethoxy-5-ethylsulfanyl-4-methoxyphenyl)ethanamine), 3,4-DMA (aka 1-(3,4-dimethoxyphenyl)propan-2-amine), 3C-BZ (aka 1-(3,5-dimethoxy-4-phenylmethoxyphenyl)propan-2-amine), 3C-E (aka 1-(4-ethoxy-3,5-dimethoxyphenyl)propan-2-amine), 4-Br-3,5-DMA (aka 1-(4-bromo-3,5-dimethoxyphenyl)propan-2-amine), 4-D (aka CAS 1020518-87-9), 4-MA (aka 1-(4-methoxyphenyl)propan-2-amine), 4-T-TRIS (aka 2-(3,5-diethoxy-4-ethylsulfanylphenyl) ethanamine), 4-TASB (aka 2-(3-ethoxy-4-ethylsulfanyl-5-methoxypheny)ethanamine), 4-TE (aka 2-(4-ethylsulfanyl-3,5-dimethoxyphenyl)ethanamine), 4-TIM (aka 2-(2,3-dimethoxy-4-methylsulfanylphenyl)ethanamine), 4-TM (aka 2-(3,5-dimethoxy-4-methylsulfanylphenyl) ethanamine), 4-TME (aka 2-(3-ethoxy-5-methoxy-4-methylsulfanylpheny)ethanamine), 4-TSB (aka 2-(3,5-diethoxy-4-methylsulfanylphenyl)ethanamine), 4T-MMDA-2 (aka 1-(5-methoxy-1,3-benzoxathiol-6-yl)propan-2-amine), 5-TASB (aka 2-(3,4-diethoxy-5-methylsulfanylphenyl) ethanamine), 5-TME (aka 2-(3-ethoxy-4-methoxy-5-methylsulfanylphenyl)ethanamine), 5-TOET (aka 1-(4-ethyl-2-methoxy-5-methylsulfanylphenyl)propan-2-amine), 5-TOM (aka 1-(2-methoxy-4-methyl-5-methylsulfanylphenyl)propan-2-amine), 25B-NBF (aka 2-(4-bromo-2,5-dimethoxyphenyl)-N-[(2-fluorophenyl)methyl]ethanamine-), 25B-NBOH (aka 2-[[2-(4-bromo-2,5-dimethoxypheny) ethylaminolmethyl]phenol), 25B-NBOMe (aka 2-(4-bromo-2,5-dimethoxyphenyl)-N[(2-methoxyphenyl)methyl] ethanamine-), 25C-NB3OMe (aka 2-(4-chloro-2,5-dimethoxyphenyl)-N-[((3-methoxypheny)methyl] ethanamine), 25C-NB4OMe (aka 2-(4-chloro-2,5-dimethoxyphenyl)-N-[(4-methoxyphenyl)methyl] ethanamine), 25C-NBF (aka 2-(4-chloro-2,5-dimethoxyphenyl)-N-[(2-fluorophenyl)methyl]ethanamine), 25C-NBOH (aka 2-(4-chloro-2,5-dimethoxyphenyl)ethylaminolmethyl]phenol), 25C-NBOMe (aka 2-(4-chloro-2,5-dimethoxyphenyl)-N[(2-methoxyphenyl)methyl] ethanamine), 25CN-NBOH (aka 4-[2-[(2-hydroxyphenyl) methylamino]ethyl]-2,5-dimethoxybenzonitrile), 25CN-NBOMe (aka CAS 1354632-16-8), 25D-NBOMe (aka 2-(2,5-dimethoxy-4-methylphenyl)-N-[(2-methoxyphenyl) methyl]ethanamine), 25E-NBOMe (aka 2-(4-ethyl-2,5-dimethoxyphenyl)-N4(2-methoxyphenyl)methyl] ethanamine), 25G-NBOMe (aka 2-(2,5-dimethoxy-3,4-dimethylphenyl)-N-[(2-methoxyphenyl)methyl] ethanamine), 25H-NBOMe (aka 2-(2,5-dimethoxyphenyl)-N-[(2-methoxyphenyl)methyl]ethanamine), 25H-NB34MD (aka N-(1,3-benzodioxol-5-ylmethyl)-2-(4-iodo-2,5-dimethoxyphenyl)ethanamine), 251-NB3OMe (aka 2-(4-iodo-2,5-dimethoxyphenyl)-N-[(3-methoxyphenyl)methyl] ethanamine), 251-NB4OMe (aka 2-(4-iodo-2,5-dimethoxyphenyl)-N-[(4-methoxyphenyl)methyl] ethanamine), 251-NBF (aka N-[(2-fluorophenyl)methyl]-2-(4-iodo-2,5-dimethoxyphenyl)ethanamine), 251-NBMD (aka N-(1,3-benzodioxol-4-ylmethyl)-2-(4-iodo-2,5-dimethoxyphenyl)ethanamine), 251-NBOH (aka 2-[[2-(4-iodo-2,5-dimethoxypheny)ethylamino]methyl]phenol), 251-NBOMe (aka 2-(4-iodo-2,5-dimethoxyphenyl)-N-[(2-methoxyphenyl)methyl]ethanamine), 25iP-NBOMe (aka 2-(2,5-dimethoxy-4-propan-2-ylphenyl)-N-[(2-methoxypheny)methyl]ethanamin-e), 25N-NBOMe (aka 2-(2,5-dimethoxy-4-nitrophenyl)-N-[(2-methoxypheny)methyl] ethanamine), 25P-NBOMe (aka 2-(2,5-dimethoxy-4-propylphenyl)-N-[(2-methoxyphenyl)methyl]ethanamine), 25TFM-NBOMe (aka 2-[2,5-dimethoxy-4-(trifluoromethyl) phenyl]-N-[(2-methoxyphenyl)methyl]et-hanamine), 2CBCB-NBOMe (aka 1-[(7R)-3-bromo-2,5-dimethoxy-7-bicyclo[4.2.0]octa-1(6),2,4-trienyl]-N-[(-2-methoxypheny) methyl]methanamine), 2CBFIy-NBOMe (aka 2-(4-bromo-2,3,6,7-tetrahydrofuro[2,3-f][1]benzofuran-8-yl)-N-[(2-methoxy-phenyl)methyl]thanamine), AEM (aka 1-(3,4,5-trimethoxyphenyl)butan-2-amine), AL (aka 2-(3,5-dimethoxy-4-prop-2-enoxyphenyl)ethanamine), ALEPH (aka 1-(2,5-dimethoxy-4-methylsulfanylphenyl)propan-2-amine; hydrochloride), ALEPH-2 (aka 1-(4-ethylsulfanyl-2,5-dimethoxyphenyl)propan-2-amine), ALEPH-4 (aka 1-(2,5-dimethoxy-4-propan-2-ylsulfanylphenyl)propan-2-amine), ALEPH-6 (aka 1-(2,5-dimethoxy-4-phenylsulfanylphenyl)propan-2-amine), ALEPH-7 (aka 1-(2,5-dimethoxy-4-propylsulfanylphenyl)propan-2-amine), ARIADNE (aka (2R)-1-(2,5-dimethoxy-4-methylphenyl)butan-2-amine), ASB (aka 2-(3,4-diethoxy-5-methoxyphenyl)ethanamine), B (aka 2-(4-butoxy-3,5-dimethoxyphenyl)ethanamine), BEATRICE (aka 1-(2,5-dimethoxy-4-methylphenyl)-N-methylpropan-2-amine), beta-D (aka 2,2-dideuterio-2-(3,4,5-trimethoxyphenyl) ethanamine), BIS-TOM (aka 1-[4-methyl-2,5-bis(methylsulfanyl)phenyl]propan-2-amine), bk-2C-B (aka 2-amino-1-(4-bromo-2,5-dimethoxyphenyl)ethanone), BOB (aka 2-(4-bromo-2,5-dimethoxyphenyl)-2-methoxyethanamine), BOD (aka 2-(2,5-dimethoxy-4-methylphenyl)-2-methoxyethanamine), BOH (aka 2-(1,3-benzodioxol-5-yl)-2-methoxyethanamine), BOHD (aka 2-amino-1-(2,5-dimethoxy-4-methylpheny)ethanol), BOM (aka 2-methoxy-2-(3,4,5-trimethoxyphenyl)ethanamine), bromo-dragonFLY (aka 1-(4-bromofuro[2,3-f][1]benzofuran-8-yl)propan-2-amine), butylone (aka 1-(1,3-benzodioxl-5-yl)-2-(methylamino)butan-1-one), CPM (aka 2-[4-(cyclopropylmethoxy)-3,5-dimethoxyphenyl]ethanamine), DESOXY (aka 2-(3,5-dimethoxy-4-methylpheny)ethanamine), DMCPA (aka 2-(2,5-dimethoxy-4-methylphenyl)cyclopropan-1-amine), DME (aka 2-amino-1-(3,4-dimethoxyphenyl)ethanol), DMMDA (aka 1-(4,7-dimethoxy-1,3-benzodioxol-5-yl)propan-2-amine), DMMDA-2 (aka 1-(6,7-dimethoxy-1,3-benzodioxol-5-yl)propan-2-amine), DMPEA (aka 2-(3,4-dimethoxyphenyl)ethanamine), DOAM (aka 1-(2,5-dimethoxy-4-pentylphenyl)propan-2-amine), DOB (aka 1-(4-bromo-2,5-dimethoxyphenyl)propan-2-amine), DOBU (aka 1-(4-butyl-2,5-dimethoxyphenyl)propan-2-amine), DOC (aka 1-(4-chloro-2,5-dimethoxyphenyl)propan-2-amine), DOEF (aka 1-[4-(2-fluoroethyl)-2,5-dimethoxyphenyl]propan-2-amine), DOET (aka 1-(4-ethyl-2,5-dimethoxyphenyl)propan-2-amine), DOF (aka 1-(4-fluoro-2,5-dimethoxyphenyl) propan-2-amine), DOI (aka 1-(4-iodo-2,5-dimethoxyphenyl)propan-2-amine), DOM (aka 1-(2,5-dimethoxy-4-methylphenyl)propan-2-amine), DON (aka 1-(2,5-dimethoxy-4-nitrophenyl)propan-2-amine), DOPR (aka 1-(2,5-dimethoxy-4-propylphenyl)propan-2-amine), DOTFM (aka 1-[2,5-dimethoxy-4-(trifluoromethyl)phenyl] propan-2-amine), E (aka 2-(4-ethoxy-3,5-dimethoxyphenyl) ethanamine), EBDP (aka 1-(1,3-benzodioxol-5-yl)-N-ethylpentan-2-amine), EEE (aka 1-(2,4,5-triethoxyphenyl) propan-2-amine), EEM (aka 1-(2,4-diethoxy-5-methoxyphenyl)propan-2-amine), EME (aka 1-(2,5-diethoxy-4-methoxyphenyl)propan-2-amine), EMM (aka 1-(2-ethoxy-4,5-dimethoxyphenyl)propan-2-amine), ETHYL-J (aka 1-(1,3-benzodioxol-5-yl)-N-ethylbutan-2-amine), ETHYL-K (aka 1-(1,3-benzodioxol-5-yl)-N-ethylpentan-2-amine), F-2 (aka 1-(5-methoxy-2-methyl-2,3-dihydro-1-benzofuran-6-yl)propan-2-amine), F-22 (aka 1-(5-methoxy-2,2-dimethyl-3H-1-benzofuran-6-yl)propan-2-amine), FLEA (aka N-[1-(1,3-benzodioxol-5-yl)propan-2-yl]-N-methylhydroxylamine), G-3 (aka 1-(4,7-dimethoxy-2,3-dihydro-1H-inden-5-yl)propan-2-amine), G-4 (aka 1-(1,4-dimethoxy-5,6,7,8-tetrahydronaphthalen-2-yl)propan-2-amine), G-5 (aka 3,6-dimethoxy-4-(2-aminopropyl) benzonorbornane), G-N(aka 1-(1,4-dimethoxynaphthalen-2-yl)propan-2-amine), GANESHA (aka 1-(2,5-dimethoxy-3,4-dimethylphenyl)propan-2-amine), HOT-17 (aka N-[2-(4-butan-2-ylsulfanyl-2,5-dimethoxypheny)ethyl] hydroxylamine), HOT-2 (aka N-[2-(4-ethylsulfanyl-2,5-dimethoxypheny)ethyl]hydroxylamine), HOT-7 (aka N-[2-(2,5-dimethoxy-4-propylsulfanylpheny)ethyl] hydroxylamine), IDNNA (aka 1-(4-iodo-2,5-dimethoxyphenyl)-N,N-dimethylpropan-2-amine), IM (aka 2-(2,3,4-trimethoxyphenyl)e thanamine), IP (aka 2-(3,5-dimethoxy-4-propan-2-yloxyphenyl)ethanamine), IRIS (aka 1-(5-ethoxy-2-methoxy-4-methylphenyl)propan-2-amine), J (aka 1-(1,3-benzodioxol-5-yl)butan-2-amine), jimscaline (aka [(1R)-4,5,6-trimethoxy-2,3-dihydro-1H-inden-1-yl] methanamine), LOPHOPHINE (aka 2-(7-methoxy-1,3-benzodioxol-5-yl)ethanamine), M (aka 2-(3,4,5-trimethoxypheny)ethanamine), MADAM-6 (aka N-methyl-1-(6-methyl-11,3-benzodioxol-5-yl)propan-2-amine), MAL (aka 2-[3,5-dimethoxy-4-(2-methylprop-2-enoxy)phenyl] ethanamine), MDA (aka 1-(1,3-benzodioxol-5-yl)propan-2-amine), MDAL (aka 1-(1,3-benzodioxol-5-yl)-N-prop-2-enylpropan-2-amine), MDBU (aka N-[1-(1,3-benzodioxol-5-yl)propan-2-yl]butan-1-amine), MDBZ (aka 1-(1,3-benzodioxol-5-yl)-N-benzylpropan-2-amine), MDCPM (aka 1-(3a,7a-dihydro-1,3-benzodioxol-5-yl)-N-(cyclopropylmethyl)propan-2-amin-e), MDDM (aka 1-(1,3-benzodioxol-5-yl)-N,N-dimethylpropan-2-amine), MDE (aka 1-(1,3-benzodioxol-5-yl)-N-ethylpropan-2-amine), MDHOET (aka 2-[1-(1,3-benzodioxol-5-yl)propan-2-ylamino]ethanol), MDIP (aka 1-(1,3-benzodioxol-5-yl)-N-propan-2-yl-propan-2-amine), MDMA (aka 1-(1,3-benzodioxol-5-yl)-N-methylpropan-2-amine), MDMC (aka 1-(2,3-dihydro-1,4-benzodioxin-6-yl)-N-methylpropan-2-amine), MDMEO (aka 1-(1,3-benzodioxol-5-yl)-N-methoxypropan-2-amine), MDMEOET (aka 1-(1,3-benzodioxol-5-yl)-N-(2-methoxyethyl)propan-2-amine), MDMP (aka 1-(1,3-benzodioxol-5-yl)-N,2-dimethylpropan-2-amine), MDOH (aka N-[1-(1,3-benzodioxol-5-yl)propan-2-yl]hydroxylamine), MDPEA (aka 2-(1,3-benzodioxol-5-yl)ethanamine), MDPH (aka 1-(1,3-benzodioxol-5-yl)-2-methylpropan-2-amine), MDPL (aka 1-(1,3-benzodioxol-5-yl)-N-prop-2-ynylpropan-2-amine), MDPR (aka 1-(1,3-benzodioxol-5-yl)-N-propylpropan-2-amine), ME (aka 2-(3-ethoxy-4,5-dimethoxyphenyl) ethanamine), MEDA (aka 1-(5-methoxy-2,3-dihydro-1,4-benzodioxin-7-yl)propan-2-amine), MEE (aka 1-(4,5-diethoxy-2-methoxyphenyl)propan-2-amine), MEM (aka 1-(4-ethoxy-2,5-dimethoxyphenyl)propan-2-amine), MEPEA (aka 2-(4-ethoxy-3-methoxyphenyl)ethanamine), META-DOB (aka 1-(5-bromo-2,4-dimethoxyphenyl)propan-2-amine), META-DOT (aka 1-(2,4-dimethoxy-5-methylsulfanylphenyl)propan-2-amine), METHYL-DMA (aka 1-(2,5-dimethoxyphenyl)-N-methylpropan-2-amine), METHYL-DOB (aka 1-(4-bromo-2,5-dimethoxyphenyl)-N-methylpropan-2-amine), METHYL-J (aka 1-(1,3-benzodioxol-5-yl)-N-methylbutan-2-amine), METHYL-K (aka 1-(1,3-benzodioxol-5-yl)-N-methylpentan-2-amine), METHYL-MA (aka 1-(4-methoxyphenyl)-N-methylpropan-2-amine), METHYL-MMDA-2 (aka 1-(6-methoxy-1,3-benzodioxol-5-yl)-N-methylpropan-2-amine), MMDA (aka 1-(7-methoxy-1,3-benzodioxol-5-yl)propan-2-amine), MMDA-2 (aka 1-(6-methoxy-1,3-benzodioxol-5-yl)propan-2-amine), MMDA-3a (aka 1-(4-methoxy-1,3-benzodioxol-5-yl)propan-2-amine), MMDA-3b (aka 1-(7-methoxy-1,3-benzodioxol-4-yl)propan-2-amine), MME (aka 1-(5-ethoxy-2,4-dimethoxyphenyl)propan-2-amine), MP (aka 2-(3,4-dimethoxy-5-propoxyphenyl)ethanamine), MPM (aka 1-(2,4-dimethoxy-5-propoxyphenyl)propan-2-amine), NBOMe-mescaline (aka N-[(2-methoxyphenyl)methyl]-2-(3,4,5-trimethoxypheny)ethanamine), ORTHO-DOT (aka 1-(4,5-dimethoxy-2-methylsulfanylphenyl)propan-2-amine), P (aka 2-(3,5-dimethoxy-4-propoxyphenyl)ethanamine), PE (aka 2-[3,5-dimethoxy-4-(2-phenylethoxy)phenyl] ethanamine), PEA (aka 2-phenylethanamine), PROPYNYL (aka 2-(3,5-dimethoxy-4-prop-2-ynoxyphenyl)ethanamine), psi-2C-T-4, psi-DOM (aka 1-(2,6-dimethoxy-4-methylphenyl)propan-2-amine), SB (aka 2-(3,5-diethoxy-4-methoxyphenyl)ethanamine), TA (aka 1-(2,3,4,5-tetramethoxyphenyl)propan-2-amine), TB (aka 2-(4-butylsulfanyl-3,5-dimethoxypheny)ethanamine), TCB-2 (aka (3-bromo-2,5-dimethoxy-7-bicyclo[4.2.0]octa-1(6), 2,4-trienyl) methanamine; hydrobromide), TMA (aka 1-(3,4,5-trimethoxyphenyl)propan-2-amine), TMA-2 (aka 1-(2,4,5-trimethoxyphenyl)propan-2-amine), TMA-3 (aka 1-(2,3,4-trimethoxyphenyl)propan-2-amine), TMA-4 (aka 1-(2,3,5-trimethoxyphenyl)propan-2-amine), TMA-5 (aka 1-(2,3,6-trimethoxyphenyl)propan-2-amine), TMA-6 (aka 1-(2,4,6-trimethoxyphenyl)propan-2-amine), TMPEA (aka 2-(2,4,5-trimethoxyphenyl)ethanamine), TOMSO (aka 1-(2-methoxy-4-methyl-5-methylsulfinylphenyl)propan-2-amine), TP (aka 2-(3,5-dimethoxy-4-propylsulfanylphenyl) ethanamine), and TRIS (aka 2-(3,4,5-triethoxyphenyl) ethanamine).

In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and derivatives thereof.

In one embodiment, serotonin acts at a serotonin receptor, e.g., by acting as a ligand at a 5-HT receptor. In one embodiment, serotonin is produced by an organism for use as a neurotransmitter within that organism. In one embodiment, the compositions and methods disclosed herein increase the activity at a serotonin receptor. In one embodiment, the compositions and methods disclosed herein decrease the activity at a serotonin receptor.

As used herein, the term "serotonin receptor" refers to a collection of proteins outside a cell capable of receiving signals and activating internal signal transduction pathways causing a cellular response. In one embodiment, a serotonin receptor is found on a cell within the central nervous system of an organism. In one embodiment, a serotonin receptor is found on a cell within the peripheral nervous system of an organism. In one embodiment, serotonin is the natural ligand for a serotonin receptor. In one embodiment, a serotonin receptor modulates the release of a neurotransmitter, e.g., glutamate, gamma-Aminobutyric acid, dopamine, epinephrine (a.k.a. norepinephrine), acetylcholine, etc. In one embodiment, a serotonin receptor modulates the release of a hormone, e.g., oxytocin, prolactin, vasopressin, cortisol, corticotropin, substance P, etc.

Examples of serotonin receptors include, but are not limited to, $5\text{-HT}_{1A}$, $5\text{-HT}_{1B}$, $5\text{-HT}_{1D}$, $5\text{-HT}_{1E}$, $5\text{-HT}_{2A}$, $5\text{-HT}_{2B}$, $5\text{-HT}_{2C}$, $5\text{-HT}_3$, $5\text{-HT}_4$, $5\text{-HT}_{5A}$, $5\text{-HT}_{5B}$, $5\text{-HT}_6$, and $5\text{-HT}_7$.

As used herein, the term "adrenergic drug" refers to a compound that binds, blocks, or otherwise influences (e.g., via an allosteric reaction) activity at an adrenergic receptor. In one embodiment, an adrenergic drug binds to an adrenergic receptor. In one embodiment, an adrenergic drug indirectly affects an adrenergic receptor, e.g., via interactions affecting the reactivity of other molecules at the adrenergic receptor. In one embodiment, an adrenergic drug is an agonist, e.g., a compound activating an adrenergic receptor. In one embodiment, an adrenergic drug is an antagonist, e.g., a compound binding but not activating an adrenergic receptor, e.g., blocking a receptor. In one embodiment, an adrenergic drug is an effector molecule, e.g., a compound binding to an enzyme for allosteric regulation. In one embodiment, an adrenergic drug acts (either directly or indirectly) at more than one type of receptor (e.g., 5HT, dopamine, adrenergic, acetylcholine, etc.).

In one embodiment, an adrenergic drug is an antidepressant.

In one embodiment, an adrenergic drug is a norepinephrine transporter inhibitor.

In one embodiment, an adrenergic drug is a vesicular monoamine transporter inhibitor.

In one embodiment, an adrenergic drug is chosen from adrenaline, agmatine, amoxapine, aptazapine, atomoxetine, bupropion, clonidine, doxepin, duloxetine, esmirtazpine, mianserin, mirabegron, mirtazapine, norepinephrine, phentolamine, phenylephrine, piperoxan, reserpine, ritodrine, setiptiline, tesofensine, timolol, trazodone, trimipramine, and xylazine.

In one embodiment, an adrenergic drug acts at an adrenergic receptor, e.g., by acting as a ligand at an adrenergic receptor. In one embodiment, adrenaline is produced by an organism for use as a neurotransmitter within that organism. In one embodiment, norepinephrine is produced by an organism for use as a neurotransmitter within that organism.

In one embodiment, the compositions and methods disclosed herein increase the activity at an adrenergic receptor. In one embodiment, the compositions and methods disclosed herein decrease the activity at an adrenergic receptor.

As used herein, the term "adrenergic receptor" refers to a collection of proteins outside a cell capable of receiving signals and activating internal signal transduction pathways causing a cellular response. In one embodiment, an adrenergic receptor is found on a cell within the central nervous system of an organism. In one embodiment, an adrenergic receptor is found on a cell within the sympathetic nervous system of an organism.

As used herein, the term "dopaminergic drug" refers to a compound that binds, blocks, or otherwise influences (e.g., via an allosteric reaction) activity at a dopamine receptor. In one embodiment, a dopaminergic drug binds to a dopamine receptor. In one embodiment, a dopaminergic drug indirectly affects a dopamine receptor, e.g., via interactions affecting the reactivity of other molecules at the dopamine receptor. In one embodiment, a dopaminergic drug is an agonist, e.g., a compound activating a dopamine receptor. In one embodiment, a dopaminergic drug is an antagonist, e.g., a compound binding but not activating a dopamine receptor, e.g., blocking a receptor. In one embodiment, a dopaminergic drug is an effector molecule, e.g., a compound binding to an enzyme for allosteric regulation. In one embodiment, a dopaminergic drug acts (either directly or indirectly) at more than one type of receptor (e.g., 5HT, dopamine, adrenergic, acetylcholine, etc.).

In one embodiment, a dopaminergic drug is a dopamine transporter inhibitor.

In one embodiment, a dopaminergic drug is a vesicular monoamine transporter inhibitor.

In one embodiment, a dopaminergic drug is chosen from amineptine, apomorphine, benzylpiperazine, bromocriptine, cabergoline, chlorpromazine, clozapine, dihydrexidine, domperidone, dopamine, fluphenazine, haloperidol, ketamine, loxapine, methamphetamine, olanzapine, pemoline, perphenazine, pergolide, phencyclidine, phenethylamine, phenmetrazine, pimozide, piribedil, a psychostimulant, reserpine, risperidone, ropinirole, tetrabenazine, and thioridazine.

In one embodiment, a dopaminergic drug acts at a dopamine receptor, e.g., by acting as a ligand at a dopamine receptor. In one embodiment, dopamine is produced by an organism for use as a neurotransmitter within that organism. In one embodiment, the compositions and methods disclosed herein increase the activity at a dopamine receptor. In one embodiment, the compositions and methods disclosed herein decrease the activity at a dopamine receptor.

As used herein, the term "dopamine receptor" refers to a collection of proteins outside a cell capable of receiving signals and activating internal signal transduction pathways causing a cellular response. In one embodiment, a dopamine receptor is found on a cell within the central nervous system of an organism.

In one embodiment, a purified terpene modulates the activity of a neurotransmitter at its native receptor, e.g., serotonin at a serotonin receptor, dopamine at a dopaminergic drug, norephedrine at an adrenergic receptor, etc.

In one embodiment, a purified terpene is active at one or more receptors, e.g., a serotonin receptor, an adrenergic receptor, a dopamine receptor, a GABAergic receptor, a glutaminergic receptor, a histaminergic receptor, a cholinergic receptor, an opioid receptor, or a glycinergic receptor.

In one embodiment, the compositions disclosed herein comprise a monoamine oxidase inhibitor.

As used herein, the term "monoamine oxidase inhibitor" refers to a molecule binding to a monoamine oxidase enzyme thereby reducing the activity of the monoamine oxidase enzyme. Within the context of this disclosure, examples of monoamine oxidase inhibitors include aurorix, deprenyl, eldepryl, emsam, humoryl, hydracarbazine, isocarboxazid, linezolid, manerix, nydrazid, phenelzine, pirazidol, procarbazine, rasagiline, and tranylcypromine. In one embodiment, monoamine oxidase catalyzes the oxidation of a monoamine, e.g., serotonin, dopamine, norepinephrine, amphetamine, adrenaline, etc.

In one embodiment, the compositions disclosed herein comprise a stabilizer. As used herein, the term "stabilizer" refers to a compound useful for preventing the degradation of an active ingredient, e.g., a compound of Formula I, a psilocybin derivative, a cannabinoid, a terpene, etc. In one embodiment, a stabilizer prevents an active ingredient from degrading. In one embodiment, a stabilizer prevents a serotonergic drug from reacting with other compounds in the composition, e.g., a cannabinoid, a terpene, a base, an acid, etc. In one embodiment, a stabilizer prevents a serotonergic drug from reacting with the ambient atmosphere, e.g., heat, light, water, and/or oxygen. In one embodiment, a stabilizer comprises an antioxidant. In one embodiment, a stabilizer comprises a pH buffer.

In one embodiment, the methods and compositions disclosed herein comprise an antioxidant. As used herein, the term "antioxidant" refers to a compound and/or a composition useful for preventing oxidation. In one embodiment, an antioxidant protects an active ingredient from "free radicals". Within the context of this disclosure, a "free radical" is an atom, molecule, or an ion with an unpaired valence electron. In one embodiment, an antioxidant is an electron donor.

In one embodiment, an antioxidant is chosen from ascorbic acid, lycopene, tocopherol, melatonin, retinol, astaxanthin, lutein, apigenin, carnosine, selenium, zinc, cucurmin, and a salt or derivative thereof.

In one embodiment, an antioxidant is ascorbic acid and/or its salts or derivatives. Within the context of this disclosure, the term "ascorbic acid" comprises Vitamin C and/or a salt or derivative thereof.

In one embodiment, an antioxidant prevents the oxidation of a composition comprising one or more compounds disclosed herein, e.g., compounds of Formula I, psilocybin derivatives, cannabinoids, terpenes, and/or mixtures thereof. For example, preventing the oxidation of a phenolic group attached to a psilocybin derivative.

As used herein, the term "oxidation" refers to the formal loss of electrons and/or the increase of the formal oxidation state and/or the addition of an oxygen atom or atoms. As used herein, "reduction" refers to the formal gain of electrons and/or the decrease of the formal oxidation state. Zumdahl, Steven S., et al. Chemistry, 7th. Cengage Learning, 2018.

In one embodiment, the methods and compositions disclosed herein comprise a pH buffer.

As used herein, the term "pH buffer" refers to a compound or a composition useful for maintaining the pH of a composition. In one embodiment, a pH buffer comprises a weak acid and a corresponding conjugate base. In one embodiment, a pH buffer comprises a weak base and a corresponding conjugate acid. In one embodiment, a pH buffer does not change the pH of a composition with the addition of a strong acid and/or base.

In one embodiment, a pH buffer maintains the pH of a composition around 7. In one embodiment, a pH buffer maintains the pH of a composition below about 7. In one embodiment, a pH buffer maintains the pH of a composition above about 7. In one embodiment, a pH buffer maintains the pH of a composition ranging from about 2 to about 6. In one embodiment, a pH buffer maintains the pH of a composition ranging from about 5 to about 7. In one embodiment, a pH buffer maintains the pH of a composition ranging from about 6 to about 8. In one embodiment, a pH buffer maintains the pH of a composition ranging from about 7 to about 10.

In one embodiment, a pH buffer comprises citric acid, acetic acid, monosodium phosphate, N-Cyclohexyl-2-aminoethanesulfonic acid, borate, hydrochloric acid, and/or sodium hydroxide.

In one embodiment, the methods disclosed herein comprise administering a composition comprising an acid.

As used herein, the term "acid" refers to a molecule or ion capable of donating a proton, i.e., $H^+$ and/or accepting electrons. In one embodiment, an "acid" refers to a Lewis acid. In one embodiment, an "acid" refers to a Bronsted acid. In one embodiment, an acid is determined by a composition's pH. In one embodiment, a pH below 7 indicates the presence of an acid.

In one embodiment, the compositions and methods disclosed herein comprise administering a formulation comprising a base.

As used herein, the term "base" refers to a molecule or ion capable of accepting a proton, i.e., an $H^+$. In one embodiment, a "base" refers to a molecule capable of donating an electron pair, i.e., a Lewis base. In one embodiment, the presence of a base is determined by a compound's pH. In one embodiment, a pH above 7 indicates the presence of a base.

In one embodiment, the compositions and methods disclosed herein comprise administering a non-water soluble composition.

In some embodiments, the compositions described herein are non-aqueous.

As used herein, the term "water soluble" refers to a compound or composition capable of dissolving in water at standard temperature and pressure. In one example, 1 g of a compound dissolves in 1 L of water. In one example, 2 g of a compound dissolves in 1 L of water. In one example, 5 g of a compound dissolves in 1 L of water. In one example, 10 g of a compound dissolves in 1 L of water. In one embodiment, a compound's solubility in water is an inherent property of a compound. In one embodiment, a compound's solubility in water is facilitated by another compound, e.g., an excipient.

In one embodiment, the compositions and methods disclosed herein comprise administering a compound of Formula I present as and/or within a homogenous mixture within a dosage formulation.

In one embodiment, the compositions and methods disclosed herein comprise administering a compound of Formula I and at least one second compound (e.g., serotonergic drug, cannabinoid, terpene, excipient, stabilizer, antioxidant, etc.) present as and/or within a homogenous mixture within a dosage formulation.

As used herein, the term "homogeneous mixture" refers to a solid, liquid, or gaseous composition that has two or more compounds present within one state or thing, e.g., a clear, colorless solution. In one embodiment, the homogeneous mixtures disclosed herein have the same proportion, concentration, and/or ratio of its components across different samples. In one embodiment, the components in the homogeneous mixture are in the same state of matter. In one embodiment, a homogeneous mixture comprises one or more compounds within a solution, e.g., a compound of Formula I and a cannabinoid within a clear solution. In one embodiment, the compositions disclosed herein are present as a homogenous mixture, e.g., a solution with no particulates, a solution with equal concentrations across samples, a powder of similar particle size, etc.

Disclosed herein is a method of modulating activity at a neurotransmitter receptor, comprising:

administering a neurotransmitter activity modulator; and administering a dosage formulation comprising a compound of Formula I to the person in need of treatment, wherein the dosage formulation modulates activity at a neurotransmitter receptor.

As used herein, the term "modulating activity of the neurotransmitter activity modulator" refers to changing, manipulating, and/or adjusting the ability of a compound or composition to affect a neurotransmitter receptor. In one embodiment, modulating the activity of a neurotransmitter activity modulator comprises administering an agonist at a neurotransmitter receptor. In one embodiment, modulating the activity of a neurotransmitter activity modulator comprises administering an antagonist at a neurotransmitter receptor.

As used herein, the term "administering" (e.g., administering a drug) refers to dosing, treating, giving, and/or providing. In one embodiment, administering a neurotransmitter activity modulator comprises providing a neurotransmitter activity modulator to an organism (e.g., a human being) with a neurotransmitter receptor. In one embodiment, administering a neurotransmitter activity modulator comprises providing a neurotransmitter activity modulator along with a compound of Formula I, e.g., a formulation having each of a neurotransmitter activity modulator and a compound of Formula I in a single dosage. In one embodiment, administering a neurotransmitter activity modulator comprises applying a transdermal composition, e.g., applying a topical composition to the skin having each of a neurotransmitter activity modulator and a compound of Formula I. In one embodiment, administering a neurotransmitter activity modulator comprises giving a transmucosal preparation, e.g., providing rapidly dissolving a tablet with an absorption enhancer having each of a neurotransmitter activity modulator and a compound of Formula I.

In one embodiment, the methods disclosed herein comprise administering a composition by inhalation for crossing a blood-brain barrier.

As used herein, the term "neurotransmitter activity modulator" refers to a compound or composition that reacts or influences activity at a neurotransmitter receptor, e.g., a compound of Formula I, a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, a neurotransmitter activity modulator binds on a neurotransmitter receptor. In one embodiment, a neurotransmitter activity modulator indirectly affects a neurotransmitter receptor, e.g., via interactions affecting the reactivity of other molecules at a neurotransmitter receptor. In one embodiment, a neurotransmitter activity modulator is an agonist. In one embodiment, a neurotransmitter activity modulator is an antagonist. In one embodiment, a neurotransmitter activity modulator acts (either directly or indirectly) at more than one type of neurotransmitter receptor.

In one embodiment, a neurotransmitter activity modulator is chosen from aripiprazole, bupropion, citalopram, clomipramine, dextroamphetamine, duloxetine, escitalopram, fluoxetine, fluvoxamine, milnacipran, mirtazapine, paroxetine, quetiapine, reboxetine, risperidone, sertraline, and venlafaxine.

As used herein, the term "first dosage formulation" refers to a compound or compounds selected for the purposes of causing a reaction, effect, and/or result, e.g., causing activity at a neurotransmitter receptor, reacting with other compounds, enhancing the effects of other active ingredients, inhibiting the biosynthesis of a compound, etc., within an organism. In one embodiment, a first dosage formulation comprises a compound of Formula I. In one embodiment, a first dosage formulation comprises a first purified cannabinoid. In one embodiment, a first dosage formulation comprises a first purified terpene. In one embodiment, a first dosage formulation comprises a compound of Formula I and a purified serotonergic derivative. In one embodiment, a first dosage formulation comprises a compound of Formula I and a first purified cannabinoid. In one embodiment, a first dosage formulation a compound of Formula I and a first purified terpene. In one embodiment, a first dosage formulation comprises a compound of Formula I, a first purified cannabinoid, and first purified terpene. In one embodiment, a first dosage formulation comprises a compound of Formula I and a neurotransmitter activity modulator.

In one embodiment, a second dosage formulation comprises a compound of Formula I. In one embodiment, a second dosage formulation comprises a second compound of Formula I. In one embodiment, a second dosage formulation comprises second serotonergic drug.

In one embodiment, the methods disclosed herein comprise administering a second dosage formulation. In one embodiment, the methods disclosed herein comprise administering a third dosage formulation. In one embodiment, the methods disclosed herein comprise administering a fourth dosage formulation. In one embodiment, the methods disclosed herein comprise administering more than four dosage formulations.

In certain embodiments, the dosage formulation contains a desired amount of at least one compound of Formula I. In certain embodiments, the dosage formulation contains from about 0.01 mg to about 1,000 mg of the compound, such as from about 0.1 mg to about 500 mg, about 0.5 mg to about 100 mg, or from about 1 mg to about 50 mg. In certain embodiments, the dosage formulation is calculated to contain an amount of a compound of Formula I based on mg of compound per kg of the subject (mg/kg). In certain embodiments, the mg/kg range can be from about 0.001 mg/kg to about 10 mg/kg, such as from about 0.01 mg/kg to about 5 mg/kg, from about 0.05 mg/kg to about 4 mg/kg, from about 0.05 mg/kg to about 3 mg/kg, from about 0.05 mg/kg to about 3 mg/kg, from about 0.05 mg/kg to about 2 mg/kg, or from about 0.05 mg/kg to about 1 mg/kg. In some embodiments, the compound is dosed in an amount that is less than about 1 mg/kg, such as from about 0.001 mg/kg to about 0.99 mg/kg, from about 0.01 mg/kg to about 0.85 mg/kg, from about 0.05 mg/kg to about 0.75 mg/kg, from about 0.01 mg/kg to about 0.50 mg/kg, from about 0.01 mg/kg to about 0.25 mg/kg, or from about 0.01 mg/kg to about 0.10 mg/kg.

In one embodiment, the methods disclosed herein comprise administering one or more active ingredients, e.g., a compound(s) of Formula I, cannabinoids, terpenes, neurotransmitter activity modulators, etc., in more than two doses.

Disclosed herein is a method of treating a psychological problem, comprising:

identifying a person in need of treatment; and administering a compound of Formula I to the person in need of treatment, wherein the compound of Formula I modulates activity at a neurotransmitter receptor.

As used herein, the term "identifying a person in need of treatment" refers to analyzing, diagnosing, and/or determining whether a person requires treatment for a disease or condition. In one embodiment, identifying a person in need of treatment comprises diagnosing a person with a medical condition, e.g., a neurological disorder, a chemical imbalance, a hereditary condition, etc. In one embodiment, identifying a person in need of treatment comprises performing a psychiatric evaluation. In one embodiment, identifying a person in need of treatment comprises performing a blood test. In one embodiment, identifying a person in need of treatment comprises determining whether a person has a compulsive disorder. In one embodiment, identifying a person in need of treatment comprises self-identifying as having a compulsive disorder.

As used herein, the term "psychological disorder" refers to a condition wherein a person exhibits a pattern of behavioral and/or psychological symptoms that impact multiple life areas and create distress for the person experiencing these symptoms. In one embodiment, a psychological disorder is caused by a genetic disorder. In one embodiment, a psychological disorder is caused by a biological condition, e.g., excess hormone production, a lack of activity at a neurotransmitter receptor, a lack of producing neurotransmitters, etc. In one embodiment, the neurotransmitter receptor is a serotonin receptor.

In one embodiment, the psychological problem is an anxiety disorder. In one embodiment, the psychological problem is a depressive disorder. In one embodiment, the psychological problem is a compulsive disorder. In one embodiment, the psychological problem is characterized by neurodegeneration.

As used herein, the term "anxiety disorder" refers to a state of apprehension, uncertainty, and/or fear resulting from the anticipation of an event and/or situation. An anxiety disorder can disrupt the physical and psychological functions of a person. These disruptions can cause a small hindrance to a debilitating handicap for a person's everyday life. An anxiety disorder can cause a physiological symptom, e.g., muscle tension, heart palpitations, sweating, dizziness, shortness of breath, etc. An anxiety disorder can also cause a psychological symptom, e.g., fear of dying, fear of embarrassment or humiliation, fear of an event occurring, etc.

In one embodiment, an anxiety disorder comprises acute stress disorder, anxiety due to a medical condition, generalized anxiety disorder, panic disorder, panic attack, a phobia, post-traumatic stress disorder, separation anxiety disorder, social anxiety disorder, substance-induced anxiety disorder, or selective mutism.

As used herein, the term "acute stress disorder" refers to a condition developed after exposure to one or more traumatic events. Examples of traumatic events include, but are not limited to, exposure to war, rape or sexual violence, a physical attack, a mugging, childhood physical or sexual violence, kidnapping or being taken hostage, terrorist attacks, torture, natural disasters, and/or severe accidents. In one embodiment, acute stress disorder occurs within a day of experiencing a traumatic event. In one embodiment, acute stress disorder occurs within three days of experiencing a traumatic event. In some instances, acute stress disorder occurs within a week of experiencing a traumatic event. In some instances, acute stress disorder occurs within a month of experiencing a traumatic event.

As used herein, the term "anxiety due to another medical condition" refers to a condition wherein anxiety symptoms are developed because of a physiological and psychological consequence of a non-related disease, injury, and/or illness, e.g., an endocrine disease, a cardiovascular disorder, respiratory illness, a metabolic disturbance, a neurological illness, etc.

As used herein, the term "generalized anxiety disorder" refers to a condition of persistent and excessive anxiety and worry about various domains, e.g., work, school, social settings, etc., that an individual finds difficult to control. In addition, the individual experiences physical symptoms including restlessness, alertness, and/or nervousness; being easily fatigued, difficulty concentrating or mind going blank, irritability, muscle tension, and sleep disturbance.

As used herein, the term "panic disorder" refers to a condition wherein an individual experiences recurrent and unexpected panic attacks. The individual is persistently concerned about having more panic attacks and changes his or her behavior in maladaptive ways because of these panic attacks, e.g. avoidance of exercise, unfamiliar locations, new people, etc.

As used herein, the term "panic attack" refers to an abrupt surge of intense fear or intense discomfort that reaches a peak within a short period of time, e.g., seconds, minutes, hours, etc. In some instances, a panic attack comprises a physical and/or cognitive symptom. Panic attacks may be predictable, such as in response to a typically feared object or situation. In some instances, a panic attack occurs for no apparent reason.

As used herein, the term "phobia" refers to a condition of being fearful, anxious about, or avoidant of a circumscribed object and/or situation. In some instances, a phobia comprises a fear, anxiety, or avoidance that is induced by a situation to a degree that is persistent and out of proportion to the actual risk posed. Examples of phobias include, but are not limited to, a fear or anxiety of an animal, a natural environment, an injection-injury, etc.

As used herein, the term "post-traumatic stress disorder" refers to a condition developed after experiencing and/or witnessing a traumatic event or learning that a traumatic event has happened to a loved one. In some instances, a person shows symptoms of post-traumatic stress disorder within a week of experiencing the traumatic event. In some instances, a person shows symptoms of post-traumatic stress disorder within a month of experiencing the traumatic event. In some instances, a person shows symptoms of post-traumatic stress disorder within a year of experiencing the traumatic event. In some instances, a person shows symptoms of post-traumatic stress disorder after a year or more of experiencing the traumatic event. In some instances, post-traumatic stress disorder comprises a person re-experiencing the trauma event through intrusive distressing recollections of the event, flashbacks, and/or nightmares. In some instances, a symptom of post-traumatic stress disorder comprises emotional numbness and avoidance of places, people, and activities that are reminders of the trauma. In some instances, a symptom of post-traumatic stress disorder comprises increased arousal such as difficulty sleeping and concentrating, feeling anxious, and being easily irritated and angered.

As used herein the term "neurodegeneration" refers to the progressive loss of structure or function of neurons, including but not limited to the death of neurons. Many neurodegenerative diseases—including amyotrophic lateral sclerosis, Parkinson's disease, Alzheimer's disease, and Huntington's disease—occur as a result of neurodegenerative processes. Such diseases are incurable, resulting in progressive degeneration and/or death of neuron cells. Some attempts have been made to treat such diseases and conditions using fungal and plant extracts. But those methods all suffer from a common flaw in that the fungal and/or plants extracts fail to provide consistent or reliable amounts of the therapeutic compounds on account of relying on the highly variable chemical compositions of particular naturally occurring organisms.

As used herein, the term "separation anxiety disorder" refers to a condition wherein an individual is fearful and/or anxious about separation from an attachment figure to a degree that is developmentally inappropriate. In some instances, a separation anxiety disorder comprises a fear or anxiety about harm coming to an attachment figure. In some instances, a separation anxiety disorder comprises a fear of an event leading to the loss of or separation from an attachment figure and reluctance to go away from attachment figures. In some instances, a separation anxiety disorder comprises a nightmare and/or psychical symptom of distress.

As used herein, the term "social anxiety disorder" refers to a condition wherein an individual is fearful, anxious about, or avoidant of social interactions and situations that involve the possibility of being scrutinized. These social interactions and situations include meeting unfamiliar people, situations in which the individual may be observed eating or drinking, situations in which the individual performs in front of others, etc. In some instances, a social anxiety disorder is caused by the fear of being negatively evaluated by others, by being embarrassed, humiliated, rejected, and/or offending others.

As used herein, the term "substance-induced anxiety disorder" refers to a condition wherein anxiety caused by a substance intoxication and/or a withdrawal or to a medical treatment. In some instances, a withdrawal from a substance increases anxiety.

As used herein, the term "selective mutism" refers to a condition characterized by an individual's consistent failure to speak in social situations in which there is an expectation to speak, e.g., school, a lecture, a meeting, etc., even though the individual speaks in other situations. Failure to speak has significant consequences on achievement in academics, occupational settings, and/or otherwise interferes with normal social communication.

In some instances, an anxiety disorder comprises a medical diagnosis based on the criteria and classification from the Diagnostic and Statistical Manual of Medical Disorders, 5th Ed. In some instances, an anxiety disorder comprises a medical diagnosis based on an independent medical evaluation. In some instances, an anxiety disorder comprises a medical diagnosis based on a self-evaluation.

In one embodiment, the methods and compositions disclosed herein comprise administering an anxiolytic drug.

As used herein, the term "anxiolytic drug" refers to a compound or composition that reacts or influences activity at a neurotransmitter receptor, e.g., a compound of Formula I, a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, an anxiolytic drug binds on a neurotransmitter receptor. In one embodiment, an anxiolytic drug indirectly affects a neurotransmitter receptor, e.g., via interactions affecting the reactivity of other molecules at a neurotransmitter receptor. In one embodiment, an anxiolytic drug is an agonist. In one embodiment, an anxiolytic drug is an antagonist. In one embodiment, an anxiolytic drug acts (either directly or indirectly) at more than one type of neurotransmitter receptor.

In one embodiment, an anxiolytic drug is chosen from alprazolam, an alpha blocker, an antihistamine, a barbiturate, a beta blocker, bromazepam, a carbamate, chlordiazepoxide, clonazepam, clorazepate, diazepam, flurazepam, lorazepam, an opioid, oxazepam, temazepam, and triazolam.

As used herein, the term "depressive disorder" refers to a condition of low mood and aversion to activity that can affect a person's thoughts, behavior, feelings, and sense of well-being lasting for a time period. In one embodiment, a depressive disorder disrupts the physical and psychological functions of a person. In one embodiment, a depressive disorder causes a physiological symptom, e.g., weight loss, aches or pains, headaches, cramps, digestive problems, etc. In one embodiment, a depressive disorder causes a psychological symptom, e.g., persistent sadness; anxiety; feelings of hopelessness and irritability; feelings of guilt, worthlessness, or helplessness; loss of interest or pleasure in hobbies and activities; difficulty concentrating, remembering, or making decisions, etc.

In one embodiment, a depressive disorder is chosen from atypical depression, bipolar disorder, catatonic depression, depressive disorder due to a medical condition, major depressive disorder, postpartum depression, premenstrual dysphoric disorder, and seasonal affective disorder.

As used herein, the term "atypical depression" refers to a condition wherein an individual shows signs of mood reactivity (i.e., mood brightens in response to actual or potential positive events), significant weight gain, increase in appetite, hypersomnia, heavy, leaden feelings in arms or legs, and/or long-standing pattern of interpersonal rejection sensitivity that results in significant social or occupational impairment. Exemplary symptoms of atypical depression include, but are not limited to, daily sadness or depressed mood; loss of enjoyment in things that were once pleasurable; major changes in weight (gain or loss) or appetite; insomnia or excessive sleep almost every day; a state of physical restlessness or being rundown that is noticeable by others; daily fatigue or loss of energy; feelings of hopelessness, worthlessness, or excessive guilt almost every day; problems with concentration or making decisions almost every day; recurring thoughts of death or suicide, suicide plan, or suicide attempt.

As used herein, the term "bipolar disorder" refers to a condition that causes an individual to experience unusual shifts in mood, energy, activity levels, and the ability to carry out day-to-day tasks. Individuals with bipolar disorder experience periods of unusually intense emotion, changes in sleep patterns and activity levels, and unusual behaviors. These distinct periods are called "mood episodes." Mood episodes are drastically different from the moods and behaviors that are typical for the person. Exemplary symptoms of mania, excessive behavior, include, but are not limited to, abnormally upbeat, jumpy, or wired behavior; increased activity, energy, or agitation; exaggerated sense of well-being and self-confidence; decreased need for sleep; unusual talkativeness; racing thoughts; distractibility; and poor decision-making—for example, going on buying sprees, taking sexual risks, or making foolish investments.

Exemplary symptoms of depressive episodes, low mood, include, but are not limited by, depressed mood, such as feelings of sadness, emptiness, hopelessness, or tearfulness; marked loss of interest or feeling no pleasure in all—or almost all—activities; significant weight loss, weight gain, or decrease or increase in appetite; insomnia or sleeping too much; restlessness or slowed behavior; fatigue or loss of energy; feelings of worthlessness or excessive or inappropriate guilt; decreased ability to think or concentrate, or indecisiveness; and thinking about, planning or attempting suicide.

As used herein, the term "catatonic depression" refers to a condition causing an individual to remain speechless and motionless for an extended period. Exemplary symptoms of catatonic depression include, but are not limited to, feelings of sadness, which can occur daily, a loss of interest in most activities, sudden weight gain or loss, a change in appetite, trouble falling asleep, trouble getting out of bed, feelings of restlessness, irritability, feelings of worthlessness, feelings of guilt, fatigue, difficulty concentrating, difficulty thinking, difficulty making decisions, thoughts of suicide or death, and/or a suicide attempt.

As used herein, the term "depressive disorder due to a medical condition" refers to a condition wherein an individual experiences depressive symptom caused by another illness. Examples of medical conditions known to cause a depressive disorder include, but are not limited to, HIV/AIDS, diabetes, arthritis, strokes, brain disorders such as Parkinson's disease, Huntington's disease, multiple sclerosis, and Alzheimer's disease, metabolic conditions (e.g. vitamin B12 deficiency), autoimmune conditions (e.g., lupus and rheumatoid arthritis), viral or other infections (hepatitis, mononucleosis, herpes), back pain, and certain cancers (e.g., pancreatic).

As used herein, the term "major depressive disorder" refers to a condition characterized by a time period of low mood that is present across most situations. Major depressive disorder is often accompanied by low self-esteem, loss of interest in normally enjoyable activities, low energy, and pain without a clear cause. In some instances, major depressive order is characterized by two weeks. In some instances, an individual experiences periods of depression separated by years. In some instances, an individual experiences symptom of depression that are nearly always present. Major depressive disorder can negatively affect a person's personal, work, or school life, as well as sleeping, eating habits, and general health. 2-7% of adults with major depressive disorder commit suicide, and up to 60% of people who commit suicide had a major depressive disorder or another related mood disorder. Dysthymia is a subtype of major depressive disorder consisting of the same cognitive and physical problems as a major depressive disorder with less severe but longer-lasting symptoms. Exemplary symptoms of a major depressive disorder include, but are not limited to, feelings of sadness, tearfulness, emptiness or hopelessness; angry outbursts, irritability or frustration, even over small matters; loss of interest or pleasure in most or all normal activities; sleep disturbances, including insomnia or sleeping too much; tiredness and lack of energy; reduced appetite, weight loss or gain; anxiety, agitation or restlessness; slowed thinking, speaking, or body movements; feelings of worthlessness or guilt, fixating on past failures or self-blame; trouble thinking, concentrating, making decisions, and remembering things; frequent thoughts of death, suicidal thoughts, suicide attempts, or suicide; and unexplained physical problems, such as back pain or headaches.

As used herein, the term "postpartum depression" refers to a condition as the result of childbirth and hormonal changes, psychological adjustment to parenthood, and/or fatigue. Postpartum depression is often associated with women, but men can also suffer from postpartum depression as well. Exemplary symptoms of postpartum depression include, but are not limited to, feelings of sadness, hopeless, emptiness, or overwhelmed; crying more often than usual or for no apparent reason; worrying or feeling overly anxious; feeling moody, irritable, or restless; oversleeping, or being unable to sleep even when the baby is asleep; having trouble concentrating, remembering details, and making decisions; experiencing anger or rage; losing interest in activities that are usually enjoyable; suffering from physical aches and pains, including frequent headaches, stomach problems, and muscle pain; eating too little or too much; withdrawing from or avoiding friends and family; having trouble bonding or forming an emotional attachment with the baby; persistently doubting his or ability to care for the baby; and thinking about harming themselves or the baby.

As used herein, the term "premenstrual dysphoric disorder" refers to a condition wherein an individual expresses mood lability, irritability, dysphoria, and anxiety symptoms that occur repeatedly during the premenstrual phase of the cycle and remit around the onset of menses or shortly thereafter. Exemplary symptoms of premenstrual dysphoric disorder include, but are not limited to, lability (e.g., mood swings), irritability or anger, depressed mood, anxiety, and tension, decreased interest in usual activities, difficulty in concentration, lethargy and lack of energy, change in appetite (e.g., overeating or specific food cravings), hypersomnia or insomnia, feeling overwhelmed or out of control, physical symptoms (e.g., breast tenderness or swelling, joint or muscle pain, a sensation of 'bloating' and weight gain), self-deprecating thoughts, feelings of being keyed up or on edge, decreased interest in usual activities (e.g., work, school, friends, hobbies), subjective difficulty in concentration, and easy fatigability.

As used herein, the term "seasonal affective disorder" refers to a condition wherein an individual experiences mood changes based on the time of the year. In some instances, an individual experiences low mood, low energy, or other depressive symptoms during the fall and/or winter season. In some instances, an individual experiences low mood, low energy, or other depressive symptoms during the spring and/or summer season. Exemplary symptoms of seasonal affective disorder include, but are not limited to, feeling depressed most of the day or nearly every day; losing interest in activities once found enjoyable; having low energy; having problems with sleeping; experiencing changes in appetite or weight; feeling sluggish or agitated; having difficulty concentrating; feeling hopeless, worthless, or guilty; and having frequent thoughts of death or suicide.

In one embodiment, a depressive disorder comprises a medical diagnosis based on the criteria and classification from Diagnostic and Statistical Manual of Medical Disorders, 5th Ed. In one embodiment, a depressive disorder comprises a medical diagnosis based on an independent medical evaluation.

In one embodiment, the methods and compositions disclosed herein comprise administering an antidepressant.

As used herein, the term "antidepressant" refers to a compound or compounds that reacts or influences activity at a neurotransmitter receptor, e.g., a compound of Formula I, a serotonergic drug, an adrenergic receptor, a dopamine receptor, a GABAergic receptor, a glutaminergic receptor, a histaminergic receptor, a cholinergic receptor, an opioid receptor, or a glycinergic receptor, etc. In one embodiment, an antidepressant binds on a neurotransmitter receptor. In one embodiment, an antidepressant indirectly affects a neurotransmitter receptor, e.g., via interactions affecting the reactivity of other molecules at a neurotransmitter receptor. In one embodiment, an antidepressant is an agonist. In one embodiment, an antidepressant is an antagonist. In one embodiment, an antidepressant acts (either directly or indirectly) at more than one type of neurotransmitter receptor.

In one embodiment, an antidepressant is chosen from bupropion, citalopram, duloxetine, escitalopram, fluoxetine, fluvoxamine, milnacipran, mirtazapine, paroxetine, reboxetine, sertraline, and venlafaxine.

Disclosed herein is a method of treating headaches and/or migraines, comprising identifying a person in need of treatment and administering a composition disclosed herein to the person in need of treatment.

Disclosed herein is a method of treating nicotine addiction, comprising identifying a person in need of treatment and administering a composition disclosed herein to the person in need of treatment.

Disclosed herein is a method of treating drug addiction, comprising identifying a person in need of treatment and administering a composition disclosed herein to the person in need of treatment.

Disclosed herein is a method of treating alcohol addiction, comprising identifying a person in need of treatment and administering a composition disclosed herein to the person in need of treatment.

The compositions disclosed herein are useful for the treatment of compulsive disorders in humans, a variety of intractable psychiatric disorders, chronic depression, post-traumatic stress disorder, and drug or alcohol dependency. The compositions disclosed herein are also useful within the context of meditative, spiritual, and religious practices within a variety of contexts.

As used herein, the term "compulsive disorder" refers to a condition wherein an individual has an obsession causing a feeling of anxiety, fear, apprehension, etc., and has a compulsion to perform tasks to relieve said feeling of anxiety. An obsession is a thought that recurs and persists despite the efforts of an individual to ignore or confront them. In some instances, an obsession is relatively vague involving a general sense of disarray or tension accompanied by a belief that life cannot proceed as normal while the imbalance remains. In other instances, an obsession is more intense and could be a preoccupation with the thought or image of someone close to them dying or intrusions related to relationship rightness. Other obsessions concern the possibility that someone or something other than oneself—such as God, the Devil, or disease—will harm either the person, the people or things that the person cares about. In some instances, individuals perform compulsive rituals because they inexplicably feel they have to. In some instances, individuals perform compulsive rituals to mitigate the anxiety that stems from a particular obsession. The person feels that these actions will somehow either prevent a dreaded event from occurring or will push the event from their thoughts.

In one embodiment, a compulsive disorder is chosen from addiction, body dysmorphic disorder, excoriation disorder, hoarding disorder, obsessive-compulsive disorder, and trichotillomania.

As used herein, the term "addiction" refers to a physical and/or psychological dependence on a substance, activity, and/or any other habit. In one embodiment, an addiction is caused by the altered brain chemistry of an individual in response to a stimulus, e.g., a substance releasing large amounts of serotonin, an activity releasing large amounts of adrenaline, etc. In one embodiment, an addiction is a dependence on a substance, e.g., a drug, an alcohol, nicotine, a food, etc. In one embodiment, an addiction is a dependence on an activity, e.g., gambling, eating, shopping, etc.

Disclosed herein is a method of treating drug addiction, comprising administering a compound described herein or a composition disclosed herein to the person in need of treatment. In certain embodiments, the drug addiction is selected from amphetamine addiction, methamphetamine addiction, opioid addiction (e.g., oxycodone, fentanyl, or heroin addiction), and cocaine addiction. In certain embodiments, the drug addiction is amphetamine addiction. In certain embodiments, the amphetamine is methamphetamine.

As used herein, the term "body dysmorphic disorder" refers to a condition characterized by the obsessive idea that some aspect of an individual's appearance is severely flawed and warrants exceptional measures to hide or fix it. Exemplary symptoms of body dysmorphic disorder includes, but are not limited to, being extremely preoccupied with a perceived flaw in appearance that to others can't be seen or appears minor; a belief that a defect in appearance makes an individual ugly or deformed; a belief that others take special notice of an individual's appearance in a negative way or mock the individual; engaging in behaviors aimed at fixing or hiding the perceived flaw that are difficult to resist or control, such as frequently checking the mirror, grooming, or skin picking; attempting to hide perceived flaws with styling, makeup, or clothes; constantly comparing one's appearance with others; always seeking reassurance about one's appearance from others; having perfectionist tendencies; seeking frequent cosmetic procedures with little satisfaction; avoiding social situations; and being so preoccupied with one's appearance that it causes major distress or problems in a person's social life, work, school, or other areas of functioning.

As used herein, the term "excoriation disorder" refers to a condition of having a repeated urge to pick at one's own skin. In some instances, an excoriation disorder causes a person to often to pick their skin to the extent that damage is caused.

As used herein, the term "hoarding disorder" refers to a condition of persistent difficulty in discarding or parting with possessions, regardless of their value. Exemplary symptoms of a hoarding disorder include, but are not limited to, inability to throw away possessions; severe anxiety when attempting to discard items; great difficulty categorizing or organizing possessions; indecision about what to keep or where to put things; distress, such as feeling overwhelmed or embarrassed by possessions; suspicion of other people touching items; obsessive thoughts and actions; fear of running out of an item or of needing it in the future; checking the trash for accidentally discarded objects; and functional impairments, e.g., loss of living space, social isolation, family or marital discord, financial difficulties, health hazards, etc.

As used herein, the term "obsessive-compulsive disorder" refers to a condition in which an individual has uncontrollable, reoccurring thoughts and behaviors that he or she feels the urge to repeat over and over. In some instances, an obsessive-compulsive disorder manifests itself as an individual needing to clean in order to reduce the fear that germs, dirt, or chemicals will contaminate the individual and the individual will spend many hours washing themselves or cleaning their surroundings. In some instances, an obsessive-compulsive disorder manifests itself as an individual needing to dispel anxiety. An individual may utter a name, phrase or repeat a behavior several times. The individual knows these repetitions will not actually prevent injury, but fear of harm will occur if the repetitions are not performed. In some instances, an obsessive-compulsive disorder manifests itself as an individual needing to reduce the fear of harming oneself or by others by, e.g., forgetting to lock the door or turning off appliances, developing checking rituals, etc. In some instances, an obsessive-compulsive disorder manifests itself as an individual needing to order and arrange his or her surroundings to reduce discomfort, e.g., putting objects in a certain order, arranging household items in a particular manner or in a symmetric fashion, etc. In some instances, an obsessive-compulsive disorder manifests itself as an individual needing to respond to intrusive obsessive thoughts, e.g., praying or saying phrases to reduce anxiety or prevent a dreaded future event. In some instances, obsessive-compulsive disorder is caused by another medical condition. In some instances, obsessive-compulsive disorder is caused by a substance.

As used herein, the term "trichotillomania" refers to a condition of self-induced and recurrent loss of hair, e.g., pulling one's own hair out. In some instances, trichotillomania comprises an individual pulling their hair out at one location. In some instances, trichotillomania comprises an individual pulling their hair out at multiple locations. Exemplary symptoms of trichotillomania include, but are not limited to, recurrent pulling out of one's hair resulting in noticeable hair loss; an increased sense of tension immediately before pulling out the hair or when resisting the behavior; pleasure, gratification, or relief when pulling out the hair; the disturbance is not accounted for by another mental disorder and is not due to a general medical condition (i.e., dermatological condition); repeated attempts have been made to decrease or stop hair pulling; disturbances caused significant distress or impairment in social, occupational, or other important areas of functioning; distress including feelings of loss of control, embarrassment, shame; and impairment due to avoidance of work, school, or other public situations.

In one embodiment, a compulsive disorder comprises a medical diagnosis based on the criteria and classification from Diagnostic and Statistical Manual of Medical Disorders, 5th Ed.

In one embodiment, a compulsive disorder comprises a medical diagnosis based on an independent medical evaluation.

In some embodiments, the compositions described herein further comprise at least one compound not acting on a serotonin receptor.

In some embodiments, the compounds and compositions described herein can be used to treat or prevent seizure disorders, such as epilepsy. Exemplary types of epilepsy include, but are not limited to, absence seizures (staring spells) such as Childhood Absence Epilepsy, with or without myoclonia, Jeavons Syndrome (absence seizures (staring spells) with eyelid myoclonia), tonic-clonic seizures (body stiffening and jerking), myoclonic seizures (sudden muscle twitches), atonic seizures (sudden loss of muscle tone causing falls), clonic seizures (repetitive jerking movements), and focal seizures which can manifest with various symptoms depending on the affected brain region, like unusual sensations or involuntary movements in a specific body part. In certain embodiments, these diseases and disorders may be associated with gene dysfunction, including one or more mutations associated with at least one gene. In certain embodiments, the seizure disorder may be associated with gene dysfunction of at least one gene selected from CHD2, Cyclin-Dependent Kinase-Like 5 (CDKL5), SCN1A, SCN2A, SCN8A, ARX, KCNA1, KCNA2, KCNT1, KCNQ2, HCN1, PCDH19, GRIN1, GRIN2A, GRIN2B, PRRT2, CACNA1A, CACNA1C, CACNA1G, CACNA1E, CACNA1H, CACNA2D2, CACNB4, STXBP1, SYNGAPI, DEPDC5, TSC1, TSC2, PNKP, SLC2A1, FOXG1, GABRG2, GABRA1, LGI1, MECP2, UBE3A, SLC12A5, ALG13, HNRNPU, PPP2R$_5$D, GRIN1, GABRB3, and KCNB1

In certain embodiments, absence epilepsies may comprise absence seizures (brief staring spells and/or loss of awareness), sometimes lasting a few seconds. In certain embodiments, this may occur several times a day. In some embodiments, the absence seizures are, unlike most types of convulsive epilepsies and seizure disorders, non-convulsive in nature. As referenced herein and unless context dictates otherwise, "non-convulsive" seizures include those such as absence seizures that do not involve convulsive movements (i.e., rhythmic jerking or stiffening of muscles). While subtle motor signs such as eye fluttering or blinking, slight lip smacking, or minor hand movements may be observed in subjects presenting absence seizures, these movements would not generally be considered convulsive in nature.

In certain embodiments, it is believed that staring spells and/or loss of awareness are generally associated with a thalamocortical circuit disruption or thalamocortical oscillations. For example, in some embodiments, absence seizures are believed to arise from abnormal rhythmic oscillations between the thalamus and cerebral cortex. The thalamus, a relay center for sensory and motor signals, plays a key role in regulating consciousness and attention. In certain embodiments, these oscillations are driven by T-type calcium channels in thalamic relay neurons, which become hyperactive during seizures, leading to excessive synchronized firing. As further discussed herein, impaired GABAergic and glutamatergic signaling, ion channel dysregulation, cortical network hyperexcitability, and genetic contributions can also be associated with thalamocortical circuit disruptions.

Thalamocortical oscillations and thalamocortical circuit disruptions both involve the functional relationship between the thalamus and the cerebral cortex, yet they represent distinct physiological processes with different implications for brain function and disease. Thalamocortical oscillations refer to rhythmic patterns of neural activity that regulate various brain states, including sleep, wakefulness, and sensory processing. These oscillations arise from the dynamic interplay between thalamic relay neurons and cortical networks, producing characteristic waveforms such as sleep spindles (12-16 Hz), delta waves (1-4 Hz), and gamma oscillations (30-100 Hz). While these oscillations are essential for normal cognition and consciousness, their dysregulation can contribute to neurological disorders. In the case of absence seizures, excessive and hypersynchronous thalamocortical oscillations-particularly in the 3 Hz spike-and-wave range—are a hallmark feature. These abnormal oscillations may lead to brief periods of impaired consciousness, causing the characteristic staring spells and lack of awareness associated with the condition.

Thalamocortical circuit disruptions, on the other hand, typically involve structural or functional impairments in the connectivity between the thalamus and the cortex. Unlike oscillations, which can be part of normal physiology, circuit disruptions generally indicate pathology and are linked to a wide range of neurological conditions, including epilepsy, neurodevelopmental disorders, and neurodegenerative diseases. A disruption in this circuitry can impair the transmission of sensory, cognitive, and/or motor information, leading to deficits in attention, awareness, and sensory perception. In the context of absence seizures, while the disorder is primarily characterized by abnormal oscillations, some researchers suggest that underlying thalamocortical circuit dysfunction may contribute to the generation and propagation of these seizures. A breakdown in inhibitory or excitatory control within the thalamocortical network may predispose the system to enter the pathological rhythmic activity seen during absence seizures.

In certain embodiments, it has been surprisingly discovered that the compounds described herein (e.g., compounds of Formula I) may be effective for treating non-convulsive absence seizures and convulsive epileptic seizures. This finding is both surprising and unexpected due to fundamental neurophysiological and mechanistic differences between these seizure types. More specifically, convulsive epileptic seizures, such as tonic-clonic or focal motor seizures, are characterized by widespread cortical excitability, excessive neuronal firing, and synchronized hyperexcitability across broad cortical and subcortical networks. These seizures typically originate in the cortex and propagate to motor regions, leading to involuntary muscle contractions, loss of postural control, and violent convulsions. Historically, treatments for convulsive seizures often focus on suppressing cortical excitability, enhancing GABAergic inhibition, or blocking sodium or calcium channels to prevent excessive neuronal firing. In contrast, absence seizures, a form of non-convulsive epilepsy, arise from abnormal thalamocortical oscillations rather than cortical hyperexcitability. These seizures are typically characterized by 3 Hz spike-and-wave discharges and are thought to result from dysregulated interactions between the thalamus and cortex, specifically involving T-type calcium channel activity and aberrant GABAergic signaling within the reticular thalamic nucleus. Unlike convulsive seizures, which manifest through motor involvement, absence seizures present as brief staring episodes, loss of awareness, and behavioral arrest without significant motor convulsions.

Given the divergent neurophysiological mechanisms underlying convulsive seizures and non-convulsive absence seizures, it would not be expected that a compound effective for convulsive seizures—likely targeting cortical excitability—would also be effective in absence seizures, which arise from thalamocortical circuit dysfunction and/or oscillations rather than generalized cortical hyperexcitability.

Indeed, it has been previously known that convulsive and non-convulsive seizure disorders are subject to distinct pathophysiologies and drug targets. For example, most known drugs for treating convulsive seizures act on sodium channels (e.g., phenytoin, carbamazepine), GABA-A receptors (e.g., benzodiazepines), or glutamate receptors to suppress high-frequency cortical firing. In contrast, absence seizures have been previously known to respond preferentially to drugs that modulate T-type calcium channels (e.g., ethosuximide) or selectively alter thalamocortical rhythm generation. Many known first-line convulsive seizure treatments fail to control absence seizures and, in some cases, worsen them (e.g., phenytoin and carbamazepine can exacerbate absence seizures).

Moreover, historical precedent has largely suggested that there is limited—if any—overlap in the known treatments for convulsive and non-convulsive seizure disorders. Clinical and pharmacological data suggest that many drugs previously described as being effective for convulsive seizures are ineffective or even counterproductive in treating absence seizures. For example, sodium channel blockers, which suppress cortical excitability in convulsive epilepsy, do not typically prevent the synchronized thalamocortical oscillations seen in absence seizures. Given this precedent, the expectation would be that compounds described herein, if effective in convulsive seizures, would not necessarily modulate thalamocortical network dysfunction in a way that otherwise treats or controls absence seizures. However, contrary to this understanding, in some embodiments, Applicant has surprisingly discovered that compounds of Formula I may be effective in treating broad seizure types (e.g., convulsive and non-convulsive), suggesting an unanticipated and novel mode of action that is distinct from conventional anti-seizure medications. Additionally, this further suggests that patients with mixed seizure types (e.g., juvenile absence epilepsy with occasional convulsive episodes) could benefit from treating with compounds of Formula I rather than requiring multiple drugs, which is often necessary to manage absence seizures separately from convulsive seizures.

Given the well-established mechanistic divergence between convulsive and non-convulsive seizure types, it was not predictable that a compound having efficacy against convulsive seizures could also be effective against absence seizures (e.g., in some embodiments, via suppression of thalamocortical oscillatory disruptions). This surprising discovery further supports the novel therapeutic potential of the compounds of Formula I.

Several mutations have been associated with absence epilepsy, particularly in forms like childhood absence epilepsy (CAE) and juvenile absence epilepsy (JAE). These genes are often involved in the regulation of ion channels or neurotransmitter signaling. Some of the key genes implicated include:

CACNA1H:
- Function: Encodes a T-type calcium channel subunit that regulates neuronal excitability and rhythmic thalamocortical activity.
- Association: Mutations can lead to hyperexcitability in thalamic neurons, a key mechanism underlying absence seizures.

CACNA1A:
- Function: Encodes a P/Q-type calcium channel subunit involved in synaptic neurotransmitter release.
- Association: Mutations in this gene are also implicated in various epilepsy syndromes, including some cases of absence epilepsy.

GABRB3:
- Function: Encodes the β3 subunit of the GABA-A receptor, which is responsible for inhibitory neurotransmission.
- Association: Mutations or deletions in this gene reduce inhibitory signaling, contributing to the generalized spike-and-wave discharges seen in absence epilepsy.

GABRG2:
- Function: Encodes the γ2 subunit of the GABA-A receptor.
- Association: Mutations in this gene disrupt inhibitory GABAergic signaling, predisposing individuals to seizures.

SCN1A and SCN2A:
- Function: Encode voltage-gated sodium channel subunits critical for action potential propagation.
- Association: While SCN1A is more strongly associated with severe epilepsies (e.g., Dravet syndrome), mutations in SCN2A have been linked to milder epilepsy syndromes, including absence epilepsy.

SLC2A1:
- Function: Encodes GLUT1, a glucose transporter essential for brain energy metabolism.
- Association: Mutations in this gene can cause GLUT1 deficiency syndrome, which may present with absence seizures as part of the clinical picture.

CHRNA4:
- Function: Encodes a subunit of the nicotinic acetylcholine receptor, involved in excitatory neurotransmission.
- Association: Rare mutations have been identified in some families with absence epilepsy.

Absence seizures are often considered a polygenic disorder, meaning multiple genes, each with a small effect, may interact to increase susceptibility. In some cases, absence seizures exhibit an autosomal dominant inheritance pattern with incomplete penetrance. The most commonly implicated genes in absence seizures are those involved in calcium channel function (e.g., CACNA1H, CACNA1A) and GABAergic inhibition (e.g., GABRB3, GABRG2).

Some other diseases or disorders that are linked to, or otherwise have symptoms or side effects associated with, thalamocortical circuit disruption include, but are not limited to, Parkinson's disease, schizophrenia, autism spectrum disorder, ADHD, obsessive-compulsive disorder (OCD), depression, Tourette Syndrome, bipolar disorder, and multiple sclerosis.

Treatment-resistant absence epilepsy, also known as refractory or drug-resistant absence epilepsy, occurs when absence seizures fail to respond adequately to first-line antiepileptic drugs (AEDs) despite optimal treatment. In certain embodiments, this means that seizures persist even after trials of at least two appropriately chosen and dosed AEDs, either alone or in combination.

In some embodiments, the seizure disease or disorder is a Developmental Epileptic Encephalopathy. Developmental Epileptic Encephalopathies (DEEs) are a group of severe childhood-onset epilepsy syndromes characterized by frequent seizures, developmental delays, and EEG abnormalities that worsen cognitive and neurological development. Below in Table 3 is a list of common DEEs that may be treated with compounds described herein, along with brief explanations for each condition:

TABLE 3

| Disease or Disorder | Description | Key Features |
|---|---|---|
| Dravet Syndrome | A severe epilepsy syndrome starting in the first year of life, often triggered by fever; commonly associated with mutations in the SCN1A gene | Prolonged seizures, developmental delays, ataxia, and a high risk of sudden unexpected death in epilepsy (SUDEP) |
| Lennox-Gastaut Syndrome (LGS) | A childhood epilepsy syndrome characterized by multiple seizure types and intellectual disability; may be associated with mutations in the SCN1A gene; may result from brain injury, malformations, or genetic conditions | Tonic (stiffening) seizures, atypical absence seizures, slow spike-wave activity on EEG, and developmental regression |
| West Syndrome | A triad of infantile spasms, developmental regression, and a specific EEG pattern (hypsarrhythmia); often associated with genetic mutations, metabolic disorders, or structural brain abnormalities | Onset typically between 3-12 months; spasms often occur in clusters |

TABLE 3-continued

| Disease or Disorder | Description | Key Features |
|---|---|---|
| Early Infantile Epileptic Encephalopathy (EIEE, or Ohtahara Syndrome) | One of the earliest and most severe forms of DEE, presenting in the neonatal period; frequently linked to genetic mutations (e.g., STXBP1, KCNQ2) or structural brain abnormalities | Tonic seizures and a burst-suppression pattern on EEG |
| Myoclonic-Astatic Epilepsy (Doose Syndrome) | A childhood epilepsy syndrome characterized by myoclonic and atonic seizures; often has a genetic component, though specific mutations are less commonly identified | Sudden falls due to atonic (drop) seizures, developmental delays, and generalized spike-wave discharges on EEG |
| Epilepsy of Infancy with Migrating Focal Seizures (EIMFS) | A rare epilepsy syndrome presenting with migrating focal seizures in infancy; frequently associated with mutations in genes like KCNT1 or SCN2A | Drug-resistant seizures, developmental delays, and focal EEG abnormalities |
| CDKL5 Deficiency Disorder | A rare genetic condition caused by mutations in the CDKL5 gene, leading to early-onset seizures and severe developmental delays | Seizures starting in the first few months of life, hypotonia, and profound intellectual disability |
| PCDH19-Related Epilepsy | A genetic epilepsy syndrome linked to mutations in the PCDH19 gene, primarily affecting females | Clustered seizures, normal early development, and variable cognitive outcomes |
| Tuberous Sclerosis Complex (TSC) | A genetic disorder caused by mutations in the TSC1 or TSC2 genes, leading to benign tumors in multiple organs | Seizures, developmental delays, and autism spectrum disorders; seizures often include focal and infantile spasms |
| Rett Syndrome | A neurodevelopmental disorder primarily affecting girls, caused by mutations in the MECP2 gene | Loss of developmental milestones, repetitive hand movements, and epilepsy; seizures typically arise later in childhood |
| Pyridoxine-Dependent Epilepsy (PDE) | A metabolic disorder caused by mutations in the ALDH7A1 gene, leading to seizures that are responsive to vitamin B6 (pyridoxine) | Neonatal or infantile-onset seizures resistant to conventional antiepileptic drugs |
| SCN8A-Related Epilepsy | Caused by mutations in the SCN8A gene, this condition leads to early-onset epilepsy and developmental delays | Seizures, hypotonia, intellectual disability, and movement disorders |
| GLUT1 Deficiency Syndrome | A metabolic disorder caused by impaired glucose transport across the blood-brain barrier due to mutations in the SLC2A1 gene | Seizures, developmental delay, and a movement disorder; symptoms improve with a ketogenic diet |
| KCNQ2 Encephalopathy | A severe epilepsy syndrome caused by mutations in the KCNQ2 gene | Neonatal seizures, developmental delays, and hypotonia; seizures may decrease with age, but developmental challenges persist |
| STXBP1 Encephalopathy | A genetic epilepsy syndrome caused by mutations in the STXBP1 gene | Early-onset epilepsy, developmental delay, and movement abnormalities |

In some embodiments, the seizure disease or disorder is also associated with intellectual disabilities (ID). In certain embodiments, the compounds described herein may be suitable for treating such seizure disorders associated with ID. In some embodiments, the seizure disease or disorder associated with ID may include Lennox-Gastaut Syndrome, Dravet Syndrome, Rett Syndrome, Tuberous Sclerosis Complex, as well as others listed below in Table 4:

TABLE 4

| Disease or Disorder | Description | Key Features |
|---|---|---|
| Angelman Syndrome | A genetic disorder characterized by developmental delays, a happy demeanor, and ataxia. | Seizures: Common, typically generalized seizures<br>ID: Severe intellectual disability and lack of speech development.<br>Onset: Infancy to early childhood.<br>Cause: Deletion or mutation in the UBE3A gene |

TABLE 4-continued

| Disease or Disorder | Description | Key Features |
|---|---|---|
| Landau-Kleffner Syndrome (LKS) | Rare childhood epilepsy syndrome associated with language regression | Seizures: Typically focal or generalized, often occurring during sleep.<br>ID: Not always present, but developmental regression can mimic intellectual disability.<br>Onset: 3-7 years.<br>Cause: Unknown, though linked to EEG abnormalities. |
| Fragile X Syndrome | A genetic disorder causing intellectual disability, behavioral issues, and sometimes epilepsy | Seizures: Often focal or generalized.<br>ID: Ranges from mild to severe.<br>Onset: Early childhood.<br>Cause: Mutation in the FMR1 gene. |
| West Syndrome (Infantile Spasms) | A severe epilepsy syndrome in infants, characterized by spasms, developmental delays, and an abnormal EEG (hypsarrhythmia) | Seizures: Infantile spasms.<br>ID: Often severe intellectual disability and developmental delays.<br>Onset: Typically between 4-8 months of age.<br>Cause: Various, including structural brain abnormalities, genetic mutations, or metabolic conditions |
| Neurofibromatosis Type 1 (NF1) | A genetic disorder causing tumors along nerves and skin changes | Seizures: Occur in some cases, often due to brain involvement.<br>ID: Learning disabilities are common; severe intellectual disability is less frequent.<br>Onset: Childhood.<br>Cause: Mutation in the NF1 gene. |
| CDKL5 Deficiency Disorder | A rare neurodevelopmental disorder associated with early-onset epilepsy. | Seizures: Severe, treatment-resistant seizures beginning in infancy.<br>ID: Profound intellectual disability and developmental delays.<br>Onset: Infancy.<br>Cause: Mutations in the CDKL5 gene. |
| Phelan-McDermid Syndrome | A rare genetic disorder caused by deletion or mutation of the SHANK3 gene | Seizures: Occur in some cases, usually focal or generalized.<br>ID: Moderate to severe intellectual disability, often with autism-like features.<br>Onset: Early childhood.<br>Cause: Genetic deletion/mutation |
| Mitochondrial Disorders | A group of disorders caused by mitochondrial dysfunction, affecting energy production | Seizures: Common and often severe.<br>ID: Ranges from mild to profound, depending on the specific condition.<br>Examples: MELAS (Mitochondrial Encephalomyopathy, Lactic Acidosis, and Stroke-like episodes) |
| Aicardi Syndrome | A rare disorder affecting brain development, found almost exclusively in females | Seizures: Infantile spasms and other seizure types.<br>ID: Severe intellectual disability and developmental delays.<br>Onset: Infancy.<br>Cause: Unknown, possibly X-linked genetic mutation |
| Pitt-Hopkins Syndrome (PTHS) | Pitt-Hopkins syndrome is a rare genetic neurodevelopmental disorder caused by mutations in the TCF4 gene, which is critical for brain development and function. Epilepsy is common, but not universal, in individuals with PTHS. Seizure types can vary and often include generalized or focal seizures | ID: PTHS is characterized by moderate to severe intellectual disability. Developmental delays are profound, with limited or absent speech and motor impairments.<br>Other Features: Breathing abnormalities, such as hyperventilation and breath-holding spells. Distinct facial features (broad nasal bridge, prominent cupid's bow). Behavioral traits resembling autism spectrum disorder. |

TABLE 4-continued

| Disease or Disorder | Description | Key Features |
|---|---|---|
| | | Onset: Developmental delays are noticeable in infancy, and seizures typically manifest in early childhood. Cause: Mutation or deletion of the TCF4 gene located on chromosome 18q21 |

In some embodiments, subjects having developmental epileptic encephalopathy (DEE) may suffer from absence seizures. In DEE, absence seizures tend to have atypical features and are often more severe and treatment-resistant compared to those in non-DEE patients.

Here's how they may present differently:

| Feature | Absence Seizures in Non-DEE (Typical Absences) | Absence Seizures in DEE (Atypical Absences) |
|---|---|---|
| Onset age | Typically 4-10 years old | Can occur in infancy or early childhood |
| Duration | Short, 5-10 seconds | Longer, up to 30 seconds or more |
| Awareness | Complete loss of awareness, but brief | May have partial awareness, slower recovery |
| Motor Symptoms | Often no motor involvement or subtle eye blinking | Can include tonic (stiffening), atonic (dropping), or myoclonic (jerking) components |
| Triggers | Hyperventilation is a common trigger | Less responsive to hyperventilation |
| EEG Patterns | 3 Hz spike-and-wave discharges | Slower spike-and-wave patterns (2.5 Hz or less), often irregular |
| Cognitive Impact | Generally normal intelligence and development | Associated with cognitive and developmental regression |
| Response to Medication | Usually responds well to ethosuximide, valproate, or lamotrigine | Often drug-resistant, requiring multiple or alternative treatments |

In some embodiments, the compositions described herein comprise a serotonergic drug, wherein the serotonergic drug is selected from Formula I. In some embodiments, the composition comprises a single serotonergic drug. In some embodiments, the serotonergic drug consists essentially of a compound of Formula I.

In some embodiments, a compound of Formula I may be administered to a subject, wherein the administration is guided by certain contraindications. As described herein, a "contraindicated" compound for a method of treatment described herein is secondary compound that should not be used in a particular patient/subject due to a high risk of harm, serious adverse effects, or potential life-threatening interactions. For example, in certain embodiments, adverse drug-drug interactions could take place when a subject receiving a compound of Formula I is also administered a monoamine oxidase inhibitor that reduces or inhibits the in vivo metabolism of the compound of Formula I. Therefore, in certain embodiments, the compounds of Formula I should only be administered to subjects that are not also receiving contraindicated secondary compounds, such as a serotonin receptor agonist, a serotonin receptor antagonist, an SNRI, an SSRI, or a monoamine oxidase inhibitor. Exemplary serotonin receptor agonists include, but are not limited to, fenfluramine, lorcaserin, and bexicaserin.

Although the disclosure has been described with reference to various exemplary embodiments, it is to be understood that these embodiments are merely illustrative of the principles and applications of the present disclosure. Those having skill in the art would recognize that various modifications to the exemplary embodiments may be made, without departing from the scope of the disclosure.

Where reference is made to a particular compound, it should be understood that this disclosure also contemplates salts and derivatives of that compound as well as degradation products, such as oxidized versions of explicitly disclosed molecules.

Moreover, it should be understood that various features and/or characteristics of differing embodiments herein may be combined with one another. It is, therefore, to be understood that numerous modifications may be made to the illustrative embodiments and that other arrangements may be devised without departing from the scope of the disclosure.

Furthermore, other embodiments of the disclosure will be apparent to those skilled in the art from consideration of the specification and practice of the disclosure disclosed herein. It is intended that the specification and examples be considered as exemplary only, with a scope and spirit being indicated by the claims.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, the terms "about" and "approximately" mean±20%, ±10%, 5%, or ±1% of the indicated range, value, or structure, unless otherwise indicated.

EXAMPLES

Example 1

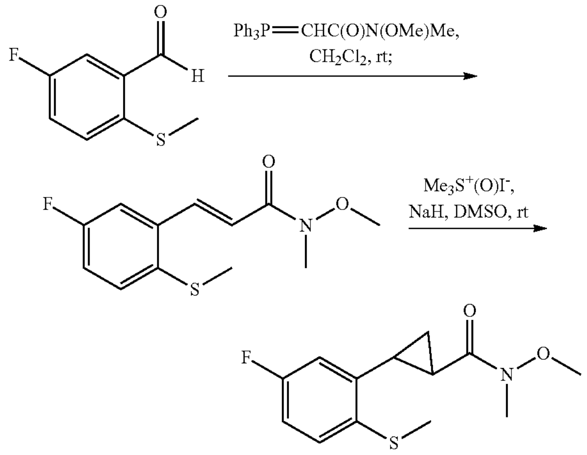

To a solution of 5-fluoro-2-(methylthio)benzaldehyde (1.0 mmol) in anhydrous dichloromethane (10 mL) was added N-methoxy-N-methyl(triphenylphosphoranylidene) acetamide (1.5 mmol), and the solution was stirred at room temperature overnight. The solution was then concentrated, and the residue was purified by silica gel chromatography using 15% ethylacetate in hexanes to afford (E)-3-(5-fluoro-2-(methylthio)phenyl)-N-methoxy-N-methylacrylamide.

Trimethylsulfoxonium iodide (1.0 mmol) is suspended in anhydrous DMSO (5 mL), and sodium hydride (1.0 mmol) was added in small portions. The mixture was stirred at room temperature for 1 hour to afford a clear solution. A solution of (E)-3-(5-fluoro-2-(methylthio)phenyl)-N-methoxy-N-methylacrylamide (0.6 mmol) in anhydrous DMSO (5 mmol) was then slowly added and the solution is stirred at room temperature overnight. Workup with water and EtOAc followed by purification by silica gel chromatography using 15% ethylacetate in hexanes afforded 2-(5-fluoro-2-(methylthio)phenyl)-N-methoxy-N-methylcyclopropane-1-carboxamide.

Example 2

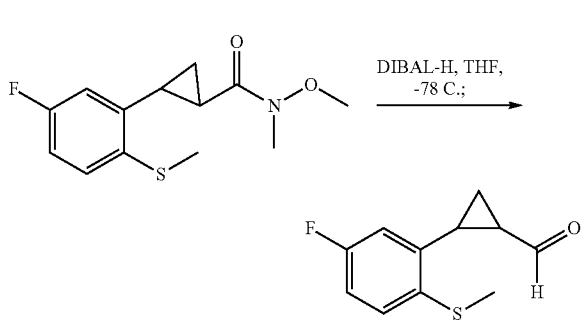

A solution of 2-(5-fluoro-2-(methylthio)phenyl)-N-methoxy-N-methylcyclopropane-1-carboxamide (0.5 mmol) in anhydrous THF (10 mL) was cooled to −78° C. under argon. To this solution was added slowly DIBAL-H (1.0 M solution in THF, 1.0 mmol) and the solution was stirred at −78° C. for 3 hours. Saturated aqueous solution of Rochelle's salt was added to quench the reaction and the mixture was warmed to room temperature, stirred for 1 hour and filtered. The solid was washed with EtOAc and the filtrate is extracted with EtOAc. The combined organic phases were washed with brine, dried over sodium sulfate, and concentrated to afford 2-(5-fluoro-2-(methylthio)phenyl)cyclopropane-1-carbaldehyde.

Example 3

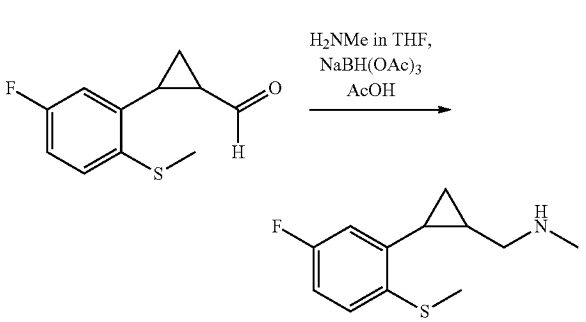

To a suspension of methyl amine (0.1 mL of 2.0M in THF) and AcOH (0.1 mL) and THF (10 mL) was added sodium triacetoxy borohydride (0.3 mmol) followed by the slow addition of 2-(5-fluoro-2-(methylthio)phenyl)cyclopropane-1-carbaldehyde (0.1 mmol) in THF (5 mL). The reaction was stirred under argon for 3 hours at room temperature before quenching with water and extracting with DCM. The organic phases were washed with brine, dried over sodium sulfate, concentrated, and purified by silica gel chromatography using 7% MeOH in DCM to afford the free base 1-(2-(5-fluoro-2-(methylthio)phenyl)cyclopropyl)-N-methylmethanamine.

Example 4

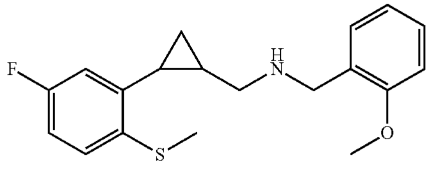 [SMILES: COc1ccccc1CNCC1CC1c1cc(F)ccc1SC]

Example 3 is repeated using 2-methoxybenzylamine as the primary amine to afford 1-(2-(5-fluoro-2-(methylthio) phenyl)cyclopropyl)-N-(2-methoxybenzyl)methanamine.

Example 5

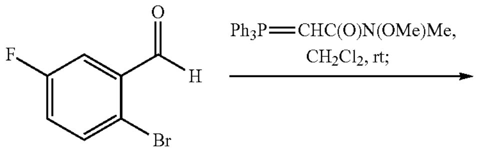

-continued

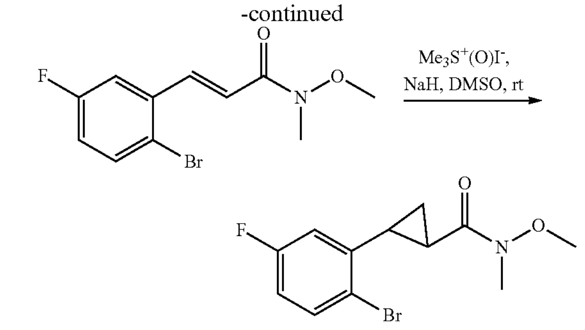

Example 1 is repeated using 2-bromo-5-fluorobenzaldehyde as the starting material to afford 2-(2-bromo-5-fluorophenyl)-N-methoxy-N-methylcyclopropane-1-carboxamide.

Example 6

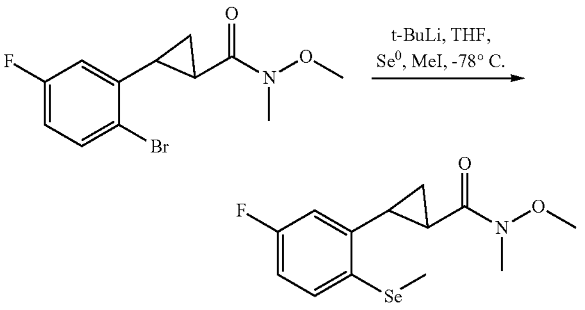

Under an inert atmosphere was added tert butyl lithium (1.25 mL of 1.6M in hexanes) to a stirred solution of 2-(2-bromo-5-fluorophenyl)-N-methoxy-N-methylcyclopropane-1-carboxamide (1 mmol) in anhydrous THF (40 mL) at −78 C. After 30 minutes the reaction was allowed to warm to room temperature and selenium (1 mmol, <5 mm) was added under a brisk stream of nitrogen and the reaction was further purged with nitrogen for 5 minutes. A solution of methyl iodide (1.2 mL of 1.0M in THF) was added slowly to the reaction mixture and 20 minutes the reaction was concentrated in vacuo, then redissolved in dichloromethane and washed with water. The organic phase was separated, dried over sodium sulfate, filtered, and concentrated before purification via silica gel chromatography with 4% MeOH in DCM to afford 2-(5-fluoro-2-(methylselanyl)phenyl)-N-methoxy-N-methylcyclopropane-1-carboxamide.

Example 7

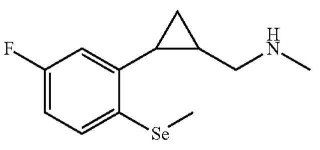

The 2-(5-fluoro-2-(methylselanyl)phenyl)-N-methoxy-N-methylcyclopropane-1-carboxamide product of Example 6 is subjected to the reaction conditions of Examples 2 and 3 to afford the 1-(2-(5-fluoro-2-(methylselanyl)phenyl)cyclopropyl)-N-methylmethanamine product.

Example 8

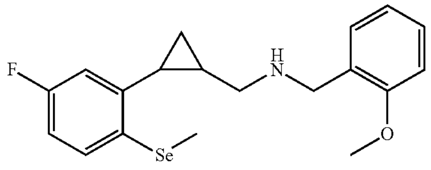 [SMILES: COc1ccccc1CNCC1CC1c1cc(F)ccc1[Se]C]

The 2-(5-fluoro-2-(methylselanyl)phenyl)-N-methoxy-N-methylcyclopropane-1-carboxamide product of Example 6 is subjected to the reaction conditions of Examples 2 and 4 to afford 1-(2-(5-fluoro-2-(methylselanyl)phenyl)cyclopropyl)-N-methylmethanamine.

Example 9

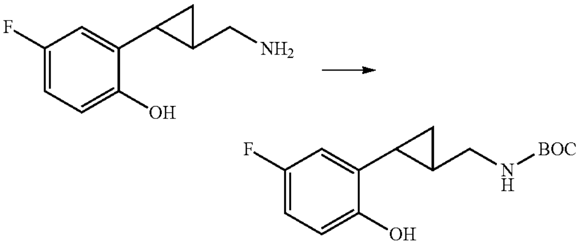

The racemic starting material, trans-2-(5-fluorophenyl-2-hydroxy)cyclopropylmethylamine, is prepared according to the procedure described in Cho et al., J. Med. Chem. 2009, 52, 1885, which is incorporated herein by reference. To a solution of trans-2-(5-fluorophenyl-2-hydroxy)cyclopropylmethylamine (55.2 mmol) and $Boc_2O$ (60.7 mmol) in $CH_2Cl_2$ is added triethylamine (221 mmol) at 0° C. The mixture is stirred at 0° C. for 30 min and then at rt for 30 min. To the resulting mixture is added sat. aq $NaHCO_3$. The organic layer is further washed with water (Å~1), dried over $Na_2SO_4$, and concentrated in vacuo. The residue is purified by flash chromatography using gradient elution from 0% EtOAc-hexane to 30% EtOAc-hexane to afford the protected carbamate as a white solid.

Example 10

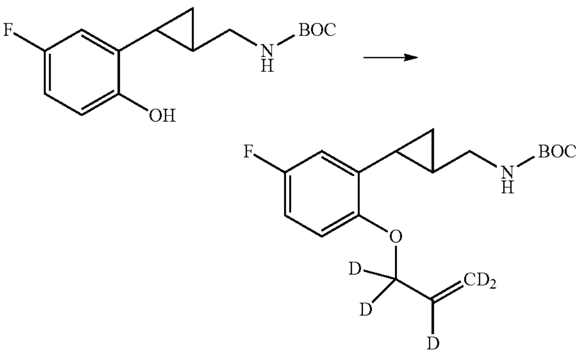

To a solution of the BOC-protected amine (17.8 mmol) in DMF are added $K_2CO_3$ (71.1 mmol) and allyl-d5 bromide (71.1 mmol). After the mixture is stirred at 60° C. in a microwave reactor for 2 hrs, the organic layer is washed with brine, dried over $Na_2SO_4$, filtered, and concentrated. The crude product is purified by flash chromatography using gradient elution from 0% EtOAc-hexane to 20% EtOAc-hexane to afford the racemic target compound.

Example 11

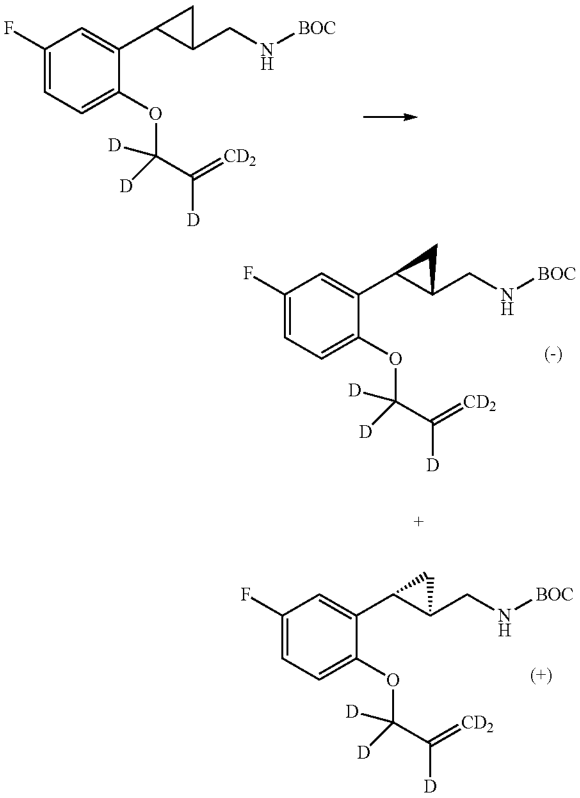

The BOC-protected racemate prepared according to the method of Example 10 is separated by chiral HPLC (Hexane/iPrOH, 96/4 isocratic, stack injections, flowrate of 12 mL/min, λ=280 nm) using chiralpak AD column to afford the (+)-isomer and the (−)-isomer.

Example 12

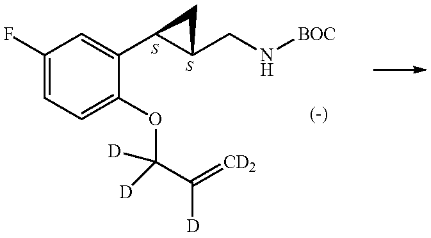

-continued

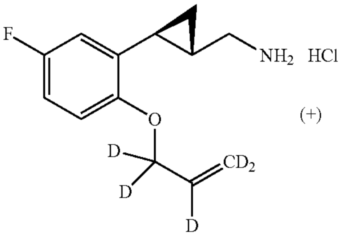

The (−) isomer produced according to Example 11 (17.3 mmol) is dissolved in a 2 N HCl solution in diethyl ether (86 mmol), and the reaction mixture is stirred at ambient temperature for 48 h. A white precipitate will form after several hours, and the mixture is stirred until the reaction was complete by TLC. The crude precipitate is filtered and purified by recrystallization from ethanol/$Et_2O$ to afford the target compound as a white powder.

Example 13

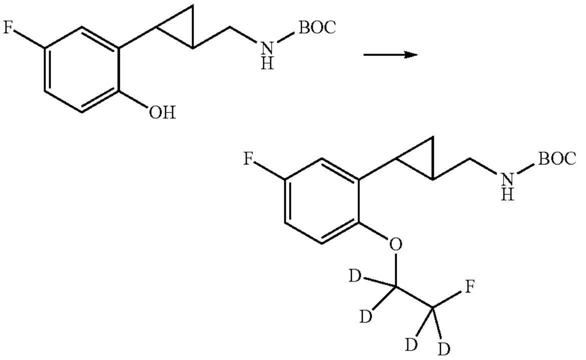

The d4 BOC racemate product is produced according to the procedure set forth in PCT Patent Publication WO2020/260196 (see, e.g., pages 30 and 31), which is incorporated herein by reference in its entirety, except phenol 1 is replaced with the BOC-protected compound prepared according to Example 9 above.

Example 14

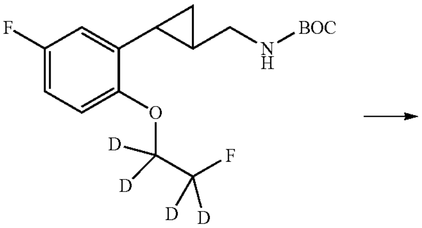

-continued

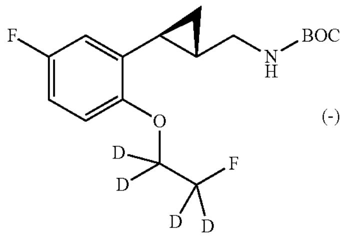

+

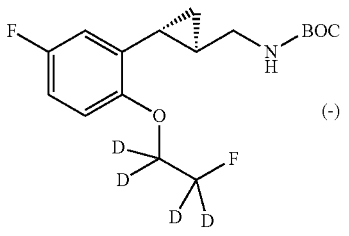

The d4 BOC-protected racemate prepared according to the method of Example 13 is separated by chiral HPLC (Hexane/iPrOH, 96/4 isocratic, stack injections, flowrate of 12 mL/min, λ=280 nm) using chiralpak AD column to afford the (+)-isomer and the (−)-isomer.

Example 15

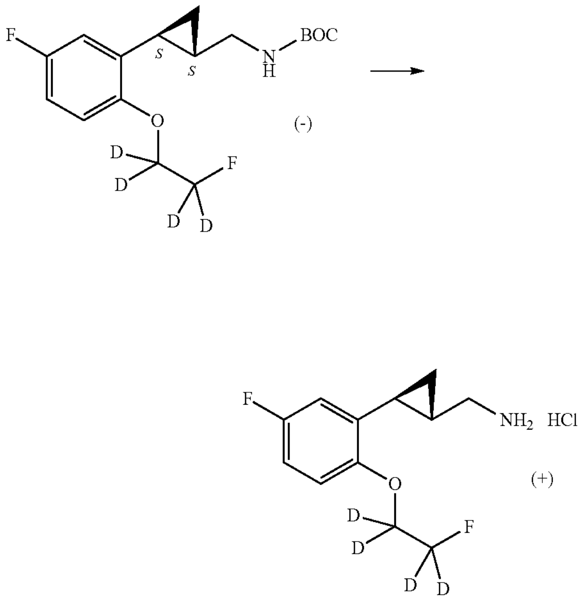

The (−) isomer produced according to Example 14 (17.3 mmol) is dissolved in a 2 N HCl solution in diethyl ether (86 mmol), and the reaction mixture is stirred at ambient temperature for 48 h. A white precipitate will form after several hours, and the mixture is stirred until the reaction was complete by TLC. The crude precipitate is filtered and purified by recrystallization from ethanol/$Et_2O$ to afford the target compound as a white powder.

Example 16

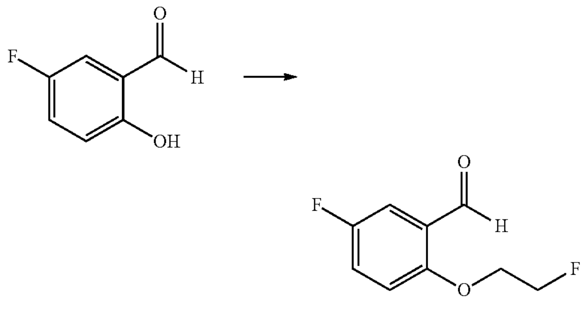

To a solution of the starting phenol (2.8 g, 20 mmol) and 2-iodo-1-fluoroethane (2 equiv) in anhydrous DMF (1 M) was added $Cs_2CO_3$ (2 equiv) at room temperature. The reaction mixture was heated at 50° C. until the reaction was complete as indicated by TLC analysis. The reaction mixture was allowed to cool to room temperature and diluted with water and diethyl ether. The phases were separated and the aqueous phase was extracted with diethyl ether (x3). The combined organic extracts were washed with water (x2) and brine, and dried over anhydrous sodium sulfate. After filtration, the solvent was removed in vacuo to provide a crude solid that was used in the next step without purification.

Example 17

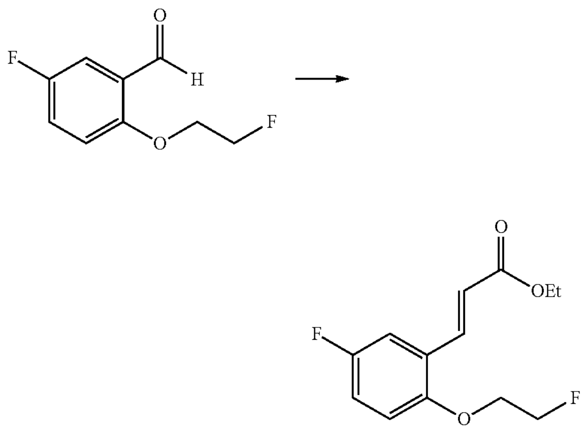

To a vigorously stirred suspension of NaH (60% mineral oil, 1.4 equiv) in THE (50 mL) was slowly added triethyl phosphonoacetate (1.2 equiv) dropwise at room temperature. Following the cessation of gas evolution, a 1 M THE solution of crude product of Example 16 was added dropwise at room temperature. The reaction was quenched after 30 min by the careful addition of water and diethyl ether. The phases were separated and the aqueous phase was extracted with diethyl ether (x3). The combined organic extracts were combined and washed with water (x2) and brine, and dried with anhydrous sodium sulfate. After filtration, the solvent was removed in vacuo to provide the crude solid product that was used in the next step without purification.

Example 18

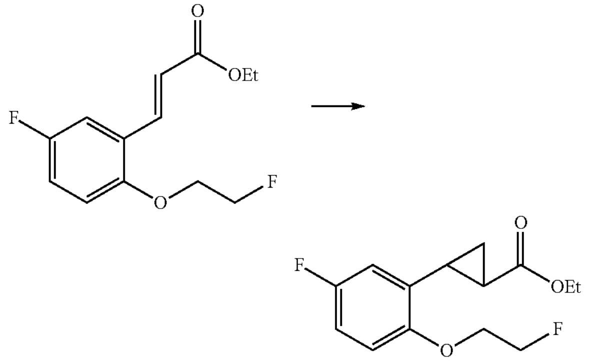

To a vigorously stirred suspension of trimethylsulfoxonium iodide (1.5 equiv) in DMSO (0.2 M) was added portion wise NaH (60% mineral oil, 1.5 equiv) at room temperature. The reaction mixture was allowed to stir until the reaction mixture became homogeneous (ca. 45-60 min) at which point a 1 M DMSO solution of the crude product produced in Example 17 was added dropwise. The reaction mixture was allowed to stir for at least 2 hours (or sooner if TLC indicated a complete reaction) and quenched by the addition of water and diethyl ether. The phases were separated, and the aqueous phase was extracted with diethyl ether (x3). The combined organic extracts were combined and washed with water (x2) and brine, and dried over anhydrous sodium sulfate. After filtration, the solvent was removed in vacuo to provide a crude oil that was purified by a flash silica gel plug (dry load, hexane then 15% EA/Hex) to provide 1.26 g of the desired ester product as colorless oil (36% yield over 3 steps).

Example 19

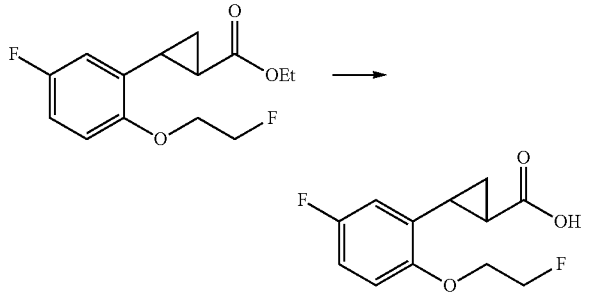

To a stirred solution of the ester product of Example 18 in THE (20 mL) was added an aqueous solution of lithium hydroxide monohydrate (3.0 equiv) in water (20 mL). The reaction mixture was heated to 60° C. and stirred overnight. The reaction mixture was then allowed to cool to room temperature and diluted with diethyl ether. The phases were separated and the organics washed with sat. aq. sodium bicarbonate (x2). The combined aqueous extracts were acidified to pH=1 and extracted with dichloromethane (x3). The combined organic extracts were dried over anhydrous sodium sulfate, filtered, and concentrate in vacuo to afford the acid product as a white solid.

Example 20

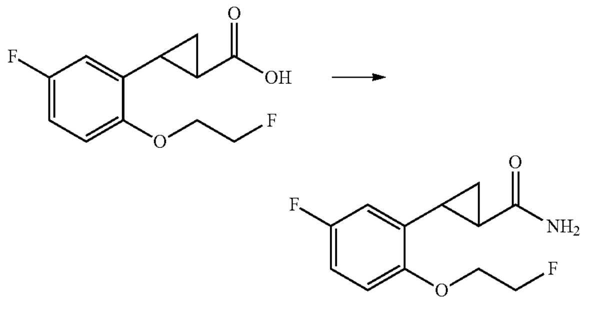

To a stirred solution of 365 mg of the acid product from Example 19 in DMF (0.1 M) at room temperature was added 1,1'-carbonyldiimidazole (2.0 equiv). The reaction mixture was allowed to stir at room temperature for 30 min before ammonium acetate (10 equiv) and triethyl amine (5 equiv) are added. The reaction mixture is allowed to stir at room temperature overnight before being quenched by the addition of diethyl ether and 1 M HCl. The phases were separated and the aqueous was extracted with diethyl ether (x3). The combined organic extracts were washed with 1 M HCl, sat. aq. sodium bicarbonate, water, and brine, and dried over anhydrous sodium sulfate. After filtration, the solvent was removed in vacuo to afford the amide product which was used in the next step without additional purification.

Example 21

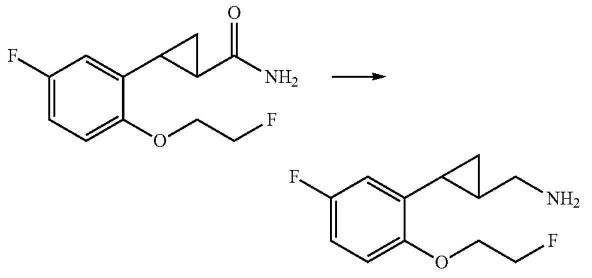

To a stirred solution of the amide produced in Example 20 in THF (0.1 M) was added dropwise $BH_3$-THF (1 M solution in THF, 5 equiv). The reaction mixture was refluxed for 4 hours before cooling to room temperature and quenching with methanol. The reaction mixture was concentrated to dryness, diluted with methanol (0.1 M) and 6 M HCl (3 mL), and refluxed for 30 min. After cooling to room temperature, the methanol was removed in vacuo and the crude mixture was basified with 3 M NaOH aqueous solution and extracted with DCM (x5). The combined organic extracts were washed with brine and dried with anhydrous sodium sulfate, filtered, and concentrated in vacuo to afford the target as solid. Formation of the free base target compound was confirmed by HRMS $(M+H)^+$ (Found: 228.1204 m/z; Calc'd: 228.1194 m/z) and $^1H$ NMR (600 MHz, $d_4$-MeOH) δ 6.94 (dd, J=9.0, 4.6 Hz, 1H), 6.89 (ddd, J=9.0, 8.0, 3.0 Hz, 1H), 6.76 (dd, J=9.4, 3.0 Hz, 1H), 4.92-4.70 (m, 2H), 4.38-4.16 (m, 2H), 3.02 (d, J=7.5 Hz, 2H), 3.05-2.99 (m, 2H), 2.16 (dt, J=9.0, 5.3 Hz, 1H), 1.31-1.22 (m, 1H), 1.18 (dt, J=8.5, 5.5 Hz, 1H), 1.04 (dt, J=9.0, 5.2 Hz, 1H).

Example 22

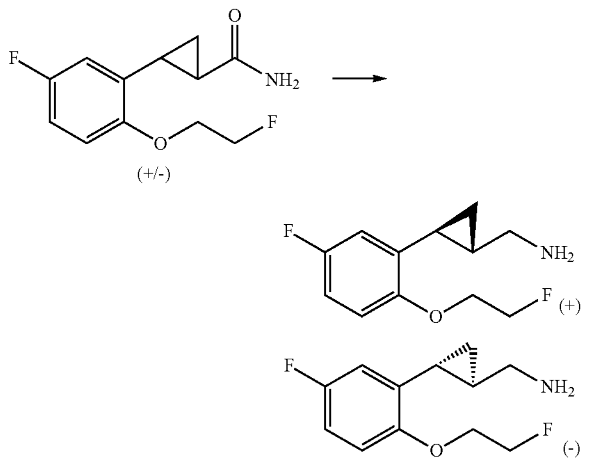

The racemate free base product prepared according to the method of Example 21 was separated by chiral HPLC, hexane/iPrOH/DEA, 90/10 (0.1% diethylamine), 5 μl injection, flowrate of 10 mL/min, λ=280 nm, using Chiralpak AD-H column to afford the (+)-isomer (20 min) and the (−)-isomer (25 min).

Example 23

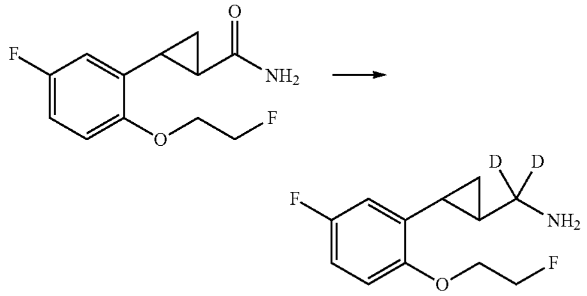

To a stirred solution of the amide produced in Example 20 in THE (0.1 M) in an ice bath was added dropwise lithium aluminium deuteride (10 equiv) portion wise. The reaction mixture was allowed to warm to room temperature and additional lithium aluminum deuteride (5 equiv) was added. The reaction mixture was quenched at 0° C. by the addition of water and basified with 3 M KOH solution. The aqueous phase was extracted with DCM (x5) and dried over anhydrous sodium sulfate, filtered, and concentrated in vacuo to afford the d2 free base racemate of the desired product as a white solid. Formation of the target d2 free base was confirmed by HRMS (ESI+) calc'd for $C_{12}H_{14}D_2F_2NO^+$ $[M+H]^+$: 230.1320; found: 230.1310; and $^1$H NMR (600 MHz, $d_4$-MeOH) δ 6.94 (dd, J=9.0, 4.6 Hz, 1H), 6.89 (ddd, J=9.0, 8.0, 3.0 Hz, 1H), 6.76 (dd, J=9.4, 3.0 Hz, 1H), 4.95-4.69 (m, 2H), 4.35-4.17 (m, 2H), 2.16 (dt, J=9.0, 5.3 Hz, 1H), 1.25 (dt, J=9.7, 4.9 Hz, 1H), 1.18 (dt, J=8.5, 5.5 Hz, 1H), 1.04 (dt, J=9.0, 5.2 Hz, 1H).

Example 24

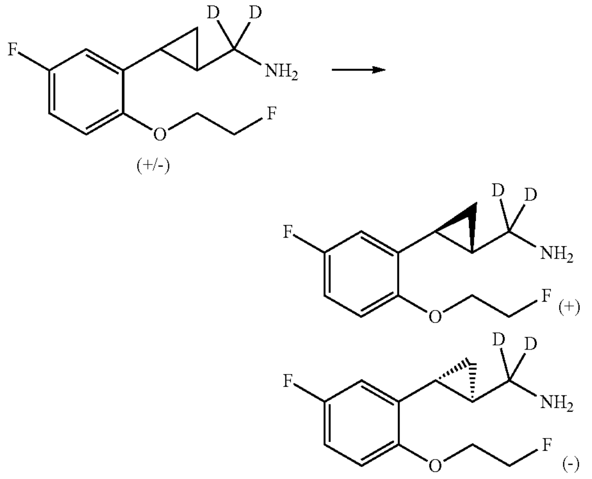

The racemate free base product prepared according to the method of Example 23 was separated by chiral HPLC, hexane/iPrOH/DEA, 90/10 (0.1% diethylamine), 5 μl injection, flowrate of 10 mL/min, λ=280 nm) using Chiralpak AD-H column to afford the (+)-isomer (20 min) and the (−)-isomer (25 min).

Example 25

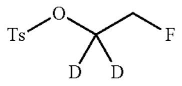 [SMILES: [2H]C([2H])(CF)OS(=O)(=O)c1ccc(C)cc1]

To a solution of ethyl fluoroacetate (10 mmol) in diethyl ether (50 mL) was added an excess of lithium aluminum deuteride (3.0 equiv) portion wise at 0° C. Upon completion of the reaction as indicated by TLC, the reaction mixture was quenched carefully with water and acidified with 1 M HCl. The phases were separated, and the aqueous phase was extracted with DCM (x3). The combined organic extracts were dried over anhydrous sodium sulfate and filtered. To the filtrate was added tosyl chloride (1.7 equiv), triethylamine (2.0 equiv) and 5 mol % DMAP. The reaction mixture was allowed to stir overnight before being concentrated and dry loaded onto a silica gel column (elution: 5, 10, 15, 25% ethyl acetate in hexane) to provide 2-fluoroethyl-1,1-d2 4-methylbenzenesulfonate as a colorless oil (73% yield).

Example 26

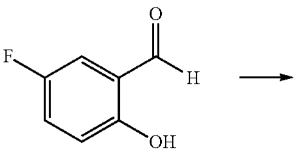

-continued

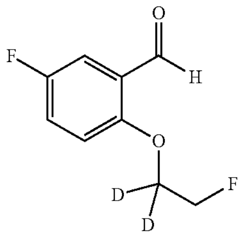

The procedure of Example 16 was repeated, except 2-iodo-1-fluoroethane was replaced with $TsOCD_2CH_2F$ prepared according to Example 25 to afford the free base of the target d2 product.

Example 27

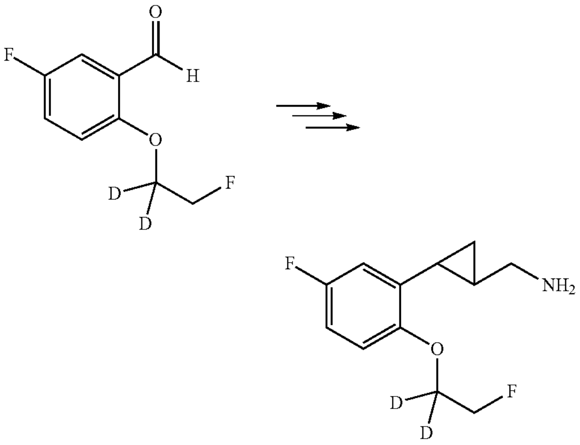

The procedure of Example 17 was repeated, except the aldehyde was replaced with the d2 aldehyde produced according to Example 26. The procedures of Examples 18 through 21 were then followed with the d2 intermediates to afford the free base of the target d2 racemate. Formation of the desired product was confirmed by HRMS ($ESI^+$) calc'd for $C_{12}H_{14}D_2F_2NO^+$ $[M+H]^+$: 230.1320; found 230.1314; and $^1H$ NMR (600 MHz, $d_4$-MeOH) δ 6.94 (dd, J=9.0, 4.6 Hz, 1H), 6.89 (ddd, J=9.0, 8.0, 3.1 Hz, 1H), 6.76 (dd, J=9.4, 3.0 Hz, 1H), 4.90-4.72 (m, 2H), 3.07-2.98 (m, 2H), 2.16 (dt, J=9.0, 5.3 Hz, 1H), 1.30-1.21 (m, 1H), 1.18 (dt, J=8.5, 5.5 Hz, 1H), 1.04 (dt, J=9.0, 5.2 Hz, 1H).

Example 28

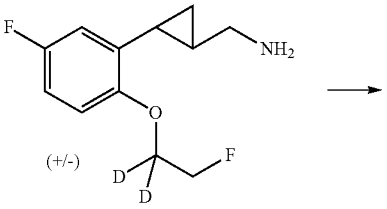

(+/-)

-continued

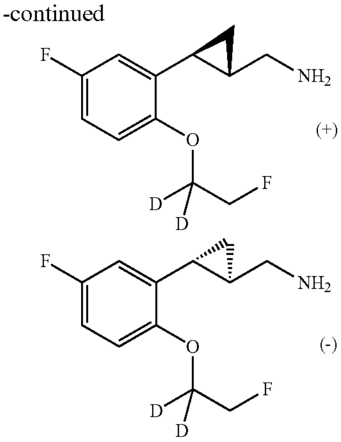

(+)

(-)

The racemate free base product prepared according to the method of Example 27 was separated by chiral HPLC, hexane/iPrOH/DEA, 90/10 (0.1% diethylamine), 5 ul injection, flowrate of 10 mL/min, λ=280 nm) using Chiralpak AD-H column to afford the (+)-isomer (20 min) and the (−)-isomer (25 min).

Example 29

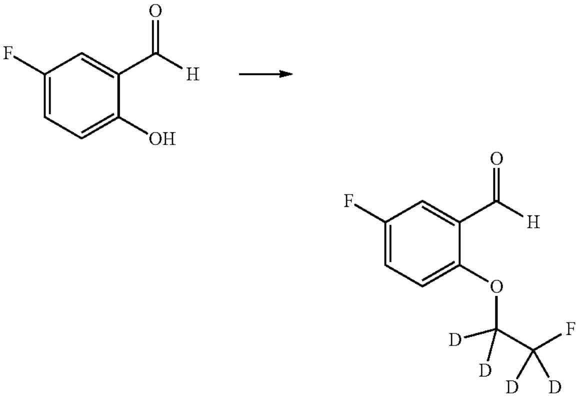

The procedure of Example 16 was repeated, except 2-iodo-1-fluoroethane was replaced with $TsOCD_2CD_2F$ prepared according to the method set forth in WO2020/260196A1 (incorporated herein by reference in its entirety), to afford the free base of the target d4 aldehyde product.

Example 30

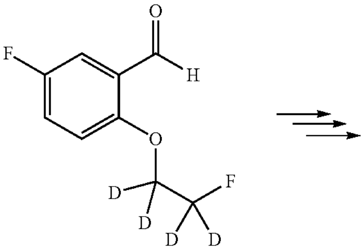

-continued

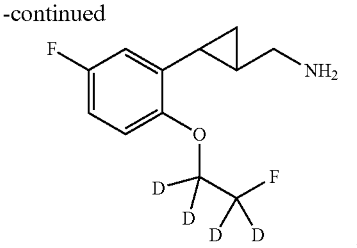

The procedure of Example 17 was repeated, except the aldehyde was replaced with the d4 aldehyde produced according to Example 29. The procedures of Examples 18 through 21 were then followed with the d4 intermediates to afford the free base of the target d4 racemate. Formation of the desired product was confirmed by HRMS (ESI$^+$) calc'd for $C_{12}H1_2D4F_2NO^+$ $[M+H]^+$: 232.1446; found 232.1440; and $^1H$ NMR (600 MHz, $d_4$-MeOH) δ 6.94 (dd, J=9.0, 4.6 Hz, 1H), 6.89 (ddd, J=9.0, 8.0, 3.1 Hz, 1H), 6.76 (dd, J=9.4, 3.1 Hz, 1H), 3.09-2.97 (m, 2H), 2.16 (dt, J=9.0, 5.3 Hz, 1H), 1.30-1.23 (m, 1H), 1.18 (dt, J=8.5, 5.5 Hz, 1H)1.04 (dt, J=9.0, 5.2 Hz, 1H).

Example 31

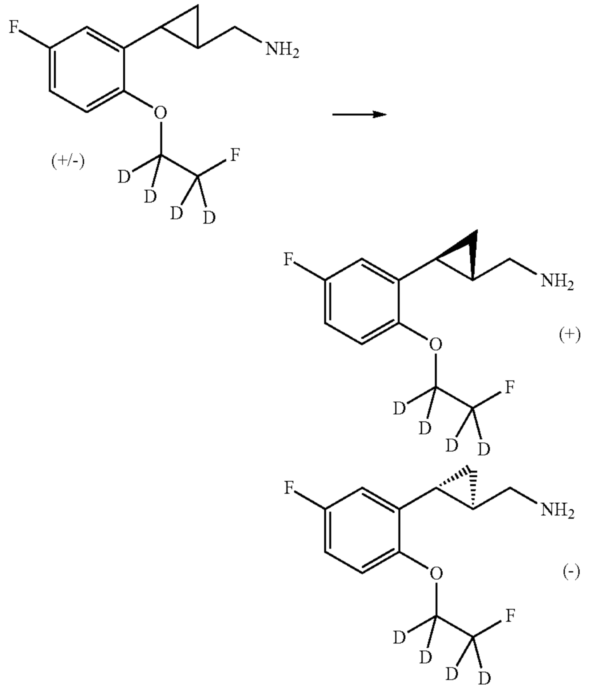

The racemate free base product prepared according to the method of Example 31 was separated by chiral HPLC, hexane/iPrOH/DEA, 90/10 (0.1% diethylamine), 5 ul injection, flowrate of 10 mL/min, λ=280 nm) using Chiralpak AD-H column to afford the (+)-isomer (20 min) and the (−)-isomer (25 min).

Example 32. Production of Hydrofumarate Salts (Aka [1:1] Fumarate Salts)

[1:1]hydrofumarate salts of each one of the compounds are separately produced from the compounds of Examples 3, 4, 7, and 8 using the following procedure:

1 equiv of the free base product is dissolved in acetone and is added dropwise to a boiling solution of fumaric acid (1 equiv) in acetone. A precipitate forms immediately and the precipitate/acetone is stored overnight at −20° C. The solids are then filtered and washed with ice-cold acetone to yield the desired hydrofumarate salt.

Example 33. Production of Fumarate Salts (Aka [2:1] Fumarate Salts)

[2:1] fumarate salts of each one of the compounds are separately produced from the compounds of Examples 3, 4, 7, and 8 using the following procedure:

1 equiv of the free base product is dissolved in acetone and is added dropwise to a boiling solution of fumaric acid (0.5 equiv) in acetone. A precipitate forms immediately and the precipitate/acetone is stored overnight at −20° C. The solids are then filtered and washed with ice-cold acetone to yield the desired fumarate salt.

Functional Assays for 5-HT2A, 5-HT2B, and 5-HT2C Receptors

To measure 5-HT2 receptor-mediated Gq activation via Gq/γ1 dissociation as measured by Bioluminescence Resonance Energy Transfer (BRET) (McCorvy J D, Wacker D, Wang S, Agegnehu B, Liu J, Lansu K, Tribo AR, Olsen RHJ, Che T, Jin J, Roth BL. Structural determinants of 5-HT2B receptor activation and biased agonism. Nat Struct Mo/Biol. 2018; 25(9): 787-96), HEK293T cells were sub-cultured in Dulbecco's Modified Eagle Medium (DMEM) supplemented with 10% dialyzed fetal bovine serum (FBS) and were co-transfected in a 1:1:1:1 ratio with Rluc8-fused human Gαq (Gαq-Rluc8), a GFP2-fused to the C-terminus of human Gγ1(Gγ1-GFP2), human Gβ1, and 5-HT2 receptor using TransiT-2020. After at least 18-24 hours, transfected cells were plated in poly-lysine coated 96-well white clear bottom cell culture plates in DMEM containing 1% dialyzed FBS at a density of 25,000-40,000 cells in 200 μL per well and incubated overnight. The following day, medium was decanted, and cells were washed with 60 μL of drug buffer (1×HBSS, 20 mM HEPES, pH 7.4), then 60 μL of drug buffer was added per well. Cells were pre-incubated at in a humidified atmosphere at 37° C. before receiving drug stimulation. Drug stimulation utilized 30 μL addition of drug (3X) diluted in McCorvy buffer (1×HBSS, 20 mM HEPES, pH 7.4, supplemented with 0.3% BSA fatty acid free, 0.03% ascorbic acid) and plates were incubated at for 1 hour at 37° C. Substrate addition occurred 15 minutes before reading and utilized 10 μL of the Rluc substrate coelenterazine 400a for Gq dissociation BRET$^2$ (Prolume/Nanolight, 5 μM final concentration). Plates were read for luminescence at 400 nm and fluorescent GFP2 emission at 510 nm at 1 second per well using a Mithras LB940 multimode microplate reader (e.g. one provided by Berthold). The BRET ratios of fluorescence/luminescence were calculated per well and were plotted as a function of drug concentration using Graphpad Prism 8 (Graphpad Software Inc., San Diego, CA). Data were normalized to % 5-HT stimulation and analyzed using nonlinear regression "log(agonist) vs. response" to yield Emax and $EC_{50}$ parameter estimates. Results are shown in Table 5, where A=<10; B=10 to <100; C=100 to 1000 and D=>1000; +++=>80%; ++=50 to 80%; and +=<50%; NA=No Activity. Gq signaling bias is reported for compounds exhibiting primary signaling for 5-HT2C via Gq-coupled signaling mechanism when compared to signaling mechanisms taking place through B-arrestin. Hallucinogenic ("Hall") or non-hallucinogenic ("N-Hall") plastogenic effect is predicted for compounds based on the level 5-HT2A agonist efficacy.

potencies of compounds and other reference compounds can also be compared statistically using an extra-sum-of-squares F-test.

TABLE 5

| | 5-HT2C | | 5-HT2B | | 5-HT2A | | 5-HT2C Gq | |
|---|---|---|---|---|---|---|---|---|
| Compound | $EC_{50}$ (nM) | Emax (%) | $EC_{50}$ (nM) | Emax (%) | $EC_{50}$ (nM) | Emax (%) | signaling bias? | Hall or N-Hall? |
| 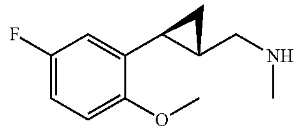 | B | ++ | B | ++ | C | ++ | Yes | N-Hall |
| 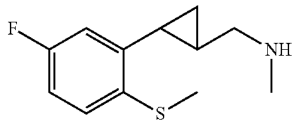 | A | ++ | NA* | NA* | C | ++ | Yes | N-Hall |
| 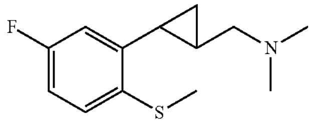 [SMILES: CSc1ccc(F)cc1C1CC1CN(C)C] | B | + | NA* | NA* | D | + | Yes | N-Hall |

*Data suggests antagonistic effect at 5-HT2B.

Biological Studies

Head-Twitch Response (HTR) Experiments.

Dose-response studies. Dose-response studies for compounds of Formula I are performed in four consecutive steps:

(a). Formulation work. A suitable (non-toxic) vehicle is identified that can be used to dissolve the compound.

(b). Pilot dose-finding study. HTR-inducing drugs typically have biphasic bell-shaped (inverted U-shaped) dose-response functions, with ascending and descending phases. To quantify the potency of a drug in a HTR dose-response study, doses covering the entire extent of the ascending phase should be included, as well as at least one dose that falls on the descending phase. A pilot dose-finding study is performed to identify a set of doses that matches those requirements. For the pilot, male C57BL/6J mice are injected with a range of doses (typically 0.3-30 mg/kg) by the IP or SC route and then behaviors are recorded in a magnetometer chamber for up to 150 minutes.

(c). Dose-response study. Groups of male C57BL/6J mice with a magnet implant are injected with vehicle or 4-5 doses of the compound (n=5-7 mice/group) by the IP or SC route and then behaviors are recorded in a magnetometer chamber for at least 30 minutes.

(d). Repeated testing. Although potency can typically be quantified based on a single dose-response study, in some instances repeated testing may be necessary. For example, the doses selected for testing may not have been ideal to calculate the median effective dose (ED50 value). If necessary, a second or third dose-response study is performed.

Analysis: The following analyses are performed for dose-response studies: HTR counts are analyzed using a 1-way ANOVA followed by a post-hoc test (Dunnett's test).

The median effective dose ($ED_{50}$ value) for the compounds (in mg/kg or moles/kg) will be calculated by non-linear regression using a gaussian or sigmoidal model. The HTR counts can be binned (e.g., blocks of 1, 2, 5, or 10 minutes) and analyzed using a 2-way ANOVA (drug×time) followed by a post-hoc test (Dunnett's test or Tukey's test). $5\text{-HT}_{2A}$ Antagonist blockade studies. Four groups of male C57BL/6J mice with a magnet implant are pretreated SC with the selective $5\text{-HT}_{2A}$ antagonist M100907 (vehicle, 0.001, 0.01, or 0.1 mg/kg). Twenty minutes later, all of the animals are injected IP or SC with one dose of the compound (n=5-7 mice/group) and then behaviors are recorded in a magnetometer chamber for 30 minutes. $5\text{-HT}_{1A}$ Antagonist blockade studies. Four groups of male C57BL/6J mice (n=5-7 mice/group) with a magnet implant are pretreated SC with the selective $5\text{-HT}_{1A}$ antagonist WAY-100635 (vehicle or 1 mg/kg). Twenty minutes later, the animals are injected IP or SC with vehicle or one dose of the compound and then behaviors are recorded in a magnetometer chamber for at least 30 minutes.

Extended time-course studies. Male C57BL/6J mice with a magnet implant are injected IP or SC with up to three different treatments (n=5-6 mice/group) and then behaviors are recorded in a magnetometer chamber for up to 5 hours (the exact assessment period used will depend on the duration-of-action of the Material being tested).

Brain penetration testing. These studies are used to test whether 5-HT2A ligands that do not induce the HTR are brain penetrant in mice. Male C57BL/6J mice with a magnet implant are pretreated IP or SC with vehicle or three doses of the 5-HT2A ligand (n=5-7 mice/group); 20 minutes later, all of the mice are injected IP with 1 mg/kg (±)-DOI HCl, and then behaviors are recorded in a magnetometer chamber for 20-30 minutes.

hERG Inhibition Studies.

All experiments are conducted manually using a HEKA EPC-10 amplifier at room temperature in the whole-cell mode of the patch-clamp technique. HEK293 cells stably expressing hKv11.1 (hERG) under G418 selection can be sourced from the University of Wisconsin, Madison. Cells are cultured in DMEM containing 10% fetal bovine serum, 2 mM glutamine, 1 mM sodium pyruvate, 100 U ml-1 streptomycin, and 500 mg ml-1 penicillin, 100 μg ml-1 G418. The cell line is not authenticated or tested for mycoplasma contamination. Before experiments, cells are grown to 60-80% confluency, lifted using TrypLE, and plated onto poly-1-lysine-coated coverslips. Patch pipettes are pulled from soda lime glass (micro-haematocrit tubes) and should exhibit resistances of 2-4 MO. For the external solution, normal sodium Ringer is used (160 mM NaCl, 4.5 mM KCl, 2 mM $CaCl_2$, 1 mM $MgCl_2$, 10 mM HEPES, pH 7.4 and 290-310 mOsm). The internal solution used is potassium fluoride with ATP (160 mM KF, 2 mM $MgCl_2$, 10 mM EGTA, 10 mM HEPES, 4 mM NaATP, pH=7.2 and 300-320 mOsm). A two-step pulse (applied every 10 s) from −80 mV initially to 40 mV for 2 s and then to −60 mV for 4 s, is used to elicit hERG currents. The percentage reduction of tail current amplitude by the compounds of Formula I that are tested is determined and data are shown as mean±s.d. (n=3-4 per data point). For all experiments, solutions of the drugs are prepared fresh from 10 mM stocks in DMSO. The final DMSO concentration never exceeds 1%.

Serotonin and Opioid Receptor Functional Assays.

Functional assay screens at 5-HT and opioid receptors are performed in parallel using the same compound dilutions and 384-well-format high-throughput assay platforms. Assays are used to assess activity at all human isoforms of the receptors, except where noted for the mouse 5-$HT_{2A}$ receptor. Receptor constructs in pcDNA vectors are generated from the Presto-Tango GPCR library39 with minor modifications. All tested compounds of Formula I are serially diluted in drug buffer (HBSS, 20 mM HEPES, pH 7.4 supplemented with 0.1% bovine serum albumin and 0.01% ascorbic acid) and dispensed into 384-well assay plates using a FLIPR Tetra automated dispenser head (Molecular Devices). Every plate includes a positive control such as 5-HT (for all 5-HT receptors), DADLE (DOR), salvinorin A (KOR), and DAMGO (MOR).

For measurements of 5-$HT_{2A}$ 5-$HT_{2B}$, and 5-$HT_{2C}$ Gq-mediated calcium flux function, HEK Flp-In 293, T-Rex stable cell lines (Invitrogen) are loaded with Fluo-4 dye for one hour, stimulated with compounds and read for baseline (0-10 s) and peak fold-over-basal fluorescence (5 min) at 25° C. on the FLIPR Tetra system. For measurement of 5-$HT_6$ Gs and 5-$HT_{7a}$ functional assays, -mediated cAMP accumulation is detected using the split-luciferase GloSensor assay in HEKT cells measuring luminescence on a Microbeta Trilux (Perkin Elmer) with a 15 min drug incubation at 25° C. For 5-$HT_{1A}$, 5-$HT_{1B}$, 5-$HT_{1F}$, MOR, KOR and DOR functional assays, Gi/o,—mediated cAMP inhibition is measured using the split-luciferase GloSensor assay in HEKT cells, conducted similarly to that above, but in combination with either 0.3 μM isoproterenol (5-$HT_{1A}$, 5-$HT_{1B}$, 5-$HT_{1F}$) or 1 μM forskolin (MOR, KOR and DOR) to stimulate endogenous cAMP accumulation. For measurement of 5-$HT_{1D}$, 5-$HT_{1E}$, 5-$HT_4$, and 5-$HT5_A$ functional assays, 1-arrestin2 recruitment is measured by the Tango assay using HTLA cells expressing tobacco etch virus (TEV) fused-β-arrestin2, as described previously with minor modifications. Cell lines are not authenticated, but they are purchased mycoplasma-free and tested for mycoplasma contamination. Data for all assays are plotted and nonlinear regression is performed using "log(agonist) vs. response" in GraphPad Prism to yield estimates of the efficacy (Emax and half-maximal effective concentration (ECSO)).

Pharmacokinetic Studies.

Male and female C57/BL6J mice (12 weeks old) are administered a compound of Formula I via i.p. injection at doses of either 50 mg kg-1, 10 mg kg-1 or 1 mg kg-1. Mice are euthanized 15 min or 3 h after injection by cervical dislocation. Two males and two females are used per dose and time point. Brain and liver are collected, flash-frozen in liquid nitrogen, and stored at −80° C. until metabolomic processing. Whole brain and liver sections are lyophilized overnight to complete dryness, then homogenized with 3.2 mm diameter stainless-steel beads using a GenoGrinder for 50 s at 1,500 rpm. Ground tissue is then extracted using 225 μl cold methanol, 190 μl water, 750 μl methyl tert-butyl ether (MTBE). Seven method blanks and seven quality-control samples (pooled human serum, BiolVT) are extracted at the same time as the samples. The nonpolar fraction of MTBE is dried under vacuum and reconstituted in 60 μl of 90:10 (v/v) methanol: toluene containing 1-cyclohexyldodecanoic acid urea as an internal standard. Samples are then vortexed, sonicated and centrifuged before analysis.

For analysis of the tested compound in liver and brain, samples are randomized before injection with method blanks and quality-control samples are analyzed between every ten study samples. A six-point calibration curve is analyzed after column equilibration using blank injections, and then after all study samples. Blanks are injected after the calibration curve to ensure no that none of the tested compound is retained on the column and carried over to samples. Reconstituted sample (5 μl) is injected onto a Waters Acquity UPLC CSH $C_{18}$ column (100 mm×2.1 mm, 1.7 μm particle size) with an Acquity UPLC CSH $C_{18}$ VanGuard precolumn (Waters) using a Vanquish UHPLC coupled to a TSQ Altis triple quadrupole mass spectrometer (Thermo Fisher Scientific). Mobile phase A consists of 60:40 v/v acetonitrile/water with 10 mM ammonium formate and 0.1% formic acid. Mobile phase B consists of 90:10 v/v isopropanol/acetonitrile with 10 mM ammonium formate and 0.1% formic acid. Gradients are run from 0-2 min at 15% B; 2-2.5 min 30% B; 2.5-4.5 min 48% B; 4.5-7.3 min 99% B; 7.3-10 min 15% B. The flow rate is 0.600 ml/min and the column is heated to 65° C. Mass spectrometer conditions are optimized for the target compound by direct infusion. Selected reaction monitoring is performed for the top five ions, with collision energy, source fragmentation, and radiofrequency optimized for the test compound. Data are processed with TraceFinder 4.1 (Thermo Fisher Scientific). Organ weights are recorded. The concentration in the brain is calculated using the experimentally determined number of moles of the target compound in the whole organ divided by the weight of the organ.

5-HT Receptor Functional Assays.

Various assays for measuring serotonin receptor activation are known to those of skill in the art, including those methods described in Olsen et al., *Nat. Chem. Biol.,* 2020 August; 16(8):841-49, incorporated herein by reference in its entirety for all purposes. The assays described therein may be utilized to measure the functional activity of any of the serotonin receptor subtypes described herein, including 5-HT1A, 5-HT2A, 5-HT2B, and 5-HT2C. In certain embodiments, serotonin (5-hydroxytryptamine) is used as the reference compound.

Cell Culture

HEK293T cells are maintained, passaged, and transfected in DMEM medium containing 10% FBS, 100 Units/mL penicillin, and 100 μg/mL streptomycin (Gibco-ThermoFisher, Waltham, MA) in a humidified atmosphere at 37° C. and 5% CO2. After transfection, cells are plated in DMEM containing 1% dialyzed FBS, 100 Units/mL penicillin, and 100 μg/mL streptomycin for BRET2, calcium, and GloSensor assays.

BRET2 Assays

Cells are plated either in six-well dishes at a density of 700,000-800,000 cells/well, or 10-cm dishes at 7-8 million cells/dish. Cells are transfected 2-4 hours later, using a 1:1:1:1 DNA ratio of receptor:Ga-RLuc8:Gs:Gy-GFP2 (100 ng/construct for six-well dishes, 750 ng/construct for 10-cm dishes), except for the Gy-GFP2 screen, where an ethanol co-precipitated mixture of Gβ1-4—is used at twice its normal ratio (1:1:2:1). Transit 2020 (Mirus Biosciences, Madison, WI) is used to complex the DNA at a ratio of 3 μL Transit/μg DNA, in OptiMEM (Gibco-ThermoFisher, Waltham, MA) at a concentration of 10 ng DNA/μL OptiMEM. The next day, cells are harvested from the plate using Versene (0.1 M PBS+0.5 mM EDTA, pH 7.4), and plated in poly-D-lysine-coated white, clear bottom 96-well assay plates (Greiner Bio-One, Monroe, NC) at a density of 30,000-50,000 cells/well.

One day after plating in 96-well assay plates, white backings (Perkin Elmer, Waltham, MA) are applied to the plate bottoms, and growth medium is carefully aspirated and replaced immediately with 60 μL of assay buffer (1x HBSS+ 20 mM HEPES, pH 7.4), followed by a 10 μL addition of freshly prepared 50 μM coelenterazine 400a (Nanolight Technologies, Pinetop, AZ). After a five-minute equilibration period, cells are treated with 30 μL of drug for an additional 5 minutes. Plates are then read in an LB940 Mithras plate reader (Berthold Technologies, Oak Ridge, TN) with 395 nm (RLuc8-coelenterazine 400a) and 510 nm (GFP2) emission filters, at 1 second/well integration times. Plates are read serially six times, and measurements from the sixth read are used in all analyses. BRET2 ratios are computed as the ratio of the GFP2 emission to RLuc8 emission.

Calcium Mobilization Assays

Cells are plated in 10-cm plates as described in the BRET2 protocol and co-transfected with receptor (1 μg) and Ga-subunit (1 μg) cDNA. The next day, cells are plated at 15,000 cells/well in poly-D-lysine coated black, clear bottom 384-well plates (Greiner Bio-One, Monroe, NC). The following day, growth medium are aspirated and replaced with 20 μL assay buffer containing 1× Fluo-4 Direct Calcium Dye (ThermoFisher Scientific, Waltham, MA) and incubated for 60 minutes at 37° C. (no $CO_2$). Plates are brought to RT for 10 minutes in the dark before being loaded into a FLIPR Tetra® liquid-handling robot and plate reader (Molecular Devices, San Jose, CA). Baseline fluorescence measurements are taken for 10 seconds followed by robotic drug addition (10 μL) and a 60-second measurement (1 measurement/second). For antagonist assays, cells are first treated with antagonist and kept in the dark at room temperature for ten minutes before agonist addition by the FLIPR Tetra® robot. Maximal response during this time is used to calculate amplitude of the calcium transients. Measurements are analyzed as percentage of maximum signal amplitude for the construct.

Glosensor cAMP Assays

Cells are plated in 10-cm plates as previously described. Cells are transfected with plasmids encoding cDNA for the Glosensor reporter (Promega, Madison, WI), receptor, and Ga-subunit at a ratio of 2:1:1 (2 μg: 1 μg: 1 μg). The next day, cells are plated in black, clear-bottom, 384-well white plates. After aspiration of the medium on the day of the assay, cells are incubated for 60 minutes at 37° C. with 20 μL of 5 mM luciferin substrate (GoldBio, St. Louis, MO) freshly prepared in assay buffer. For Gas activity, 10 μL of drugs are added using the FLIPR Tetra@liquid-handling robot and read after 15 minutes in a Spectramax luminescence plate reader (Molecular Devices, San Jose, CA) with a 0.5 second signal integration time. For Gai activity, 10 μL of drugs are added for a 15-minute incubation period. Subsequently, 10 μL of isoproterenol (final concentration of 200 nM) are added and incubated for an additional 15-minute period before reading.

Hepatocyte Stability Assay

Purpose: Measure the in vitro metabolic stability of test compound(s) in different species of hepatocytes Materials and reagents: Compounds of Formula I described herein are selected for study. Control compound verapamil is purchased from Sigma Chemical Co. Cryopreserved Hepatocytes are purchased from BioIVT or RILD and stored at in a liquid nitrogen container. The hepatocytes of interest are listed in the table below:

| Species | Strain | Sex | Source |
|---|---|---|---|
| Mouse | ICR/CD-1 | Male | BioIVT |
| Rat | Sprague Dawley | Male | BioIVT |
| Dog | Beagle | Male | BioIVT |
| Monkey | Cynomolgus | Male | RILD |
| Human | N/A | Mixed | BioIVT |

William's E Medium, human recombinant insulin, HEPES, DPBS and GlutaMAX are purchased from Gibco. Isotonic Percoll is purchased from Solarbio. Fetal bovine serum is purchased from Avantor. Dexamethasone is purchased from Solarbio. 96-well plates are purchased from Corning.

Experimental Procedure: Preparation of Working Solutions—Prepare 10 mM stock solutions of test compound(s) and positive controls in appropriate solvent (DMSO). In 96-well plates, diluted to 100 μM by combining 198 μL of 50% acetonitrile/50% water and 2 μL of 10 mM positive controls. Preparation of Hepatocytes—Place incubation medium (William's E Medium supplemented with GlutaMAX) and hepatocyte thawing medium in a 37° C. water bath, and allow warming for at least 15 minutes prior to use. Remove a vial of cryopreserved hepatocytes from storage, ensuring that vials remain at cryogenic temperatures until thawing process ensues. Thaw the cells by placing the vial in a 37° C. water bath and gently shaking the vials for 2 minutes. After thawing is completed, spray vial with 70% ethanol, transfer the vial to a biosafety cabinet. Use wide-bore pipette tip to transfer hepatocytes into 50 mL conical tube containing thawing medium. Place the 50 mL conical tube into a centrifuge and spin at 80 g for 8 minutes. Upon completion of spin, aspirate thawing medium and resuspend hepatocytes in enough incubation medium to yield ~$1.5\times10^6$ cells/mL. Using an AO/PI staining solution, count cells and determine the viable cell density. Cells with poor viability (<75% viability) are not acceptable for use. Dilute cells with incubation medium to a working cell density of $0.5\times10^6$ viable cells/mL. Compound Incubation—Pipette 198 μL of hepatocytes into each well of a 96-well non-coated plate. Place the plate in the incubator on an orbital shaker to allow the hepatocytes to warm for 10 minutes. Pipette 2 μL of the 100 μM test compound(s) or positive control into respective wells of the 96-well plate to start the reaction. The final test concentration is 1 μM. Return the plate to the incubator and place on an orbital shaker. The reaction for each compound will be performed in duplicate. Procedure for Stability Determination—Remove 25 μL aliquots of reaction mixture at time points of 0, 15, 30, 60, 90 and 120 minutes. The aliquots are then mixed with 6 volumes (150 μL) of acetonitrile containing internal standards (IS: 100 nM tolbutamide, 200 nM labetalol, 100 nM ketoprofen, 200 nM imipramine and 200 nM diclofenac) to terminate the reaction. Centrifuge the plate for 45 minutes at 3,220 g. Aliquots of 100 μL of the supernatants will be mixed with 100 μL ultrapure water and used for LC/MS/MS analysis.

Data Analysis: All calculations are carried out using Microsoft Excel. Peak areas are determined from extracted ion chromatograms. Determine the in vitro half-life ($t_{1/2}$) of parent compound by regression analysis of the percent parent disappearance vs. time curve. The in vitro half-life (in vitro $t_{1/2}$) is determined from the slope value:

$$\text{in vitro } t_{1/2} = -0.693/k$$

Conversion of the in vitro $t_{1/2}$ (in mi) into the in vitro intrinsic clearance (in vitro $CL_{int}$, in μL/min/$10^6$ cells) is done using the following equation (mean of duplicate determinations):

$$\text{in vitro } CL_{int} = kV/N$$

Where V=incubation volume (0.2 mL); N=number of hepatocytes per well ($0.1\times10^6$ cells).

Example: This Hepatocyte Stability assay is conducted on the compounds of Formula I, with the results set forth in the following table:

| Compound | Species | In vitro $T_{1/2}$ (min) | In vitro Clint (uL/min/$10^6$ cells) | Scale-up Clint (mL/min/kg) |
|---|---|---|---|---|
| 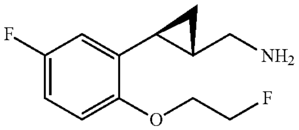 [SMILES: NC[C@H]1C[C@@H]1c1cc(F)ccc1OCCF] | Human<br>Mouse | RP<br>RP | RP<br>RP | RP<br>RP |
| 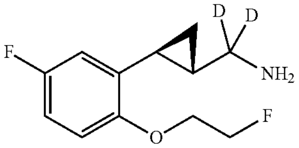 [SMILES: [2H]C([2H])(N)[C@H]1C[C@@H]1c1cc(F)ccc1OCCF] | Human<br>Mouse | RP<br>RP | RP<br>RP | RP<br>RP |
| 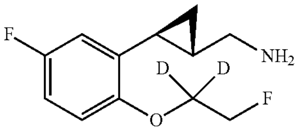 [SMILES: [2H]C([2H])(CF)Oc1ccc(F)cc1[C@H]1C[C@@H]1CN] | Human<br>Mouse | RP<br>RP | RP<br>RP | RP<br>RP |
| 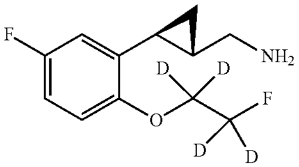 [SMILES: [2H]C([2H])(F)C([2H])([2H])Oc1ccc(F)cc1[C@H]1C[C@@H]1CN] | Human<br>Mouse | RP<br>RP | RP<br>RP | RP<br>RP |

*RP = results pending

Metabolite Identification Assays

Purpose: The objective of this study is to identify the potential metabolites of test article (TA) and to predict the possible metabolic pathways of test article in mouse, rat, dog, monkey and human hepatocytes.

Experimental Procedure: Materials—compounds of Formula I are provided for testing. Acetonitrile and methanol are purchased from Fisher Scientific. Cryopreserved Hepatocytes are purchased from BiolVT or RILD and stored at in a liquid nitrogen container. The hepatocytes of interest are listed in the table below:

| Species | Strain | Sex | Source |
|---|---|---|---|
| Mouse | ICR/CD-1 | Male | BioIVT |
| Rat | Sprague Dawley | Male | BioIVT |
| Dog | Beagle | Male | BioIVT |
| Monkey | Cynomolgus | Male | RILD |
| Human | N/A | Mixed | BioIVT |

Sample preparation—The stock solution of test compound is prepared in acetonitrile/DMSO at the concentration of 2 mM. The final test concentration will be 10 μM. Prepare hepatocytes thawing medium by mixing ingredients in table below. Prepare incubation medium by mixing 49.5 mL Williams E Medium and 0.5 mL glutaMAX. Place thawing medium and incubation medium in a 37° C. water bath, then allow warming for at least 15 minutes prior to use.

| Reagent | Initial Conc. | Final Conc. | Quantities of Reagents |
|---|---|---|---|
| Williams' Medium E | — | — | 31.2 mL |
| Isotonic Percoll | — | 30% | 13.5 mL |
| DPBS(10×) | — | — | 1.5 mL |
| GlutaMAX ™-1(100×) | 200 mM/100× | 2 mM | 500 μL |
| HEPES | 1M | 15 mM | 750 μL |

-continued

| Reagent | Initial Conc. | Final Conc. | Quantities of Reagents |
|---|---|---|---|
| FBS | — | 5% | 2.5 mL |
| Human recombination insulin | 4 mg/mL | 4 μg/mL | 50 μL |
| 10 mM Dexamethasone | 10 mM | 1 μM | 5 μL |

Remove the vial of hepatocytes from storage, ensuring that vials remain at cryogenic temperatures until thawing process ensues. As quickly as possible, thaw the cells by placing the vial in a 37° C. water bath and gently shaking the vials. Vials should remain in water bath until all ice crystals have dissolved and are no longer visible. Open the vial and pour the contents into the conical tube containing 50 mL thawing medium, then centrifuge at 80 g for 6 minutes. Upon completion of spin, aspirate thawing medium and resuspend hepatocytes in enough incubation medium to yield ~$1.5\times10^6$ cells/mL. Using Cellometer® Vision, count cells and determine the viable cell density. Cells with poor viability (<75% viability) are not acceptable for use. Dilute cells with incubation medium to a working cell density of $1\times10^6$ viable cells/mL. For the 0-min sample, aliquots (199 μL) of hepatocytes suspension will be transferred into a 24-well plate, 600 μL of acetonitrile containing 0.1% formic acid will be added into corresponding wells, and then 1 μL of test article working solution (2 mM) will be added. For the 120 min, 240 min and blank (240 min) samples, the 120 min, 240 min samples are started with the addition of 1 μL of 2 mM compound solution into 24-well plate contain of 199 μL of hepatocytes suspension. and the blank samples are started with the addition of 1 μL acetonitrile/DMSO solution into 199 μL of hepatocytes suspension. The incubations will be carried out in an incubator (37° C., 5% $CO_2$) on an orbital shaker at ~500 rpm. The reaction will be quenched by adding 600 μL of acetonitrile containing 0.1% formic acid into respective well at the corresponding time points. The supernatant is used for UHPLC-UV-MS/MS analysis (If needed, the supernatants (600 μL) will be transferred and placed in the evaporator under steady stream of nitrogen at room temperature until dry. The dried residues will be reconstituted with 100 μL of diluents (acetonitrile: water (v/v)=1:4). If acetonitrile: water (v/v)=1:4 cannot reconstitute the sample well, other diluents will be used. Then samples will be centrifuged at 16,000×g for 30 minutes. The supernatant will be transferred and analyzed by UHPLC-UV-MS/MS. The control compound verapamil is included in the experiment with sample incubation method. The time points are 0 min and 240 min. The remaining percentage of verapamil will be used to monitor the hepatocytes activity. Noted that the incubation time should be compound dependent, guided by hepatocytes stability, target % parent remaining ~50% compared with 0 min sample.

Instrumentation—UHPLC-MS/MS analysis is conducted using a Dionex UltiMate 3000 UHPLC system/Vanquish UHPLC system (Thermo Scientific, USA). Thermo Scientific Q Exactive/Orbitrap Exploris 120/240 (Thermo Scientific, USA) fitted with a HESI probe. Mass Spectrometry Analysis—All analyses are carried out with a high-resolution mass spectrometric instrument. Both data from positive and negative ionization mode will be collected. Compound dependent parameters will be optimized by test article. Parallel reaction monitoring (PRM) will be used to acquire $MS^2$ spectra. UHPLC-UV was used to collect the UV peak area of parent drug and metabolites (if the product content was too low, there might be no UV signal).

Data Analysis: A common method in metabolite identification includes the production of metabolites by in vitro or in vivo experiments, collection of samples at different time points and analysis of the samples by using full-scan MS. The metabolites are identified by comparison of the ion chromatograms between a blank and the other samples under consideration of the expected metabolites according to predicted gains and losses in molecular mass of the parent drug. Once molecular ions for possible metabolites are detected, they can be subjected to analysis by MS/MS and the product ion MS/MS spectra of the parent compound can subsequently compared with the corresponding fragmentation pattern of metabolite structures. The specific fragment ion that showed a shift in its m/z helps to identify the site of the modification of the molecule. Data will be acquired and processed using Xcalibur software (Thermo Fisher Scientific) and Compound Discoverer (Thermo Fisher Scientific). The relative peak areas are determined from extracted ion chromatograms of hepatocytes samples at 240 min.

Data Presentation: A Microsoft PowerPoint report will be prepared, which includes a summary of the material and bioanalytical method; metabolite screening results; the MS/MS spectra of parent drug and potential metabolites; and the MS/MS spectra analysis of parent drug and potential metabolites.

Protocol for Rodent-Based EEG Assay for Lennox-Gastaut Syndrome (LGS)

1.1. Objective to Test the Efficacy of Compounds of Formula I in Reducing Seizure Activity and Improving EEG Readouts in a Rodent Model of Lennox-Gastaut Syndrome (LGS).

1.2. Materials and Equipment

- Rodent model of LGS (e.g., Scn1a+/−, Stxbpl+/− mice, or chemical-induced models using kainic acid or pilocarpine).
- Surgical tools for electrode implantation.
- Wireless EEG monitoring system and data acquisition software.
- Drug formulation and delivery equipment.
- Video monitoring system for behavioral correlation.
- Data analysis software for EEG quantification (e.g., spectral analysis tools).

1.3. Methodoloqy 1.3.1. Pre-Study Preparation

1. Select a validated LGS rodent model with a history of spontaneous seizures or induced epileptiform activity.
2. Perform surgical implantation of EEG electrodes:
   - Implant cortical electrodes bilaterally to capture generalized seizure activity.
   - Place reference and ground electrodes appropriately.
   - Allow rodents to recover for 7-10 days post-surgery.
3. Divide animals into treatment groups: vehicle control, positive control (e.g., cannabidiol or clobazam), and Formula I drug groups.

1.3.2. Baseline EEG Monitoring

1. Record baseline EEG for 24-48 hours to document spontaneous seizures, slow spike-and-wave discharges (1.5-2.5 Hz), and paroxysmal fast activity.

2. Quantify seizure frequency, duration, and severity during baseline monitoring.

1.3.3. Drug Administration

1. Administer the compound of Formula I at the desired dose and frequency (e.g., daily for 2 weeks) via oral gavage or intraperitoneal injection.
2. Include a dose-escalation cohort to determine the optimal therapeutic dose.

1.3.4. Post-Treatment EEG Monitoring

1. Perform continuous EEG monitoring for 24-48 hours post-treatment to evaluate changes in seizure burden and EEG patterns.
2. Analyze specific EEG readouts:
   - Seizure frequency: Reduction in the number of spontaneous seizures.
   - Seizure duration: Shorter seizure events post-treatment.
   - Spike-and-wave discharges: Decrease in the frequency or amplitude of slow spike-and-wave discharges.
   - Paroxysmal fast activity: Reduction in fast rhythmic activity during sleep.
   - Spectral power: Normalization of spectral power in specific frequency bands (e.g., delta, theta).

1.3.5. Behavioral Correlation

1. Correlate EEG findings with behavioral observations (e.g., motor seizures, atonic drops, absence seizures).
2. Use video recordings to confirm seizure types and assess drug effects on seizure severity.

1.3.6. Safety and Tolerability

1. Monitor body weight, food intake, and general behavior daily.
2. Evaluate drug-related adverse effects, such as sedation or motor impairment.

1.4. Data Analysis

1. Quantify EEG parameters using automated or manual scoring methods.
2. Perform statistical analysis (e.g., paired t-tests or ANOVA) to compare pre- and post-treatment EEG metrics across groups.
3. Identify EEG changes indicative of therapeutic efficacy, such as:
   - Significant reduction in seizure frequency and duration.
   - Decrease in slow spike-and-wave discharges and paroxysmal fast activity.
   - Normalization of spectral power in abnormal frequency bands.

1.5. Reporting Results

1. Present EEG data (e.g., representative traces, heatmaps of spectral power, seizure frequency graphs).
2. Summarize behavioral correlations and safety outcomes.
3. Compare Formula I drug effects to positive and vehicle controls.

Protocol for Rodent-Based EEG Assay for Dravet Syndrome (DS)

When adapting the protocol for Dravet Syndrome (DS) instead of Lennox-Gastaut Syndrome (LGS), the following specific changes should be made:

2.1. Rodent Model Selection

Replace LGS-specific models (e.g., Stxbpl+/– or pilocarpine-induced models) with Dravet-specific models:

- Scnla+/–Mice: This is the most commonly used genetic model for Dravet Syndrome, mimicking the SCN1A mutations seen in human patients.
- These mice exhibit spontaneous seizures, hyperthermia-induced seizures, and developmental delays characteristic of DS.

2.2. EEG Readouts

While many EEG metrics overlap between LGS and DS, the following are specific to DS:

- Spontaneous Seizures: Focus on generalized tonic-clonic seizures (GTCS) and myoclonic seizures, which are more typical of DS.
- Hyperthermia-Induced Seizures: Include a protocol to induce hyperthermia (e.g., heating the rodent to 39-42° C.) to assess the drug's ability to prevent or reduce thermally induced seizures.
- Interictal Epileptiform Discharges (IEDs): Measure the frequency and duration of interictal spikes, which are more pronounced in DS models.

2.3. Behavioral Correlation

Include additional assessments specific to DS, such as:

- Developmental Milestones: Monitor motor and cognitive development delays, which are hallmark features of DS.
- Motor Dysfunction: Assess motor coordination and gait abnormalities, which are often impaired in DS models.

2.4. Biomarkers

Add specific biomarker analyses relevant to DS:

- Inflammatory Markers: IL-1 and TNF-α, which may play a role in seizure exacerbation in DS.
- Neuronal Injury Markers: Increased focus on markers of oxidative stress and excitotoxicity, which are prominent in DS pathophysiology.

2.5. Safety and Tolerability

DS models are highly sensitive to environmental stressors, so emphasize careful monitoring of hyperthermia-induced seizures and increased sensitivity to drug side effects, such as sedation or respiratory depression.

Biomarker and Behavioral Assays for Testing New Drugs for Treating Pitt-Hopkins Syndrome (PTHS)

3.1. Objective to Evaluate the Efficacy of Compounds of Formula I in Reducing Seizures and Improving Neurological Outcomes in Rodent Models of Pitt-Hopkins Syndrome (PTHS), with a Focus on EEG-Based Protocols and Behavioral Assays.

3.2. Materials and Equipment

- Rodent model of PTHS (e.g., Tcf4+/– mice or other validated genetic models).
- EEG monitoring system with wireless capability.
- Behavioral testing apparatus (e.g., open field, rotarod, elevated plus maze).
- Drug formulation and administration tools (oral gavage, intraperitoneal injection tools).
- Data acquisition and analysis software for EEG and behavioral data.
- Molecular analysis tools (e.g., ELISA kits, Western blot, qPCR setup).

3.3. Methodology

A. Pre-study Preparation

1. Select a validated PTHS rodent model (e.g., Tcf4+/– mice) that exhibits seizures, motor impairments, and other neurological features associated with PTHS.
2. Acclimate animals to the laboratory environment for at least 7 days before the study begins.
3. Divide animals into treatment groups: vehicle control, positive control (e.g., standard anti-epileptic drug like valproate), and experimental Formula I drug groups.

B. Surgical Preparation for EEG Monitoring

1. Implant EEG electrodes surgically:
   - Cortical electrodes for monitoring generalized seizures.
   - Hippocampal electrodes if focal seizure activity is of interest.

2. Allow 7-10 days of recovery post-surgery before starting baseline recordings.

C. Baseline EEG Monitoring

1. Record baseline EEG activity for 24-48 hours to assess spontaneous seizure frequency, duration, and severity.
2. Analyze the following EEG features:
   - Spontaneous seizure frequency and interictal epileptiform discharges (IEDs).
   - Abnormal EEG patterns, such as high-amplitude slow waves and spike-wave discharges.

D. Drug Administration

1. Administer the Formula I test drug at the desired dose and schedule (e.g., daily for 2-4 weeks).
2. Include dose-escalation studies to determine the optimal therapeutic window.
3. Ensure consistent timing of administration to minimize variability.

E. Post-Treatment EEG Monitoring

1. Record EEG continuously for 24-48 hours after the drug treatment period.
2. Evaluate changes in seizure frequency, duration, and severity compared to baseline.
3. Analyze EEG readouts such as:
   - Reduction in interictal spike-wave discharges.
   - Decrease in seizure-related high-amplitude slow waves.
   - Changes in spectral power (e.g., normalization of delta and theta band activity).

F. Behavioral Assays

1. Seizure Monitoring and Severity Scoring:
   - Use video recordings to confirm behavioral correlates of EEG-identified seizures.
   - Score seizure severity using a modified Racine scale.
2. Cognitive and Motor Assessments:
   - Perform rotarod testing to evaluate motor coordination and balance.
   - Conduct open field testing to assess locomotor activity and anxiety-like behavior.
3. Social Interaction Tests:
   - Assess social deficits using a three-chamber sociability assay, as PTHS often involves social impairments.

G. Molecular and Biomarker Analysis

1. Collect brain and blood samples at the end of the study for biomarker analysis:
   - Evaluate inflammatory markers (e.g., IL-6, TNF-$\alpha$) and neuronal injury markers (e.g., GFAP, NSE).
   - Assess expression levels of Tcf4 and downstream target genes using qPCR or Western blot.

H. Safety Assessment

1. Monitor body weight, food intake, and general health daily.
2. Assess potential side effects, such as sedation or ataxia, using a standardized scoring system.

3.4. Data Analysis

1. Quantify EEG parameters, including:
   - Total seizure frequency and duration.
   - Interictal spike-wave discharges.
   - Spectral power analysis.
2. Perform statistical comparisons (e.g., paired t-tests or ANOVA) between baseline and post-treatment EEG data.
3. Analyze behavioral and biomarker results to correlate with EEG findings.

3.5. Reporting Results

1. Summarize key findings in a comprehensive report, including:
   - EEG data (e.g., representative traces, seizure frequency graphs).
   - Behavioral assay outcomes.
   - Biomarker changes.
   - Safety and tolerability data.

Testing Drugs for Absence Seizures with or without Myoclonia (Modifications of the Pitt-Hopkins Syndrome Protocol)

4.1. Rodent Model Selection

- Replace the Pitt-Hopkins-specific rodent model (e.g., Tcf4+/− mice) with models suitable for absence seizures:
  - Genetic Absence Epilepsy Rats from Strasbourg (GAERS).
  - WAG/Rij rats.
  - Scn8a mutant mice for models incorporating both absence seizures and myoclonic activity.

4.2. EEG Metrics and Seizure Types

- Focus on specific EEG patterns associated with absence seizures:
  - Spike-and-Wave Discharges (SWDs):
    - Measure the frequency, duration, and amplitude of SWDs, a hallmark feature of absence seizures.
  - Amplitude and Spectral Analysis:
    - Evaluate theta and delta bands for changes in EEG background activity.
  - For myoclonia, include burst-like discharges in the EEG assessment.

4.3. Behavioral Correlation

- Prioritize behaviors directly linked to absence seizures:
  - Seizure-Related Behaviors:
    - Immobility, staring spells, and twitching during SWDs.
  - Myoclonia Observation:
    - Quantify myoclonic jerks using video recordings and a severity scoring system.
- Retain behavioral assessments such as rotarod and open field tests to evaluate motor coordination and general locomotor activity.

4.4. Positive Control Drug

- Replace standard Pitt-Hopkins positive controls with drugs effective in absence seizures:
  - Ethosuximide or valproate.

4.5. Molecular and Biomarker Analysis

- Focus on ion channel and neurotransmitter-related biomarkers:
  - T-type calcium channels (Cav3.1, Cav3.2).
  - Sodium channel expression and function (e.g., NaV1.6 in Scn8a models).
  - Neurotransmitters such as GABA and glutamate.

4.6. EEG Analysis Timeframes

- Modify continuous EEG monitoring:
  - Conduct baseline recordings for 24-48 hours.
  - Repeat monitoring post-drug administration for similar timeframes to evaluate SWD reduction and behavioral changes.

4.7. Safety and Tolerability

Assess sedative or motor impairments more thoroughly: Monitor for ataxia or changes in locomotion due to the known effects of some absence seizure drugs (e.g., ethosuximide).

Additional Embodiments

Embodiment 1: A compound of Formula I:

Formula I

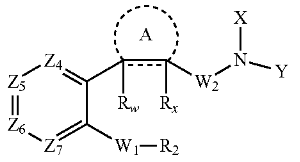

wherein

X and Y are each independently selected from hydrogen, deuterium, optionally substituted $C_1$-$C_8$ alkyl, optionally substituted $C_2$-$C_8$ alkenyl, or optionally substituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from $CF_2$, $NR_1$, 0, 5, S(O), $SO_2$, Se, Se(O), and $SeO_2$;

$W_2$ is absent or $C(R_3)(R_{3'})$;

$Z_4$ is selected from N and $CR_4$;

$Z_5$ is selected from N and CRS;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —$C(O)N(R_9)_2$, —$SOR_8$, and —$SO_2R_8$; $R_2$, $R_4$, $R_5$, $R_6$, and $R_7$ are each independently selected from hydrogen, deuterium, —$N(R_9)_2$, —$SR_9$, halo, optionally substituted $C_1$-$C_8$ alkyl, -$C_1$-$C_8$ alkoxy, optionally substituted $C_2$-$C_8$ alkenyl, optionally substituted $C_2$-$C_8$ alkynyl, optionally substituted aryl, optionally substituted heteroaryl, hydroxyl, —$OC(O)R_8$, —$OC(O)OR_8$, —$OP(O)(OR_9)_2$, and —$OSO_2R_8$, or $R_2$ is a residue selected from Formula III Formula III

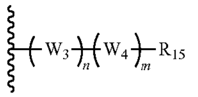

wherein $W_3$ is, for each occurrence, independently selected from optionally substituted alkylene, optionally substituted arylene, optionally substituted heteroarylene, optionally substituted cycloalkylene, optionally substituted heterocycloalkylene, and

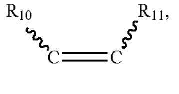

wherein n is an integer selected from 1 to 10, $W_4$ is, for each occurrence, independently selected from O, S, Se, $C(R_{12})(R_{13})$, optionally substituted arylene, optionally substituted heteroarylene, optionally substituted cycloalkylene, optionally substituted heterocycloalkylene, and

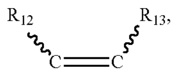

wherein m is an integer selected from 0 to 10, and $R_{10}$, $R_{11}$, $R_{12}$, $R_{13}$, and $Ra_5$ are, for each occurrence, independently selected from optionally substituted $C_1$-$C_8$alkyl, hydrogen, deuterium, halo, and hydroxyl, or $R_4$ is taken together with $R_5$ and the carbons therebetween to form 3- to 7-membered carbocyclic or heterocyclic ring optionally including 1 to 2 additional ring heteromoieties selected from O, S, S(O), $SO_2$, and $NR_9$, or $R_5$ is taken together with $R_6$ and the carbons therebetween to form 3- to 7-membered carbocyclic or heterocyclic ring optionally including 1 to 2 additional ring heteromoieties selected from O, S, S(O), $SO_2$, and $NR_9$, or $R_6$ is taken together with $R_7$ and the carbons therebetween to form 3- to 7-membered carbocyclic or heterocyclic ring optionally including 1 to 2 additional ring heteromoieties selected from O, S, S(O), $SO_2$, and $NR_9$;

$R_3$ and $R_{3'}$ are each, independently, selected from hydrogen, deuterium, —$N(R_9)_2$, —$SR_9$, halo, optionally substituted $C_1$-$C_8$alkyl, -$C_1$-$C_8$ alkoxy, and optionally substituted $C_2$-$C_8$ alkenyl, or Y is absent and $R_3$ taken together with carbon to which it is attached and the nitrogen atom to which X is attached form a 3- to 7-membered heterocyclic ring optionally including 1 to 2 additional ring heteromoieties selected from O, S, S(O), $SO_2$, and $NR_9$, or $R_3$ and $R_{3'}$ are taken together with the carbon to which they are attached to form a keto group;

$R_x$ and $R_w$ are each, independently, absent or selected from hydrogen, deuterium, —$N(R_9)_2$, —$SR_9$, halo, optionally substituted $C_1$-$C_8$alkyl, -$C_1$-$C_8$ alkoxy, optionally substituted $C_2$-$C_8$ alkenyl, and optionally substituted $C_2$-$C_8$ alkynyl, or $R_2$ is taken together with $W_1$ and the carbon to with $R_x$ is attached, and the carbons therebetween, to form a 3- to 7-membered heterocyclic ring optionally including 1 to 2 additional ring heteromoieties selected from O, S, S(O), $SO_2$, and $NR_9$;

$R_8$ is selected from optionally substituted $C_1$-$C_8$alkyl, optionally substituted $C_2$-$C_8$ alkenyl, and optionally substituted aryl;

$R_9$ is independently selected from hydrogen, deuterium, optionally substituted $C_1$-$C_8$ alkyl, optionally substituted $C_2$-$C_8$ alkenyl, and optionally substituted aryl;

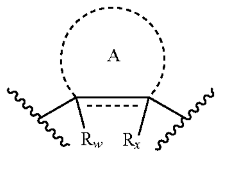

represents a fused ring chosen from an optionally substituted cycloalkanyl, optionally substituted cycloalkenyl, optionally substituted heterocyclyl, optionally substituted aryl, and optionally substituted heteroaryl;

the ------ is a single or double bond, wherein $R_x$ and $R_w$ are absent when it is a double bond;

and salts, solvates, hydrates, prodrugs, and enantiomers thereof.

Embodiment 2: A compound of Formula I:

Formula I

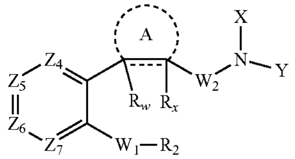

wherein

X and Y are each independently selected from hydrogen, deuterium, optionally substituted $C_1$-$C_8$ alkyl, optionally substituted $C_2$-$C_8$ alkenyl, or optionally substituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from $CF_2$, $NR_1$, O, S(O), $SO_2$, Se, Se(O), and $SeO_2$;

$W_2$ is absent or $C(R_3)(R_{3'})$;

$Z_4$ is selected from N and $CR_4$;

$Z_5$ is selected from N and $CR_5$;

$Z_6$ is selected from N and $CR_6$;

$Z_7$ is selected from N and $CR_7$;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —$C(O)N(R_9)_2$, —$SOR_8$, and —$SO_2R_8$;

$R_2$, $R_4$, $R_5$, $R_6$ and $R_7$ are each independently selected from hydrogen, deuterium, —$N(R_9)_2$, —$SR_9$, halo, optionally substituted $C_1$-$C_8$ alkyl, -$C_1$-$C_8$ alkoxy, and optionally substituted $C_2$-$C_8$ alkenyl, or $R_4$ is taken together with $R_5$ and the carbons therebetween to form 3- to 7-membered carbocyclic or heterocyclic ring optionally including 1 to 2 additional ring heteromoieties selected from O, S, S(O), $SO_2$, and $NR_9$, or $R_5$ is taken together with $R_6$ and the carbons therebetween to form 3- to 7-membered carbocyclic or heterocyclic ring optionally including 1 to 2 additional ring heteromoieties selected from O, S, S(O), $SO_2$, and $NR_9$, or $R_6$ is taken together with $R_7$ and the carbons therebetween to form 3- to 7-membered carbocyclic or heterocyclic ring optionally including 1 to 2 additional ring heteromoieties selected from O, S, S(O), $SO_2$, and $NR_9$;

$R_3$ and $R_{3'}$ are each, independently, selected from hydrogen, deuterium, —$N(R_9)_2$, —$SR_9$, halo, optionally substituted $C_1$-$C_8$ alkyl, -$C_1$-$C_8$ alkoxy, and optionally substituted $C_2$-$C_8$ alkenyl;

$R_x$ and $R_w$ are each, independently, absent or selected from hydrogen, deuterium, —$N(R_9)_2$, —$SR_9$, halo, optionally substituted $C_1$-$C_8$ alkyl, -$C_1$-$C_8$ alkoxy, and optionally substituted $C_2$-$C_8$ alkenyl, or $R_2$ is taken together with $W_1$ and the carbon to with $R_x$ is attached, and the carbons therebetween, to form a 3- to 7-membered heterocyclic ring optionally including 1 to 2 additional ring heteromoieties selected from O, S, S(O), $SO_2$, and $NR_9$;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$ alkyl, optionally substituted $C_2$-$C_8$ alkenyl, and optionally substituted aryl;

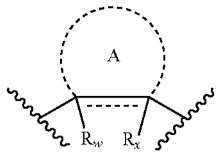

represents a fused ring chosen from an optionally substituted cycloalkanyl, optionally substituted cycloalkenyl, optionally substituted heterocyclyl, optionally substituted aryl, and optionally substituted heteroaryl;

the ------ is a single or double bond, wherein $R_x$ and $R_w$ are absent when it is a double bond, and salts, solvates, hydrates, prodrugs, and enantiomers thereof.

Embodiment 3: The compound according to Embodiment 1 or 2, wherein

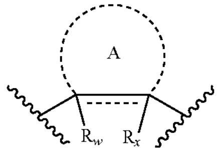

is selected from

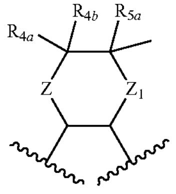
,
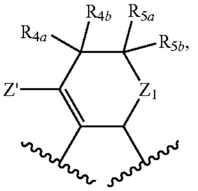
,
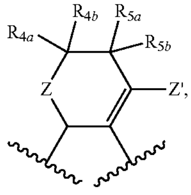
,
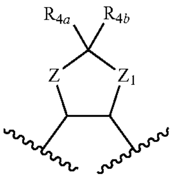
,

-continued

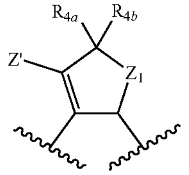

,

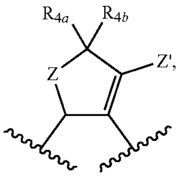

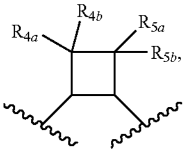

and

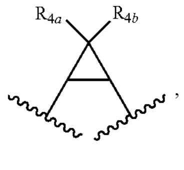

, wherein Z and $Z_1$ are independently selected from O, S and $-CZ'_2-$, and $R_{4a}$, $R_{4b}$, $R_{5a}$, $R_{5b}$ and Z' are each independently selected from hydrogen, deuterium, halogen, hydroxyl, branched or unbranched $C_1$-$C_8$ alkyl, and branched or unbranched $C_2$-$C_8$ alkenyl.

Embodiment 4: The compound according to any one of the preceding Embodiments, wherein the ⩦ is a double bond and $R_x$ and $R_w$ are absent.

Embodiment 5: The compound according to any one of the preceding Embodiments, wherein the ⩦ is a single bond.

Embodiment 6: The compound according to Embodiment 4, wherein $R_w$ and $R_x$ are hydrogen.

Embodiment 7: The compound according to Embodiment 6, wherein

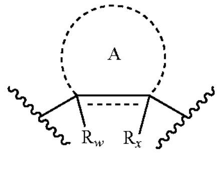

is

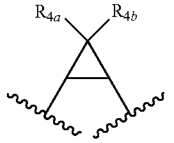

.

Embodiment 8: The compound according to any one of Embodiments 3-7, wherein $R_{4a}$, $R_{4b}$, $R_{5a}$ and $R_{5b}$ are each independently selected from hydrogen, halogen, hydroxyl, deuterium, and $C_1$-$C_4$ alkyl.

Embodiment 9: The compound according to any one of the preceding Embodiments, wherein $R_2$ is selected from optionally substituted $C_1$-$C_4$ alkyl and optionally substituted $C_2$-$C_4$ alkenyl.

Embodiment 10: The compound according to Embodiment 9, wherein $R_2$ is substituted with at least one fluorine or at least one deuterium.

Embodiment 11: The compound according to Embodiment 9, wherein $R_2$ is selected from methyl, ethyl, propyl, and allyl, each of which are optionally substituted with at least one fluorine or at least one deuterium.

Embodiment 12: The compound according to Embodiment 9, wherein $R_2$ is selected from methyl, $CF_3$, $CD_3$, ethyl, fluorinated ethyl, deuterated ethyl, propyl, fluorinated propyl, deuterated propyl, allyl and deuterated allyl.

Embodiment 13: The compound according to any one of Embodiments 1-8, wherein $R_2$ is taken together with $W_1$ and the carbon to with $R_x$ is attached, and the carbons therebetween, to form a 3- to 7-membered heterocyclic ring optionally including 1 to 2 additional ring heteromoieties selected from O, S, S(O), $SO_2$, and $NR_9$.

Embodiment 14: The compound according to Embodiment 13, wherein the compound of Formula I is selected from compounds of Formula IX:

Formula IX

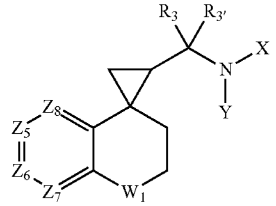

Embodiment 15: The compound according to any one of the preceding Embodiments, wherein at least one of $Z_4$, $Z_5$ $Z_6$ or $Z_7$ is N.

Embodiment 16: The compound according to Embodiment 15, wherein $Z_7$ is N.

Embodiment 17: The compound according to any one of Embodiments 1-14, wherein $Z_4$ is $CR_4$, $Z_5$ is $CR_5$, $Z_6$ is $CR_6$, and $Z_7$ is $CR_7$.

Embodiment 18: The compound according to Embodiment 17, wherein $R_4$, $R_5$ and $R_6$ are each independently selected from hydrogen and halo.

Embodiment 19: The compound according to any one of Embodiments 17-18, wherein $R_5$ is fluoro.

Embodiment 20: The compound according to any one of Embodiments 17-19, wherein $R_4$ is selected from hydrogen, chloro, and fluoro.

Embodiment 21: The compound according to any one of Embodiments 17-20, wherein $R_7$ is hydrogen.

Embodiment 22: The compound according to any one of the preceding Embodiments, wherein $W_2$ is $C(R_3)(CR_{3'})$.

Embodiment 23: The compound according to Embodiment 22, wherein $R_3$ and $R_{3'}$ are selected from hydrogen and deuterium.

Embodiment 24: The compound according to any one of the preceding Embodiments, wherein X and Y are each independently selected from hydrogen, deuterium, unsubstituted $C_1$-$C_8$ alkyl, unsubstituted $C_2$-$C_8$ alkenyl, and unsubstituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$.

Embodiment 25: The compound according to any one of the preceding Embodiments, wherein X and Y are each independently selected from hydrogen, deuterium, and $C_1$-$C_4$ alkyl.

Embodiment 26: The compound according to any one of Embodiments 1-24, wherein X and Y are independently selected from hydrogen, deuterium, and $-CD_3$.

Embodiment 27: The compound according to any one of the preceding Embodiments, wherein X is hydrogen.

Embodiment 28: The compound according to any one of the preceding Embodiments, wherein Y is hydrogen.

Embodiment 29: The compound according to any one of the preceding Embodiments, wherein $W_1$ is O.

Embodiment 30: The compound according to any one of Embodiments 1-28, wherein $W_1$ is selected from Se, Se(O), $SeO_2$, S, S(O), and $SO_2$.

Embodiment 31: The compound according to Embodiment 30, wherein $W_1$ is Se.

Embodiment 32: The compound according to Embodiment 30, wherein $W_1$ is S.

Embodiment 33: The compound according to any one of the preceding Embodiments, wherein $W_3$ is an optionally substituted alkylene.

Embodiment 34: The compound according to Embodiment 33, wherein the optionally substituted alkylene is $C(R_{10})(R_{11})$.

Embodiment 35: The compound according to any one of the preceding Embodiments, wherein $W_4$ is an optionally substituted alkylene.

Embodiment 36: The compound according to Embodiment 35, wherein the optionally substituted alkylene is $C(R_{12})(R_{13})$.

Embodiment 37: The compound according to any one of the preceding Embodiments, wherein at least one of $R_{10}$, $R_{11}$, $R_{12}$, $R_{13}$ or $R_{15}$ is deuterium.

Embodiment 38: The compound according to Embodiments 34-37, wherein n is 1, $W_3$ is $C(R_{10})(R_{11})$, and at least one of $R_{10}$ or $R_{11}$ is deuterium.

Embodiment 39: The compound according to Embodiment 38, wherein $R_{10}$ and $R_{11}$ are both deuterium.

Embodiment 40: The compound according to any one of Embodiments 37-39, wherein $Ra_5$ is selected from hydrogen, deuterium, and fluoro.

Embodiment 41: The compound according to any one of Embodiments 37-40, wherein m is an integer selected from 0 to 2.

Embodiment 42: The compound according to any one of Embodiments 1-34 or 37-41, wherein $W_4$ is selected from $C(R_{12})(R_{13})$ and

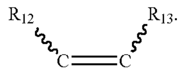

Embodiment 43: The compound according to any one of the preceding Embodiments, wherein $R_{12}$ and $R_{13}$ are, for each occurrence, independently selected from hydrogen, deuterium, and fluoro.

Embodiment 44: The compound according to any one of preceding Embodiments 1-13 or 15-43, wherein the compound is selected from compounds of Formula V:

Formula V

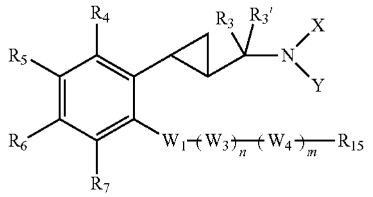

Embodiment 45: The compound according to Embodiment 44, wherein $R_3$ and $R_{3'}$ are selected from hydrogen and deuterium.

Embodiment 46: The compound according to any one of Embodiments 44-45, wherein X and Y are each hydrogen.

Embodiment 47: The compound according to any one of Embodiments 44-46, wherein at least one of $R_5$ or $R_6$ is fluoro.

Embodiment 48: The compound according to any one of Embodiments 44-47, wherein $W_3$ is $C(R_{10})(R_{11})$ and wherein at least one of $R_3$, $R_{3'}$, $R_{10}$ or $R_{11}$ is deuterium.

Embodiment 49: The compound according to Embodiment 48, wherein n is 1.

Embodiment 50: The compound according to any one of Embodiments 44-49, wherein the compound of Formula V is selected from compounds of Formula VI:

Formula VI

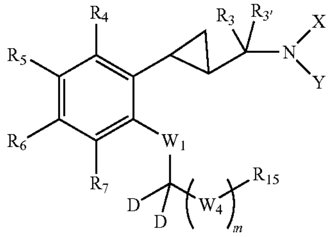

Embodiment 51: The compound according to Embodiment 50, wherein m is an integer selected from 0, 1 or 2 and $R_{15}$ is selected from hydrogen, deuterium, and fluoro.

Embodiment 52: The compound according to any one of Embodiments 50-51, wherein m is an integer selected from 1 and 2.

Embodiment 53: The compound according to any one of Embodiments 50-52, wherein $W_4$ is $C(R_{12})(R_{13})$

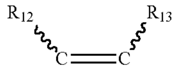

and at least one occurrence of $R_{12}$ or $R_{13}$ is fluoro.

Embodiment 54: The compound according to any one of Embodiments 44-53, wherein $W_1$ is S.

Embodiment 55: The compound according to any one of Embodiments 44-53, wherein $W_1$ is O.

Embodiment 56: The compound according to any one of Embodiments 50-55, wherein the compound of Formula VI is selected from compounds of Formula VI(a):

Formula VI(a)

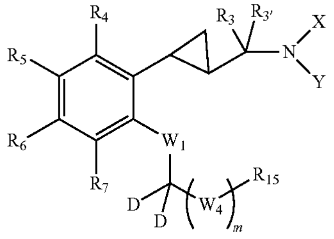

Embodiment 57: A compound selected from Formula VIII:

Formula VIII

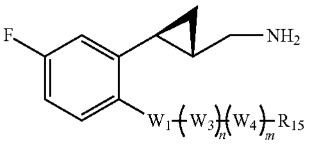

wherein $W_1$ is selected from $CF_2$, $NR_1$, O, S, S(O), $SO_2$, Se, Se(O), and $SeO_2$;

$W_3$ is, for each occurrence, independently selected from optionally substituted alkylene, optionally substituted arylene, optionally substituted heteroarylene, optionally substituted cycloalkylene, optionally substituted heterocycloalkylene, and

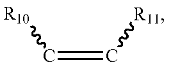

wherein n is an integer selected from 1 to 10;

$W_4$ is, for each occurrence, independently selected from O, S, Se, optionally substituted alkylene, optionally substituted arylene, optionally substituted heteroarylene, optionally substituted cycloalkylene, optionally substituted heterocycloalkylene, and

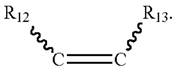

wherein m is an integer selected from 0 to 10; and $R_{10}$, $R_{11}$, $R_{12}$, $R_{13}$ and $R_{15}$ are, for each occurrence, independently selected from optionally substituted $C_1$-$C_8$ alkyl, hydrogen, deuterium, halo, and hydroxyl, and salts, solvates, hydrates, prodrugs, and enantiomers thereof.

Embodiment 58: The compound according to Embodiment 57, wherein $W_3$ is an optionally substituted alkylene.

Embodiment 59: The compound according to Embodiment 58, wherein the optionally substituted alkylene is $C(R_{10})(R_{11})$.

Embodiment 60: The compound according to any one of Embodiments 57-59, wherein $W_4$ is an optionally substituted alkylene.

Embodiment 61: The compound according to Embodiment 60, wherein the optionally substituted alkylene is $C(R_{12})(R_{13})$.

Embodiment 62: The compound according to any one of Embodiments 57-61, wherein at least one of $R_{10}$, $R_{11}$, $R_{12}$, $R_{13}$ or $R_{15}$ is deuterium.

Embodiment 63: The compound according to any one of Embodiments 57-62, wherein n is 1, $W_3$ is $C(R_{10})(R_{11})$, and at least one of $R_{10}$ or $R_{11}$ is deuterium.

Embodiment 64: The compound according to Embodiment 63, wherein $R_{10}$ and $R_{11}$ are both deuterium.

Embodiment 65: The compound according to any one of Embodiments 57-64, wherein $R_{15}$ is selected from hydrogen, deuterium and fluoro.

Embodiment 66: The compound according to any one of Embodiments 57-65, wherein m is an integer selected from 0 to 2.

Embodiment 67: The compound according to any one of Embodiments 57-66, wherein $W_4$ is selected from $C(R_{12})(R_{13})$ and

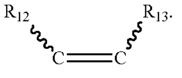

Embodiment 68: The compound according to any one of Embodiments 57-67, wherein $R_{12}$ and $R_{13}$ are, for each occurrence, independently selected from hydrogen, deuterium, and fluoro.

Embodiment 69: The compound according to any one of Embodiments 57-68, wherein the compound is selected from:

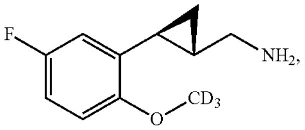

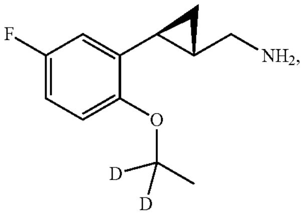

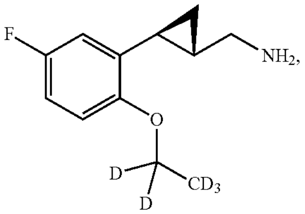

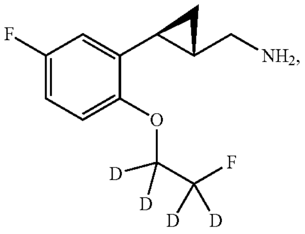

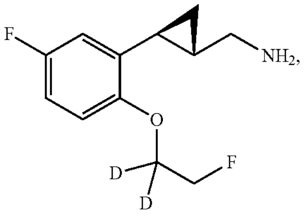

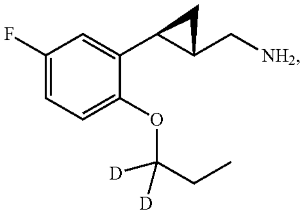

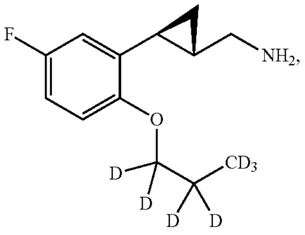

-continued

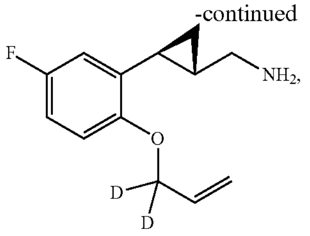

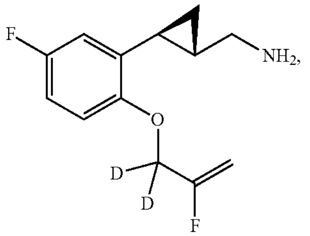

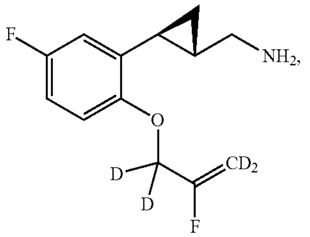

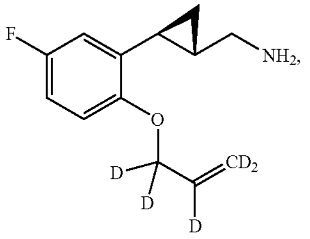

and salts, solvates, hydrates, prodrugs, and enantiomers thereof.

Embodiment 70: The compound according to any one of Embodiments 1-69, wherein the compound comprises a salt.

Embodiment 71: The compound according to any one of Embodiments 1-70, wherein the compound is crystalline.

Embodiment 72: The compound according to any one of Embodiments 1-71, wherein the compound comprises at least one deuterium atom, and wherein the compound exhibits a plasma half life ($T_{1/2}$) in CB-1 mice that is greater than a plasma half life ($T_{1/2}$) in CB-1 mice for a comparative compound having the same molecular structure except for the replacement of the at least one deuterium atom with at least one hydrogen atom.

Embodiment 73: The compound according to Embodiment 72, wherein the compound is selected from;

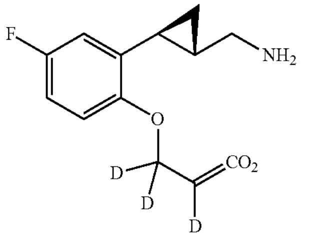 and

-continued

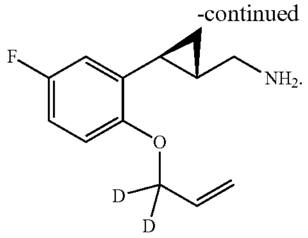

Embodiment 74: The compound according to Embodiment 73, wherein the comparative compound comprises:

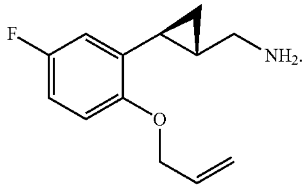 [SMILES: C=CCOc1ccc(F)cc1[C@H]1C[C@@H]1CN]

Embodiment 75: The compound according to Embodiment 72, wherein the compound is selected from:

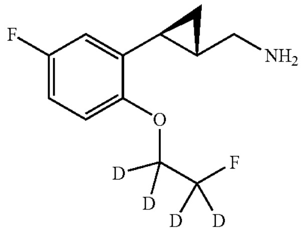 and

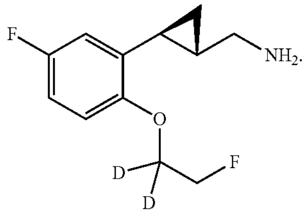

Embodiment 76: The compound according to Embodiment 75, wherein the comparative compound comprises:

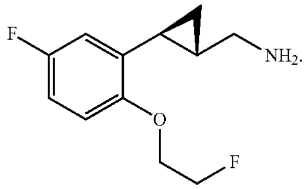 [SMILES: NC[C@H]1C[C@@H]1c1cc(F)ccc1OCCF]

Embodiment 78: The compound according to any one of Embodiments 72-76, wherein the plasma $T_{1/2}$ of the compound is at least 10% greater than the plasma $T_{1/2}$ of the comparative compound.

Embodiment 79: The compound according to any one of Embodiments 72-76, wherein the plasma $T_{1/2}$ of the compound is at least 20% greater than the plasma $T_{1/2}$ of the comparative compound.

Embodiment 80: The compound according to any one of Embodiments 72-76, wherein the plasma $T_{1/2}$ of the compound is at least 25% greater than the plasma $T_{1/2}$ of the comparative compound.

Embodiment 81: The compound according to any one of Embodiments 72-76, wherein the plasma $T_{1/2}$ of the compound is at least 40% greater than the plasma $T_{1/2}$ of the comparative compound B.

Embodiment 82: The compound according to any one of Embodiments 72-76, wherein the plasma $T_{1/2}$ of the compound is at least 50% greater than the plasma $T_{1/2}$ of the comparative compound.

Embodiment 83: The compound according to any one of Embodiments 72-76, wherein the plasma $T_{1/2}$ of the compound is at least two times (2×) greater than the plasma $T_{1/2}$ of the comparative compound.

Embodiment 84: The compound according to any one of Embodiments 72-76, wherein the plasma $T_{1/2}$ of the compound is at least three times (3×) greater than the plasma $T_{1/2}$ of the comparative compound.

Embodiment 85: The compound according to any one of Embodiments 72-76, wherein the plasma $T_{1/2}$ of the compound is at least four times (4×) greater than the plasma $T_{1/2}$ of the comparative compound.

Embodiment 86: The compound according to any one of Embodiments 72-76, wherein the plasma $T_{1/2}$ of the compound is at least five times (5×) greater than the plasma $T_{1/2}$ of the comparative compound.

Embodiment 87: The compound according to any one of Embodiments 72-76, wherein the plasma $T_{1/2}$ is based on oral dosing of both compounds to CB-1 mice.

Embodiment 88: The compound according to Embodiment 87, wherein both compounds are each separately dosed orally at 5 mg/kg.

Embodiment 89: The compound according to Embodiment 87, wherein both compounds are each separately dosed orally at 10 mg/kg.

Embodiment 90: A composition comprising, consisting essentially of, or consisting of a compound according to any one of Embodiments 1-89, and a pharmaceutically acceptable carrier.

Embodiment 91: The composition according to Embodiment 90, wherein the composition comprises an oral dosage form.

Embodiment 92: The composition according to Embodiment 91, wherein the oral dosage form comprises a tablet or capsule.

Embodiment 93: A method of treating or preventing a disease or disorder, comprising administering a pharmaceutically acceptable amount of a compound or composition according to any of the preceding Embodiments to a subject in need thereof.

Embodiment 94: The method according to Embodiment 93, wherein the disease or disorder is a psychological disease or disorder.

Embodiment 95: The method according to any one of Embodiments 93-94, wherein the disease or disorder can be treated or prevented by modulation of 5-HT2C receptors.

Embodiment 96: The method according to Embodiment 95, wherein the compound is a 5-HT2C receptor agonist.

Embodiment 97: The method according to any one of Embodiments 93-96, wherein the compound is a 5-HT2C receptor agonist that induces a $G_q$-mediated signaling bias when compared to p-arrestin-mediated signaling.

Embodiment 98: The method according to any one of Embodiments 93-97, wherein the disease or disorder is selected from a psychotic disorder, seizures, obesity, gastrointestinal disorder, sleep apnea, hypertension, hyperlipidemia, a cardiovascular disease, dementia, memory deficit, mild cognitive impairment, Parkinson's Disease, Alzheimer's Disease, an intellectual deficit associated with Alzheimer's disease, Huntington's Disease, dyskinesia, chronic pain, migraine, epilepsy, abuse or addiction to alcohol and drugs, or sexual dysfunction in males or females.

Embodiment 99: The method according to any one of Embodiments 93-98, wherein the compound or composition is contained in an oral dosage form.

Embodiment 100: The method according to Embodiment 99, wherein the oral dosage form is administered once or twice daily.

Embodiment 101: The method according to Embodiment 99, wherein the oral dosage form is administered once daily.

Embodiment 102: The method according to any one of Embodiments 93-101, wherein the subject is administered from about 5 mg to about 250 mg of the compound per day.

Embodiment 103: The method according to any one of Embodiments 93-101, wherein the subject is administered from about 20 mg to about 200 mg of the compound per day.

Embodiment 104: The method according to any one of Embodiments 93-101, wherein the subject is administered from about 40 mg to about 150 mg of the compound per day.

Embodiment 105: The method according to any one of Embodiments 93-104, wherein the compound is administered to the subject in an amount of from about 0.1 mg/kg to about 10 mg/kg per day.

Embodiment 106: The method according to any one of Embodiments 93-104, wherein the compound is administered to the subject in an amount of from about 0.25 mg/kg to about 5 mg/kg per day.

Embodiment 107: The method according to any one of Embodiments 93-104, wherein the compound is administered to the subject in an amount of from about 0.5 mg/kg to about 2.5 mg/kg per day.

Embodiment 108: The method according to any one of Embodiments 99-107, wherein the oral dosage form comprises a solid capsule or solid tablet.

Embodiment 109: The method according to Embodiment 108, wherein the subject is administered from about 40 mg to about 80 mg of the compound in a solid capsule or solid tablet twice per day.

Embodiment 110: The method according to any one of Embodiments 93-98, wherein the subject is administered from about 40 mg to about 80 mg of the compound twice per day.

Embodiment 111: The method according to any one of Embodiments 93-98, wherein the subject is administered from about 25 mg to about 100 mg of the compound twice per day.

Embodiment 112: The method according to any one of Embodiments 93-111, wherein the compound is administered with food.

Embodiment 113: The method according to any one of Embodiments 93-111, wherein the compound is administered to the subject when the subject has at least some food in the subject's stomach.

Embodiment 114: The method according to any one of Embodiments 93-113, wherein the subject is administered a dose of from about 0.25 mg/kg to about 2.50 mg/kg once or twice per day.

Embodiment 115: The method according to any one of Embodiments 93-113, wherein the subject is administered a dose of from about 0.25 mg/kg to about 2.50 mg/kg twice per day.

Embodiment 116: The method according to any one of Embodiments 93-115, wherein the disease or disorder is obesity.

Embodiment 117: The method according to any one of Embodiments 93-115, wherein the disease or disorder is a disease or disorder associated with seizures.

Embodiment 118: The method according to Embodiment 117, wherein the disease or disorder is a Developmental Epileptic Encephalopathy.

Embodiment 119: The method according to Embodiment 117, wherein the disease or disorder is Dravet Syndrome.

Embodiment 120: The method according to Embodiment 117, wherein the disease or disorder is Lennox Gastaut Syndrome.

Embodiment 121: The method according to Embodiment 117, wherein the disease or disorder is Tuberous sclerosis.

Embodiment 122: The method according to Embodiment 117, wherein the disease or disorder is CDKL5 deficiency disorder.

Embodiment 123: The method according to Embodiment 117, wherein the disease or disorder is associated with absence seizures.

Embodiment 124: The method according to Embodiment 123, wherein the absence seizures are associated with or without myoclonia.

Embodiment 125: The method according to Embodiment 117, wherein the disease or disorder is West Syndrome.

Embodiment 126: The method according to Embodiment 117, wherein the disease or disorder is Ohtahara Syndrome.

Embodiment 127: The method according to Embodiment 117, wherein the disease or disorder is Doose Syndrome.

Embodiment 128: The method according to Embodiment 117, wherein the disease or disorder is Epilepsy of Infancy with Migrating Focal Seizures (EIMFS).

Embodiment 129: The method according to Embodiment 117, wherein the disease or disorder is CDKL5 Deficiency Disorder.

Embodiment 130: The method according to Embodiment 117, wherein the disease or disorder is PCDH19-Related Epilepsy.

Embodiment 131: The method according to Embodiment 117, wherein the disease or disorder is Rett Syndrome.

Embodiment 132: The method according to Embodiment 117, wherein the disease or disorder is Pyridoxine-Dependent Epilepsy (PDE).

Embodiment 133: The method according to Embodiment 117, wherein the disease or disorder is a SCN8A-Related Epilepsy.

Embodiment 134: The method according to Embodiment 117, wherein the disease or disorder is GLUT1 Deficiency Syndrome.

Embodiment 135: The method according to Embodiment 117, wherein the disease or disorder is KCNQ2 Encephalopathy.

Embodiment 136: The method according to Embodiment 117, wherein the disease or disorder is STXBP1 Encephalopathy.

Embodiment 137: The method according to Embodiment 117, wherein the disease or disorder is a neurodevelopmental disorder associated with one or more mutations of the TCF4 gene.

Embodiment 138: The method according to Embodiment 137, wherein the disease or disorder is associated with intellectual disabilities.

Embodiment 139: The method according to Embodiment 137 or 138, wherein the disease or disorder is Pitt-Hopkins Syndrome (PTHS).

Embodiment 140: The method according to Embodiment 117, wherein the disease or disorder is associated with the dysfunction of at least one gene selected from CACNA1H, CACNA1A, GABRB3, GABRG2, SCN1A, SCN2A, SCC2A1, or CHRNA4.

Embodiment 141: The method according to Embodiment 117 or 140, wherein the disease or disorder is associated with polygenic mutations.

Embodiment 142: The method according to any one of Embodiments 117 and 140-141, wherein the disease or disorder is absence seizures.

Embodiment 143: The method according to Embodiment 142, wherein the disease or disorder is treatment-resistant absence seizures.

Embodiment 144: The method according to Embodiment 143, wherein the treatment-resistant absence seizures are associated with dysfunction of at least one gene selected from CACNA1H orGABRB3.

Embodiment 145: The method according to Embodiment 117, wherein the disease or disorder is associated with the dysfunction of at least one gene selected from CACNA1H, GABRB3, SCN1A, orTCF4.

Embodiment 146: The method according to Embodiment 145, wherein the disease or disorder is selected from Lennox-Gastaut Syndrome and Dravet Syndrome.

Embodiment 147: The method according to Embodiment 145, wherein the disease or disorder is selected from absence seizures and Pitt-Hopkins Syndrome.

Embodiment 148: The method according to any one of Embodiments 145-147, wherein the subject has one or more single nucleotide polymorphisms in a gene.

Embodiment 149: The method according to any one of Embodiments 145-147, wherein the subject has a chromosomal deletion including at least a portion of a gene.

Embodiment 150: The method according to any one of Embodiments 145-147, wherein the subject has a complete deletion of a gene.

Embodiment 151: The method according to any one of Embodiments 145-147, wherein the subject has a chromosomal translocation comprising at least a portion of a gene.

Embodiment 152: The method according to any one of Embodiments 145-147, wherein the subject has a translocation, frameshift, or non-sense mutation in a gene.

Embodiment 153: The method according to any one of Embodiments 145-152, wherein the gene is the TCF4 gene.

Embodiment 154: The method according to any one of Embodiments 145-152, wherein the gene is the SCN1A gene.

Embodiment 155: The method according to any one of Embodiments 145-152, wherein the gene is the GABRB3.

Embodiment 156: The method according to any one of Embodiments 145-152, wherein the gene is the CACNA1H.

Embodiment 157: The method according to any one of Embodiments 93-156, wherein the subject is an infant or pediatric subject.

Embodiment 158: The method according to any one of Embodiments 93-157, wherein the subject has an age selected from about 16 years of age or less, about 12 years of age or less, about 8 years of age or less, about 5 years of age or less, and about 2 years of age or less.

Embodiment 159: The method according to any one of Embodiments 93-156, wherein the subject is an adult subject.

Embodiment 160: The method according to Embodiment 159, wherein the adult subject is at least 18 years old.

Embodiment 161: A method of treating seizures in a subject exhibiting dysfunction with one or more genes selected from CACNA1H, CACNA1A, GABRB3, GABRG2, SCN1A, SCN2A, SCC2A1, CHRNA4, and TCF4, the method comprising administering to a subject a therapeutically effective amount of the compound according to any one of Embodiments 1-92.

Embodiment 162: The method according to any one of Embodiments 93-115, wherein the disease or disorder is a psychotic disorder.

Embodiment 163: The method according to Embodiment 162, wherein the psychotic disorder is schizophrenia.

Embodiment 164: A prodrug of a compound according to any one of Embodiments 1-92.

Embodiment 165: The prodrug according to Embodiment 164, wherein the prodrug is selected from compounds of Formula VIIa:

Formula VIIa

[A-]

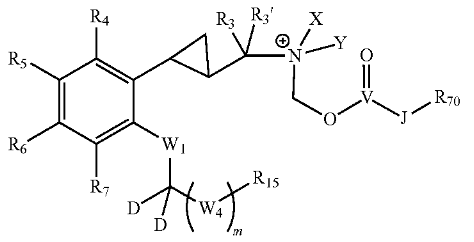

wherein

[A-] is a pharmaceutically acceptable anion;

V is selected from C and $P(R_{75})$, wherein $R_{75}$ is selected from —$O^-$ and -OM, wherein M is a pharmaceutically acceptable cation, provided that [A-] is absent when V is $P(R_{75})$ and $R_{75}$ is —$O^-$;

J is absent or is selected from 0, S, and $NR_9$; and $R_{70}$ is selected from hydrogen, optionally substituted alkyl that is branched or unbranched, and optionally substituted alkenyl that is branched or unbranched.

Embodiment 166: The prodrug according to Embodiment 165, wherein V is C.

Embodiment 167: The prodrug according to any one of Embodiments 165-166, wherein J is absent and $R_{70}$ is an optionally substituted $C_1$-$C_{24}$ alkyl.

Embodiment 168: The prodrug according to Embodiment 165, wherein V is $P(R_{75})$.

Embodiment 169: The prodrug according to Embodiment 168, wherein $R_{75}$ is —$O^-$, J is O, and $R_{70}$ is hydrogen, wherein the compound is zwitterionic and [A-] is absent.

Embodiment 170: The prodrug according to any one of Embodiments 165-169, wherein $W_1$ is O, $R_5$ is F, m is an integer selected from 1 to 3, and $R_{15}$ is selected from fluorine, hydrogen, and deuterium.

Embodiment 171: The prodrug according to any one of Embodiments 165-169, wherein $W_1$ is selected from 0, S, and Se.

Embodiment 172: A method of treating a seizure disease or disorder comprising administering to a subject in need thereof a therapeutically effective amount of a 5-HT2C receptor agonist compound that induces a $G_q$-mediated signaling bias when compared to p-arrestin-mediated signaling, wherein the 5-HT2C receptor agonist compound is selected from compounds of Formula VI:

Formula VI

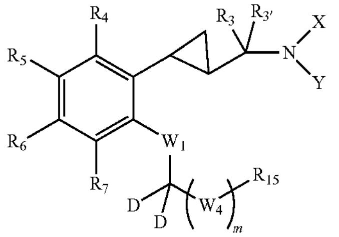

wherein

X and Y are each independently selected from hydrogen, deuterium, optionally substituted $C_1$-$C_8$ alkyl, optionally substituted $C_2$-$C_8$ alkenyl, and optionally substituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and NRq;

$W_1$ is selected from O, S, S(O), $SO_2$, Se, Se(O), and $SeO_2$;

$W_4$ is, for each occurrence, independently selected from O, S, Se, $C(R_{12})(R_{13})$, optionally substituted arylene, optionally substituted heteroarylene, optionally substituted cycloalkylene, optionally Y Ysubstituted heterocycloalkylene, and

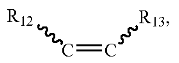

wherein m is an integer selected from 0 to 10;

$R_{12}$, $R_{13}$ and $R_{15}$ are, for each occurrence, independently selected from hydrogen, deuterium, halo, and hydroxyl;

$R_4$, $R_5$, $R_6$ and $R_7$ are each independently selected from hydrogen, deuterium, —$N(R_9)_2$, —$SR_9$, halo, optionally substituted $C_1$-$C_8$ alkyl, -$C_1$-$C_8$ alkoxy, optionally substituted $C_2$-$C_8$ alkenyl, optionally substituted $C_2$-$C_8$ alkynyl, optionally substituted aryl, optionally substituted heteroaryl, hydroxyl, —$OC(O)R_8$, —$OC(O)OR_8$, —$OP(O)(OR_9)_2$, and -$OSO2R_8$, or $R_4$ is taken together with $R_5$ and the carbons therebetween to form 3- to 7-membered carbocyclic or heterocyclic ring optionally including 1 to 2 additional ring heteromoieties selected from O, S, S(O), $SO_2$, and $NR_9$, or $R_5$ is taken together with $R_6$ and the carbons therebetween to form 3- to 7-membered carbocyclic or heterocyclic ring optionally including 1 to 2 additional ring heteromoieties selected from O, S, S(O), $SO_2$, and $NR_9$, or $R_6$ is taken together with $R_7$ and the carbons therebetween to form 3- to 7-membered carbocyclic or heterocyclic ring optionally including 1 to 2 additional ring heteromoieties selected from O, S, S(O), $SO_2$, and $NR_9$;

$R_3$ and $R_{3'}$ are each, independently, selected from hydrogen, deuterium, —$N(R_9)_2$, —$SR_9$, halo, optionally substituted $C_1$-$C_8$alkyl, -$C_1$-$C_8$ alkoxy, and optionally substituted $C_2$-$C_8$ alkenyl;

$R_9$ is independently selected from hydrogen, deuterium, optionally substituted $C_1$-$C_8$ alkyl, optionally substituted $C_2$-$C_8$ alkenyl, and optionally substituted aryl;

and salts, solvates, hydrates, prodrugs, and enantiomers thereof.

Embodiment 173: The method according to Embodiment 172, wherein $R_4$, $R_5$, $R_6$ and $R_7$ are each independently selected from hydrogen, deuterium, —$N(R_9)_2$, —$SR_9$, halo, optionally substituted $C_1$-$C_8$alkyl, -$C_1$-C alkoxy, optionally substituted $C_2$-$C_8$ alkenyl, optionally substituted $C_2$-$C_8$ alkynyl, optionally substituted aryl, and optionally substituted heteroaryl.

Embodiment 174: The method according to any one of Embodiments 172-173, wherein X and Y are hydrogen.

Embodiment 175: The method according to any one of Embodiments 172-174, wherein $W_1$ is selected from S and Se.

Embodiment 176: The method according to any one of Embodiments 172-174, wherein $W_1$ is O.

Embodiment 177: The method according to any one of Embodiments 172-176, wherein $R_3$ and $R_{3'}$ are selected from hydrogen and deuterium.

Embodiment 178: The method according to any one of Embodiments 172-177, wherein $R_4$, $R_5$, $R_6$ and $R_7$ are selected from hydrogen, deuterium, and halo.

Embodiment 179: The method according to any one of Embodiments 172-178, wherein $R_5$ is fluoro.

Embodiment 180: The method according to any one of Embodiments 172-179, wherein $R_4$, $R_6$ and $R_7$ are each hydrogen.

Embodiment 181: The method according to Embodiment 180, wherein $W_1$ is selected from S and Se.

Embodiment 182: The method according to Embodiment 180, wherein $W_1$ is O.

Embodiment 183: The method according to any one of Embodiments 172-182, wherein $W_4$ is, for each occurrence, independently selected from $C(R_{12})(R_{13})$ and

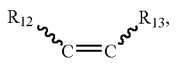

wherein m is an integer selected from 0 to 3, and $R_{12}$ and $R_{13}$ are independently selected from hydrogen, deuterium, and fluoro for each occurrence.

Embodiment 184: The method according to Embodiment 183, wherein $R_{15}$ is selected from hydrogen, fluoro, and deuterium.

Embodiment 185: The method according to any one of Embodiments 172-182, wherein $R_5$ is fluoro, $R_4$ is hydrogen, $R_6$ is hydrogen, and $R_7$ is hydrogen; $R_3$ and $R_{3'}$ are each hydrogen; X and Y are each hydrogen; and $W_4$ is, for each occurrence, independently selected from $C(R_{12})(R_{13})$ and

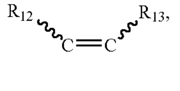

wherein m is an integer selected from 0 to 3, and $R_{12}$ and $R_{13}$ are independently selected from hydrogen, deuterium, and fluoro for each occurrence; and $R_{15}$ is selected from hydrogen, fluoro and deuterium.

Embodiment 186: The method according to Embodiment 185, wherein m is an integer selected from 1 and 2, and $R_{15}$ is selected from hydrogen and fluoro.

Embodiment 187: The method according to Embodiment 186, wherein $W_1$ is selected from S and Se.

Embodiment 188: The method according to Embodiment 186, wherein $W_1$ is O.

Embodiment 189: The method according to any one of Embodiments 172-188, wherein the subject exhibits dysfunction with at least one gene selected from CACNA1H or GABRB3.

Embodiment 190: The method according to any one of Embodiments 172-189, wherein seizure disease or disorder comprises absence seizures.

Embodiment 191: The method according to Embodiment 190, wherein the absence seizures are associated with myoclonia.

Embodiment 192: The method according to Embodiment 191, wherein the absence seizures are associated with eyelid myoclonia.

Embodiment 193: The method according to any one of Embodiments 172-188, wherein the subject exhibits dysfunction with at least one gene selected from CACNA1H, GABRB3, SCN1A, or TCF4.

Embodiment 194: The method according to any one of Embodiments 172-188 and 193, wherein the seizure disease or disorder is selected from Lennox-Gastaut Syndrome, Dravet Syndrome and Pitt-Hopkins Syndrome.

Embodiment 195: The method according to any one of Embodiments 172-194, wherein the subject is orally administered the compound in an amount of about 0.25 mg/kg to about 2.50 mg/kg once or twice per day.

Embodiment 196: The method according to any one of Embodiments 172-194, wherein the subject is orally administered the compound in an amount of about 0.25 mg/kg to about 2.50 mg/kg once per day.

Embodiment 197: The method according to any one of Embodiments 172-196, wherein the subject is at least 18 years old.

Embodiment 198: The method according to any one of Embodiments 172-197, wherein the subject is administered from about 40 mg to about 80 mg of the compound once per day.

Embodiment 199: The method according to any one of Embodiments 172-198, wherein the compound is administered in a solid capsule or solid tablet.

Embodiment 200: The method according to any one of Embodiments 172-197, wherein the subject is administered about 40 mg to about 80 mg of the compound twice per day.

Embodiment 201: The method according to Embodiment 200, wherein the compound is administered in a solid capsule or solid tablet.

Embodiment 202: The method according to any one of Embodiments 172-188, wherein the seizure disease or disorder is associated with dysfunction with one or more genes selected from CACNA1H, CACNA1A, GABRB3, GABRG2, SCN1A, SCN2A, SCC2A1, CHRNA4, and TCF4.

Embodiment 203: A method of treating a syndrome selected from Lennox-Gastaut Syndrome, Dravet Syndrome, and Pitt-Hopkins Syndrome, comprising orally administering to a subject in need thereof from about 0.25 mg/kg to about 2.50 mg/kg of a compound of Formula II:

Formula II

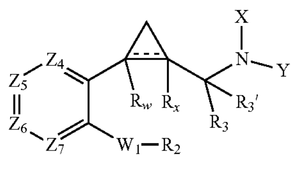

wherein

X and Y are each hydrogen;

$W_1$ is selected from O, S, S(O), $SO_2$, Se, Se(O), and $SeO_2$;

$Z_4$ is selected from N and $CR_4$;

$Z_5$ is selected from N and $CR_5$;

$Z_6$ is selected from N and $CR_6$;

$Z_7$ is selected from N and $CR_7$;

$R_2$, $R_4$, $R_5$, $R_6$ and $R_7$ are each independently selected from hydrogen, deuterium, halo, —$N(R_9)_2$, —$SR_9$, optionally substituted $C_1$-$C_8$alkyl, -$C_1$-$C_8$ alkoxy, optionally substituted $C_2$-$C_8$ alkenyl;

$R_3$, $R_{3'}$, $R_x$ and $R_w$, are each, independently, selected from hydrogen, deuterium, —$N(R_9)_2$, —$SR_9$, halo, optionally substituted $C_1$-$C_8$alkyl, -$C_1$-$C_8$ alkoxy, and optionally substituted $C_2$-$C_8$ alkenyl, optionally substituted $C_2$-$C_8$ alkynyl, optionally substituted aryl, and optionally substituted heteroaryl;

$R_9$ is independently selected from hydrogen, deuterium, optionally substituted $C_1$-$C_8$ alkyl, optionally substituted $C_2$-$C_8$ alkenyl, and optionally substituted aryl;

------ is a single bond;

and salts, solvates, hydrates, prodrugs, and enantiomers thereof.

Embodiment 204: The method according to Embodiment 203, wherein $Z_4$ is $CR_4$;

$Z_5$ is $CR_5$;

$Z_6$ is $CR_6$;

$Z_7$ is $CR_7$; and $R_4$, $R_5$, $R_6$ and $R_7$ are each independently selected from hydrogen, deuterium, —$N(R_9)_2$, —$SR_9$, halo, optionally substituted $C_1$-$C_8$alkyl, -$C_1$-$C_8$ alkoxy, optionally substituted $C_2$-$C_8$ alkenyl, optionally substituted $C_2$-$C_8$ alkynyl, optionally substituted aryl, and optionally substituted heteroaryl.

Embodiment 205: The method according to any one of Embodiments 203-204, wherein $R_4$, $R_5$, $R_6$, and $R_7$ are selected from hydrogen, deuterium, and halo.

Embodiment 206: The method according to any one of Embodiments 203-205, wherein $R_5$ is fluoro.

Embodiment 207: The method according to any one of Embodiments 203-206, wherein $R_4$, $R_6$, and $R_7$ are each hydrogen.

Embodiment 208: The method according to any one of Embodiments 203-207, wherein $R_2$ is $C_1$-$C_4$ alkyl substituted with at least two deuteriums.

Embodiment 209: The method according to any one of Embodiments 203-208, wherein $R_3$ and $R_{3'}$ are each independently selected from hydrogen and deuterium.

Embodiment 210: The method according to any one of Embodiments 203-209, wherein $R_2$ is optionally substituted $C_1$-$C_4$ alkyl.

Embodiment 211: The method according to Embodiment 210, wherein $R_2$ is $C_1$-$C_4$ alkyl substituted with at least one group selected from cycloalkyl, aryl, and heteroaryl.

Embodiment 212: The method according to Embodiment 211, wherein the $C_1$-$C_4$ alkyl is further optionally substituted with at least one deuterium or fluoro.

Embodiment 213: The method according to any one of Embodiments 210-212, wherein $R_2$ is $C_1$-$C_4$ alkyl substituted with a cyclopropyl or phenyl group.

Embodiment 214: The method according to any one of Embodiments 210-213, wherein $R_2$ is selected from

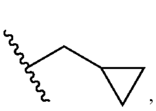
,
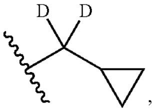
,

-continued

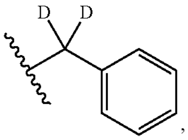
,
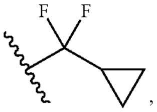
,
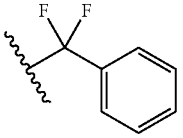
and
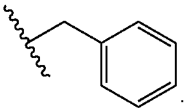
.

Embodiment 215: The method according to any one of Embodiments 203-213, wherein $R_2$ is substituted with at least one deuterium.

Embodiment 216: The method according to Embodiment 215, wherein $R_2$ is substituted with at least two deuteriums.

Embodiment 217: The method according to any one of Embodiments 203-213 or 215-216, wherein $R_2$ is optionally substituted with at least one halo.

Embodiment 218: The method according to Embodiment 217, wherein $R_2$ is substituted withe fluoro.

Embodiment 219: The method according to any one of Embodiments 203-218, wherein $W_1$ is selected from S and Se.

Embodiment 220: The method according to any one of Embodiments 203-218, wherein $W_1$ is O.

Embodiment 221: The method according to any one of Embodiments 203-220, wherein the subject exhibits dysfunction with at least one gene selected from CACNA1H, GABRB3, SCN1A, or TCF4.

Embodiment 222: The method according to any one of Embodiments 203-221, wherein the syndrome is Lennox-Gastaut Syndrome.

Embodiment 223: The method according to any one of Embodiments 203-221, wherein the syndrome is Dravet Syndrome.

Embodiment 224: The method according to any one of Embodiments 203-221, wherein the syndrome is Pitt-Hopkins Syndrome.

Embodiment 225: The method according to any one of Embodiments 203-224, wherein the subject is orally administered the at least one compound in an amount of from about 0.25 mg/kg to about 2.50 mg/kg once or twice per day.

Embodiment 226: The method according to any one of Embodiments 203-224, wherein the subject is orally administered the at least one compound in an amount of from about 0.25 mg/kg to about 2.50 mg/kg once per day.

Embodiment 227: The method according to any one of Embodiments 203-226, wherein the subject is at least 18 years old.

Embodiment 228: The method according to any one of Embodiments 203-227, wherein the at least one compound is administered with food.

Embodiment 229: The method according to any one of Embodiments 203-228, wherein the subject is administered from about 40 mg to about 80 mg of the at least one compound once per day.

Embodiment 230: The method according to any one of Embodiments 203-229, wherein the at least one compound is administered in a solid capsule or solid tablet.

Embodiment 231: The method according to any one of Embodiments 203-228, wherein the subject is administered from about 40 mg to about 80 mg of the at least one compound twice per day.

Embodiment 232: The method according to any one of Embodiments 203-228 and 231, wherein the at least one compound is administered in a solid capsule or solid tablet.

Embodiment 233: A method of treating a disease or disorder, comprising orally administering to a subject in need thereof a therapeutically effective amount at least one compound, wherein the at least one compound is selected from compounds of Formula V:

Formula V

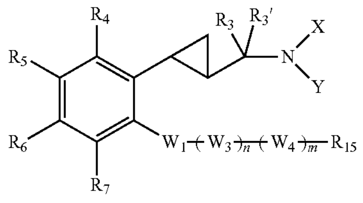

wherein

X and Y are each independently selected from hydrogen, deuterium, optionally substituted $C_1$-$C_8$ alkyl, optionally substituted $C_2$-$C_8$ alkenyl, or optionally substituted $C_2$-$C_8$ alkynyl, or Y is taken together with X and the nitrogen atom therebetween to form a 3- to 7-membered heterocyclic ring optionally including 1 to 2 additional ring heteromoieties selected from O, S, S(O), $SO_2$, and $NR_9$;

$W_1$ is selected from $CF_2$, $NR_1$, 0, 5, S(O), $SO_2$, Se, Se(O), and $SeO_2$;

$W_3$ is, for each occurrence, independently selected from optionally substituted alkylene, optionally substituted arylene, optionally substituted heteroarylene, optionally substituted cycloalkylene, optionally substituted heterocycloalkylene, and

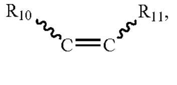

wherein n is an integer selected from 1 to 10;

$W_4$ is, for each occurrence, independently selected from O, S, Se, $C(R_{12})(R_{13})$, optionally substituted arylene, optionally substituted heteroarylene, optionally substituted cycloalkylene, optionally substituted heterocycloalkylene, and

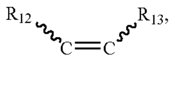

wherein m is an integer selected from 0 to 10;

$R_{10}$, $R_{11}$, $R_{12}$, $R_{13}$ and $R_{15}$ are, for each occurrence, independently selected from $C_1$-$C_8$ alkyl, hydrogen, deuterium, halo, and hydroxyl;

$R_1$ is selected from hydrogen, deuterium, optionally substituted $C_1$-$C_8$ alkyl, optionally substituted $C_2$-$C_8$ alkenyl, —$C(O)R_8$, —$C(O)OR_8$, —$P(O)(OR_9)_2$, —C(O)$N(R_9)_2$, —$SOR_8$, and —$SO_2R_8$;

$R_4$, $R_5$, $R_6$, and $R_7$ are each independently selected from hydrogen, deuterium, —$N(R_9)_2$, —$SR_9$, halo, optionally substituted $C_1$-$C_8$ alkyl, -$C_1$-$C_8$ alkoxy, and optionally substituted $C_2$-$C_8$ alkenyl, or $R_4$ is taken together with $R_5$ and the carbons therebetween to form 3- to 7-membered carbocyclic or heterocyclic ring optionally including 1 to 2 additional ring heteromoieties selected from O, S, S(O), $SO_2$, and $NR_9$, or $R_5$ is taken together with $R_6$ and the carbons therebetween to form 3- to 7-membered carbocyclic or heterocyclic ring optionally including 1 to 2 additional ring heteromoieties selected from O, S, S(O), $SO_2$, and $NR_9$, or $R_6$ is taken together with $R_7$ and the carbons therebetween to form 3- to 7-membered carbocyclic or heterocyclic ring optionally including 1 to 2 additional ring heteromoieties selected from O, S, S(O), $SO_2$, and $NR_9$;

$R_3$ and $R_{3'}$ are each, independently, selected from hydrogen, deuterium, —$N(R_9)_2$, —$SR_9$, halo, optionally substituted $C_1$-$C_8$ alkyl, -$C_1$-$C_8$ alkoxy, and optionally substituted $C_2$-$C_8$ alkenyl;

$R_8$ is selected from optionally substituted $C_1$-$C_8$ alkyl, optionally substituted $C_2$-$C_8$ alkenyl, and optionally substituted aryl;

$R_9$ is independently selected from hydrogen, deuterium, optionally substituted $C_1$-$C_8$ alkyl, optionally substituted $C_2$-$C_8$ alkenyl, and optionally substituted aryl;

and salts, solvates, hydrates, prodrugs, and enantiomers thereof.

Embodiment 234: The method according to Embodiment 233, wherein X and Y are each hydrogen.

Embodiment 235: The method according to any one of Embodiments 233-234, wherein $W_1$ is selected from 0, S, and Se.

Embodiment 236: The method according to any one of Embodiments 233-235, wherein $R_4$, $R_5$, $R_6$, and $R_7$ are each independently selected from hydrogen, deuterium, and halo.

Embodiment 237: The method according to any one of Embodiments 233-236, wherein $R_3$ and $R_{3'}$ are each, independently, selected from hydrogen and deuterium.

Embodiment 238: The method according to any one of Embodiments 233-237, wherein the at least one compound of Formula V is selected from compounds of Formula VI(a):

Formula VI(a)

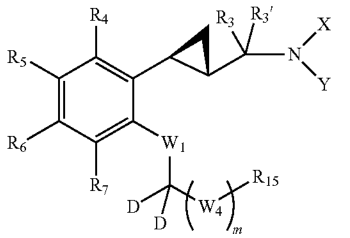

and salts, solvates, hydrates, prodrugs, and enantiomers thereof.

Embodiment 239: The method according to any one of Embodiments 233-238, wherein $R_4$, $R_5$, $R_6$, and $R_7$ are each independently selected from hydrogen, deuterium, and fluoro.

Embodiment 240: The method according to Embodiment 239, wherein $R_5$ is fluoro.

Embodiment 241: The method according to Embodiment 240, wherein $W_1$ is selected from S and Se.

Embodiment 242: The method according to Embodiment 240, wherein $W_1$ is O.

Embodiment 243: The method according to any one of Embodiments 233-242, wherein $R_3$ and $R_{3'}$ are each hydrogen.

Embodiment 244: The method according to any one of Embodiments 233-243, wherein $R_4$, $R_6$, and $R_7$ are each hydrogen.

Embodiment 245: The method according to Embodiment 244, wherein $W_1$ is selected from S and Se.

Embodiment 246: The method according to Embodiment 244, wherein $W_1$ is O.

Embodiment 247: The method according to any one of Embodiments 233-246, wherein $W_4$ is, for each occurrence, independently selected from $C(R_{12})(R_{13})$ and

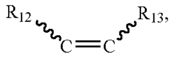

wherein m is an integer selected from 0 to 3, and $R_{12}$ and $R_{13}$ are each independently selected from hydrogen, deuterium, and fluoro for each occurrence.

Embodiment 248: The method according to any one of Embodiments 233-247, wherein $R_{15}$ is selected from hydrogen, fluoro, and deuterium.

Embodiment 249: The method according to Embodiment 233, wherein $R_5$ is fluoro, $R_4$ is hydrogen, $R_6$ is hydrogen, and $R_7$ is hydrogen; $R_3$ and $R_{3'}$ are each hydrogen; and $W_4$ is, for each occurrence, independently selected from $C(R_{12})(R_{13})$ and

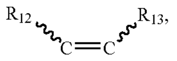

wherein m is an integer selected from 0 to 3, and $R_{12}$ and $R_{13}$ are each independently selected from hydrogen, deuterium, and fluoro for each occurrence; and $R_{15}$ is selected from hydrogen, fluoro, and deuterium.

Embodiment 250: The method according to Embodiment 249, wherein m is an integer selected from 1 and 2, and $R_{15}$ is selected from hydrogen and fluoro.

Embodiment 251: The method according to any one of Embodiments 249-250, wherein $W_1$ is selected from S and Se.

Embodiment 252: The method according to any one of Embodiments 249-250, wherein $W_1$ is O.

Embodiment 253: The method according to any one of Embodiments 233-252, wherein the subject exhibits dysfunction with at least one gene selected from CACNA1H, CACNA1A, GABRB3, GABRG2, SCN1A, SCN2A, SCC2A1, CHRNA4, and TCF4.

Embodiment 254: The method according to any one of Embodiments 233-253, wherein the subject is an infant or pediatric subject under the age of 18 years.

Embodiment 255: The method according to any one of Embodiments 233-254, wherein the subject is an adult subject that is aged at least 18 years.

Embodiment 256: The method according to any one of Embodiments 233-255, wherein the at least one compound is orally administered.

Embodiment 257: The method according to any one of Embodiments 233-256, wherein the at least one compound is administered in an amount of about 0.25 mg/kg to about 2.50 mg/kg.

Embodiment 258: The method according to any one of Embodiments 233-257, wherein the subject is orally administered the at least one compound in an amount of about 0.25 mg/kg to about 2.50 mg/kg once or twice per day.

Embodiment 259: The method according to any one of Embodiments 233-257, wherein the subject is orally administered the at least one compound in an amount of about 0.25 mg/kg to about 2.50 mg/kg once per day.

Embodiment 260: The method according to any one of Embodiments 233-259, wherein the subject is administered about 40 mg to about 80 mg of the at least one compound once per day.

Embodiment 261: The method according to any one of Embodiments 233-259, wherein the subject is administered about 40 mg to about 80 mg of the at least one compound twice per day.

Embodiment 262: The method according to any one of Embodiments 233-261, wherein the disease or disorder is associated with food intake.

Embodiment 263: The method according to any one of Embodiments 233-261, wherein the disease or disorder is a seizure disease or disorder, and/or symptoms associated therewith.

Embodiment 264: The method according to any one Embodiments 233-261, wherein the disease or disorder is staring spells and/or loss of awareness associated with a thalamocortical circuit disruption and/or thalamocortical oscillations.

Embodiment 265: The method according to Embodiments 264, wherein the staring spells and/or loss of awareness are associated with eyelid myoclonia.

Embodiment 266: The method according to any one of Embodiments 233-265, wherein the at least one compound is crystalline.

Embodiment 267: The method according to any one of Embodiments 233-266, wherein the at least one compound is a crystalline salt.

Embodiment 268: The method according to any one of Embodiments 264-267, wherein the thalamocortical oscillations are associated with absence seizures.

Embodiment 269: The method according to any one of Embodiments 264-268, wherein the thalamocortical oscillations associated with non-convulsive seizures.

Embodiment 270: The method according to any one of Embodiments 233-263, wherein the disease or disorder is absence seizures.

Embodiment 271: The method according to any one of Embodiments 233-263, wherein the disease or disorder is Developmental Epileptic Encephalopathy.

Embodiment 272: The method according to any one of Embodiments 233-263, wherein the disease or disorder is at least one symptom associated with Developmental Epileptic Encephalopathy.

Embodiment 273: The method according to any one of Embodiments 233-272, wherein the at least one compound is administered in a liquid oral dosage form comprising sucrose and water.

Embodiment 274: The method according to any one of Embodiments 233-273, wherein the at least one compound is administered at least two times per day.

Embodiment 275: The method according to any one of Embodiments 233-273, wherein the at least one compound is administered one to three times per day.

Embodiment 276: The method according to any one of Embodiments 233-273, wherein the at least one compound is administered once per day.

Embodiment 277: The method according to any one of Embodiments 233-272, wherein the at least one compound is administered in an extended release tablet further comprising a pharmaceutically-acceptable carrier.

Embodiment 278: The method according to Embodiments 277, wherein the extended release tablet delivers at least some of the at least one compound to the small intestine of the subject.

Embodiment 279: The method according to any one of Embodiments 277-278, wherein the extended release tablet releases the at least one compound over a time period of from about 8 hrs to about 36 hrs.

Embodiment 280: The method according to any one of Embodiments 277-278, wherein the extended release tablet releases the at least one compound over a time period of from about 12 hrs to about 24 hrs.

Embodiment 281: The method according to any one of Embodiments 277-280, wherein the at least one compound is administered once per day.

Embodiment 282: The method according to any one of Embodiments 233-281, wherein the at least one compound induces a $G_q$-mediated signaling bias at 5-HT2C receptors when compared to p-arrestin-mediated signaling.

Embodiment 283: The method according to any one of Embodiments 233-282, wherein the at least one compound is a 5-HT2C receptor agonist.

Embodiment 284: The method according to Embodiments 270 and 273-283, wherein the absence seizures are associated with Developmental Epileptic Encephalopathy.

Embodiment 285: The method according to Embodiment 284, wherein the absence seizures are atypical.

Embodiment 286: The method according to any one of Embodiments 284-285, wherein the subject exhibits EEG spike-and-wave patterns of about 2.5 Hz or less.

Embodiment 287: The method according to any one of Embodiments 270 and 273-283, wherein the absence seizures are typical.

Embodiment 288: The method according to Embodiment 287, wherein the subject exhibits EEG spike-and-wave patterns of about 3.0 Hz or more.

Embodiment 289: The method according to any one of Embodiments 264-265, wherein the wherein the staring spells occur for from about 5 seconds to about 90 seconds.

Embodiment 290: The method according to any one of Embodiments 262 or 273-283, wherein the disease or disorder is obesity.

Embodiment 291: The method according to Embodiment 291, wherein the disease or disorder is obesity and at least one comorbidity.

Embodiment 292: The method according to Embodiment 291, wherein the at least one comorbidity is selected from hypertension, Type II diabetes, dyslipidemia, stroke, gout, osteoarthritis, and sleep apnea.

Embodiment 293: The method according to any one of Embodiments 290-292, wherein the subject has a body mass index (BMI) of about 27 $kg/m^2$ or more.

Embodiment 294: The method according to any one of Embodiments 290-292, wherein the subject has a body mass index (BMI) of about 30 $kg/m^2$ or more.

Embodiment 295: The method according to any one of Embodiments 290-294, further comprising administering to the subject at least one GLP-1 receptor agonist.

Embodiment 296: The method according to Embodiment 295, wherein the at least one GLP-1 receptor agonist is selected from semaglutide, liraglutide, tirzepatide, exenatide, albiglutide, dulaglutide, and lixisenatide.

Embodiment 297: The method according to any one of Embodiments 290-296, wherein the at least one compound is

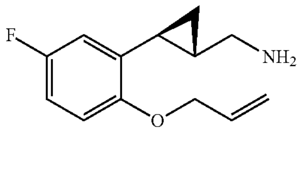 [SMILES: C=CCOc1ccc(F)cc1[C@H]1C[C@@H]1CN]

or a salt, solvate, hydrate, or prodrug thereof.

Embodiment 298: The method according to any one of Embodiments 290-296, wherein the at least one compound is selected from

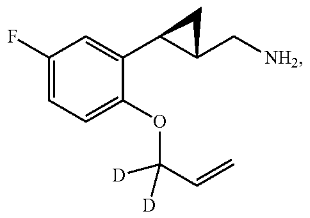

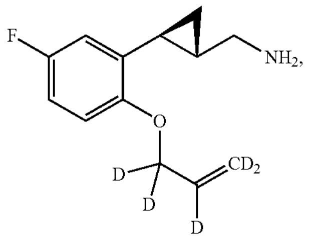

and salts, solvates, hydrates, or prodrugs thereof.

Embodiment 299: The method according to any one of Embodiments 264-265, wherein the disease or disorder is starting spells and/or loss of awareness associated with absence seizures with eyelid myoclonia.

Embodiment 300: The method according to Embodiment 299, wherein the subject has Jeavons Syndrome.

Embodiment 301: The method according to any one of Embodiments 273-276, wherein the liquid oral dosage form comprises the at least one compound at a concentration of from about 1 mg/ml to about 25 mg/ml.

Embodiment 302: The method according to any one of Embodiment 273-276, wherein the liquid oral dosage form comprises the at least one compound at a concentration of from about 5 mg/ml to about 15 mg/ml.

Embodiment 303: The method according to any one of Embodiment 273-276, wherein the liquid oral dosage form comprises the at least one compound at a concentration of from about 8 mg/ml to about 12 mg/ml.

Embodiment 304: The method according to any one of Embodiment 273-276, wherein the liquid oral dosage form comprises the at least one compound at a concentration of about 10 mg/ml.

Embodiment 305: The method according to any one of Embodiments 233-304, wherein use of a secondary drug is contraindicated, wherein the secondary drug is selected from at least one of a serotonin receptor agonist, a serotonin receptor antagonist, an SNRI, an SSRI, and a monoamine oxidase inhibitor.

Embodiment 306: The method according to any one of Embodiments 268-272, wherein the absence seizures are refractory absence seizures.

Embodiment 307: The method according to Embodiment 273, wherein the at least one compound is administered two or three times per day.

Finally, it is noted that, as used in this specification and the appended claims, the singular forms "a," "an," and "the," include plural referents unless expressly and unequivocally limited to one referent and vice versa. As used herein, the term "include" or "comprising" and its grammatical variants are intended to be non-limiting, such that recitation of an item or items is not to the exclusion of other like items that can be substituted or added to the recited item(s).

What is claimed:

1. A method of treating staring spells and/or loss of awareness associated with thalamocortical oscillations, comprising orally administering to a human subject in need thereof at least one compound selected from compounds of Formula V:

Formula V

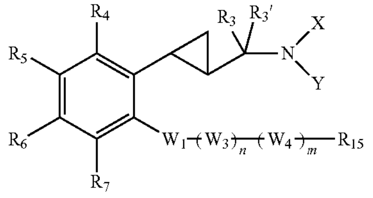

wherein

X and Y are each hydrogen;

$W_1$ is O;

$W_3$ is —$C(R_{10})(R_{11})$ wherein n is an integer selected from 1 to 4;

$W_4$ is

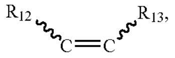

wherein m is 0 or 1;

$R_{10}$, $R_{11}$, $R_{12}$, and $R_{13}$ are, for each occurrence, independently selected from hydrogen, deuterium, and fluoro;

$R_{15}$ is selected from hydrogen, deuterium, and fluoro;

$R_4$, $R_6$, and $R_7$ are each hydrogen;

$R_5$ is fluoro;

$R_3$ and $R_{3'}$ are each, independently, selected from hydrogen and deuterium;

and salts, solvates, hydrates, prodrugs, and enantiomers thereof.

2. The method of claim 1, wherein at least one of $R_3$, $R_{3'}$, $R_{10}$ or $R_{11}$ is deuterium.

3. The method of claim 1, wherein $R_3$ and $R_{3'}$ are each hydrogen.

4. The method of claim 1, wherein $R_{15}$ is selected from hydrogen and fluoro.

5. The method of claim 1, wherein the subject is an infant or pediatric subject under the age of 18 years.

6. The method of claim 1, wherein the subject is an adult subject that is aged at least 18 years.

7. The method of claim 1, wherein the subject is administered the at least one compound in an amount of about 0.25 mg/kg to about 2.50 mg/kg one to three times per day.

8. The method of claim 1, wherein the subject is administered the at least one compound in an amount of about 0.25 mg/kg to about 2.50 mg/kg once per day.

9. The method of claim 1, wherein the subject is administered about 40 mg to about 80 mg of the at least one compound once per day.

10. The method of claim 1, wherein the subject is administered about 40 mg to about 80 mg of the at least one compound twice per day.

11. The method of claim 1, wherein the staring spells occur for about 5 seconds to about 90 seconds.

12. The method of claim 7, wherein the at least one compound is administered in a liquid oral dosage form comprising a sugar and water.

13. The method of claim 12, wherein the at least one compound is administered in a liquid oral dosage form comprising sucrose and water, wherein the at least one compound is present at a concentration of about 5 mg/ml to about 15 mg/ml of the liquid oral dosage form.

14. The method of claim 8, wherein the at least one compound is administered in an extended release tablet further comprising a pharmaceutically-acceptable carrier.

15. The method of claim 14, wherein the extended release tablet delivers at least some of the at least one compound to the small intestine of the subject.

16. The method of claim 2, wherein $R_3$ and $R_{3'}$ are deuterium.

17. The method of claim 2, wherein $R_{10}$ and $R_{11}$ are deuterium.

18. The method of claim 1, wherein the thalamocortical oscillations are associated with non-convulsive absence seizures.

19. The method of claim 1, wherein the subject is administered about 0.25 mg/kg to about 2.50 mg/kg of the at least one compound.

20. The method of claim 3, wherein the cyclopropyl ring in the compound of Formula V has S,S absolute stereochemistry.

21. The method of claim 20, wherein n is an integer selected from 1 and 2.

22. The method of claim 21, wherein m is 0.

23. The method of claim 22, wherein $R_{15}$ is fluoro.

24. The method of claim 20, wherein n is 1.

25. The method of claim 24, wherein m is 1.

26. The method of claim 25, wherein $R_{15}$ is hydrogen.

27. The method of claim 23, wherein $R_{10}$ and $R_{11}$ are hydrogen for each occurrence.

28. The method of claim 18, wherein the non-convulsive absence seizures are non-convulsive myoclonic absence seizures.

29. The method of claim 1, wherein the thalamocortical oscillations are associated with refractory absence seizures.

* * * * *